US012479866B2

(12) United States Patent
Hormann et al.

(10) Patent No.: US 12,479,866 B2
(45) Date of Patent: Nov. 25, 2025

(54) BORON-CONTAINING RHO KINASE INHIBITORS

(71) Applicant: Percipiad, Inc., Warminster, PA (US)

(72) Inventors: Robert Eugene Hormann, Melrose Park, PA (US); Malla Padidam, Chalfont, PA (US)

(73) Assignee: Percipiad, Inc.

( * ) Notice: Subject to any disclaimer, the term of this patent is extended or adjusted under 35 U.S.C. 154(b) by 897 days.

(21) Appl. No.: 17/627,537

(22) PCT Filed: Jul. 17, 2020

(86) PCT No.: PCT/US2020/042538
§ 371 (c)(1),
(2) Date: Jan. 14, 2022

(87) PCT Pub. No.: WO2021/011873
PCT Pub. Date: Jan. 21, 2021

(65) Prior Publication Data
US 2022/0389035 A1 Dec. 8, 2022

Related U.S. Application Data

(60) Provisional application No. 62/875,270, filed on Jul. 17, 2019.

(51) Int. Cl.
*C07F 5/02* (2006.01)
*A61K 45/06* (2006.01)
*A61P 25/28* (2006.01)
*A61P 27/06* (2006.01)

(52) U.S. Cl.
CPC .............. *C07F 5/025* (2013.01); *A61K 45/06* (2013.01)

(58) Field of Classification Search
CPC . C07F 5/025; C07F 5/02; A61K 45/06; A61P 27/06; A61P 25/28
See application file for complete search history.

(56) References Cited

U.S. PATENT DOCUMENTS 3,639,532 A * 2/1972 Oertal .................. C08K 5/5353 987/153
2010/0280011 A1 11/2010 Delong et al.
2017/0137443 A1 5/2017 Wang et al.

FOREIGN PATENT DOCUMENTS

WO WO-2010028005 A1 * 3/2010 ................ A61P 9/00
WO WO-2010126626 A2 * 11/2010 .............. A61P 35/00

OTHER PUBLICATIONS

Jiang et al. "Boron-Based 4-Hydroxytamoxifen Bioisosteres for Treatment of de Novo Tamoxifen Resistant Breast Cancer" ACS Medicinal Chemistry Letters 2012, vol. 3, pp. 392-396. https://pubs.acs.org/doi/10.1021/ml3000287, Retrieved Jan. 11, 2022.
Oliveira et al. "Synthesis and pharmacological evaluation of novel isoquinoline N-sulphonylhydrazones designed as ROCK inhibitors", Journal of enzyme inhibition and medicinal chemistry, 2018. vol. 33, No. 1, pp. 1181-1193., http://dx.doi.org/10.1080/14756366.2018.1490732., Retrieved Jan. 11, 2022.
Extended European Search Report issued on Jun. 7, 2023 in counterpart Application No. 20841243.
Dayal, Neetu, et al., "Potently inhibiting cancer cell migration with novel 3H-pyrazolo[4,3-f]quinoline boronic acid ROCK inhibitors", European Journal of Medicinal Chemistry, Elsevier, Amsterdam, NL, vol. 180, Jun. 29, 2019 (Jun. 29, 2019), pp. 449-456.

* cited by examiner

*Primary Examiner* — Jeffrey S Lundgren
*Assistant Examiner* — Alexander K. Showalter
(74) *Attorney, Agent, or Firm* — The Belles Group, P.C.

(57) ABSTRACT

The present invention provides boron-containing isoquinoline compounds as protein kinase-modulating compounds. These compounds are useful as neuroprotective and neuroregenerative agents for the amelioration of glaucoma and other ocular neuropathies.

20 Claims, 15 Drawing Sheets

BORON-CONTAINING RHO KINASE INHIBITORS

CROSS-REFERENCE TO RELATED APPLICATION

This application claims the benefit of priority from U.S. Provisional Application No. 62/875,270, filed Jul. 17, 2019, the contents of which are hereby incorporated herein by reference in their entirety.

FIELD OF THE DISCLOSURE

The present disclosure generally relates to protein kinase-modulating compounds including boron-containing compounds, which are useful as neuroprotective and neuro-regenerative agents for the amelioration of glaucoma and other ocular neuropathies.

BACKGROUND

Glaucoma is a worldwide health issue with significant economic burden. Glaucoma is one of the major causes of blindness worldwide; greater than 60 million people are affected. According to a 2006 estimate irreversible sight impairment costs the United States approximately $50B annually, with glaucoma as a significant contributor. The market for glaucoma medications in the U.S. was ca. $2.5B in 2015.

Commercial glaucoma medications are designed to reduce intraocular pressure. Drugs for glaucoma can be organized according to target class: alpha adrenergic agonists (reduce aqueous humor production, increases outflow) beta-adrenergic blockers (reduce aqueous humor production), carbonic anhydrase inhibitors (reduce aqueous humor production), miotics (increase aqueous humor outflow), prostaglandins (increase uveoscleral outflow), sympathomimetics (reduce aqueous humor production, increase outflow) and more recently under development, adenosine A1 receptor agonists (increase aqueous humor outflow) and rho kinase inhibitors (increase aqueous humor outflow, decreased production). Several of these classes have multiple targets and modes of action. As is the case with many ocular medications, some glaucoma medications were originally considered for systemic indications and have been repurposed for ophthalmology.

One developmental medication designed to ameliorate increased ocular pressure (IOP) also demonstrates neuroprotection in the posterior eye: Rhopressa (netarsudil). Netarsudil is an IOP-lowering agent that also has been shown to promote blood flow to the optic nerve head, retinal ganglion cell survival, and axon regeneration in rats. In its primary IOP-lowering function, netarsudil inhibits rho kinase (ROCK) in the trabecular meshwork to increase aqueous humor outflow and also the norepinephrine transporter (NET) in the ciliary body to reduce aqueous humor production. Hence, the primary IOP targets (ROCK, NET) are in the anterior segment of the eye. In contrast, the secondary neuroprotective targets are in the posterior of the eye (ROCK).

A primary endpoint in clinical trials of netarsudil has been the reduction of IOP. Toward this end, netarsudil is constructed as a lipophilic pro-drug administered as a topical solution. The pro-moiety increases log P in order to maximize transcellular permeability. Since lipophilic molecules tend to favor corneal rather than conjunctival permeation, and since the IOP-lowering targets are anterior, the presumptive route of entry is through the cornea. Importantly, both the parent molecule and more polar pro-drug analogs are much less effective in lowering IOP in rabbit studies, a reflection of bioavailability rather than potency. Despite the design orientation toward the anterior eye, in rats, netarsudil must also reach the retina, as evidenced by retinal ganglion cell survival, and axon regeneration. A common but mild side effect of netarsudil is conjunctival hyperemia.

AR-13154, another ROCK inhibitor, also targets Janus kinase (JAK), platelet-derived growth factor kinase (PDGFR), protein kinase C (PKC), and also ROCK. AR-13154 is intended for treatment of wet age-related macular degeneration (AMD) and retinal neovascularization in proliferative diabetic retinopathy (PDR). The sponsors of AR-13154 intend that it be administered as an implant to reach its retinal targets.

Numerous design strategies have been implemented to improve the bioavailability and convenience of ocular drugs. These can be categorized according to two parameters: (a) elaborations of the active ingredient, i.e., API, API modifications such as pro-drug moieties, drug delivery systems, and (b) mode/locus of administration. Because the eye is externally visible and because geometrical distances to interior ocular compartments are short, the human eye gives the impression of accessibility. Quite to the contrary, effective drug delivery to eye tissue is very difficult due to multiple, layered, and orthogonally-selective static and dynamic barriers. Delivery to posterior tissues of the eye is especially difficult.

Therefore, there remains a need to achieve or increase the neuroprotective effect of topical ROCK inhibitors; and reduce the side effects (e.g. hyperemia, etc.) associated therewith. Embodiments of the present invention are designed to meet these, and other, needs.

SUMMARY

The present invention provides boron-containing isoquinoline compounds. A significant subset contains an amino-acid, peptide or peptide-like prodrug moiety.

The present invention also provides compositions comprising a boron-containing compound and one or more excipients. In a further aspect, the composition is a pharmaceutically acceptable composition.

In another aspect, the present invention provides boron-containing isoquinoline compounds for use as rho kinase inhibitors. An advantage of the present invention is that it provides a means to regulate signaling pathways that involve rho kinase and are located in cells and tissues in the posterior segment of the eye.

In another aspect, the present invention provides boron-containing compounds that vary in physical properties, membrane transporter recognition, and mucoadhesion properties.

In another aspect, the present invention provides methods of regulating rho kinase in an isolated host cell or a non-human organism, comprising contacting the host cell or a non-human organism with a boron-containing compound of the current invention, or composition thereof.

In another aspect, the present invention provides boron-containing compounds that are operative with systemic, topical ocular, ocular injective, and ocular implant modes of administration.

In another aspect, the present invention provides methods of treating a disease, disorder, injury, or condition in a subject, comprising administering to the subject a boron-containing compound of the invention, or composition thereof.

In another aspect, the present invention provides methods of treating a rho kinase-modulated disease, disorder, injury, or condition in a subject, comprising administering to the subject a boron-containing compound of the invention, or composition thereof.

In another aspect, the present invention provides boron-containing compounds, or composition thereof, for use in treating a disease, disorder, injury, or condition.

In another aspect, the present invention provides boron-containing compounds, or composition thereof, for use in the manufacture of a medicament for treating a disease, disorder, injury, or condition.

BRIEF DESCRIPTION OF THE DRAWINGS

The following detailed description of various embodiments of the invention will be better understood when read in conjunction with the appended drawings. For the purpose of illustrating the invention, certain embodiments are shown in the drawings. It should be understood, however, that the invention is not limited to the precise arrangements and instrumentalities of the embodiments shown in the drawings.

Figure 1:
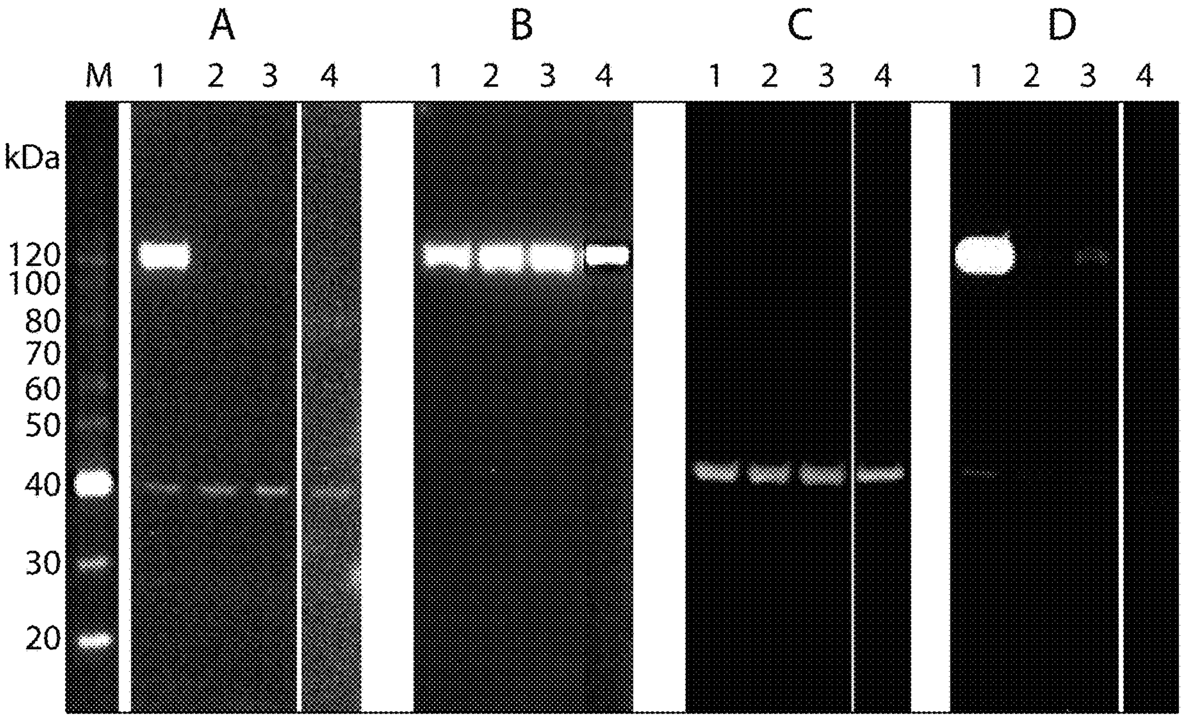
FIG. 1 Detection of phosphorylated MYPT1 Thr853, total MYPT1, and beta-actin on western blot in human trabecular meshwork cells. (A) MYPT1 Thr853 (~115 kDa) incubated with 10 μM compound 10.2HCl, Netarsudil.2HCl, or Netarsudil-M1-racemate.2HCl. (B) total MYPT1 (~115 kDa) incubated with 10 μM compound 10.2HCl, Netarsudil.2HCl, or Netarsudil-M1-racemate.2HCl. (C) Beta-actin (~42 kDa) incubated with 10 μM compound 10.2HCl, Netarsudil.2HCl, or Netarsudil-M1-racemate.2HCl. (D) MYPT1 Thr853 (~115 kDa) incubated with 2.5 μM compound 10.2HCl, Netarsudil.2HCl, or Netarsudil-M1-racemate.2HCl. Lane 1 is DMSO control; lane 2 is a Netarsudil-M1-racemate.2HCl; lane 3 is compound 10.2HCl; and lane 4 is Netarsudil.2HCl. Lane M is ThermoFisher MagicMark™ XP Western Protein Standard (cat #LC5602). Approximate molecular weights are given next to standard lane. Phospho-MYPT1 Thr853 antibody cross reacts with an unidentified protein of ~40 kDa.

All drawings are not necessarily to scale. It should be understood that the various aspects are not limited to the compositions, arrangements, and instrumentality shown in the figures.

DETAILED DESCRIPTION

The term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-10}$ alkyl groups include methyl (including $—CD_3$), ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

The term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include $—CH_2CH_2NO_2$, $—CH_2CH_2CO_2H$, $—CH_2CH_2SO_2CH_3$, $—CH_2CH_2COPh$, $—CH_2C_6H_{11}$, and the like.

The term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

The term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent.

The term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl, cyclohexenyl and the like.

The term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

The term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

The term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

The term “alkoxyalkyl” as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

The term “haloalkoxy” as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

The term “dialkylamino” as used by itself or as part of another group refers to —NR'R", wherein R' and R" are each independently alkyl or R' and R" are taken together to form a 3- to 8-membered optionally substituted heterocyclo.

In some embodiments, compounds of the present invention containing a boronic acid group —$B(OH)_2$, oxaborolane, or oxaborole, are likely to display ionization equilibrium in water because of the acidic character of the boron functionality. By way of illustration, and not limitation, certain compounds of the invention may exist either as a neutral trivalent species or as an anionic tetrahedral species (Equations 1-3).

boronic acid

Eq. 1

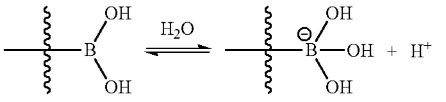

oxaborolane

Eq. 2

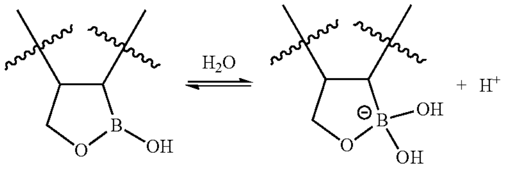

oxaborole

Eq. 3

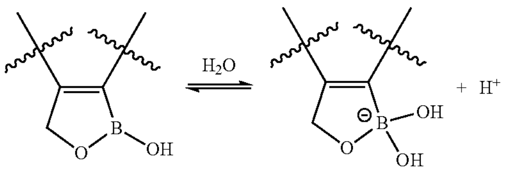

Embodiments of the present invention encompass both neutral trivalent species and anionic tetrahedral species of boronic acids, oxaborolanes, oxaboroles, and related ring systems as illustrated in Equations 1-3. In some embodiments, compounds of the present invention having a boronic acid substituent exist as an anionic tetrahedral species in water. In other embodiments, compounds of the present invention having an oxaborolane substituent exist as an anionic tetrahedral species in water. In further embodiments, compounds of the present invention having an oxaborole substituent exist as an anionic tetrahedral species in water. Thus, in a pharmaceutical composition comprising a boron-containing compounds and water (and optionally one or more additional excipients), compounds of the present invention may be present in the neutral trivalent form, the anionic tetrahedral form, or both.

Embodiments of the present invention encompass structures containing both a boronic acid and an amino group or nitrogen-containing heterocycle. Depending on pH, these may exist as a cationic species, a neutral species without formal charge, a zwitterionic neutral species, or an anionic species. Pharmaceutical compositions comprising boron and amino-containing compounds of the present invention may be present in any of these forms.

The present disclosure encompasses various forms of boron-containing rings, including open- and closed-ring forms which may exist in equilibria with one another depending on various conditions, e.g., solvent, pH, temperature, as illustrated in Equation 4A. Compounds of the present disclosure are meant to include both open- and closed-ring forms that may exist under various conditions, as illustrated in Equations 4A & 4B.

Eq. 4A

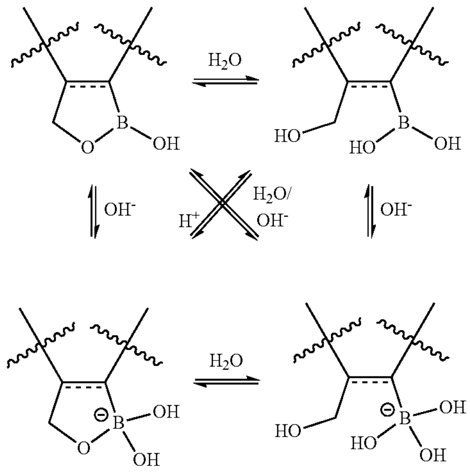

Eq. 4B

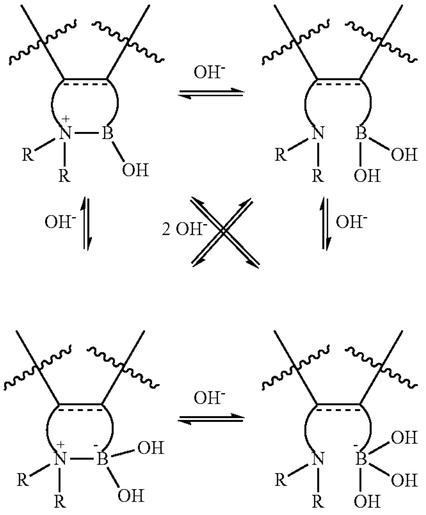

The present disclosure also encompasses various di- and trimeric forms of boronic acids, oxaborolanes, oxaboroles, azaboroles, and related boron-containing ring systems. In one embodiment, Compounds of the Disclosure form boroxines, for example, a compound of Formula B:

B

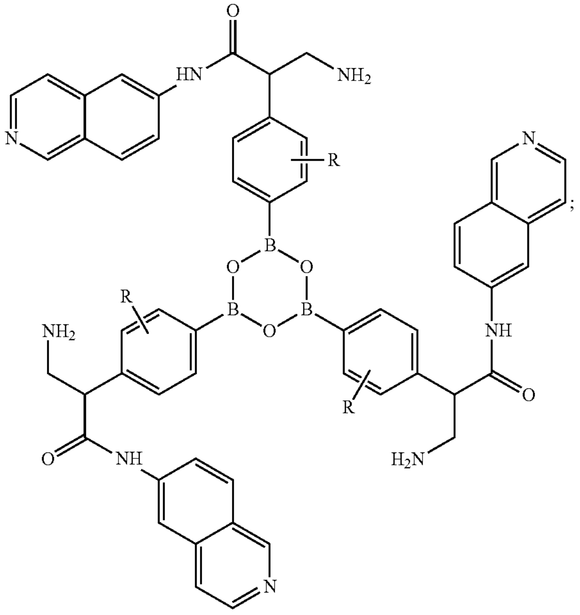

or an anhydride of Formula C or Formula D:

C

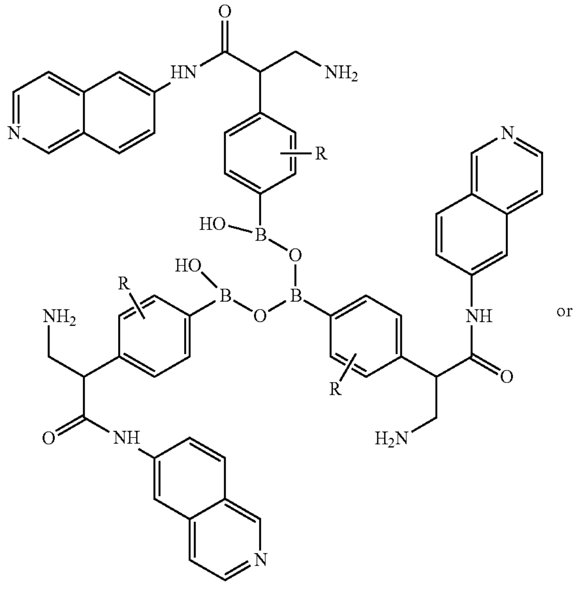

or

-continued

D

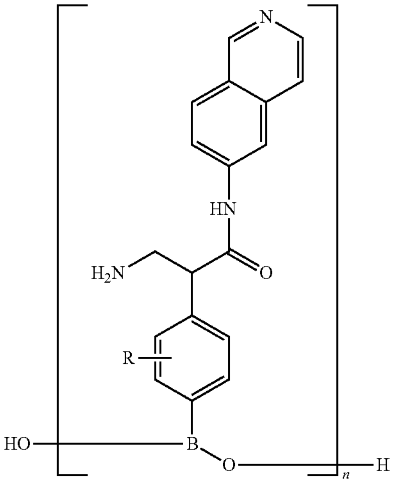

wherein n is 1 to 1000, or 1 to 500, or 1 to 250, or 1 to 100, or 1 to 50.

For the purpose of the instant disclosure, the term "boroxine" is meant to refer to a cyclotrimeric anhydride of a boronic acid-containing compound having Formula 1.

The term "monovalent cation" as used herein refers to inorganic cations such as, but not limited to, alkaline metal ions, e.g., $Na^+$ and $K^+$, as well as organic cations such as, but not limited to, ammonium and substituted ammonium ions, e.g., $NH_4^+$, $NHMe_3^+$, $NH_2Me_2^+$, $NHMe_3^+$ and $NMe_4^+$.

Compounds of the present disclosure may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers.

The present disclosure encompasses the preparation and use of salts of the compounds of the present disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as lithium salt, sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as bicarbonate, hydrochloride, hydrobromide, hydroiodide, nitrate, phosphate, diphosphate, bisulfate, hemisulfate, sulphate and the like; organic acid salts such as citrate, lactate, tartrate, maleate, fumarate, mandelate, acetate, dichloroacetate, trifluoroacetate, oxalate, formate, adipate, ascorbate, benzoate, butyrate, camphorate, cyclohexyl sulfamate, glycolate, heptanoate, hexanoate, hydroxymaleate, malate, pamoate, persulfate, phenylacetate, picrate, pivalate, propionate, quinate, salicylate, stearate, succinate, sulfamate, sulfanilate, and undecanoate, and the like; sulfonates such as camphorsulfonate, methanesulfonate, ethanesulfonate, 2-naphthalenesulfonate, 2-hydroxyethylsulfonate, benzenesulfonate, p-toluenesulfonate and the like; and amino acid salts such as arginate, asparginate, choline, glutamate, lysine, meglumine, and the like. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product. For a review on suitable salts see Berge et al, J. Pharm. Sci., 1977 66:1-19 and G. S. Paulekuhn et al. J. Med. Chem. 2007 50:6665.

As used herein, the term "pharmaceutically acceptable salt" is meant to include boronic acid salts having the general formula:

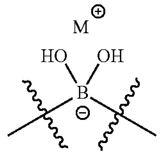

wherein $M^+$ is $H^+$ or a monovalent cation.

The present disclosure encompasses the preparation and use of solvates of the compounds described herein. Solvates typically do not significantly alter the physiological activity or toxicity of the compounds, and as such may function as pharmacological equivalents. The term "solvate" as used herein is intended to mean a combination, physical association and/or solvation of a compound of the present disclosure with a solvent molecule such as, e.g. a desolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

Compounds of the present disclosure can be present as solvated forms with a pharmaceutically acceptable solvent, such as water, methanol, ethanol, and the like, and it is intended that the disclosure includes both solvated and unsolvated forms of the compounds described herein. One type of solvate is a hydrate.

As used herein, a "hydrate" relates to a particular subgroup of solvates where the solvent molecule is water. Solvates typically can function as pharmacological equivalents. Preparation of solvates is known in the art. See, for example, M. Caira et al, J. Pharmaceut. Sci., 93 (3): 601-611 (2004), which describes the preparation of solvates of fluconazole with ethyl acetate and with water. Similar preparation of solvates, hemisolvates, hydrates, and the like are described by E. C. van Tonder et al., AAPS Pharm. Sci. Tech., 5 (1): Article 12 (2004), and A. L. Bingham et al., Chem. Commun. 603-604 (2001). A typical, non-limiting, process of preparing a solvate would involve dissolving a compound of the present disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The term "aqueous" typically denotes an aqueous composition wherein the carrier is to an extent of >50%, more preferably >75% and in particular >90% by weight water.

As used herein, the term "composition" is intended to include the formulation of the active component/compound or a pharmaceutically acceptable salt thereof, with a pharmaceutically acceptable carrier. For example, compositions of the present invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

As used herein, the term "excipient" refers to any ingredient in a composition other than a compound of the present invention. An excipient is typically an inert substance added to a composition to facilitate processing, handling, administration, etc., of a compound. Useful excipients include, but are not limited to, adjuvants, antiadherents, binders, carriers, disintegrants, fillers, flavors, colors, diluents, lubricants, glidants, preservatives, sorbents, solvents, surfactants and sweeteners.

As used herein, the terms "ophthalmic formulation" and "ocular formulation" are interchangeable.

As used herein, the term "rho kinase-modulated disease, disorder, injury, or condition" refers to generally adverse physiological conditions for which rho kinase exerts a regulatory or contributing role.

As used herein, the term "para-ocular rho kinase-modulated disease, disorder, injury, or condition" refers to generally adverse physiological conditions for which rho kinase exerts a regulatory or contributing role, but which do not necessarily have ocular effects.

As used herein, the term "tear substitute" refers to molecules or compositions which lubricate, "wet," approximate the consistency of endogenous tears, aid in natural tear build-up, or otherwise provide temporary relief of dry eye symptoms and conditions upon ocular administration.

Exemplary Compounds

The present invention provides a compound having Formula 1:

Formula 1

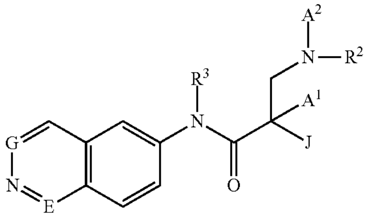

or a stereoisomer, tautomer, or pharmaceutically acceptable salt or solvate thereof, wherein:

E is selected from the group consisting of CH, C—OH, N, or NH,

G is CH, or, when E is NH, G is absent;

J is $-(CH_2)_n$-$A^6$, or

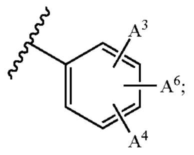

$A^1$, $A^2$, $R^2$ and $R^3$ are each —H or C1-C6 alkyl;

$A^3$ and $A^4$ are each selected from the group consisting of hydrogen, halo, C1-C6 alkyl, nitro, cyano, hydroxy, amino, optionally substituted alkyl, haloalkyl, hydroxyalkyl, alkoxy, alkylthio, alkoxyalkyl, alkylaminoalkyl, dialkylaminoalkyl, alkylaminoalkenyl, dialkylaminoalkenyl,

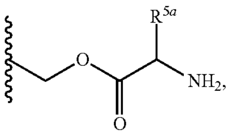
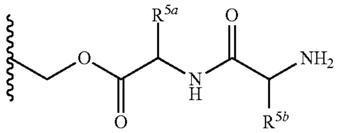
,
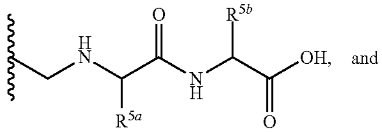
and
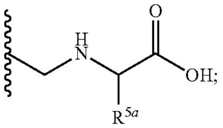

$R^{5a}$ and $R^{5b}$ are selected from a side chain of any natural amino acid, C1-C6 alkyl, trifluoro-C1-C6 alkyl, $-(CH_2)_nSH$, $-(CH_2)_nNH-C(=NH)NH_2$, $-(CH_2)_nCO_2H$, $-(CH_2)_nNH_2$, $-(CH_2)_nCH(NH_2)(CO_2H)$, $-(CH_2)_nSO_3H$, $-(CH_2)_nNR^6R^7$, $-(CH_2)_n$-pyridyl, $-(CH_2)_nONO_2$;

$A^6$ is $-(CR^6R^7)_nB(R^8R^9)$,

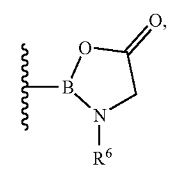
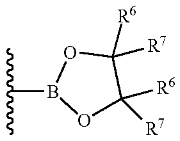
, or
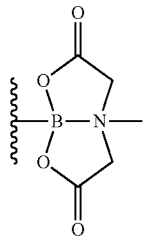
;

or $A^6$ together with either $A^3$ or $A^4$ form $-BR^8O(CR^6R^7)_nO-$, $-BR^8O(CR^6R^7)_nNR^6-$, $-BR^8O(CR^6R^7)_n-$, $-BR^8NR^6(CR^6R^7)_nO-$, $-BR^8NR^6(CR^6R^7)_nNR^6-$, $-BR^8NR^6(CR^6R^7)_n-$, $-B(R^8)_2N(R^6)_2(CR^6R^7)_nO-$, $-B(R^8)_2N(R^6)_2(CR^6R^7)_nNR^6-$, $-B(R^8)_2N(R^6)_2(CR^6R^7)_n-$, $-BR^8-O-N{=}CH-$, $-BR^8NR^6N{=}CH-$, $-B(R^8)_2N(R^6)_2N{=}CH-$, $-BR^8-O-CR^6{=}N-$, $-BR^8NR^6CR^6{=}N-$, $-BR^8-O-C(=O)NR^6-$, $-BR^8NR^6C(=O)NR^6-$, $-BR^8-O-C(NR^6){=}N-$, $-BR^8NR^6C(NR^6){=}N-$, $-B(R^8)_2N(R^6)_2CR^6{=}N-$, $-B(R^8)_2N(R^6)_2C(=O)-N-$, $-B(R^8)_2N(R^6)_2C(NR^6){=}N-$, $-BR^8-O-NR^6-$, $-B(OH)-O-NH-C(O)-$, $-B(OH)NR^6NHC(O)-$, $-B(OH)_2N(R^6)_2NHC(O)-$, $-OBR^8CH{=}CH-$, $-NR^6BR^8CH-CH-$, $-N(R^6)_2B(R^8)_2CH-CH-$, $-OBR^8(CR^6R^7)_nO-$, $-OBR^8(CR^6R^7)_nNR^6-$, $-OBR^8(CR^6R^7)_n-$, $-NR^6BR^8(CR^6R^7)_nO-$, $-NR^6BR^8(CR^6R^7)_nNR^6-$, $-NR^6BR^8(CR^6R^7)_n^-$, $-N(R^6)_2B(R^8)_2(CR^6R^7)_nO-$, $-N(R^6)_2B(R^8)_2(CR^6R^7)_nNR-$, $-N(R^6)_2B(R^8)_2(CR^6R^7)_n-$, $-BR^8-O-CH{=}CH-$, $-BR^8NR^6CH{=}CH-$, $-B(R^8)_2N(R^6)_2CH-CH-$;

$R^6$ and $R^7$ are each H, C1-C6 alkyl, C1-C6 alkenyl, C1-C6 alkynyl, trifluoro C1-C6 alkyl, acetyl, phenyl, or C1-C6 alkylsulfonyl;

$R^8$ and $R^9$ are each fluoro, hydroxy or alkoxy; or $-B(R^8R^9)$ forms a fluoride adduct, hydroxy acid adduct, or an amino acid adduct;

n and m are each 0, 1, 2, 3, or 4.

In one aspect, a compound of Formula 2 is provided:

Formula 2

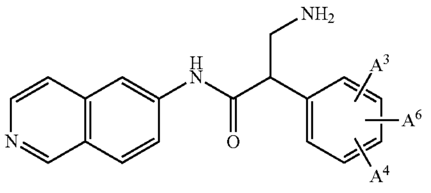

In a preferred embodiment, a compound of Formula 2 is a compound of any of Formulae 3-8:

Formula 3

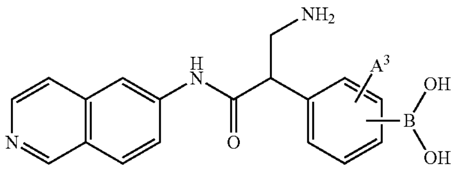

Formula 4

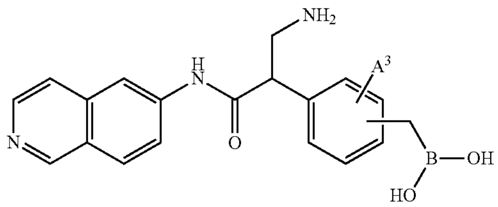

Formula 5

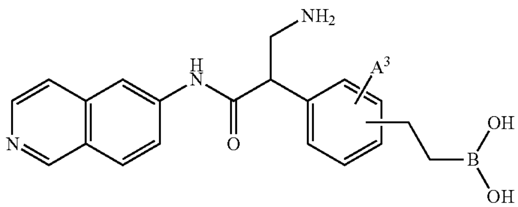

-continued
Formula 6
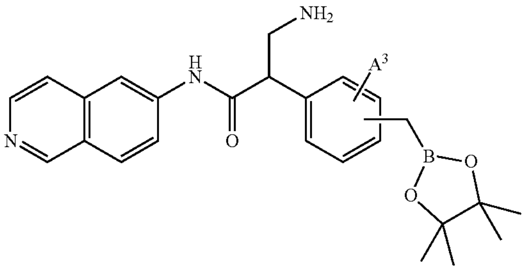
Formula 7
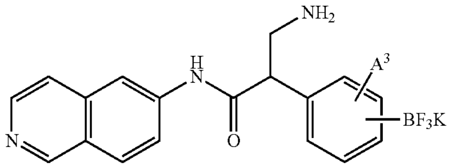
Formula 8
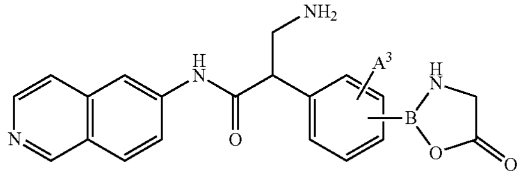
In a preferred embodiment, a compound of Formula 2 is a compound of any of Formulae 9-11:
Formula 9
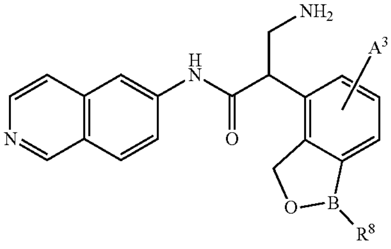
Formula 10
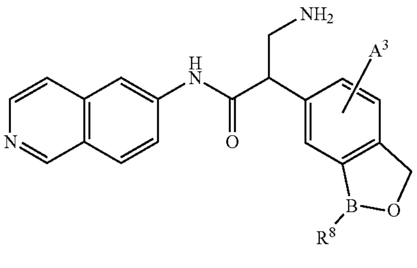
Formula 11
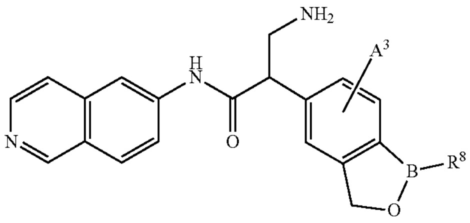
In a preferred embodiment, a compound of Formula 2 is a compound of any of Formulae 12-14:
Formula 12
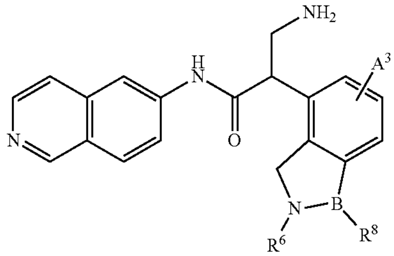
Formula 13
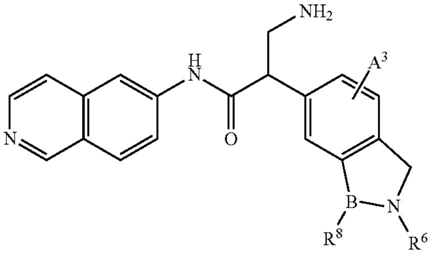
Formula 14
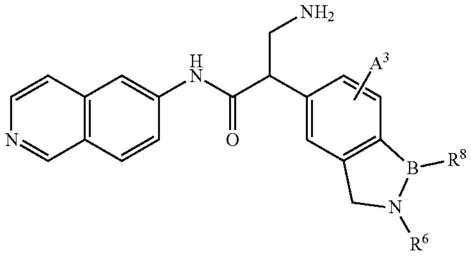
In a preferred embodiment, a compound of Formula 2 is a compound of any of Formulae 15-17:
Formula 15
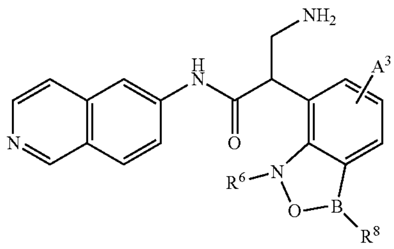
Formula 16
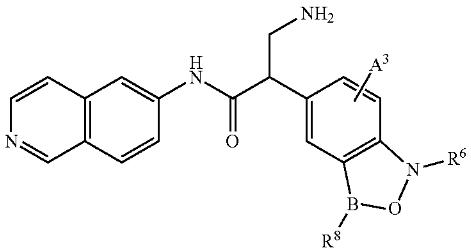

-continued
Formula 17
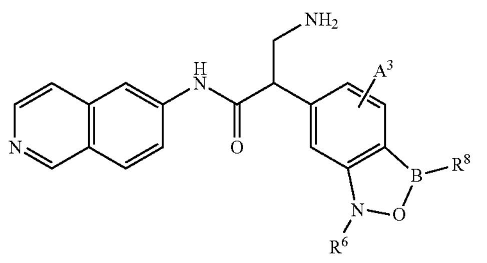
In a preferred embodiment, a compound of Formula 2 is a compound of any of Formulae 18-20:
Formula 18
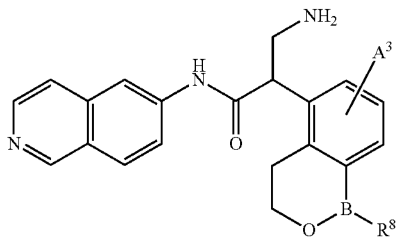
Formula 19
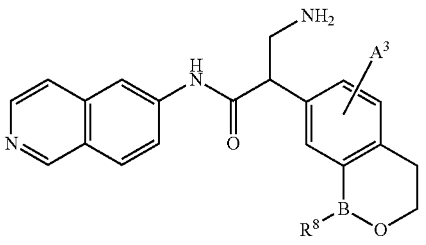
Formula 20
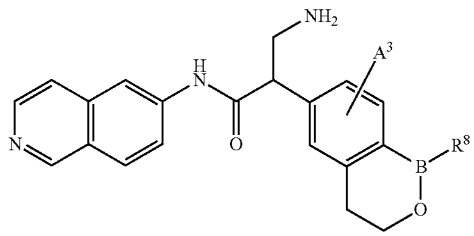
Formula 21
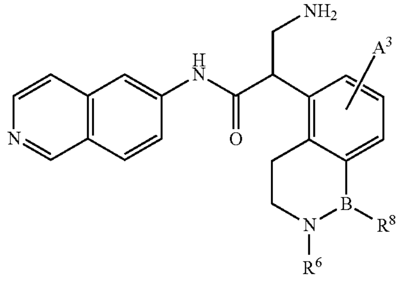
-continued
Formula 22
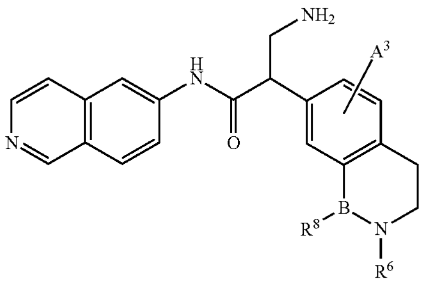
Formula 23
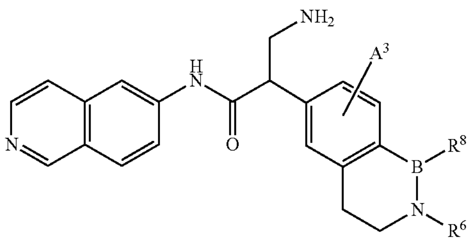
In a preferred embodiment, a compound of Formula 2 is a compound of any of Formulae 24-26:
Formula 24
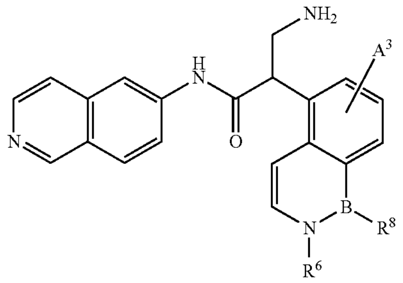
Formula 25
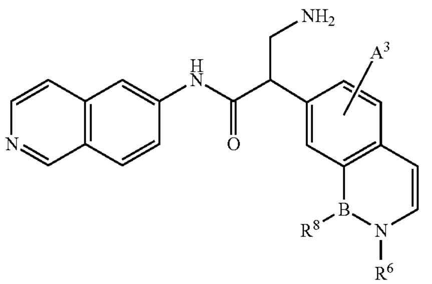
Formula 26
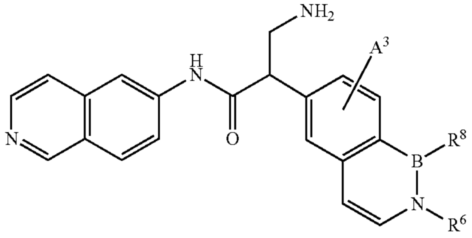

In a preferred embodiment, a compound of Formula 2 is a compound of any of Formulae 27-32:
Formula 27
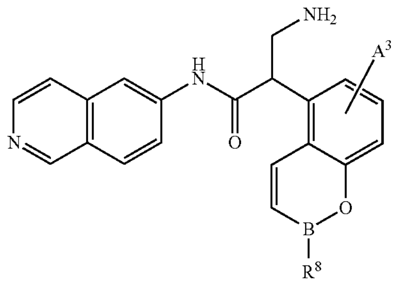
Formula 28
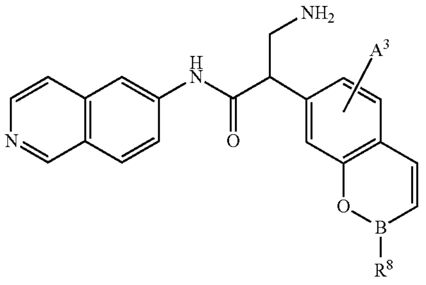
Formula 29
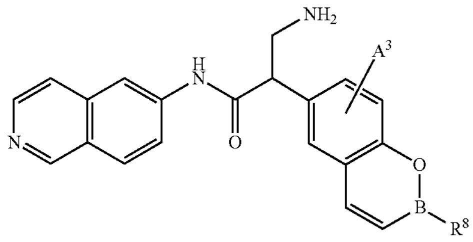
Formula 30
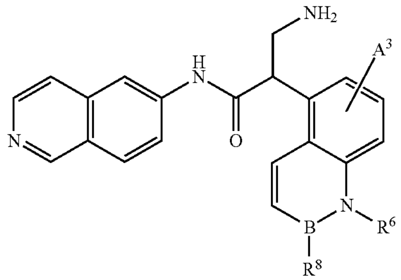
Formula 31
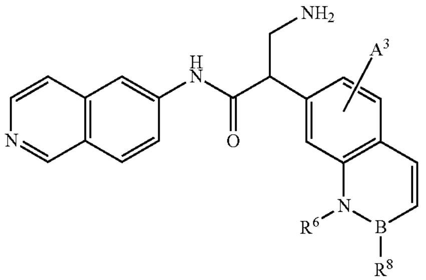
-continued
Formula 32
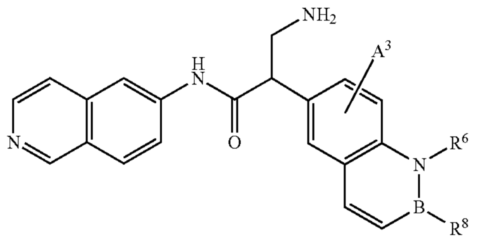
In a preferred embodiment, a compound of Formula 2 is a compound of any of Formulae 33-38:
Formula 33
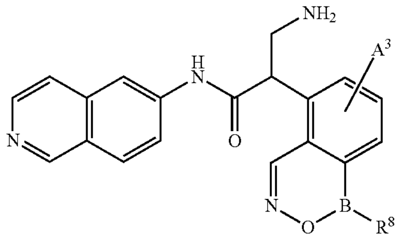
Formula 34
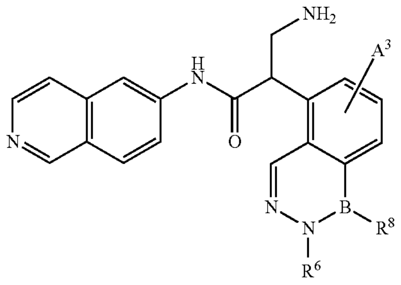
Formula 35
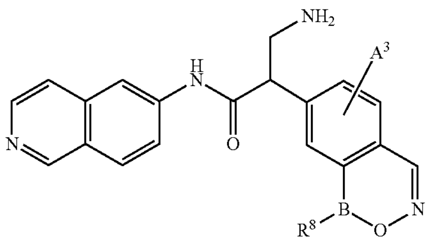
Formula 36
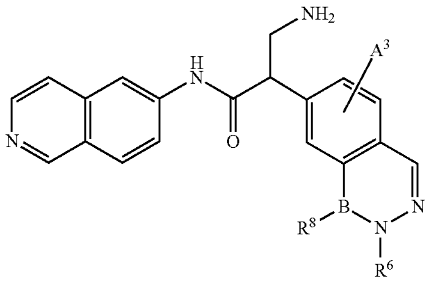

-continued
Formula 37
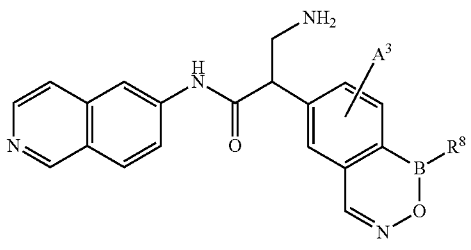
Formula 38
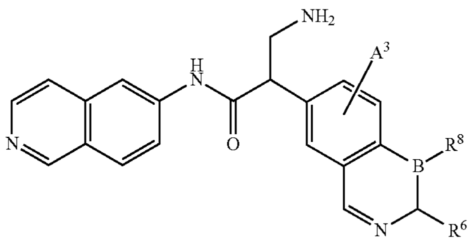
In a preferred embodiment, a compound of Formula 2 is a compound of any of Formulae 39-41:
Formula 39
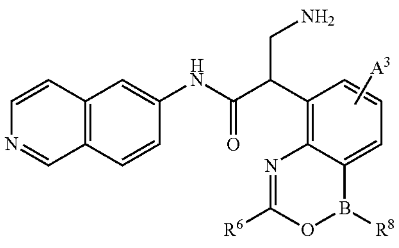
Formula 40
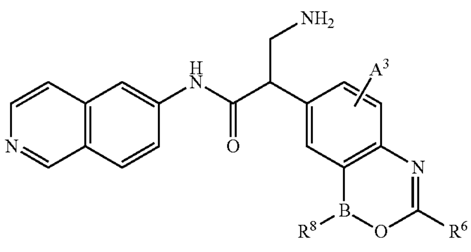
Formula 41
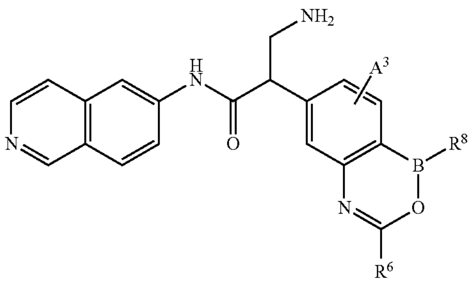
In a preferred embodiment, a compound of Formula 2 is a compound of any of Formulae 42-47:
Formula 42
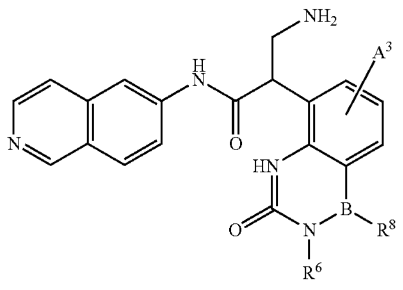
Formula 43
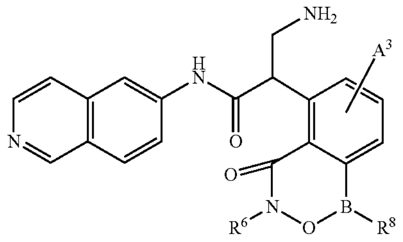
Formula 44
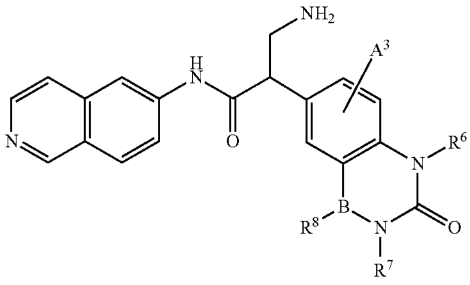
Formula 45
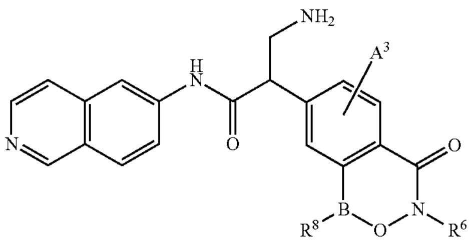
Formula 46
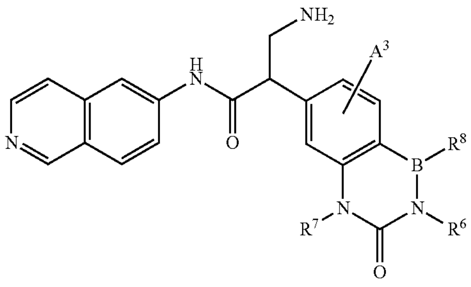

-continued
Formula 47
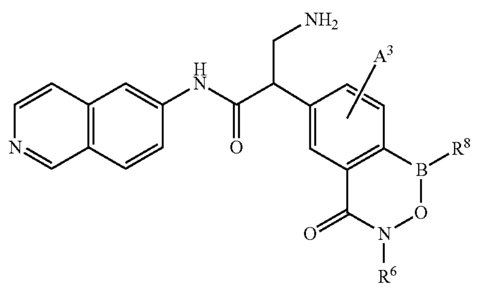
In a preferred embodiment, a compound of Formula 2 is a compound of any of Formulae 48-56:
Formula 48
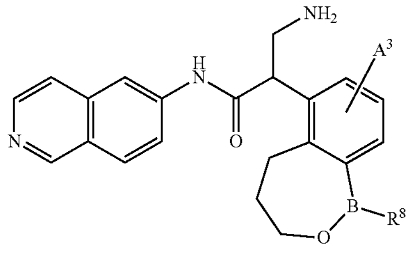
Formula 49
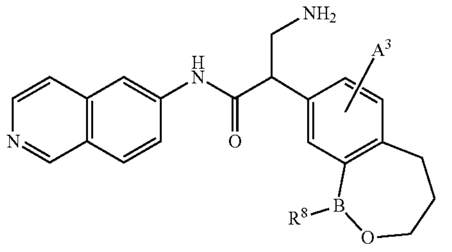
Formula 50
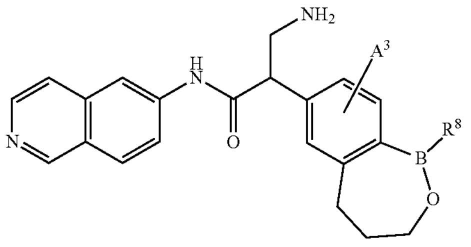
Formula 51
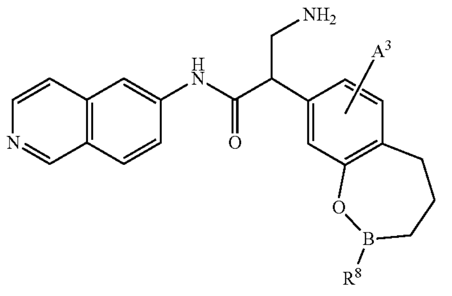
-continued
Formula 52
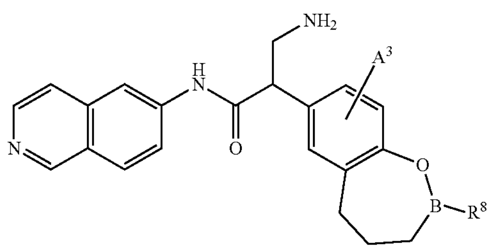
Formula 53
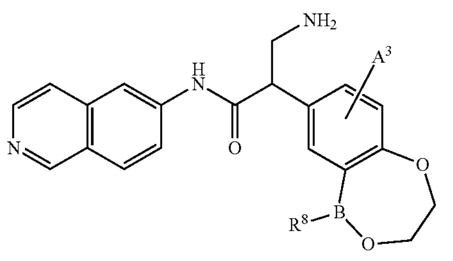
Formula 54
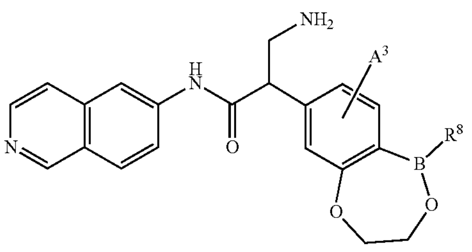
Formula 55
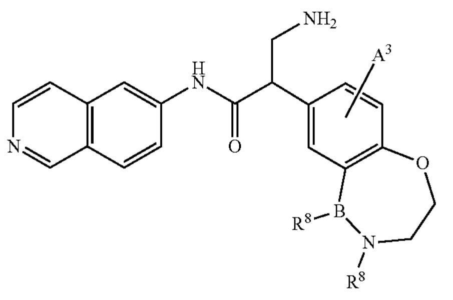
Formula 56
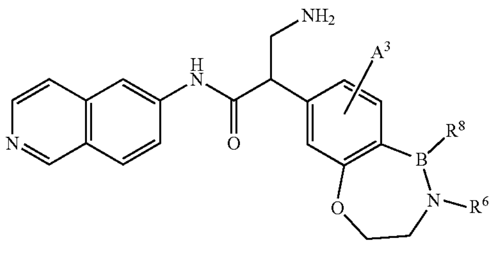

In a preferred embodiment, a compound of Formula 1 is a compound of Formula 67:
Formula 67
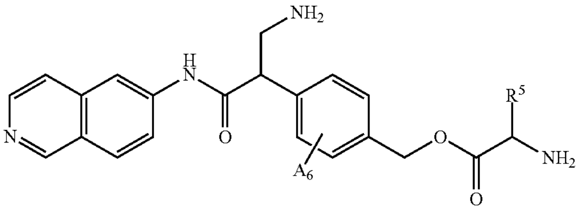
Examples of a compound of Formulae 1-56 and 67 are illustrated below.
| # | Structure |
|---|---|
| 198 | 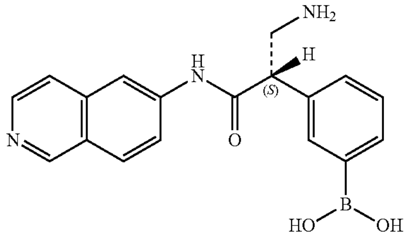 |
| 199 | 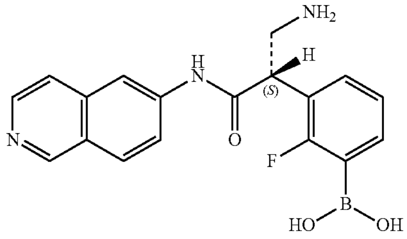 |
| 200 | 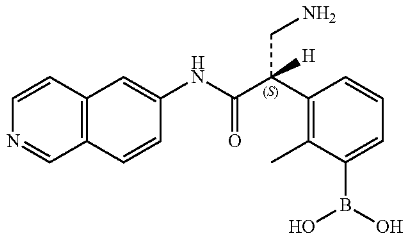 |
| 201 | 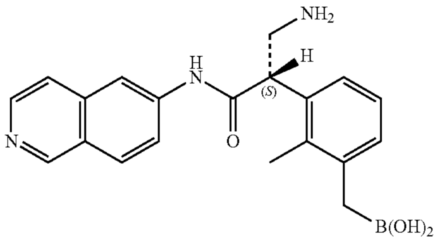 |
-continued
| # | Structure |
|---|---|
| 202 | 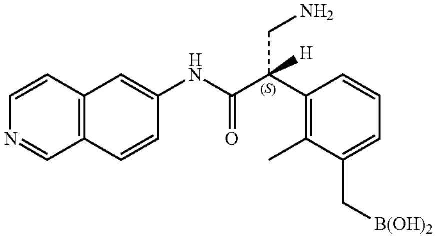 |
| 203 | 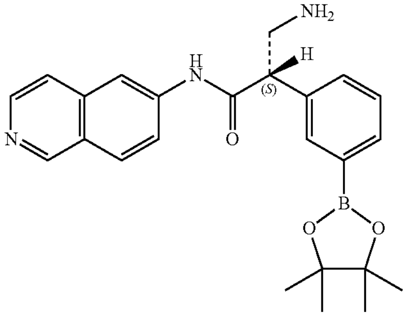 |
| 204 | 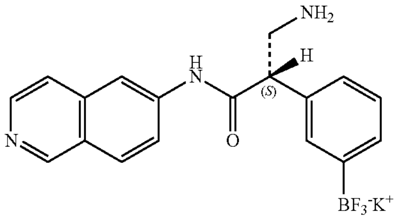 |
| 205 | 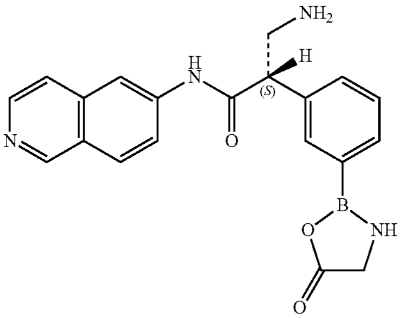 |
| 206 | 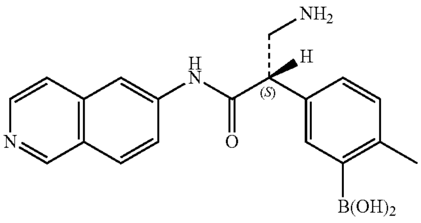 |
| 207 | 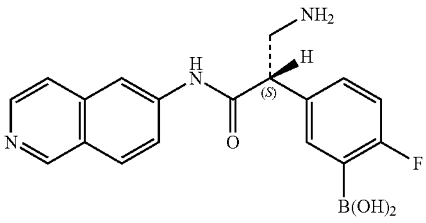 |

-continued
| # | Structure |
|---|---|
| 208 | 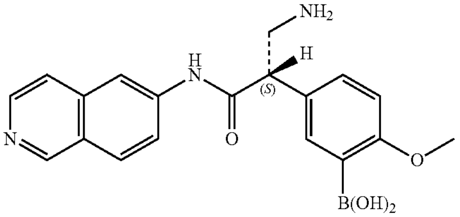 |
| 209 | 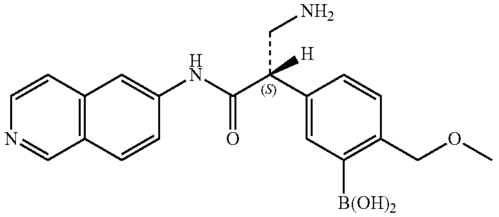 |
| 210 | 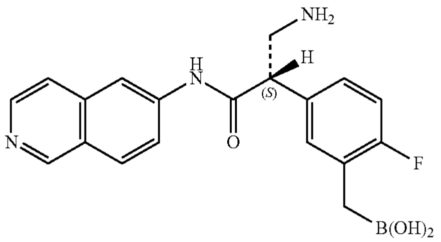 |
| 211 | 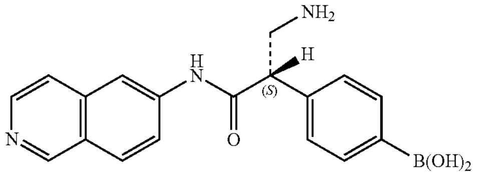 |
| 212 | 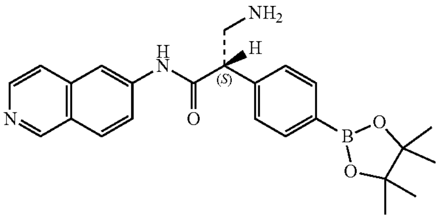 |
| 213 | 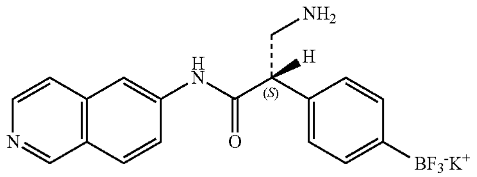 |
| 214 | 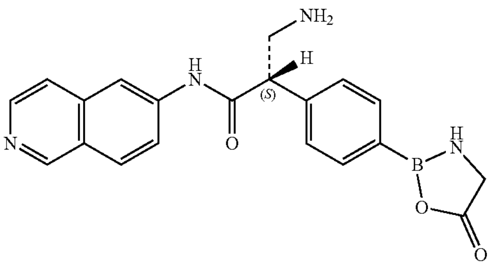 |
-continued
| # | Structure |
|---|---|
| 215 | 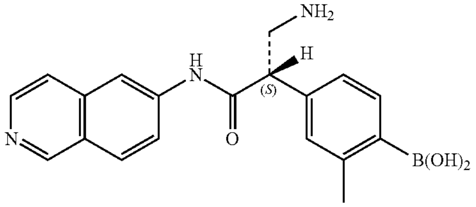 |
| 216 | 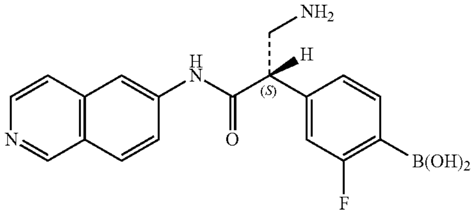 |
| 217 | 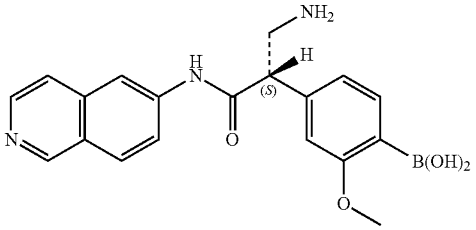 |
| 218 | 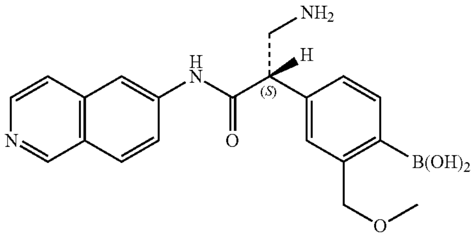 |
| 219 | 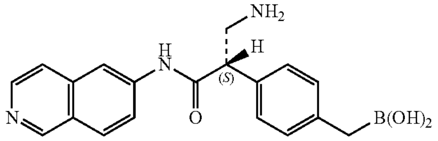 |
| 220 | 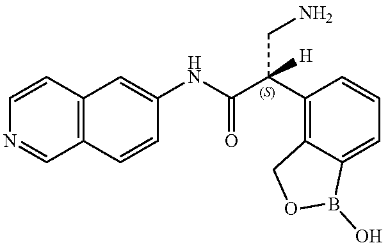 |
| 221 | 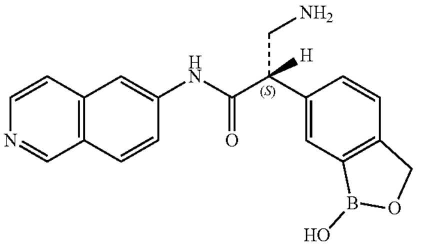 |

-continued
| # | Structure |
|---|---|
| 222 | 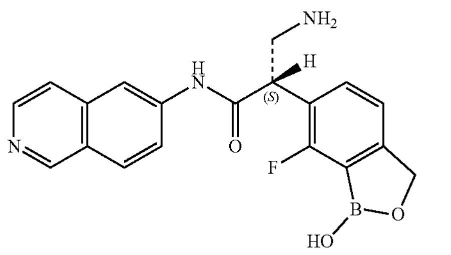 |
| 223 | 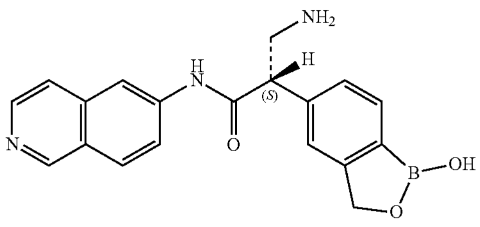 |
| 224 | 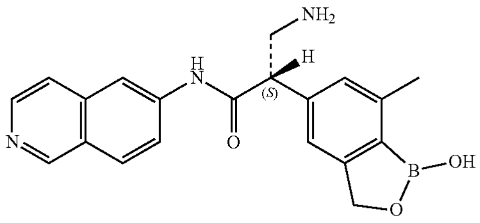 |
| 225 | 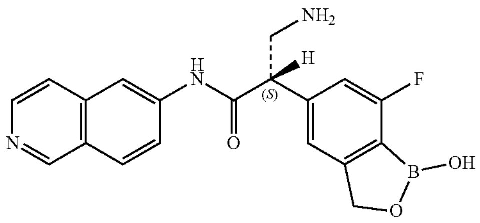 |
| 226 | 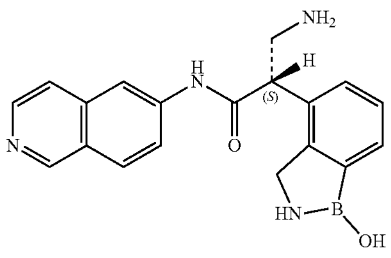 |
| 227 | 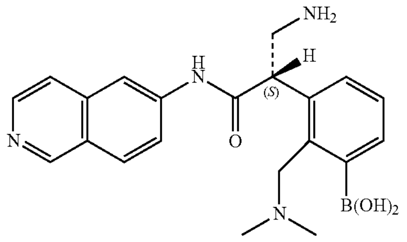 |
-continued
| # | Structure |
|---|---|
| 228 | 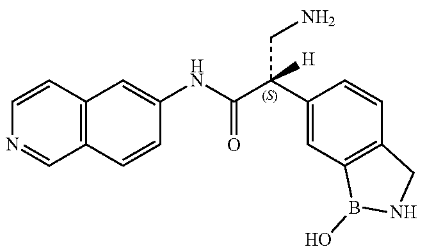 |
| 229 | 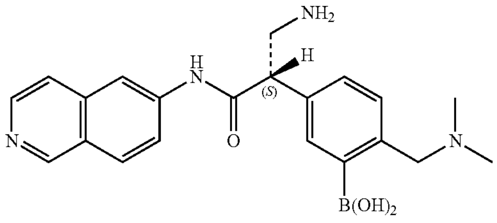 |
| 230 | 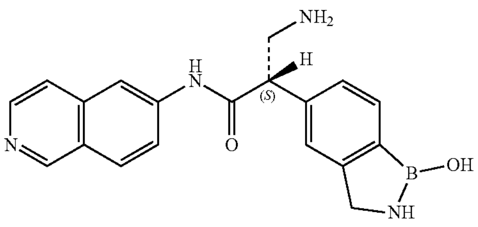 |
| 231 | 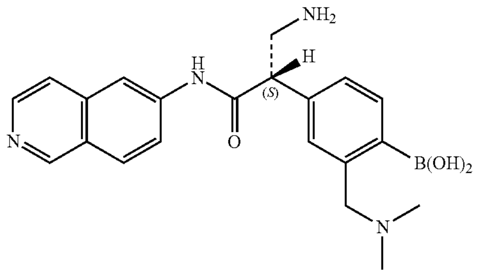 |
| 232 | 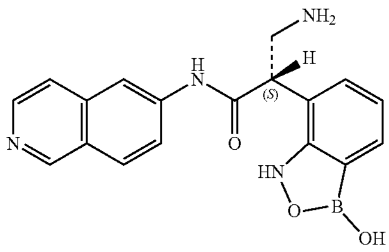 |
| 233 | 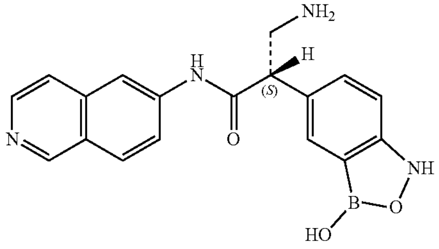 |

-continued
| # | Structure |
|---|---|
| 234 | 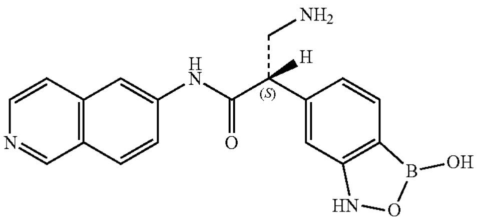 |
| 235 | 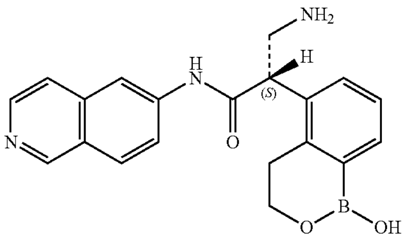 |
| 236 | 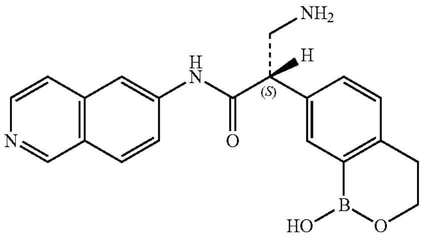 |
| 237 | 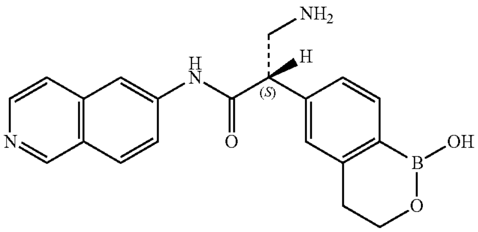 |
| 238 | 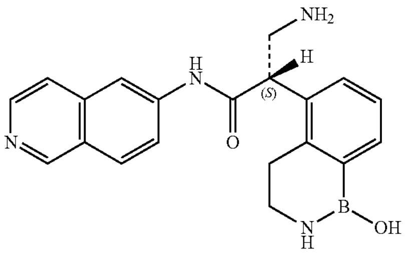 |
| 239 | 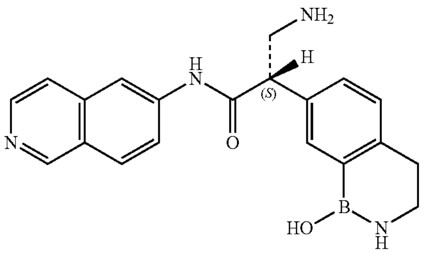 |
-continued
| # | Structure |
|---|---|
| 240 | 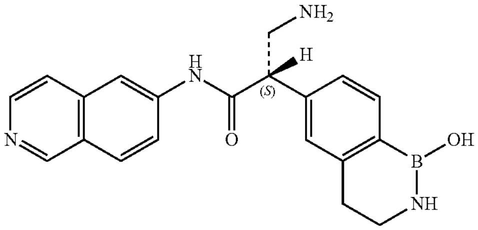 |
| 241 | 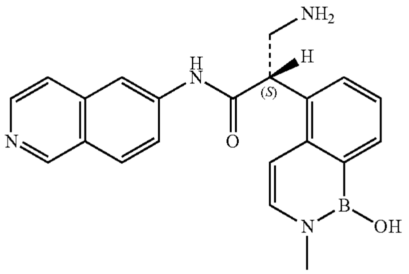 |
| 242 | 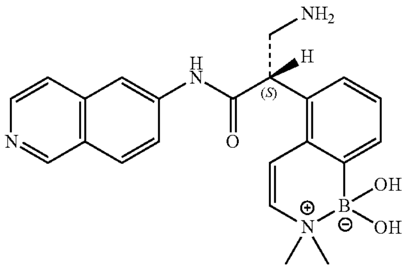 |
| 243 | 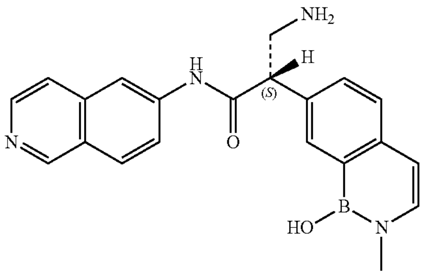 |
| 244 | 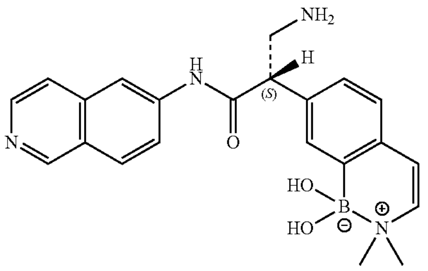 |
| 245 | 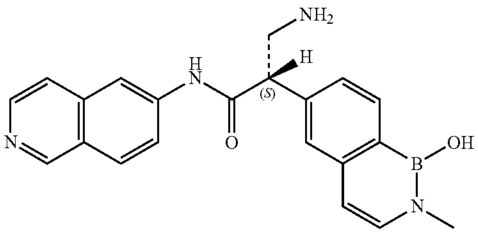 |

-continued
| # | Structure |
|---|---|
| 246 | 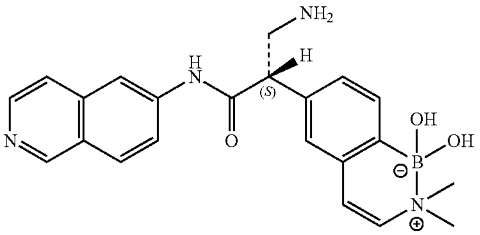 |
| 247 | 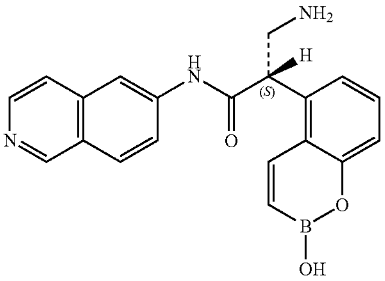 |
| 248 | 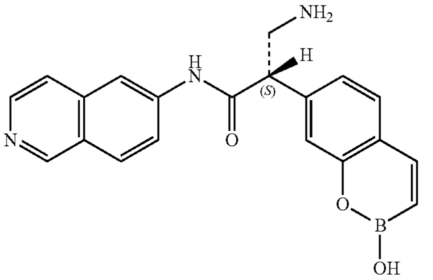 |
| 249 | 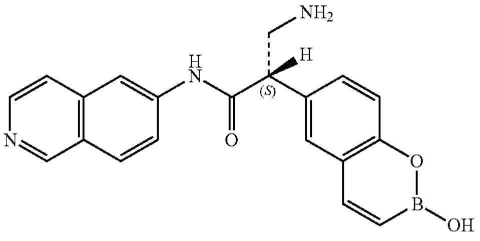 |
| 250 | 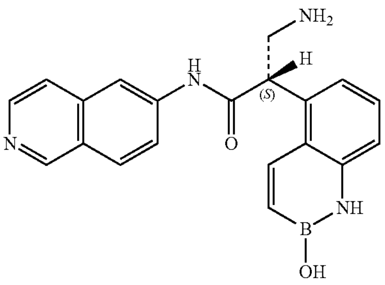 |
-continued
| # | Structure |
|---|---|
| 251 | 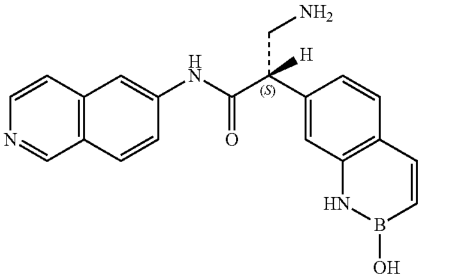 |
| 252 | 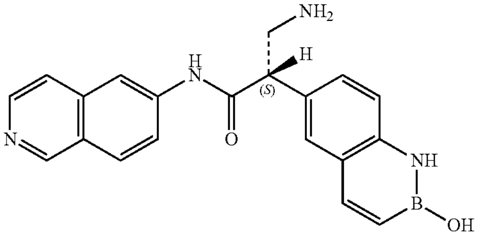 |
| 253 | 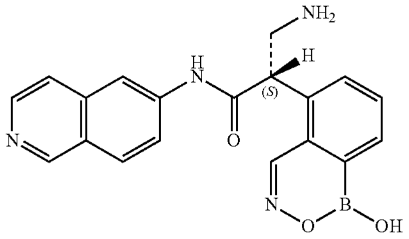 |
| 254 | 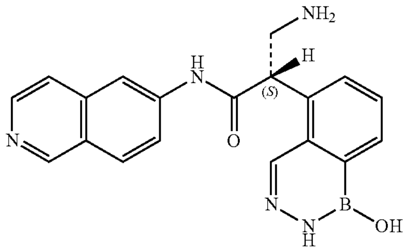 |
| 255 | 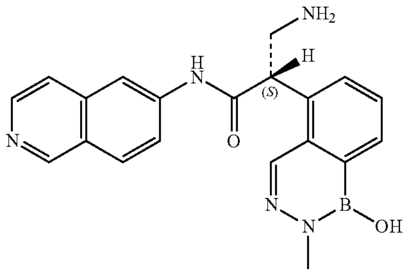 |
| 256 | 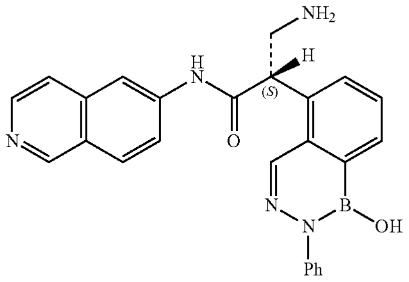 |

-continued
| # | Structure |
|---|---|
| 257 | 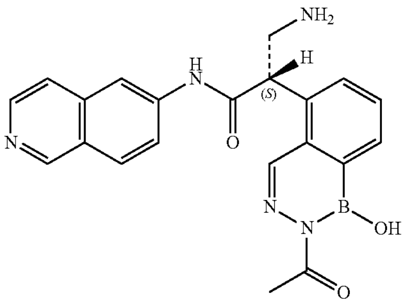 |
| 258 | 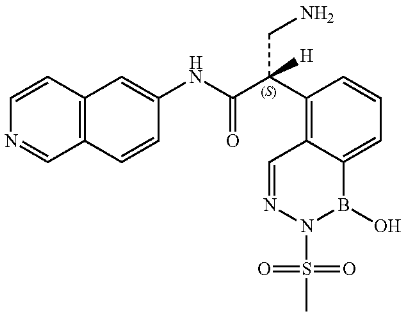 |
| 259 | 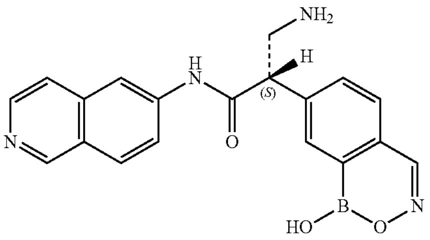 |
| 260 | 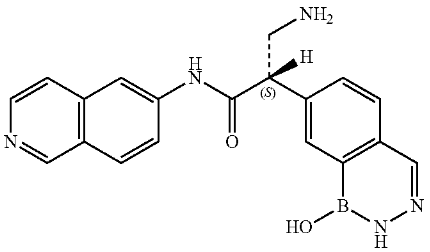 |
| 261 | 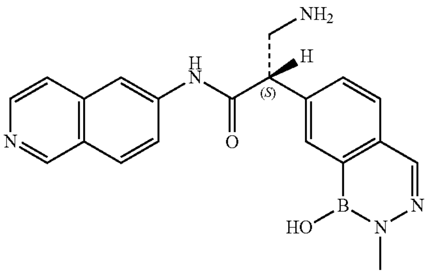 |
-continued
| # | Structure |
|---|---|
| 262 | 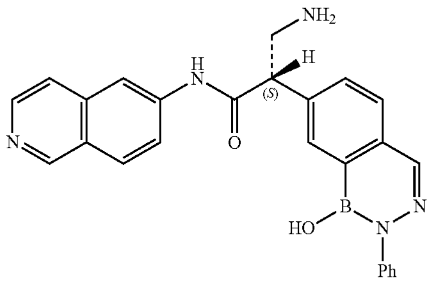 |
| 263 | 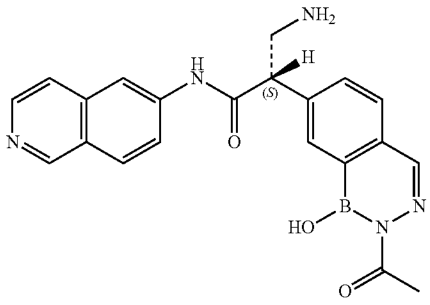 |
| 264 | 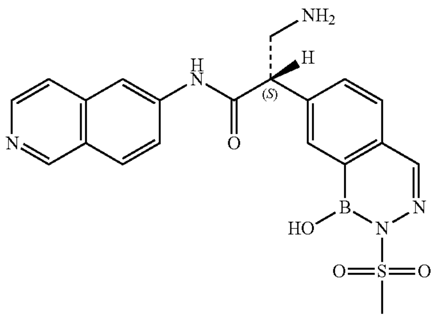 |
| 265 | 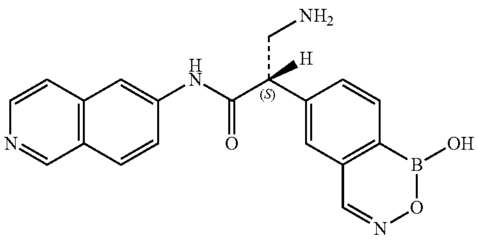 |
| 266 | 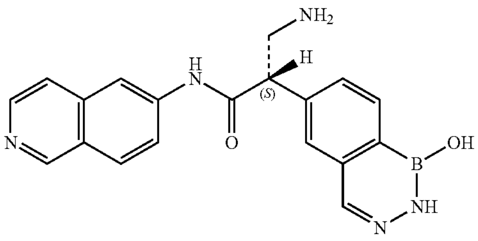 |

-continued
| # | Structure |
|---|---|
| 267 | 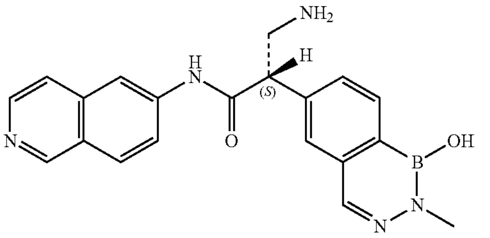 |
| 268 | 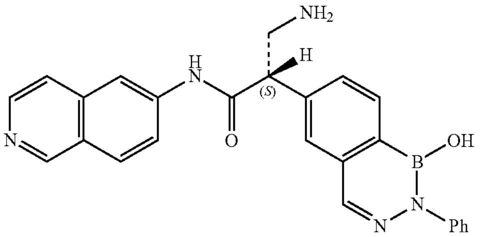 |
| 269 | 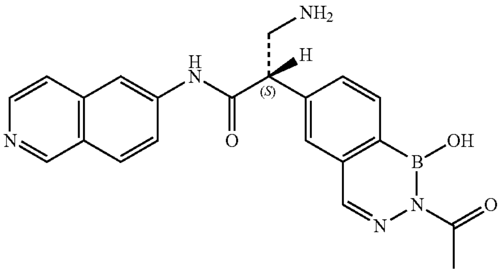 |
| 270 | 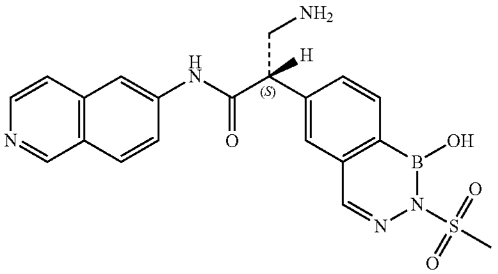 |
| 271 | 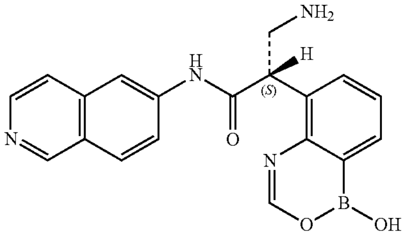 |
| 272 | 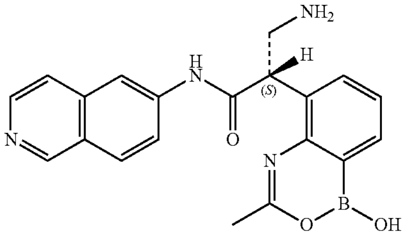 |
| 273 | 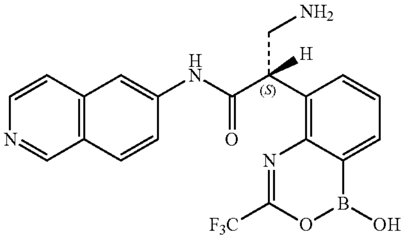 |
| 274 | 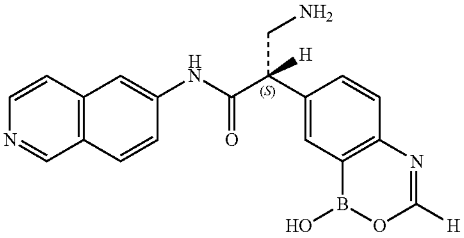 |
| 275 | 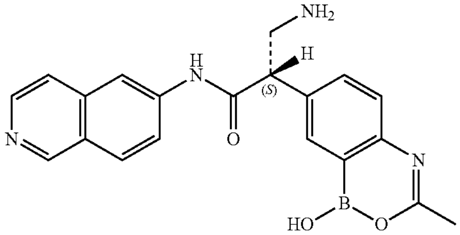 |
| 276 | 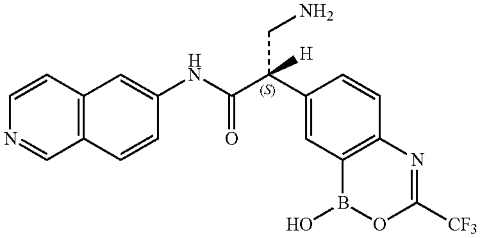 |
| 277 | 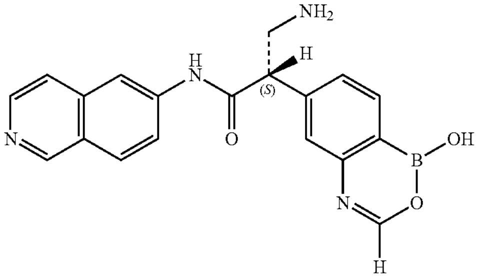 |
| 278 | 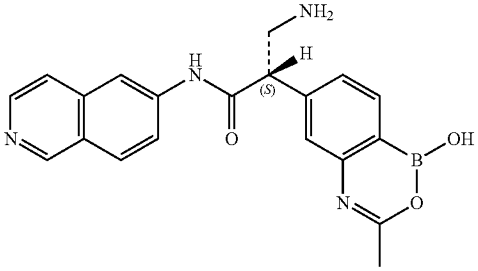 |

-continued
| # | Structure |
| --- | --- |
| 279 | 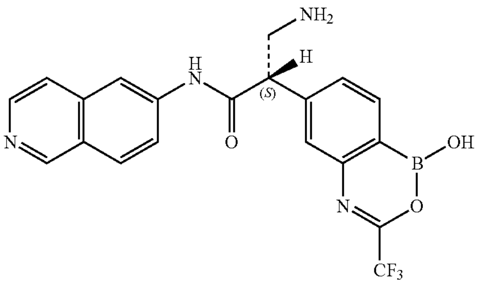 |
| 280 | 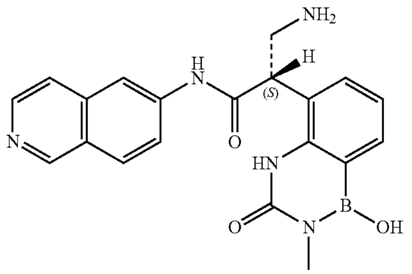 |
| 281 | 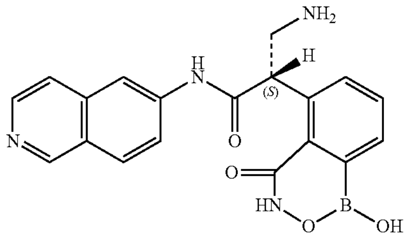 |
| 282 | 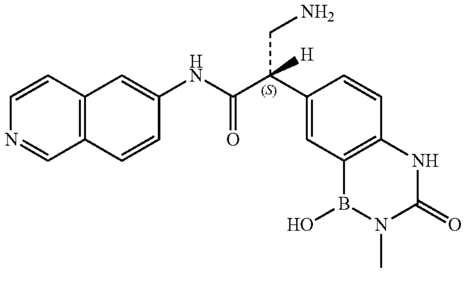 |
| 283 | 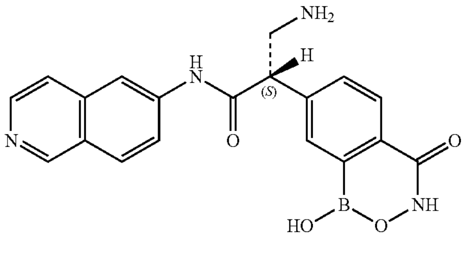 |
-continued
| # | Structure |
| --- | --- |
| 284 | 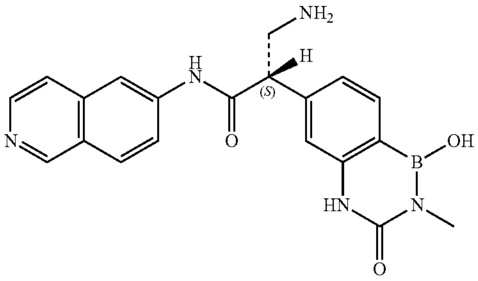 |
| 285 | 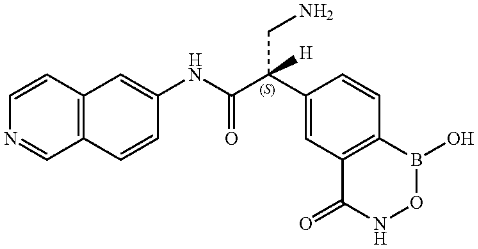 |
| 286 | 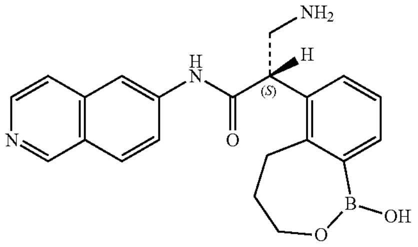 |
| 287 | 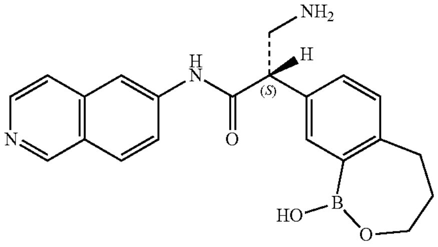 |
| 288 | 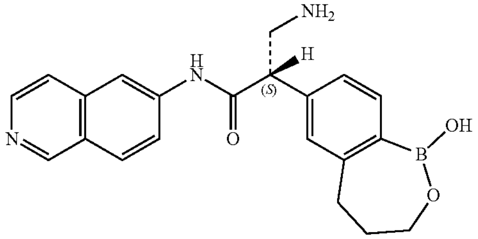 |
| 289 | 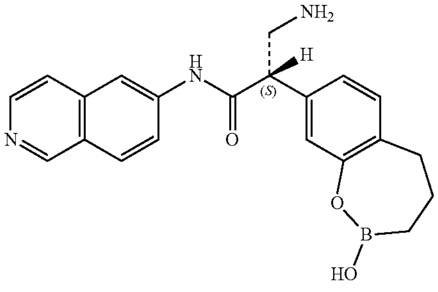 |

-continued

| # | Structure |
| --- | --- |
| 290 | 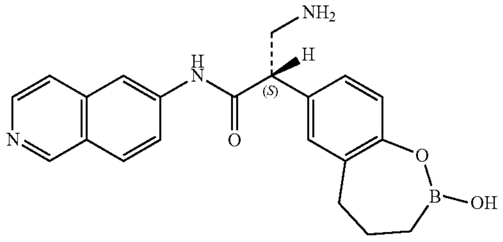 |
| 291 | 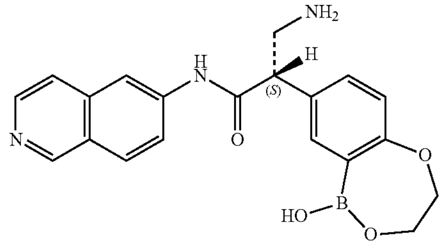 |
| 292 | 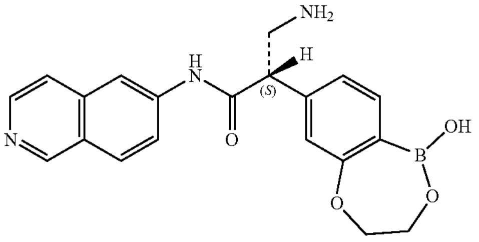 |
| 293 | 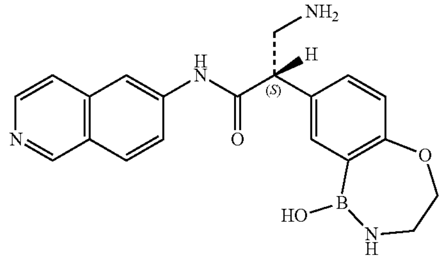 |
| 294 | 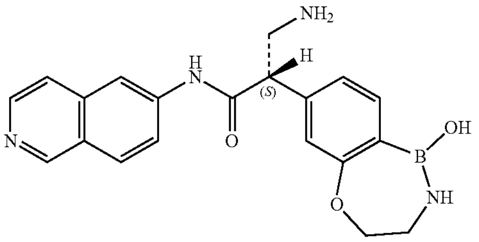 |
| | 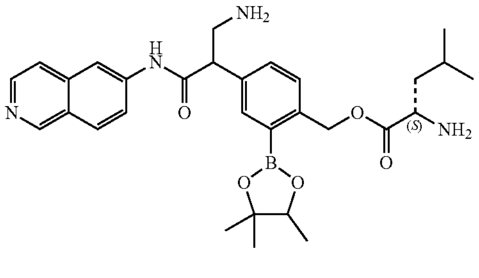<br>222-1 (Type I) |

-continued

| # | Structure |
| --- | --- |
| | 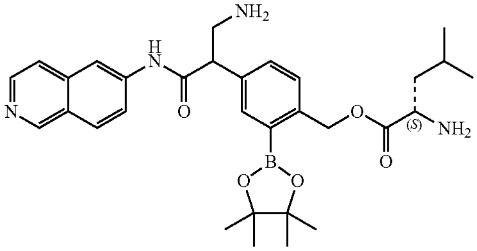<br>222-2 (Type I) |
| | 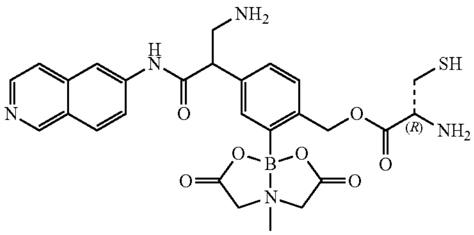<br>222-3 (Type I) |

In a preferred embodiment, a compound of Formula 1 is a compound of Formulae 57:

Formula 57

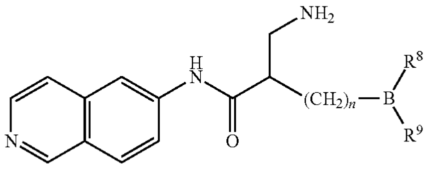

In some embodiments, the present invention provides a compound as described in Table 1 or Table 2 (above), or a stereoisomer, tautomer, or pharmaceutically acceptable salt or solvate thereof.

In other embodiments, the present invention provides micronized compounds, and compositions thereof. In some embodiments, the average particle size distribution of the micronized form of a compound of invention is about 100 μm or less, preferably 20 μm or less, e.g., about 19 μm, about 18 μm, about 17 μm, about 16 μm, about 15 μm, about 14 μm, about 13 μm, about 12 μm, or about 11 μm, or less. In some embodiments, the average particle size distribution is about 50 μm or less, preferably 10 μm or less, e.g., about 9 μm, about 8 μm, about 7 μm, about 6 μm, or about 5 μm, or less. In other embodiments, the average particle size distribution is about 25 μm or less, preferably 5 μm or less, e.g., about 4 μm, about 3 μm, about 2 μm, or about 1 μm, or less. In further embodiments, the average particle size distribution is about 1 μm or less, e.g., about 0.9 μm, about 0.8 μm, about 0.7 μm, about 0.6 μm, about 0.5 μm, about 0.4 μm, about 0.3 μm, about 0.2 μm, about 0.1 μm, about 0.09 μm, about 0.08 μm, about 0.07 μm, about 0.06 μm, about 0.05 μm, about 0.04 μm, about 0.03 μm, about 0.02 μm, or about 0.01 μm or less.

In some embodiments, the present invention provides polymorphic solid forms of the compounds described herein. In other embodiments, the compounds of invention are the lowest energy crystalline form. In further embodiments, the compounds of invention are not the lowest energy crystalline form. In yet other embodiments, the compounds of invention are an amorphous form. In still other embodiments, the compounds of invention are in a solvate form.

Technical and scientific terms used herein have the meaning commonly understood by one of skill in the art to which the present disclosure pertains, unless otherwise defined. Reference is made herein to various methodologies and materials known to those of skill in the art.

The starting materials and reagents used in preparing these compounds generally are either available from commercial suppliers, such as Aldrich Chemical Co., or are prepared by methods known to those skilled in the art following procedures set forth in references. Peptides of natural and commercially-prepared amino acids are generally available from suppliers such as Bachem AG, either as off-the-shelf materials or by custom synthesis. Other materials, reagents and the like to which reference are made in the following examples are obtainable from commercial sources, unless otherwise noted.

General synthetic procedures have been described in treatises such as Fieser and Fieser's Reagents for Organic Synthesis; Wiley & Sons: New York, Volumes 1-28; Comprehensive Organic Transformations, R. C. Larock, 3rd edition Wiley-VCH, New York 2017; Comprehensive Organic Synthesis, Molander & Knochel (Eds.) Elsevier, 2014; Boronic Acids, D. G. Hall, Wiley, 2011; and Organic Reactions, Wiley & Sons: New York, 2012, Volumes 1-77 and will be familiar to those skilled in the art.

Synthetic procedures specific to organoboron chemistry are described in Boronic Acids: Preparation and Applications in Organic Synthesis, Medicine and Materials, 2nd Ed., Dennis G. Hall (Ed.), 2011, Wiley. An overview of organotrifluoroborates is provided by Molander, G. A., Ellis, N.; Organotrifluoroborates: Protected Boronic Acids That Expand the Versatility of the Suzuki Coupling Reaction, Acc. Chem. Res. 2007, 40, 275-286. Use of alpha- and beta-carbonyl protected boronic acids is explained in (a) He, Z., Yudin, A. K., Amphoteric a-Boryl Aldehydes, J. Am. Chem. Soc., 2011, 133 (35), 13770-13773; He, Z., Zajdlik, A., St. Denis, J. D., Assem, N., Yudin, A. K., (b) Boroalkyl Group Migration Provides a Versatile Entry into a-Aminoboronic Acid Derivatives, J. Am. Chem. Soc., 2012, 134 (24), 9926-9929, and (c) St. Denis, J. D. Zajdlik, A., Tan, J., Trinchera, P., Lee, C. F., He, Z., Adachi, S., Yudin, A. K., Boron-Containing Enamine and Enamide Linchpins in the Synthesis of Nitrogen Heterocycles, J. Am. Chem. Soc., 2014, 136 (50), pp 17669-17673. Synthetic routes for the preparation of boron-containing ring systems are described or reviewed in (a) Chellappan, S. K., Hormann, R. E., Shulman, I., U.S. Pat. No. 9,127,024 (2015), (b) James, R. A., Chellappan, S. K., Hormann, R. E., U.S. patent application No. 20160083403-A1 2016, (c) Adamczyk-Woźniak, A., Borys, K. M., Sporzyński, A., Recent Developments in the Chemistry and Biological Applications of Benzoxaboroles, Chem. Rev. 2015, 115, 5224-5247, (d) Groziak, M. P., Boron Heterocycles as Platforms for Building New Bioactive Agents, in Progress in Heterocyclic Chemistry, 2000, 12, 1-21, Gribble, G. W., Gilchirst, T. L., Eds., Elsevier, and (e) Wisniewski, S. R., Guenther, C. L., Argintaru, O. A., and Molander, G. A., A Convergent, Modular Approach to Functionalized 2,1-Borazaronaphthalenes from 2-Aminostyrenes and Potassium Organotrifluoroborates, J Org Chem. 2014, 79, 1, 365-378.

Protecting group methods have been described in *Greene's Protective Groups in Organic Synthesis,* 5$^{th}$ Ed., P. G. Wuts, 2014. Specific protection of amino acid functionality has been described in Amino Acid-Protecting Groups, A. Isidro-Llobet, M. A'Ivarez, F. Albericio, Chem. Rev. 2009, 109, 2455-2504. The choice of protecting groups described in the synthesis schemes is representative and expedient. Based on the listed literature sources, one skilled in the art would recognize alternate, functionally equivalent protection schemes are available to effect the depicted transformations. In general, treatment with $(nBu)_4N^+F^-$ at the last step is expected to remove both the Teoc group as well as the Fmoc. Should Fmoc prove resistant under these conditions, it can be removed by treatment with piperidine or morpholine.

Boronic acid protecting group schemes and methodologies are illustrated in (a) Tobisu. M., Chatani, N., Devising Boron Reagents for Orthogonal Functionalization through Suzuki-Miyaura Cross-Coupling, Angew. Chem. Int. Ed. 2009, 48, 3565, (b) Churches, Q. I., Craig A., Hutton. C. A.; Introduction, Interconversion and Removal of Boron Protecting Groups, in Boron Reagents in Synthesis, ACS Symposium Series, 2016 Vol. 1236, Chapter 11, pp 357-377, and (c) Molloy, J. J., Watson, A. J. B., B-Protected Boronic Acids: Methodology Development and Strategic Application, in Boron Reagents in Synthesis, ACS Symposium Series, 2016, Vol. 1236, Chapter 12, pp 379-413.

Peptide synthesis has been described in *Amino Acids, Peptides and Proteins in Organic Chemistry*, A. B. Hughes, 2013, Wiley-VCH, among many other publications. Many of the target compounds lend themselves to preparation by solid phase synthesis. Peptide conjugates may be prepared by solid phase synthesis, by methods described in, for example, *Solid-Phase Synthesis: A Practical Guide,* 1st Ed., F. Albericio, Ed., CRC Press, 2000. In the schemes below, the reagents for amide coupling chemistry are represented by a few among many possible conditions. For example, alternate coupling agents are dicyclohexylcarbodiimide (DCC), diisopropylcarbodiimide (DIC); 1-hydroxy-benzotriazole (HOBt), 1-hydroxy-7-aza-benzotriazole (HOAt), 2-(1H-benzotriazol-1-yl)-1,1,3,3-tetramethyluronium hexafluorophosphate (HBTU), 1-[Bis(dimethylamino)methylene]-1H-1,2,3-triazolo[4,5-b]pyridinium 3-oxid hexafluorophosphate (HATU), 2-(6-Chlor-1H-benzotriazol-1-yl)-1,1,3,3-tetramethylaminium-hexafluorophosphat (HCTU), N,N,N',N'-Tetramethyl-O-(benzotriazol-1-yl) uronium tetrafluoroborate (TBTU), benzotriazol-1-yl-oxytripyrrolidinophosphonium hexafluorophosphate (PyBOP), (1-Cyano-2-ethoxy-2-oxoethylidenaminooxy)dimethylaminomorpholino carbenium hexafluorophosphate (COMU), or O-[(Ethoxycarbonyl)cyanomethylenamino]-N,N,N',N'-tetramethyluronium tetrafluoroborate TOTU (Oxyma Pure). The following table summarizes a few optional amide coupling conditions:

| Substrate | Coupling agents | Base | Solvent |
|---|---|---|---|
| RC(=O)Cl + R'$NH_2$ | — | TEA trimethylamine | dichloromethane ($CH_2Cl_2$, DCM) |
| RC(O)OPf + R'$NH_2$ | — | aqueous $K_2CO_3$ | Biphasic aqueous, |

-continued

| Substrate | Coupling agents | Base | Solvent |
|---|---|---|---|
| (Note 1) | | | $CH_2Cl_2$ |
| RCO(O)Pf + R'NH2 | — | DIPEA | DMF |
| $RCO_2H$ + $R'NH_2$ | BOP, (Benzotriazol-1-yloxy)tris(dimethylamino) phosphonium hexafluorophosphate; HOBt, hydroxybenzotriazole | diisopropylethylamine (DIPEA) | DMF |
| $RCO_2H$ + $R'NH_2$ | PyBOP, (Benzotriazol-1-yloxy)tripyrrolidinophosphonium hexafluorophosphate | diisopropylethylamine (DIPEA) | DMF |

Note 1.
Pf = pentafluroophenyl; prepared from CO2H, PfOH, using DCC to couple.

For asymmetric syntheses, the antipodal targets can be prepared by use of the opposite-enantiomer starting material, chiral catalyst, or chiral auxiliary. Enantiomers can also be obtained by standard preparative chiral chromatography.

Deuteriated scaffolds or scaffold fragments can be prepared by standard reactions using deuteriated starting materials or by scrambling methods such as those described in (a) Atzrodt, J., Derdau, V., Fey, T., Zimmermann, J., The Renaissance of H/D Exchange, Angew. Chemie Int. Ed. 2007, 46, 41, 7744-7765, (b) Rosales A., Rodríguez-García I., *$Cp_2TiCl/D_2O/Mn$ , a formidable reagent for the deuteration of organic compounds*, Beilstein J Org Chem. 2016; 12, 1585-9, and related articles.

Standard reference works setting forth the general principles of pharmacology include *Goodman and Gilman's The Pharmacological Basis of Therapeutics*, 12th Ed., McGraw Hill Companies Inc., New York (2011).

General methods and conditions for the borylation of arenes, aryl halides, and aryl triflates, particularly using palladium-ligand catalyst systems with BpinH [4,4,5,5-Tetramethyl-1,3,2-dioxaborolane] or $B(pin)_2$ [Bis(pinacolato) diboron] are described in (a) Boronic Acids: Preparation and Applications in Organic Synthesis, Medicine and Materials, 2nd Ed., Dennis G. Hall (Ed.), 2011, Wiley, (b) Chellappan, S. K., Hormann, R. E., Shulman, I., U.S. Pat. No. 9,127,024 (2015), (c) James, R. A., Chellappan, S. K., Hormann, R. E., U.S. patent application No. 20160083403-A1 2016.

The following abbreviations are used throughout the application.

$B(pin)_2$=Bis(pinacolato)diboron
BpinH=4,4,5,5-Tetramethyl-1,3,2-dioxaborolane
DCC=Dicyclohexylcarbodiimide
DIPEA=diisopropylethylamine
Dman=1-Dimethylamino-8-methylaminonaphthalene
DMF=dimethylformamide
dppf=dppf=1,1'-Ferrocenediyl-bis(diphenylphosphine)
Fmoc=9-Fluorenylmethoxycarbonyl
HATU=1-[Bis(dimethylamino)methylene]-1H-1,2,3-triazolo[4,5-b]pyridinium 3-oxid hexafluorophosphate
NBS=N-bromosuccinimide
NMP=N-methyl pyrrolidine
PyBOP=(Benzotriazol-1-yloxy)tripyrrolidinophosphonium hexafluorophosphate
Suben=ω-5-Dibenzosuberenyl
TBDMS=t-butyl,dimethylsilyl
tBoc=t-butoxycarbonyl
Teoc=2-(trimethylsilyl) ethoxycarbonyl
TFA=trifluoroacetic acid Linear boronic acid compound 197 can be prepared according to the following:

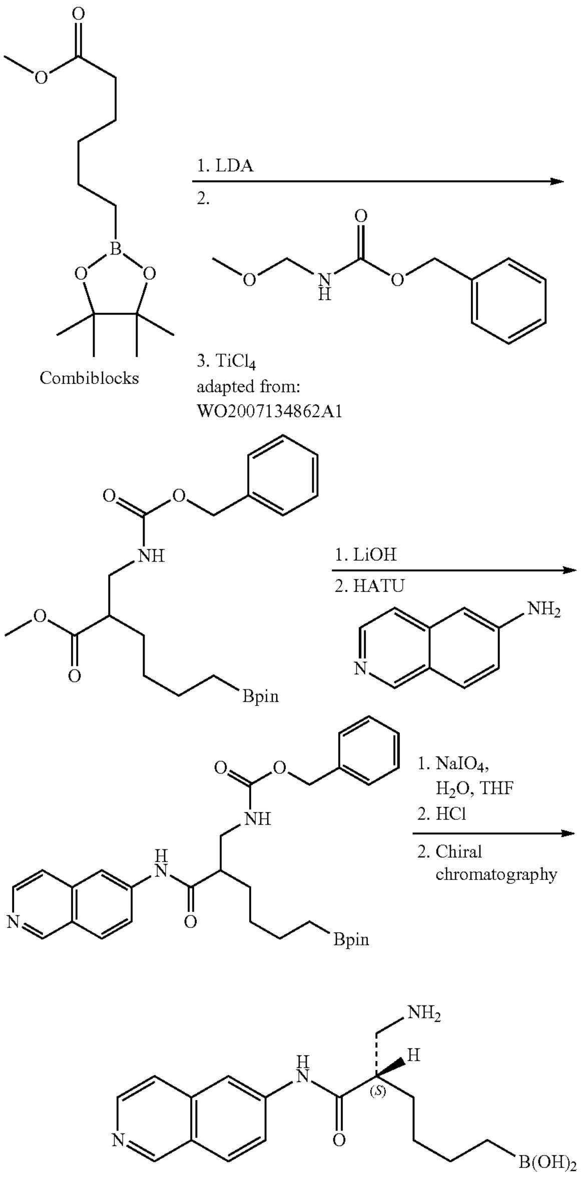

197

Compounds 198-219 can be prepared by first preparing the functionalized building blocks according to the following general scheme:
Building block preparation
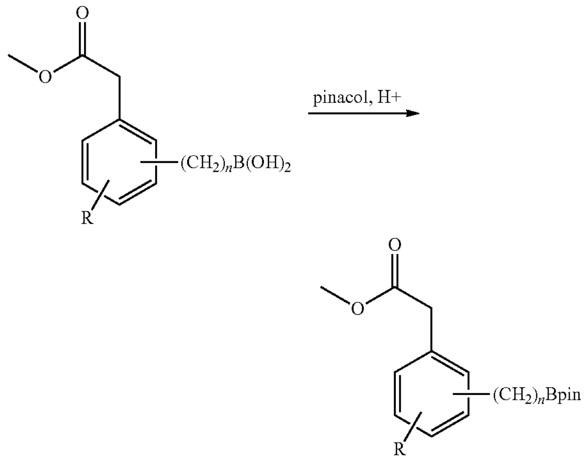
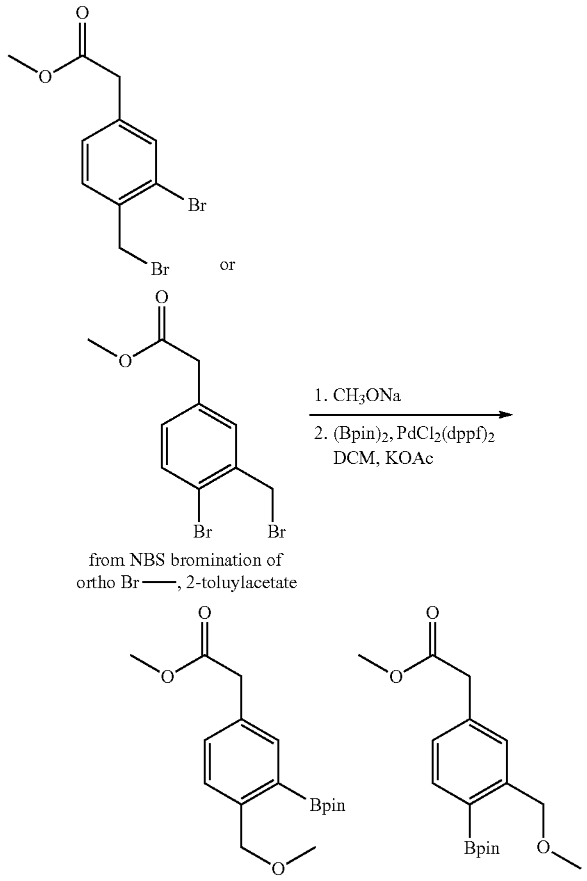
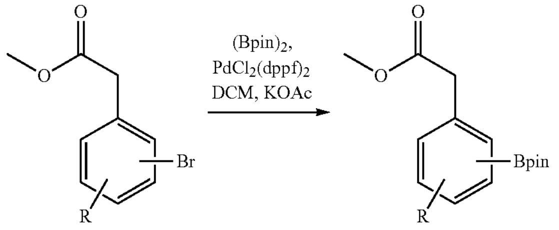
-continued
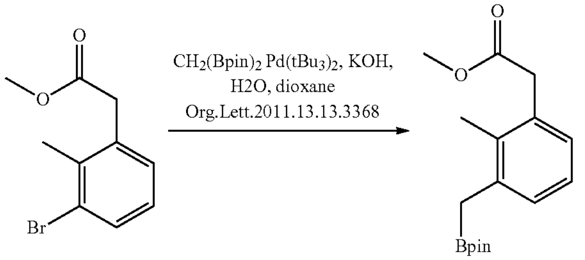
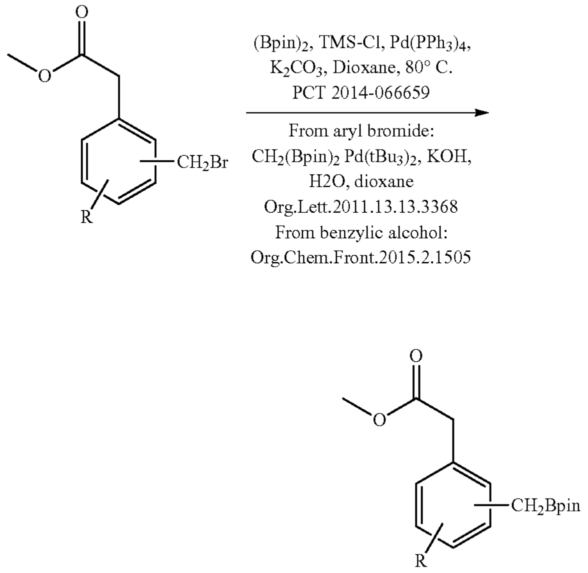
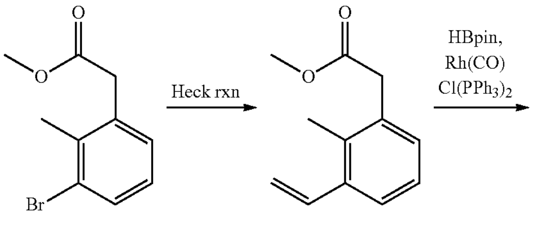
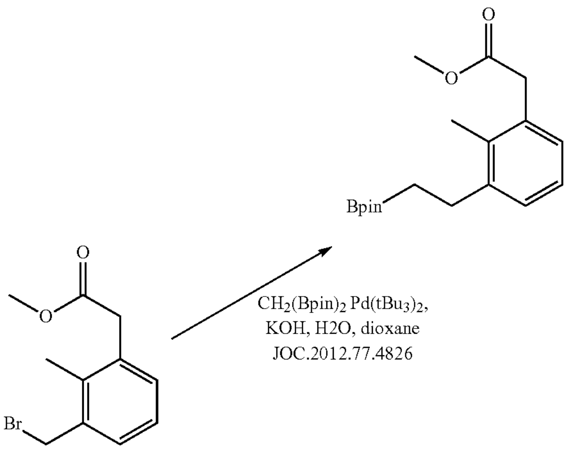

The isoquinoline portion is then introduced.
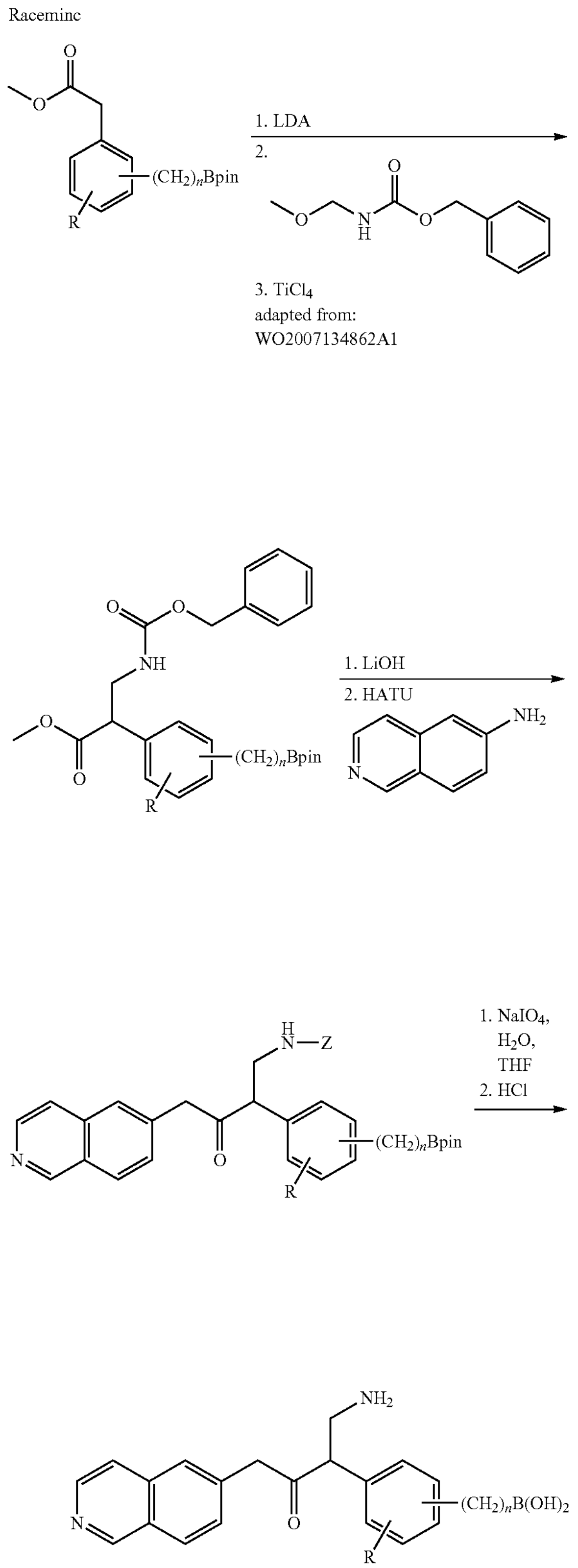
197
n = 0, unless
otherwise indicated
-continued
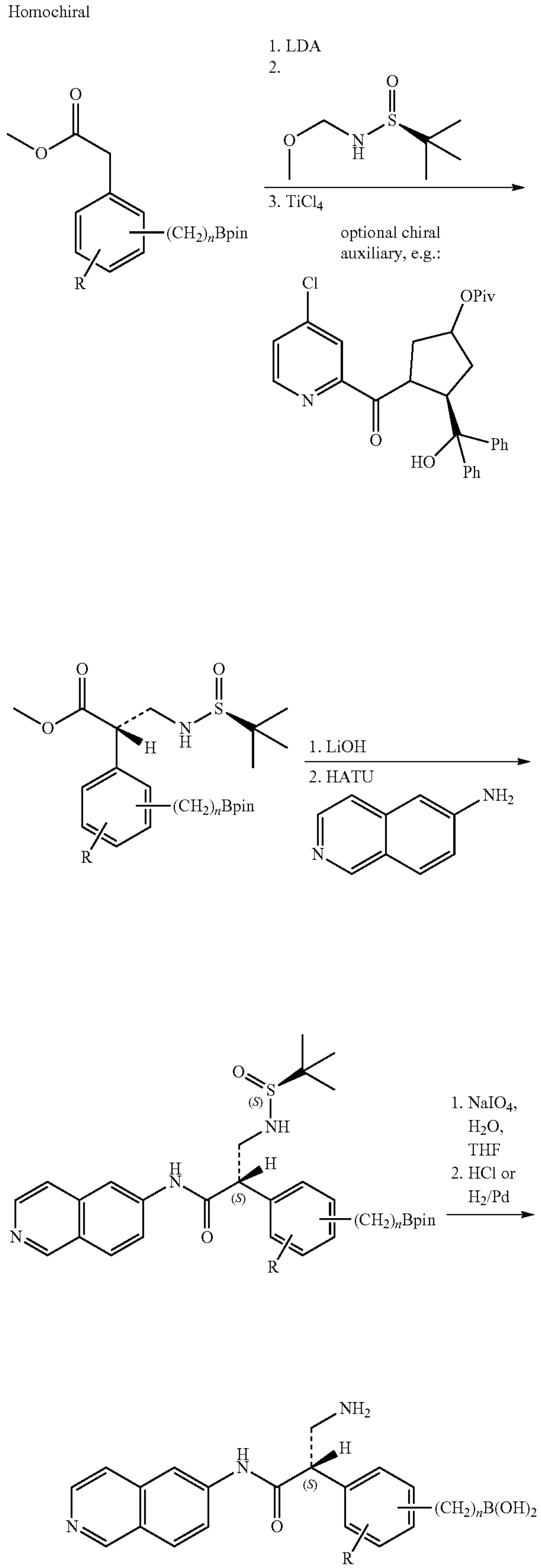

Optionally, the sulfinamide is converted to a more resilient protecting group.

The boronic acids can be further manipulated.

Post-Assembly Processing

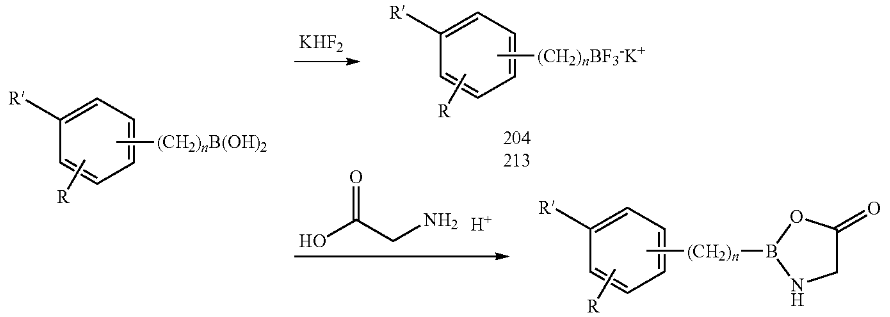

204
213

205
214

Oxazorole compounds 220-225 may likewise prepared by first preparing the boronic acid building blocks:

Building Block Preparation

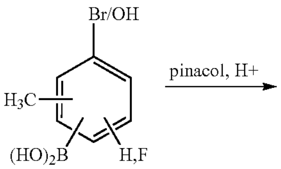

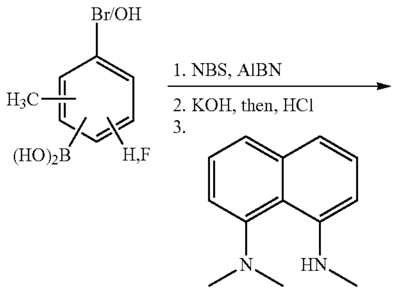

RSC.Adv.2013.3.21331

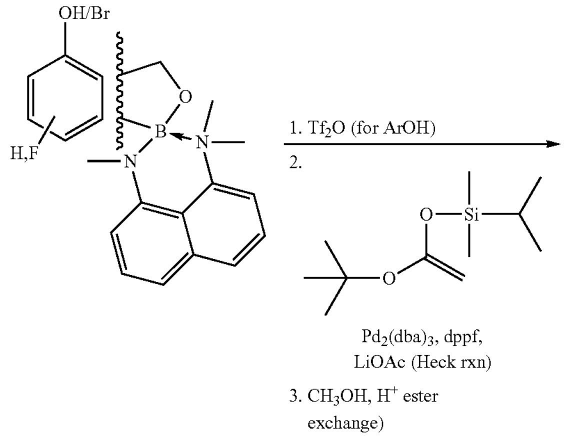

-continued

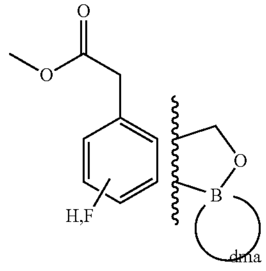

| Raw Materials | | |
|---|---|---|
| 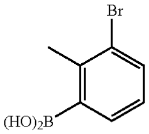 Enamine AK Sci. Small Molecules FCH Group | 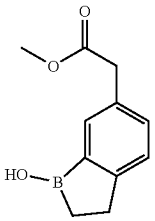 Anisyn FCH Group | 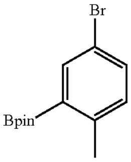 many vendors |

| | | |
|---|---|---|
| 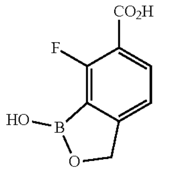 WO.2014144380.A1 Arndt-Eistert or Kowalski homologation to obtain ArCH2CO2R | 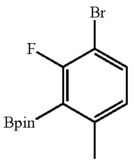 not known | 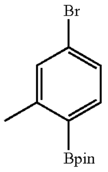 Astatech Fluorochem Small Molecules others |

-continued
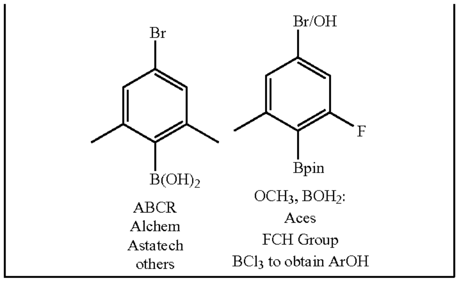
The isoquinoline portion is then installed.
Raceminc
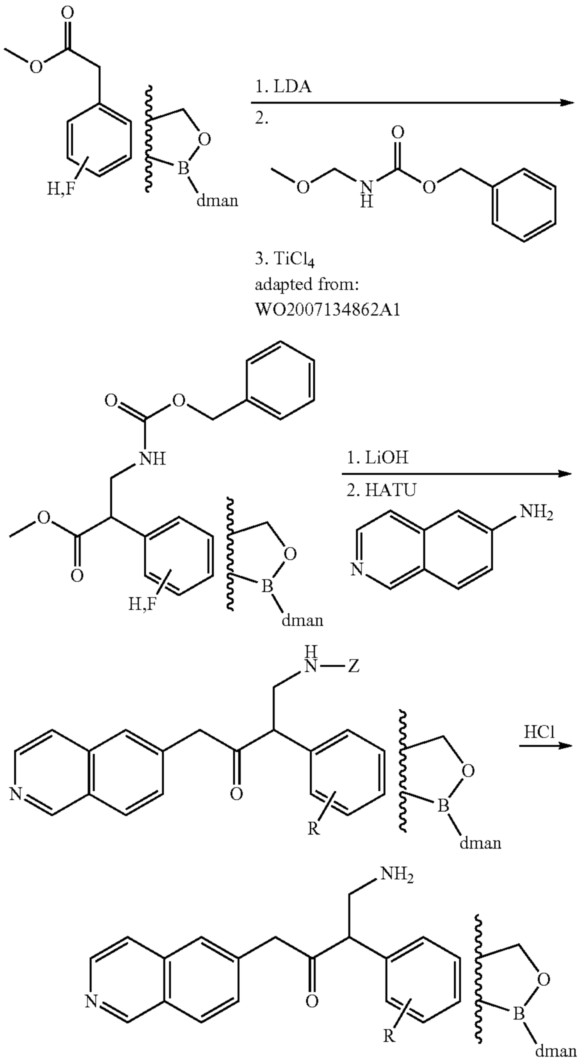
197
| Substitution | Cmpd # |
|---|---|
| 2-CH2OB(OH)-3 | 220 |
| 3-B(OH)OCH2-4 | 221 |
| 2-F, 3-B(OH)OCH2-4 | 222 |
| 3-CH2OB(OH)-4, | 223 |
| 3-CH2OB(OH)-4, 5-CH3 | 224 |
| 3-CH2OB(OH)-4, 5-F | 225 |
dman = 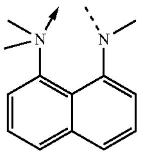
-continued
Homochiral
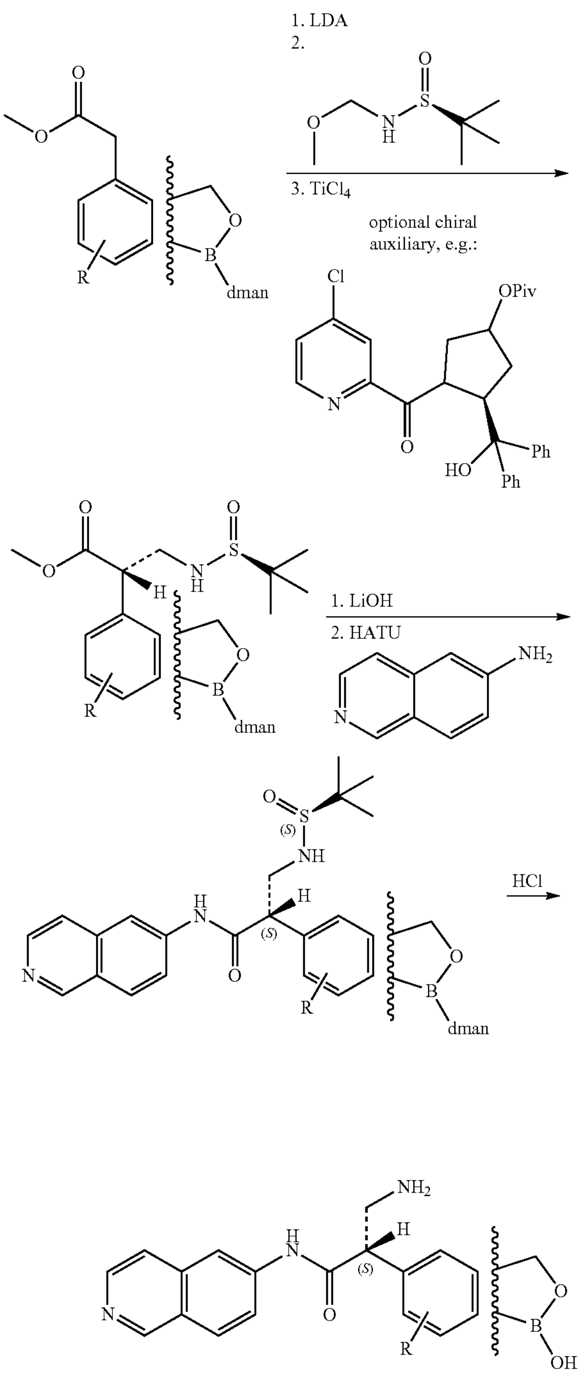
dman = 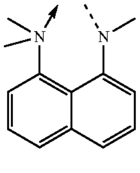

Azaborole compounds 226-231 may be prepared in a similar manner.
Building Block Preparation
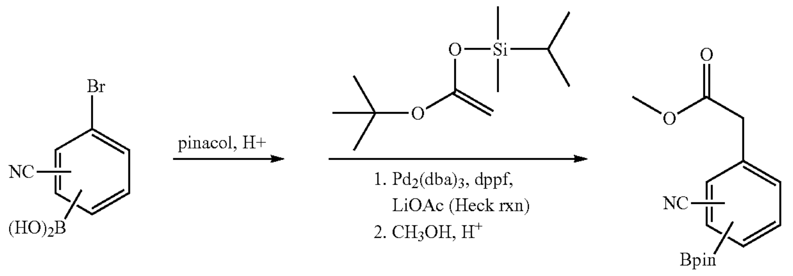
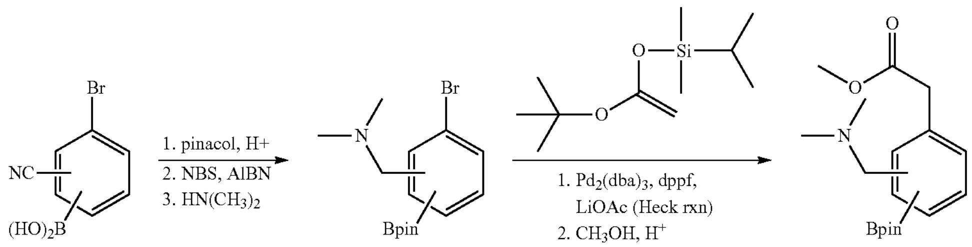
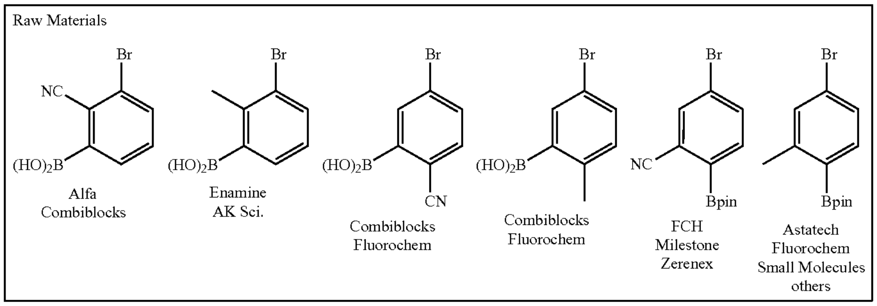
The building blocks can then be attached to the isoquinoline portions:
Raceminc
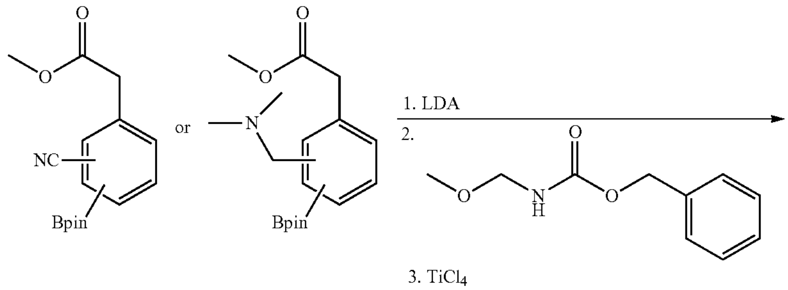
adapted from:
WO2007134862A1

-continued
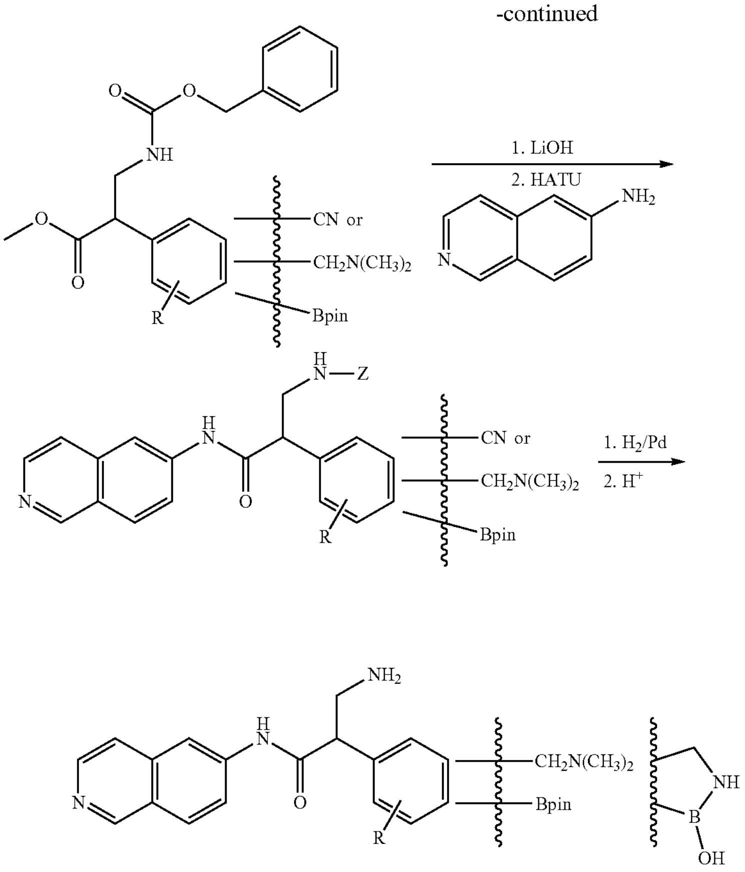
| Substitution | Cmpd # |
|---|---|
| 2-$CH_2NHB(OH)$-3 | 226 |
| 2-$CH_2N(CH_3)_2$ 3-$B(OH)_2$ | 227 |
| 3-$B(OH)NHCH_2$-4 | 228 |
| 3-$B(OH)_2$ 4-$CH_2N(CH_3)_2$ | 229 |
| 3-$CH_2NHB(OH)$-4 | 230 |
| 3-$CH_2N(CH_3)_2$ 4-$B(OH)_2$ | 231 |
Homochiral
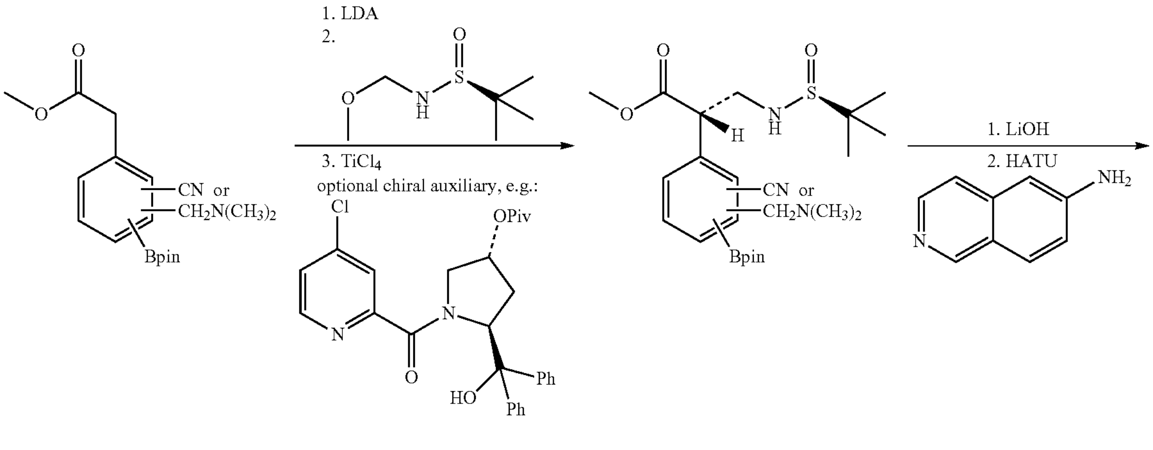

-continued
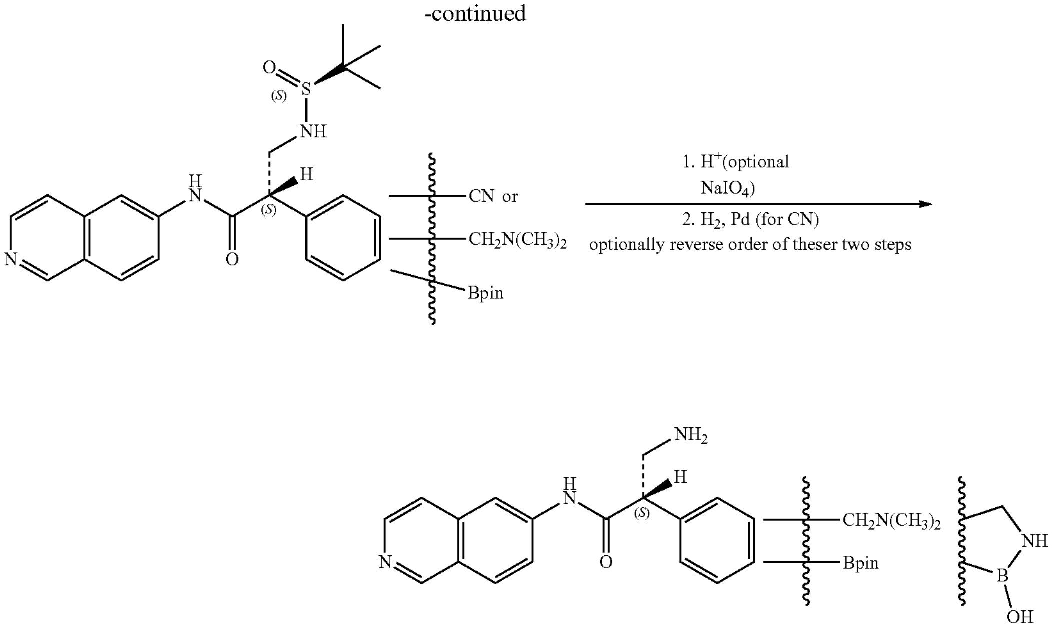
Optionally, the sulfinamide is converted to a more resilient protecting group.
Oxazaborole compounds 232-234 can be prepared as follows:
Building Block Preparation
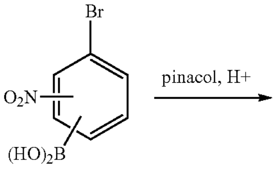
-continued
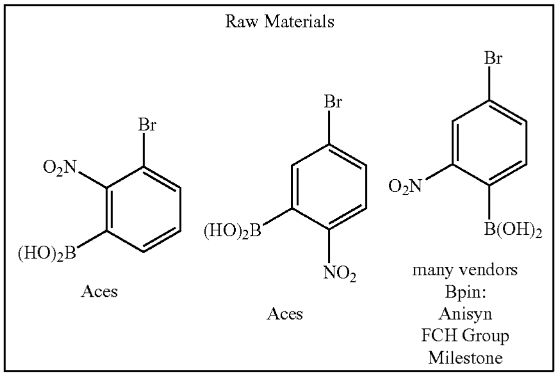
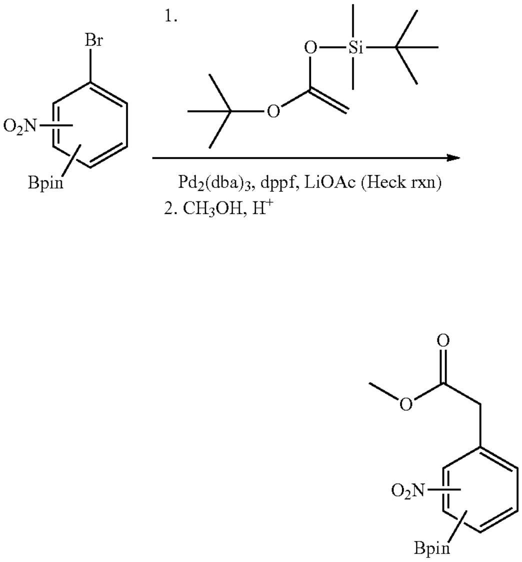
Raceminc
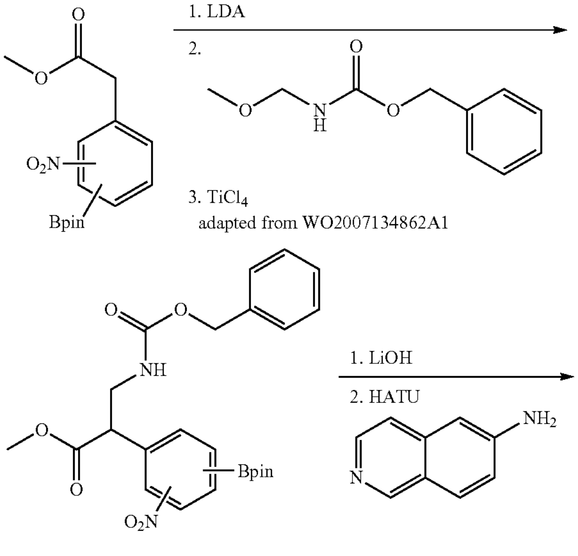
Scheme 36. 1,2,6-Oxazaborine, diazaborine, racemic -continued
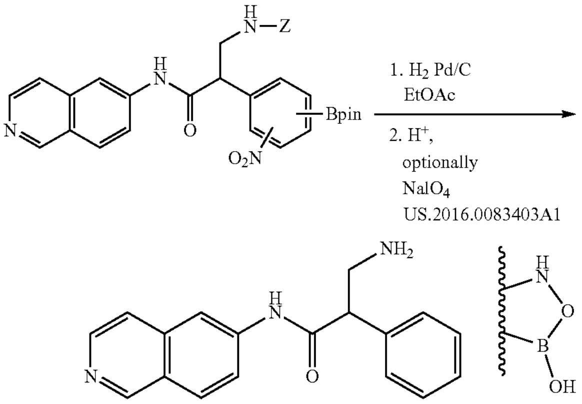
| Substitution | Cmpd # |
| --- | --- |
| 2-NHOB(OH)-3 | 232 |
| 3-B(OH)NHCO-4 | 233 |
| 3-NHOB(OH)-4 | 234 |
Homochiral
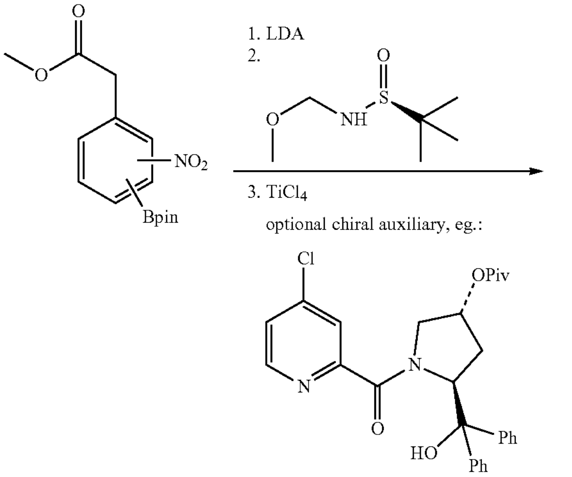
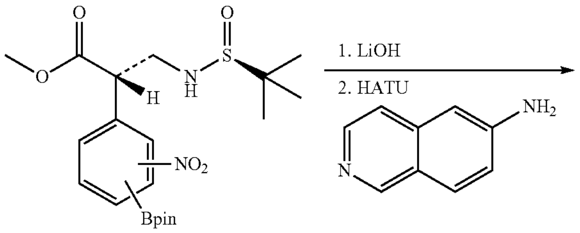
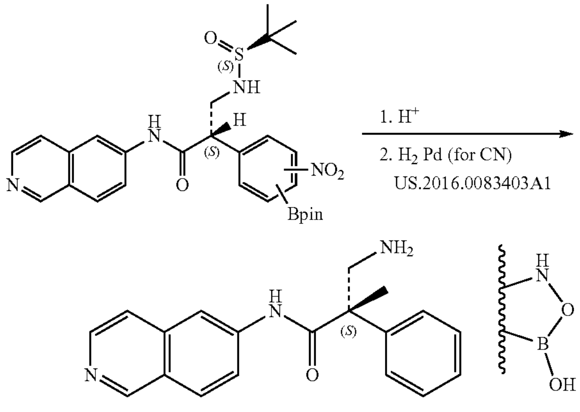
Optionally, the sulfinamide is converted to a more resilient protecting group.
[H]-Oxaborine and azaborine compounds 235-240 can be prepared as follows:
Building Block Preparation
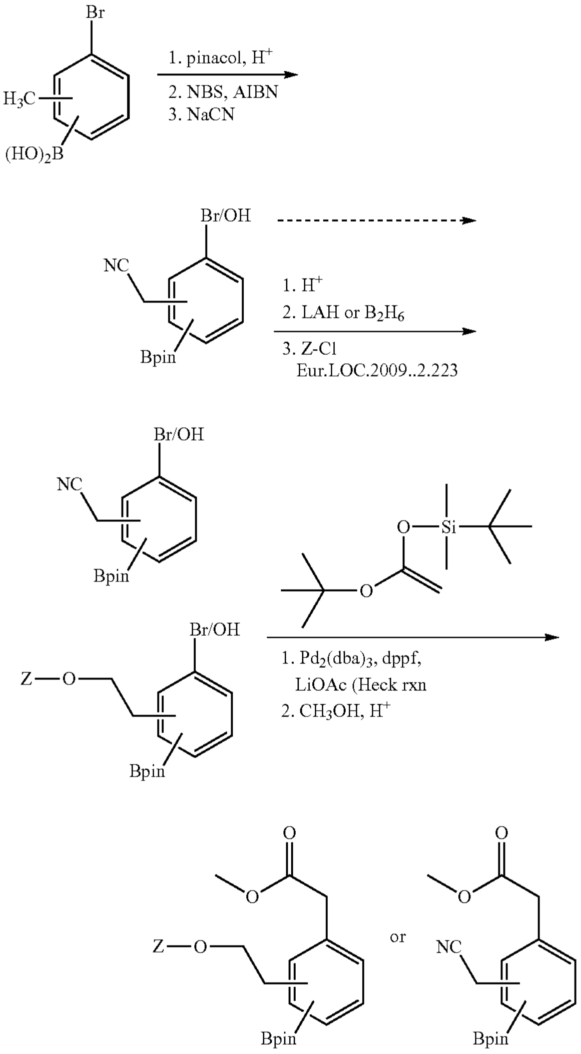
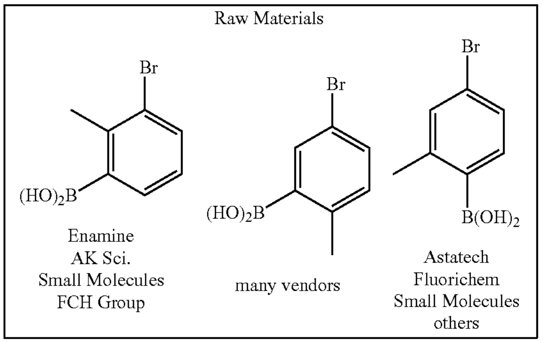
Racemic -continued
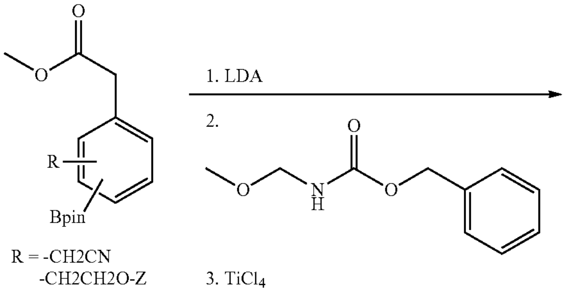
adapted from: WO2007134862A1
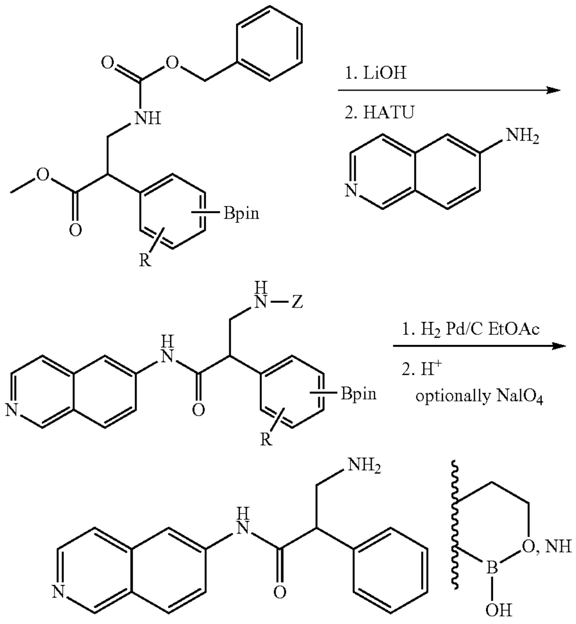
| Substitution | Cmpd # |
| --- | --- |
| 2- $CH_2CH_2OB(OH)$-3 | 235 |
| 3- $B(OH)OCH_2CH_2$-4 | 236 |
| 4- $B(OH)OCH_2CH_2$-3 | 237 |
| 2- $CH_2CH_2NHB(OH)$-3 | 238 |
| 4- $B(OH)NHCH_2CH_2$-3 | 239 |
| 3- $B(OH)NHCH_2CH_2$-4 | 240 |
Homochiral
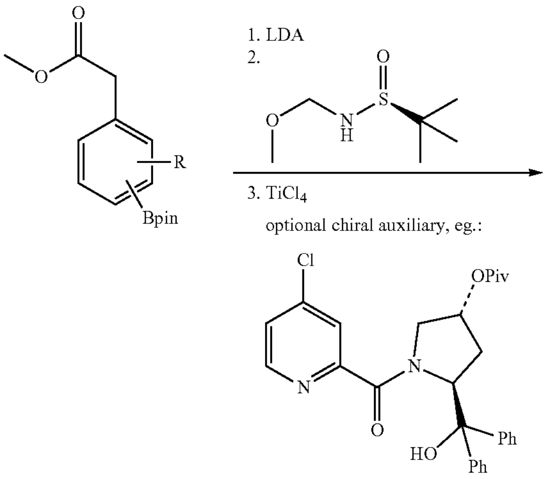
-continued
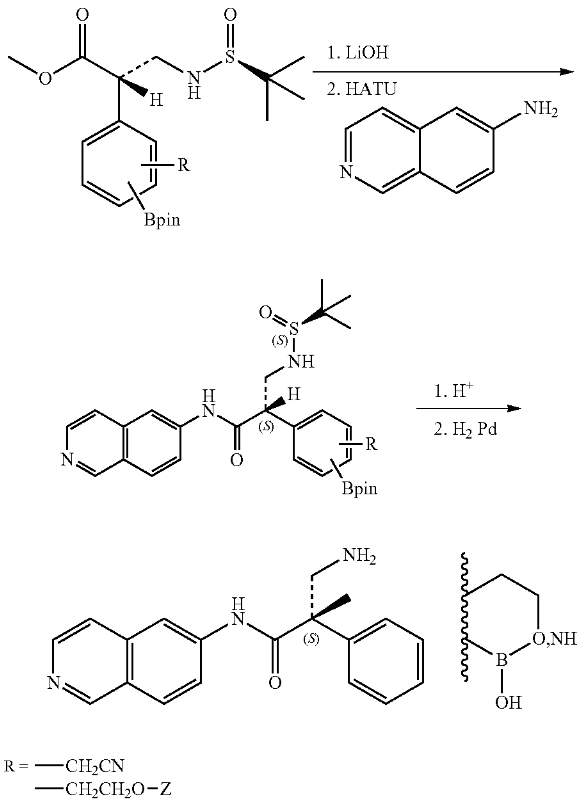
Optionally, the sulfonamide is converted to a more resilient protecting group.
The unsaturated azaborine and azaborinium compounds 241-246 can be prepared according to the following:
Building Block Preparation
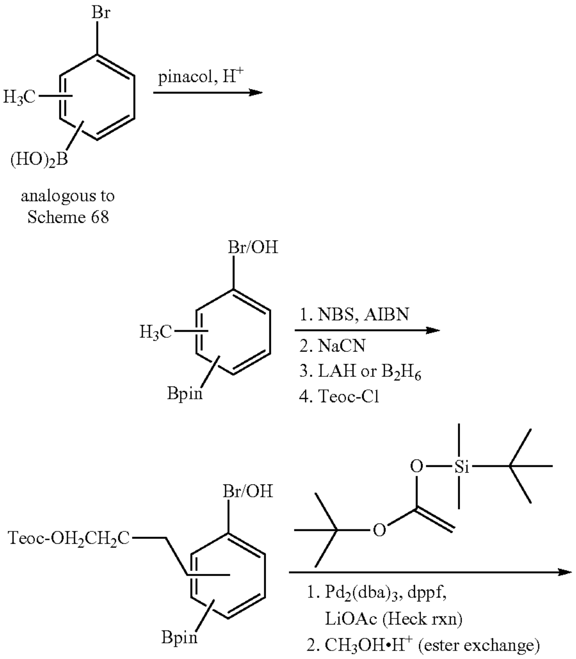

-continued

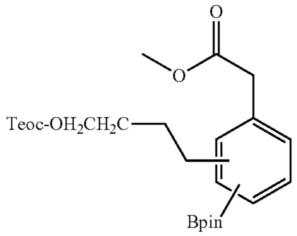

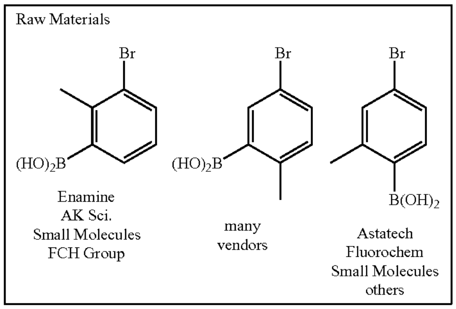

Alternate method to attach protected R—$OCH_2CH_2$— group on aryl ring: reaction of $ROCH_2CH_2$-Bpin with aryl bromide and Pd catalysis.

The building blocks are then attached to the isoquinoline portions:

Raceminc

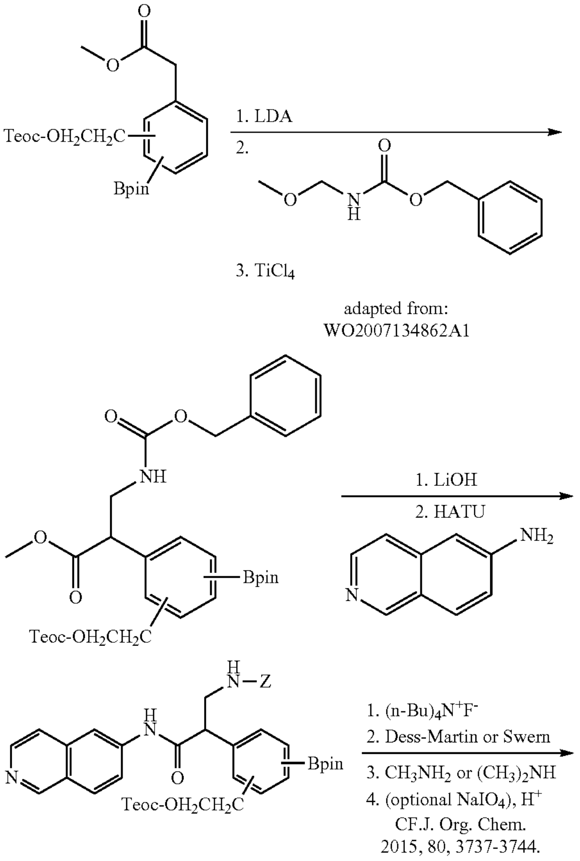

-continued

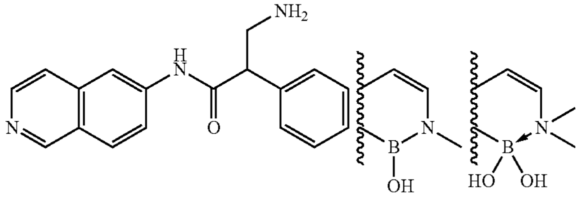

| Substitution | Cmpd # |
|---|---|
| $2-CH=CHN(CH_3)B(OH)-3$ | 241 |
| $2-CH=CHN(CH_3)_2^+B(OH)_2^--3$ | 242 |
| $3-B(OH)N(CH_3)CH=CH-4$ | 243 |
| $3-B(OH)_2^-N(CH_3)_2^+CH=CH-4$ | 244 |
| $4-B(OH)N(CH_3)CH=CH-3$ | 245 |
| $4-B(OH)_2^-N(CH_3)_2^+CH=CH-3$ | 246 |

Homochiral

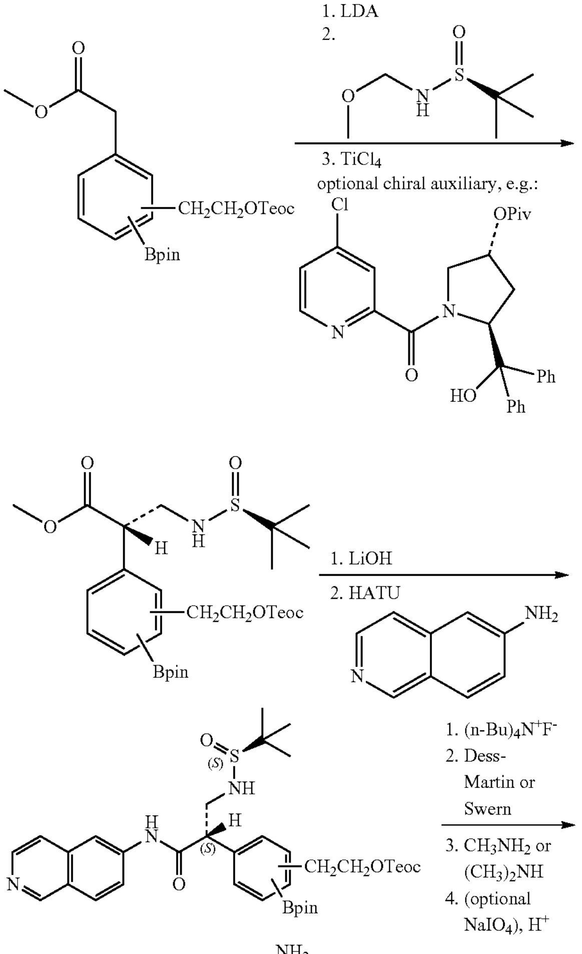

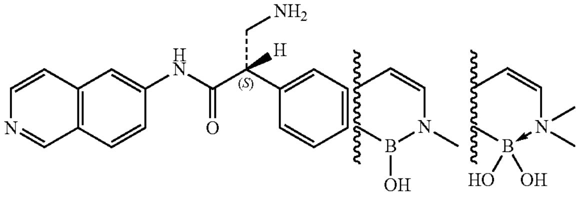

Optionally, the sulfonamide is converted to a more resilient protecting group.

The preparation of unsaturated oxaborine and azaborine compounds 247-252 is shown in the schemes below:
Building Block Preparation
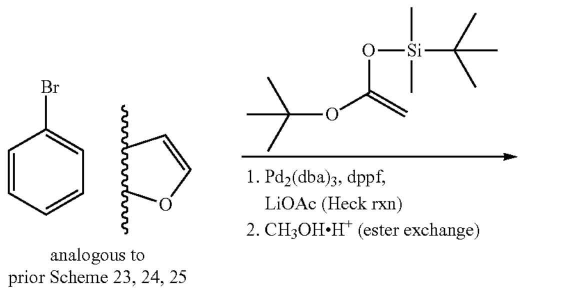
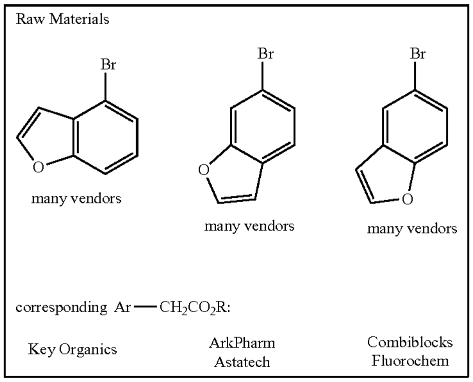
Raceminc
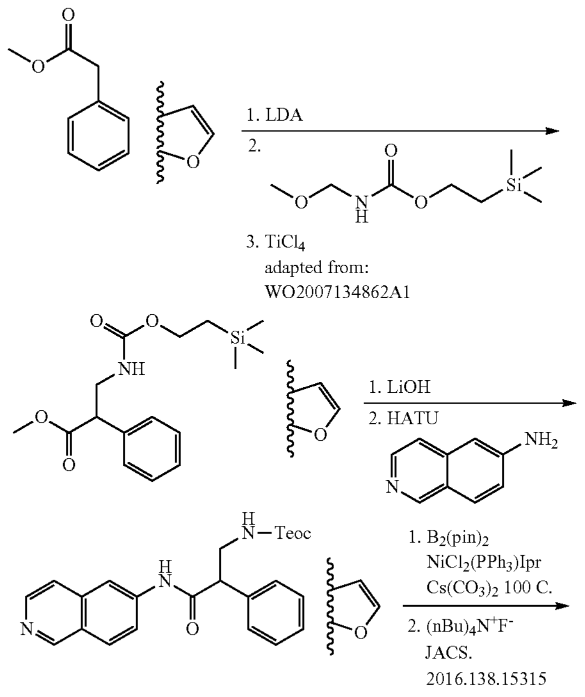
-continued
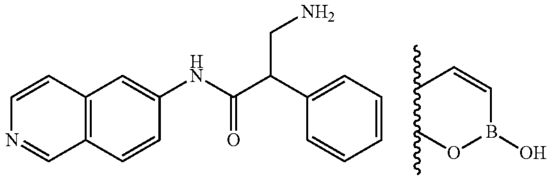
| Substitution | Cmpd# |
| --- | --- |
| 2-CH═CHB(OH)NH-3 | 250 |
| 3-NHB(OH)CH═CH-4 | 251 |
| 4-NHB(OH)CH═CH-3 | 252 |
Homochiral
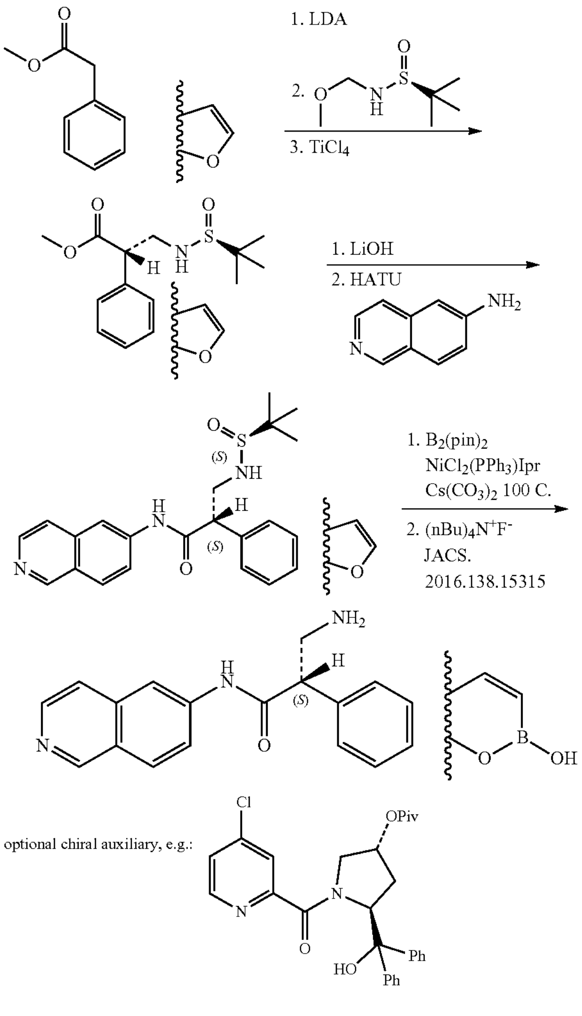
Optionally, the sulfinamide is converted to a more resilient protecting group.
Building Block Preparation
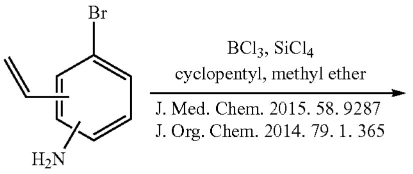

-continued
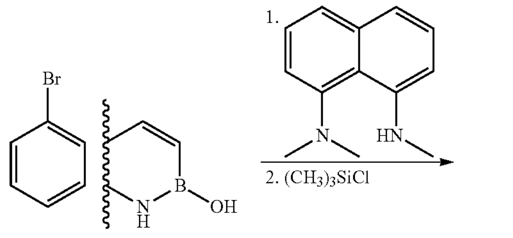
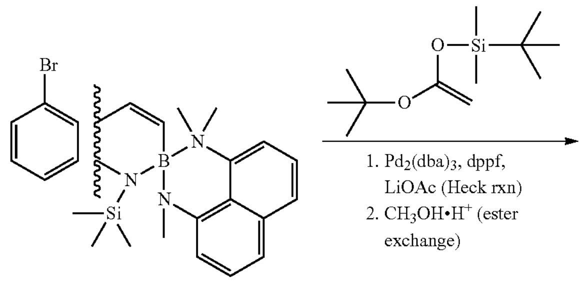
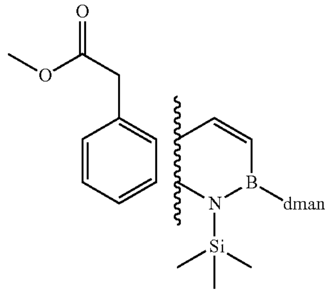
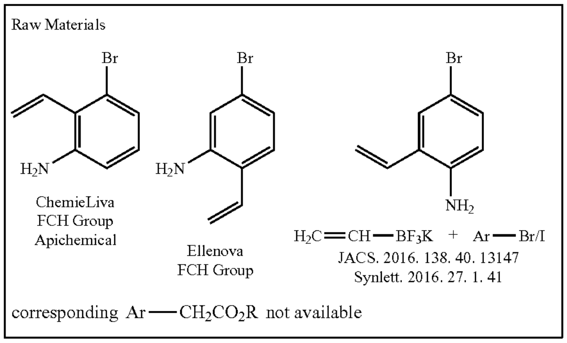
Racemine
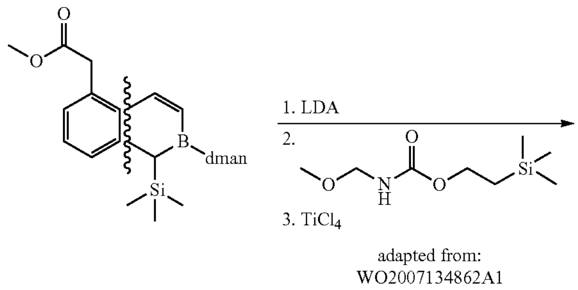
-continued
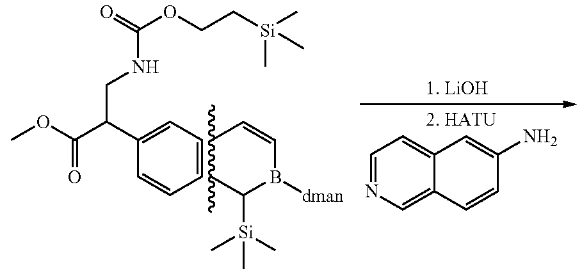
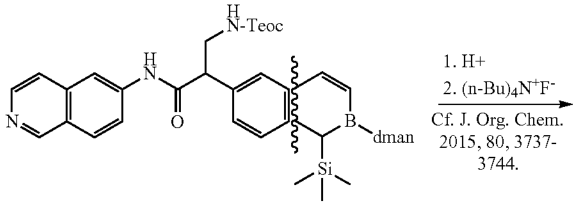
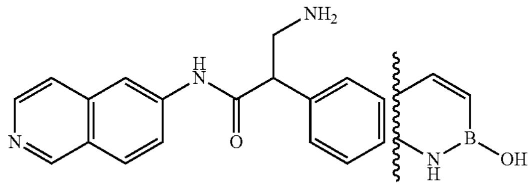
| Substitution | Cmpd # |
|---|---|
| 2-CH═CHB(OH)NH-3 | 250 |
| 3-NHB(OH)CH═CH-4 | 251 |
| 4-NHB(OH)CH═CH-3 | 252 |
Homochiral
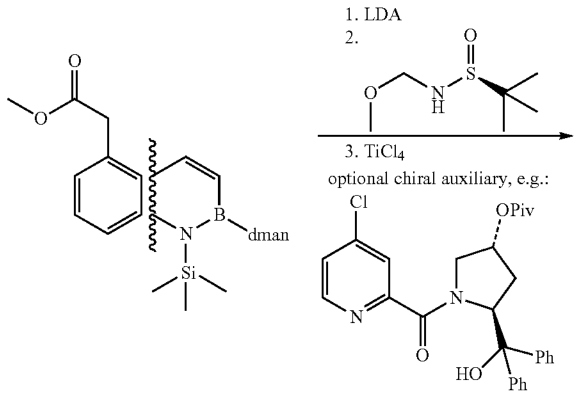
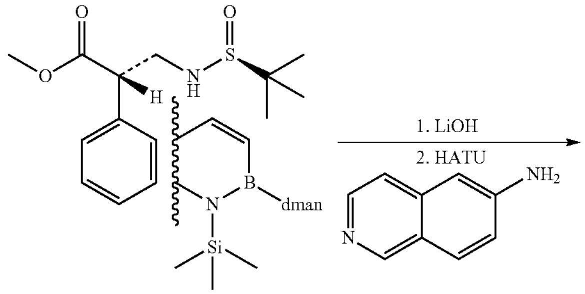

-continued

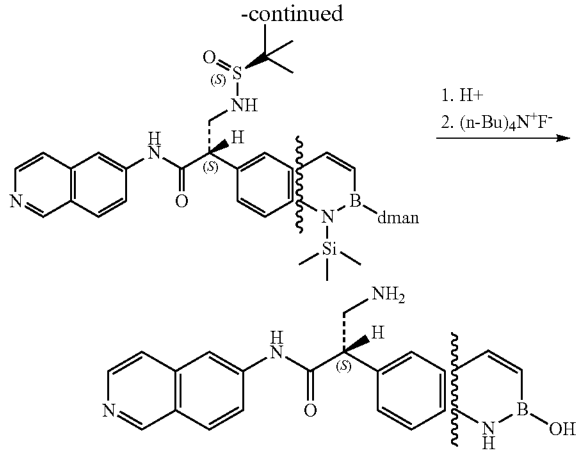

Optionally, the sulfinamide is converted to a more resilient protecting group.

Similarly, 1,2,6-oxazaborine and diazaborine compounds 253-270 can be prepared as follows:

Building Block Preparation

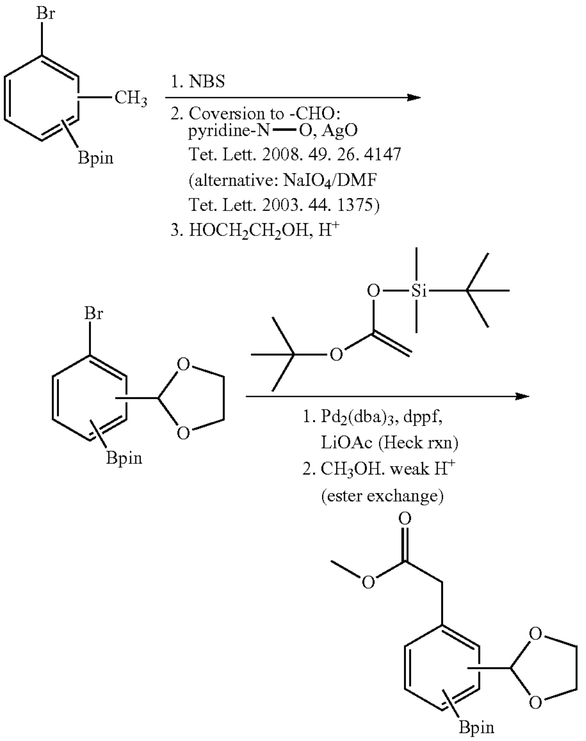

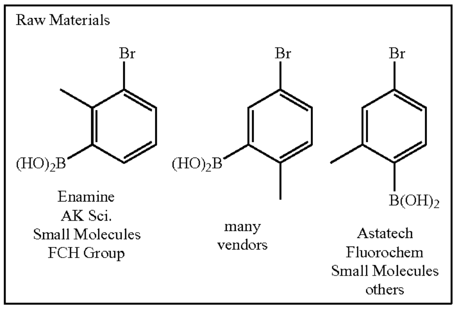

Alternative to prepare RCHO: double bromination with NBS, conversion to ethylene acetal using $HOCH_2CH_2O$—Na.

Alternative to ester exchange: Hydrolysis with NaOH or $(nBu)_4N^+OH^-$, treatment with $CH_3I$ or $CH_2N_2$.

Further assembly is shown below:

Raceminc

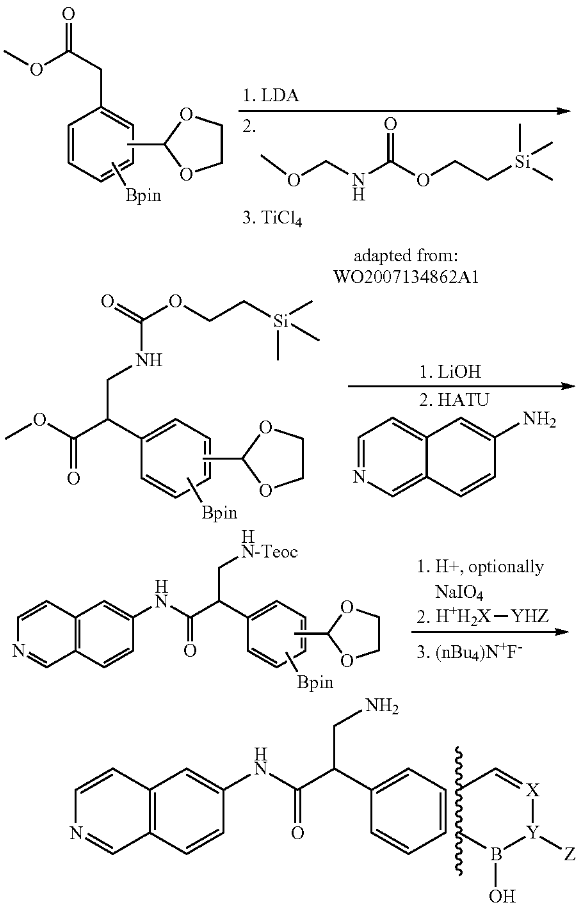

2,3- 3,4- & 4,3- isomers

| $H_2X$—YH—Z | | |
|---|---|---|
| $H_2N$—OH | 2-CH=N—O—B(OH)-3 | 253 |
| $H_2N$—$NH_2$ | 2-CH=N—NH—B(OH)-3 | 254 |
| $H_2N$—$NHCH_3$ | 2-CH=N—N($CH_3$)—B(OH)-3 | 255 |
| $H_2N$—NHPh | 2-CH=N—N(Ph)—B(OH)-3 | 256 |
| $H_2N$—NHC(O)$CH_3$ | 2-CH=N—N(C=O$CH_3$)—B(OH)-3 | 257 |
| $H_2N$—$NHSO_2CH_3$ | 2-CH=N—N($SO_2CH_3$)—B(OH)— | 258 |
| | 4-CH=N—O—B(OH)-3 | 259 |
| | 4-CH=N—NH—B(OH)-3 | 260 |
| | 4-CH=N—N($CH_3$)—B(OH)-3 | 261 |
| | 4-CH=N—N(Ph)—B(OH)-3 | 262 |
| | 4-CH=N—N(C=O$CH_3$)—B(OH)-3 | 263 |
| | 4-CH=N—N($SO_2CH_3$)—B(OH)— | 264 |
| | 3-CH=N—O—B(OH)-4 | 265 |
| | 3-CH=N—NH—B(OH)-4 | 266 |
| | 3-CH=N—N($CH_3$)—B(OH)-4 | 267 |
| | 3-CH=N—N(Ph)—B(OH)-4 | 268 |
| | 3-CH=N—N(C=O$CH_3$)—B(OH)-4 | 269 |
| | 3-CH=N—N($SO_2CH_3$)—B(OH)-4 | 270 |

Homochiral

-continued

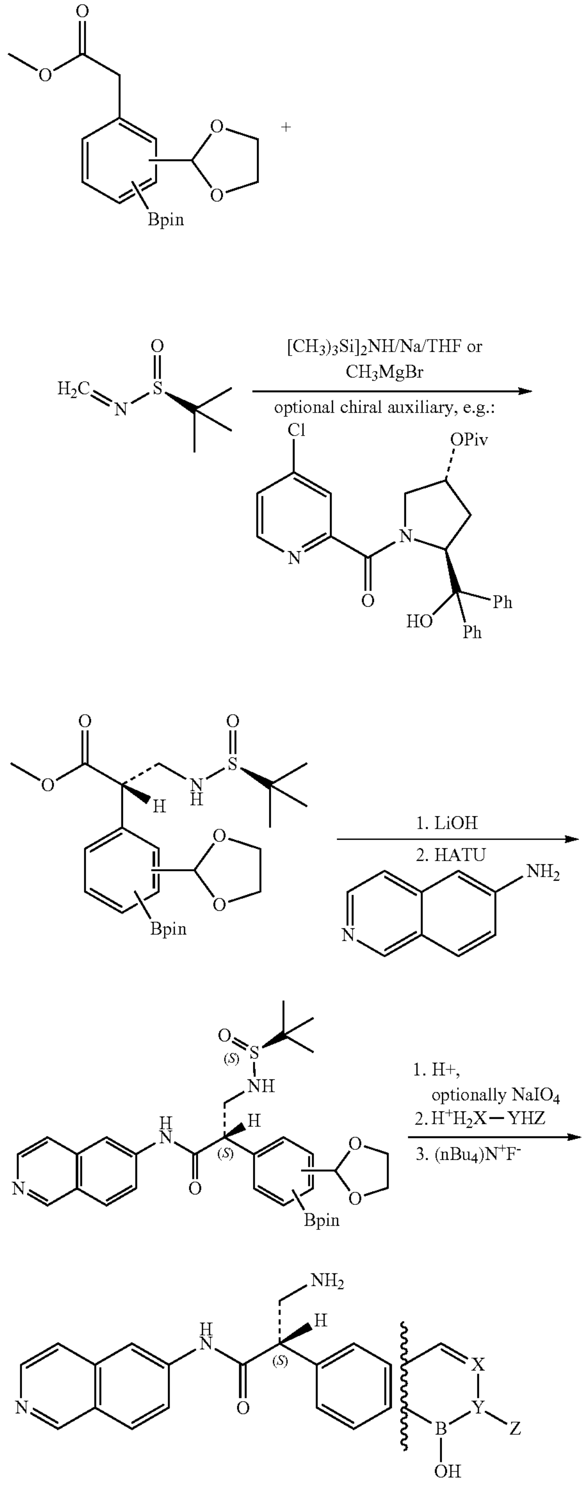

| $H_2X$—YH—Z |
|---|
| $H_2N$—OH |
| $H_2N$—$NH_2$ |
| $H_2N$—$NHCH_3$ |
| $H_2N$—NHPh |
| $H_2N$—$NHC(O)CH_3$ |
| $H_2N$—$NHSO_2CH_3$ |

Optionally, the sulfonamide is converted to a more resilient protecting group.

1,3,6-Oxazaborine and diazaborine compounds 271-279 can be prepared according to the following:

Raceminc

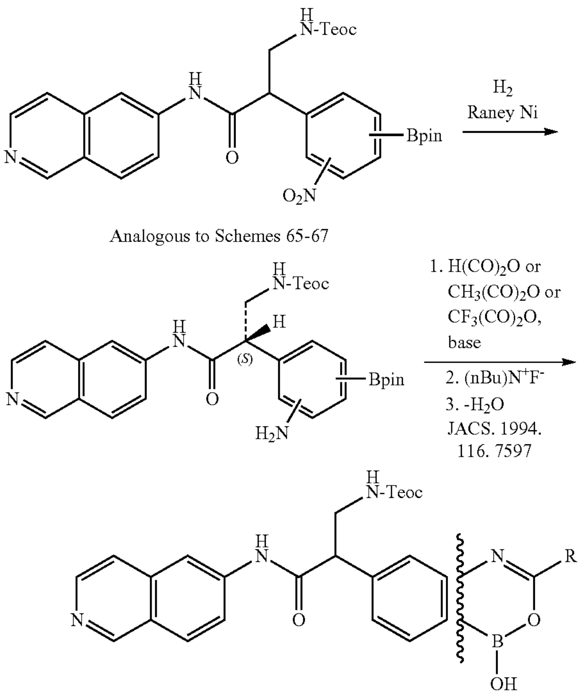

R = H, $CH_3$, $CF_3$

| | |
|---|---|
| 2-N═CH—OB(OH)-3 | 271 |
| 2-N═C($CH_3$)—OB(OH)-3 | 272 |
| 2-N═C($CF_3$)—OB(OH)-3 | 273 |
| 4-N═CH—OB(OH)-3 | 274 |
| 4-N═C($CH_3$)—OB(OH)-3 | 275 |
| 4-N═C($CF_3$)—OB(OH)-3 | 276 |
| 3-N═CH—OB(OH)-4 | 277 |
| 3-N═C($CH_3$)—OB(OH)-4 | 278 |
| 3-N═C($CF_3$)—OB(OH)-4 | 279 |

Homochiral

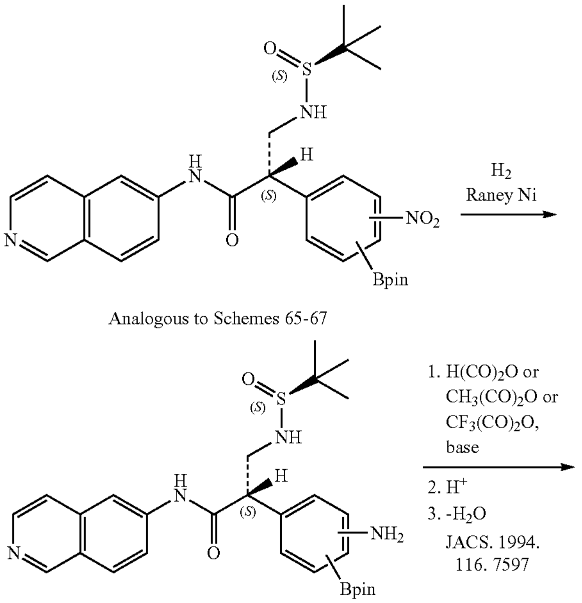

-continued

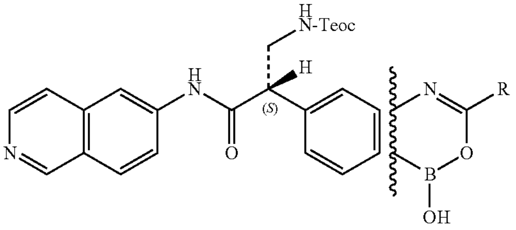

R = H, $CH_3$, $CF_3$

Optionally, the sulfinamide to a more resilient protecting group.

1,2,6-Oxazaborine and 1,3,6-diazaborine compounds 280-285 can be prepared as follows:

1,3,6-Diazaborine, racemic:

Raceminc

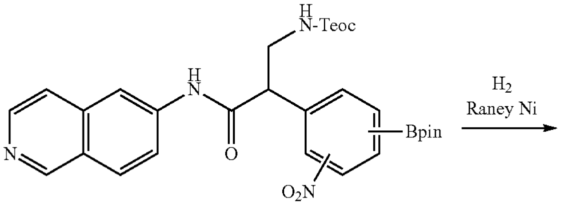

Analogous to Schemes 65-67

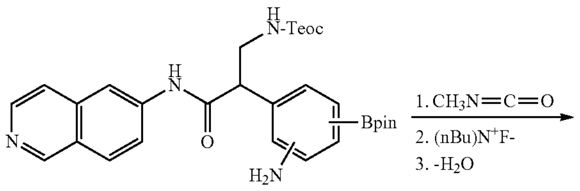

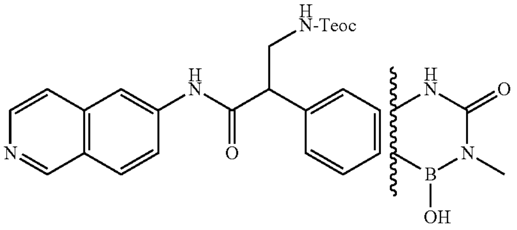

2-NH(C=O)—N($CH_3$)—B(OH)-3 280
4-NH(C=O)—N($CH_3$)—B(OH)-3 282
3-NH(C=O)—N($CH_3$)—B(OH)-4 284

1,3,6-Diazaborine, homochiral:

Homochiral

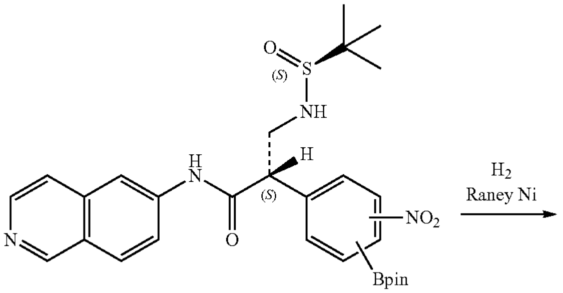

Analogous to Schemes 65-67

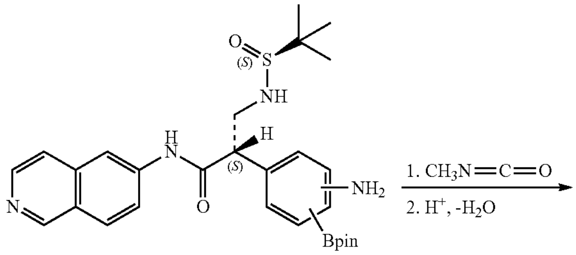

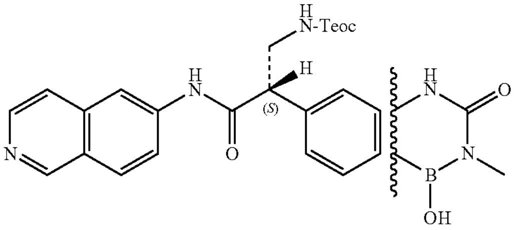

Optionally, the sulfonamide is converted to a more resilient protecting group.

1,2,6-Oxazaborine, building blocks can be prepared as follows:

Building Block Preparation

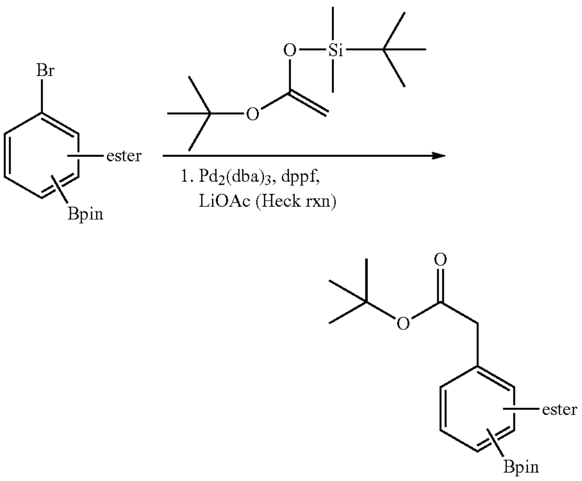

-continued
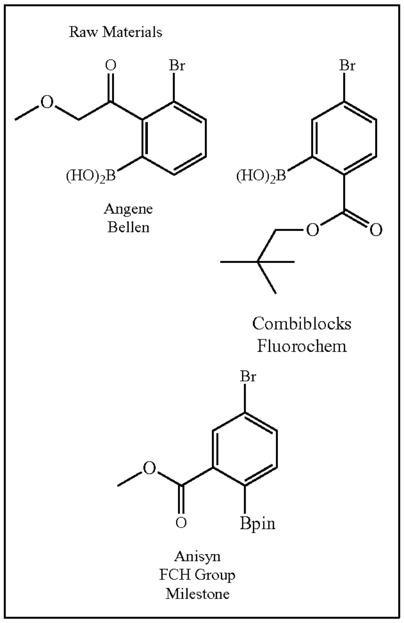
1,2,6-Oxazaborine (racemic and homochiral) may be prepared as shown below:
Raceminc
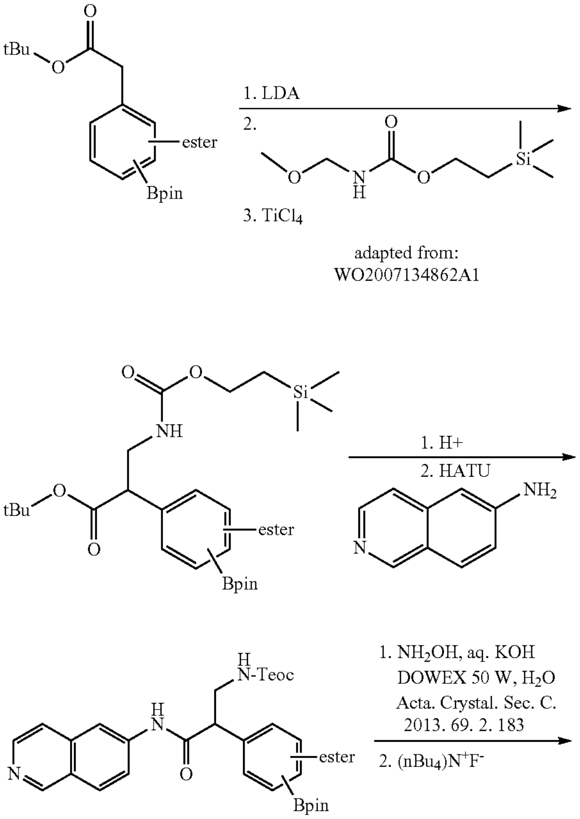
-continued
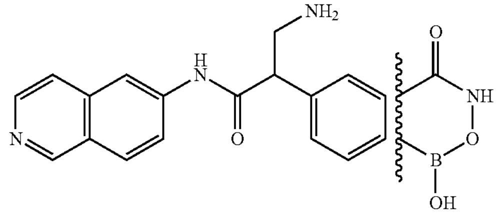
2,3- 3,4- & 4,3- isomers
2-(C═O)NHO—B(OH)-3 281
4-(C═O)NHO—B(OH)-3 283
3-(C═O)NHO—B(OH)-4 285
Homochiral
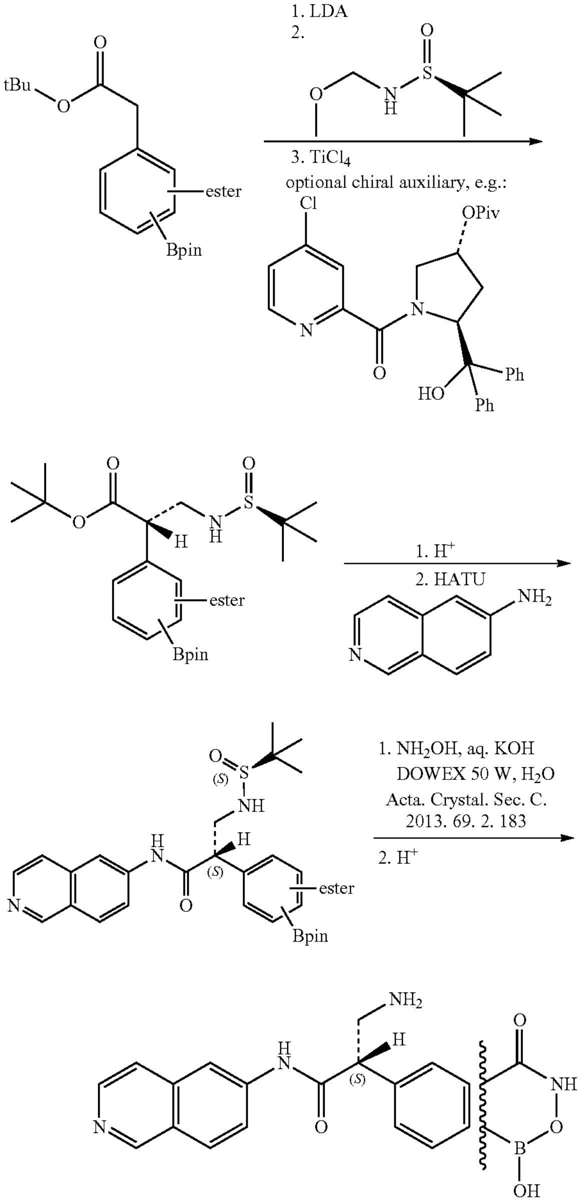
Optionally, the sulfonamide is converted to a more resilient protecting group.

Oxaborepine, dioxaborepine, and oxazaborepine compounds 286-294 may be prepared as shown below:

Oxaborepines, Building Blocks:

Building Block Preparation

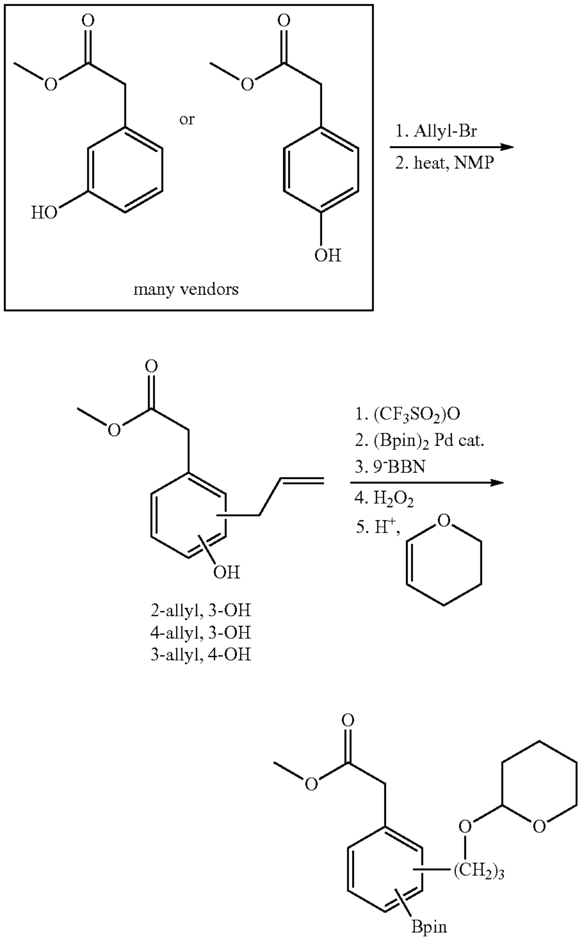

2-allyl, 3-OH
4-allyl, 3-OH
3-allyl, 4-OH 2,3-, 4, 3- &
3, 4-THP-
$(CH_2)_3$, Bpin Oxaborepines (racemic and homochiral) compounds may be prepared as shown below:

Raceminc

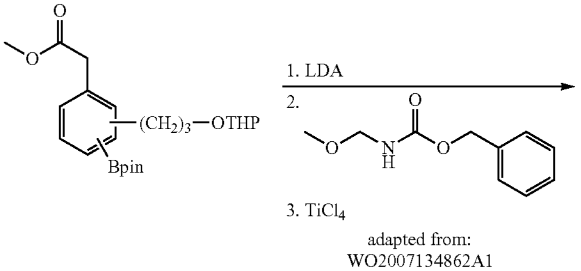

adapted from:
WO2007134862A1

-continued

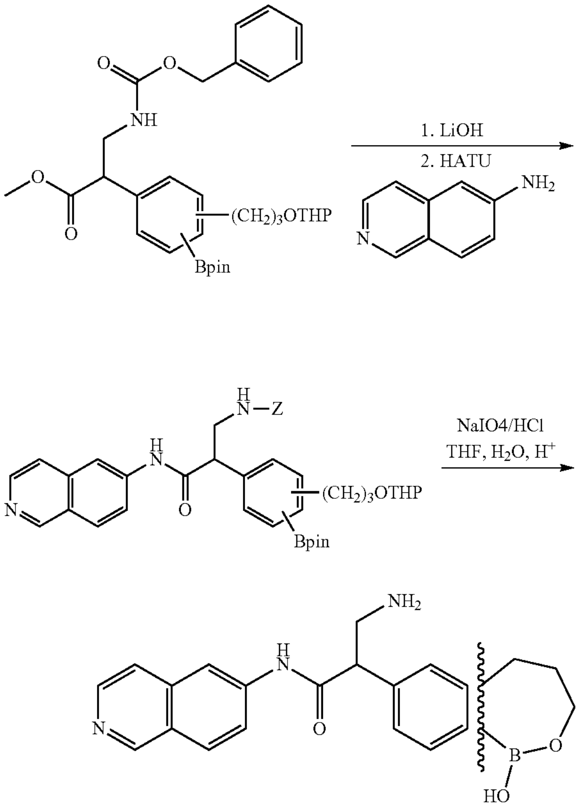

2-$CH_2CH_2CH_2OB(OH)$-2 286
3-$B(OH)OCH_2CH_2CH_2$-4 287
4-$B(OH)OCH_2CH_2CH_2$-3 288

Homochiral

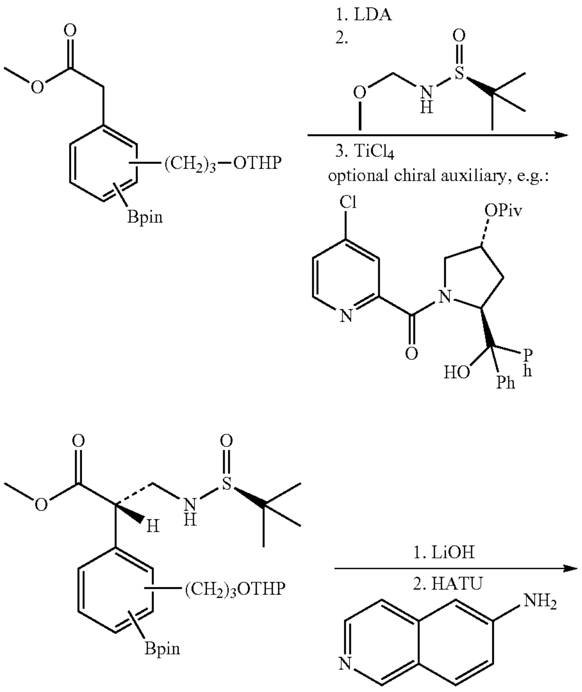

-continued

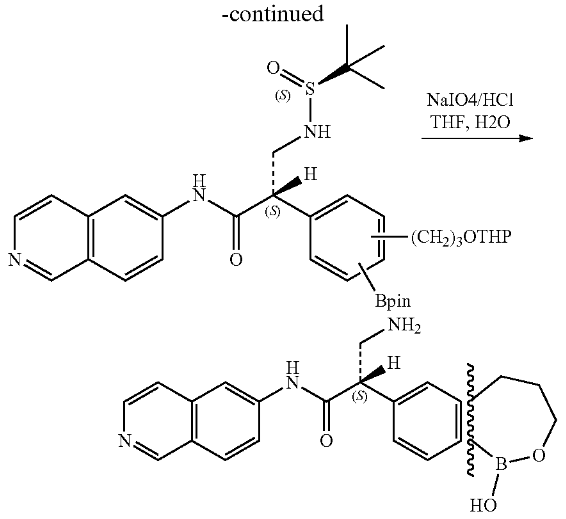

Optionally, the sulfinamide is converted to a more resilient protecting group.

The reverse oxaborepines building blocks can be prepared as shown below:

Building Block Preparation

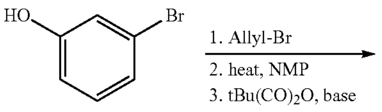

many vendors

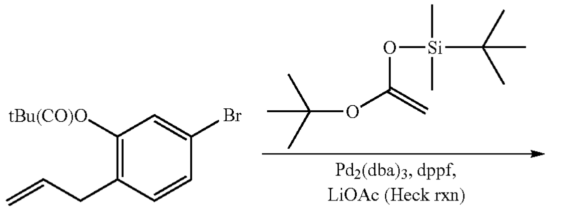

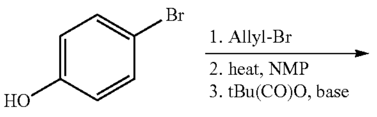

many vendors

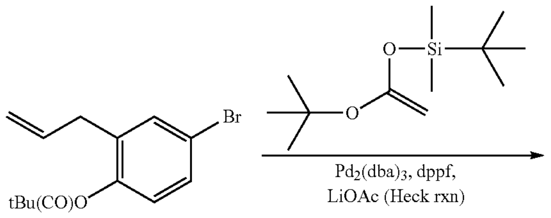

-continued

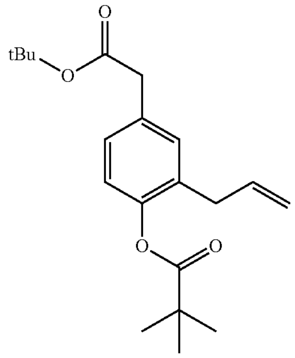

The reverse oxaborepines compounds (racemic and homochiral) can then be prepared as shown below:

Racemine

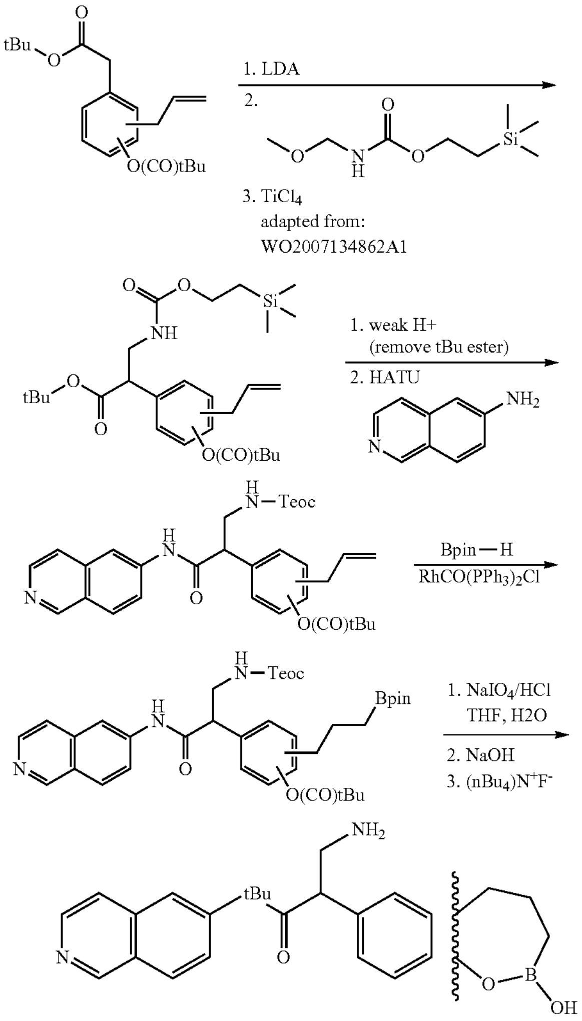

3-OB(OH)$CH_2CH_2CH_2$-4 289
4-OB(OH)$CH_2CH_2CH_2$-3 290

Homochiral

-continued
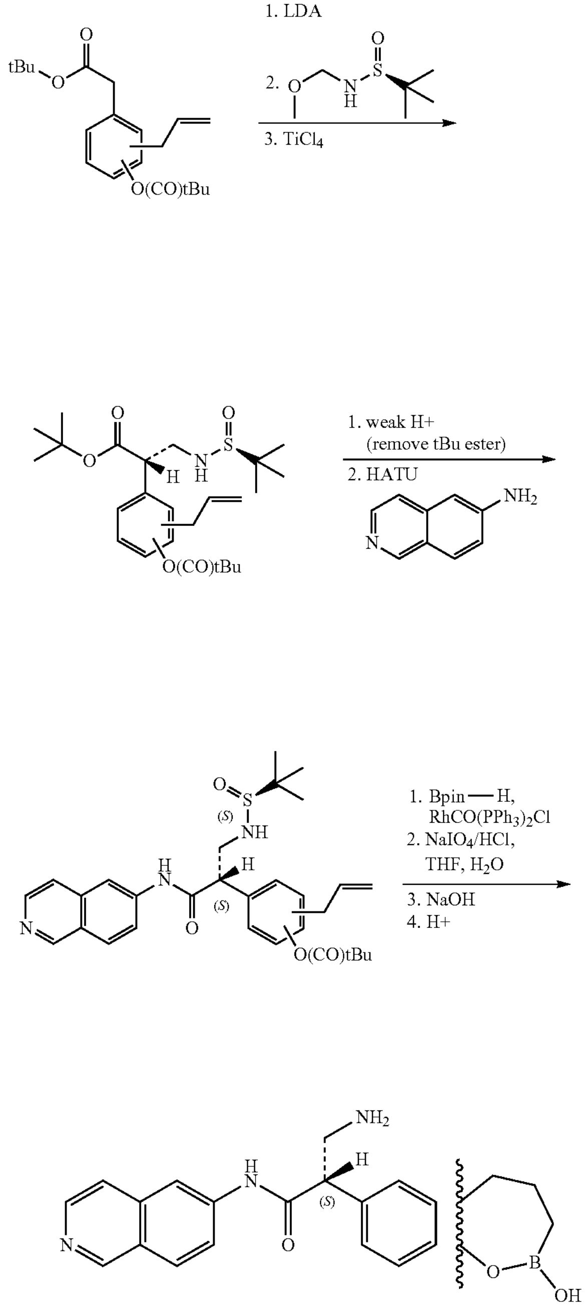
optional chiral auxiliary, e.g.:
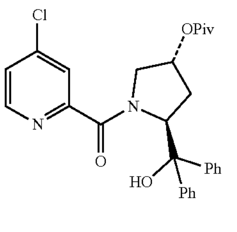
Optionally, the sulfinamide is converted to a more resilient protecting group.
The building blocks for the dioxaborepines and oxazaborepines compounds can be prepared as shown below:
Building Block Preparation
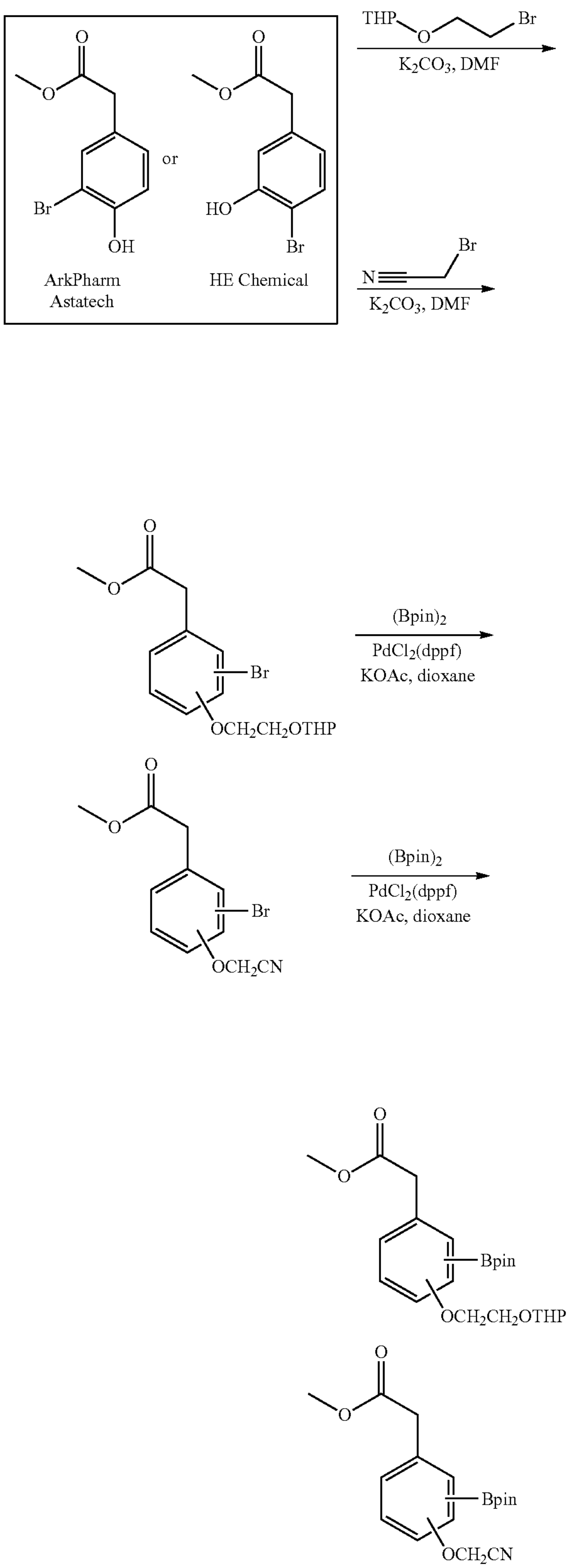

The preparation of the dioxaborepines and oxazaborepines can be prepared as shown below:
Raceminc
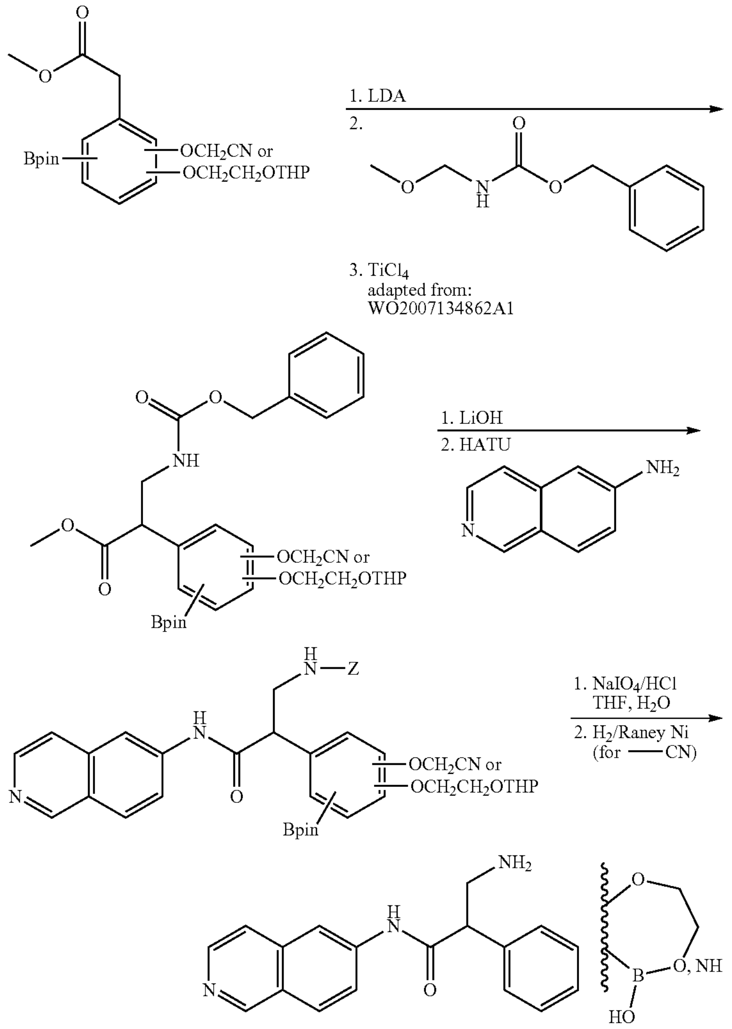
3-B(OH)$OCH_2CH_2O$-4 291
4-B(OH)$OCH_2CH_2O$-3 292
3-B(OH)$NHCH_2CH_2O$-4 293
4-B(OH)$NHCH_2CH_2O$-3 294
Homochiral
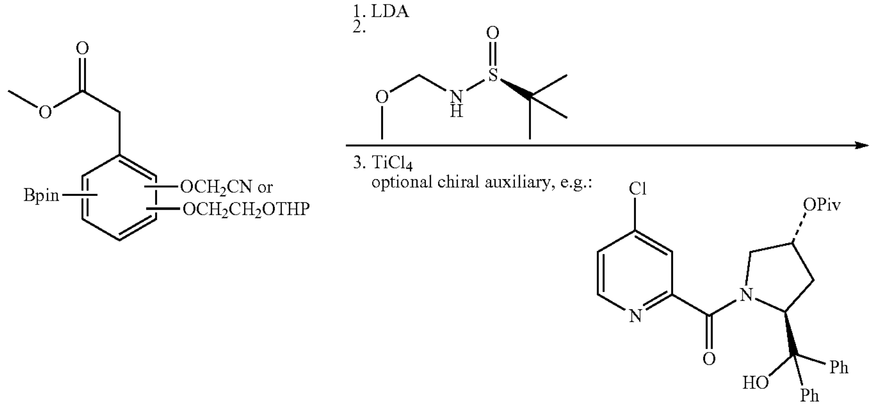

-continued
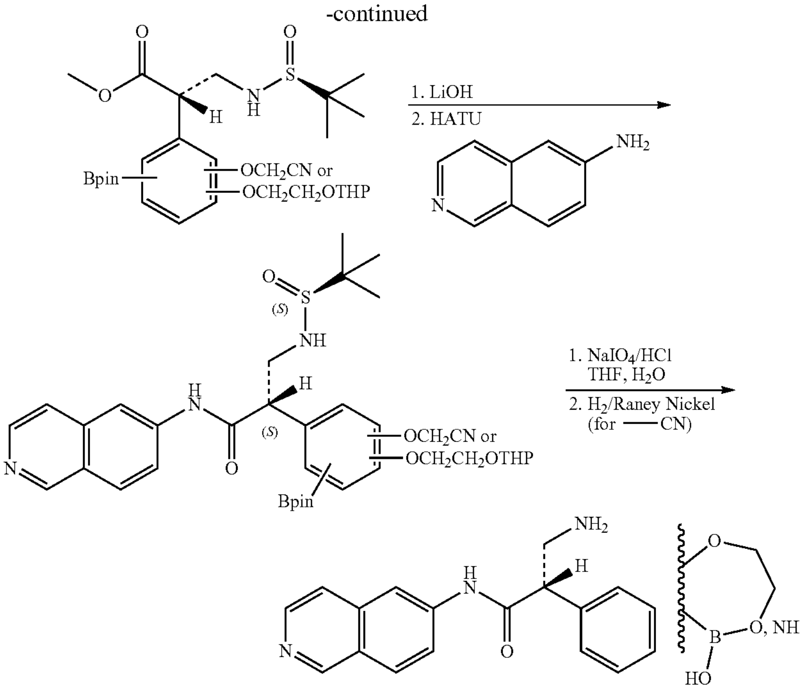
Optionally, the sulfinamide is converted to a more resilient protecting group.
Compounds 222-1, 222-2 and 222-3 are prepared following similar methods.
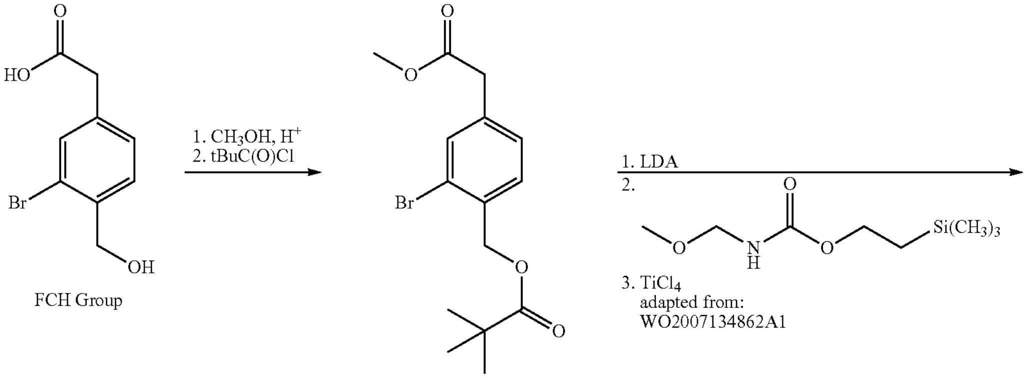
FCH Group
alternately, using Z group, with removal by hydrogenation
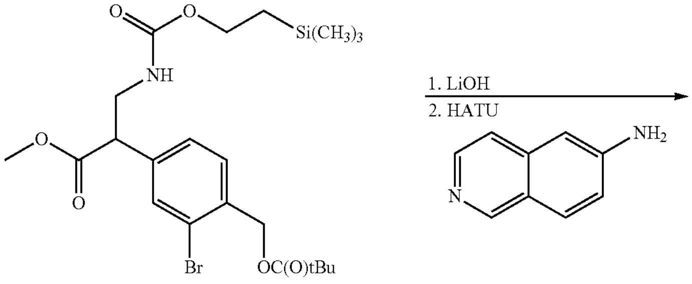

-continued

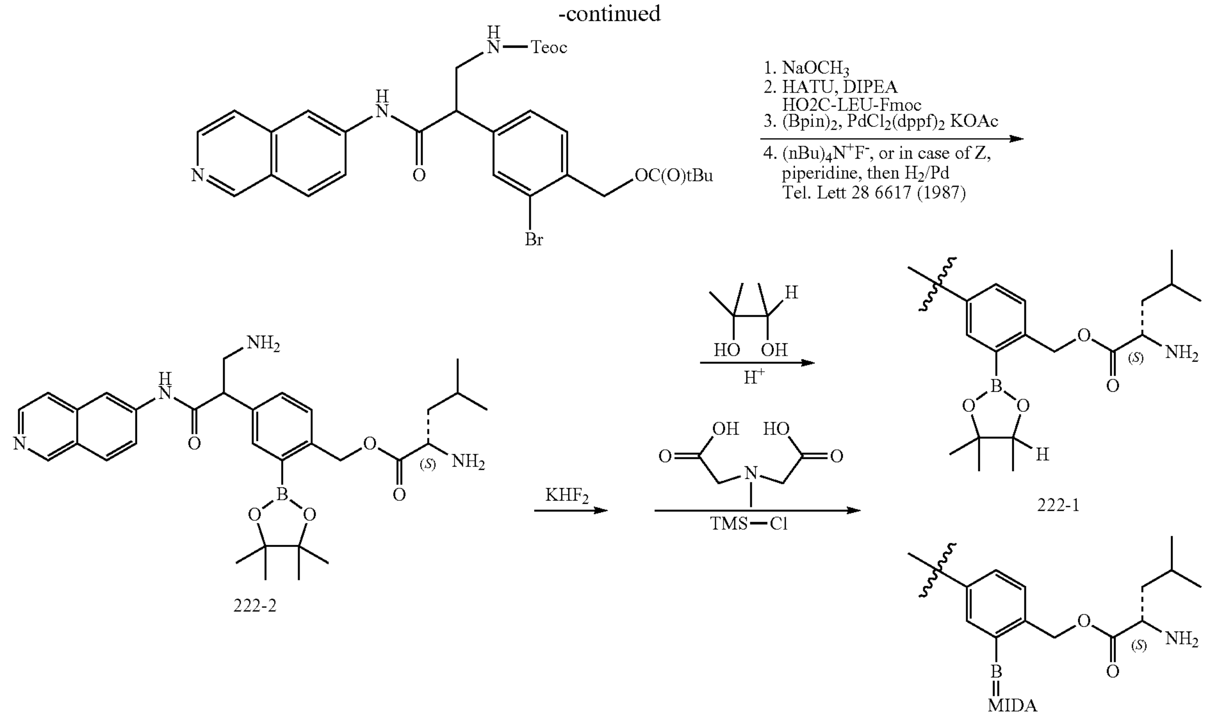

222-2

222-1

222-3

Those skilled in the art would understand that the synthetic methods of preparing the compounds of invention are not limited to those described herein.

Route of Administration

In some embodiments, a compound of present invention is delivered to a target site in the eye of a subject through systemic administration. In other embodiments, the delivered is to a non-ocular target site of a subject through systemic administration. In certain embodiments, and for both ocular or non-ocular targets, a pharmaceutical formulation comprising a compound of invention is optionally administered by multiple administration routes, including, but not limited to, oral and parenteral (e.g., intravenous, subcutaneous, intramuscular, transdermal, intradermal, sublingual, buccal, vaginal, rectal, intrapulmonary, inhalation, insufflation, topically, intranasally, intraperitoneally, intraarterial, intrathoracially, epidurally, intrathecally, intracerebroventricularly, intralesional, and by injection into the joints) routes of administration. Parenteral injections optionally involve bolus injections or continuous infusions.

In some embodiments, a compound of present invention is delivered to a target site in the eye of a subject through local ocular administration. In certain embodiments, a pharmaceutical formulation comprising a compound of invention is optionally administered by multiple ocular administration routes, including, but not limited to, topical, transscleral, intravitreal, intracanalicular, intracameral, suprachoroidal, punctal (tear duct), subretinal, periocular (subconjunctival, subtenon, retrobulbar, peribulbar, posterior juxtascleral).

Excipients

In some embodiments, the pharmaceutical compositions of the present invention can be in unit dosage form. In such form, the composition may be divided into unit doses containing appropriate quantities of the active component. In other embodiments, the unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

The dosage will depend on the route of administration, the severity of the disease, age and weight of the patient and other factors normally considered by the attending physician, when determining the individual regimen and dosage level as the most appropriate for a particular patient.

In some embodiments, the dosage range for systemic administration is from about 0.001 to about 100 mg/kg body weight, from about 0.01 to about 10 mg/kg per body weight, from about 0.05 to about 5 mg/kg body weight per day. Transdermal dosages will be designed to attain similar serum or plasma levels, based upon techniques known to those skilled in the art of pharmacokinetics and transdermal formulations. Plasma levels for systemic administration are expected to be in the range of 0.1 to 1000 ng/mL, from 0.5 to 500 ng/ml and from 1 to 100 ng/mL. While these dosages are based upon a daily administration rate, weekly or monthly accumulated dosages may also be used to calculate the clinical requirements.

In some embodiments, the dose of a compound of invention is about 0.001% by weight to about 10% by weight of the ophthalmic formulation. In some embodiments, the dose of a compound of invention is about 0.001% by weight to about 5% by weight of the ophthalmic formulation.

Dosages may be varied based on the patient being treated, the condition being treated, the severity of the condition being treated, the route of administration, etc. to achieve the desired effect.

The compounds of invention further provide veterinary compositions comprising at least one active ingredient as above defined together with a veterinary carrier therefor. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally, topically to the eye, or by any other desired route.

Compositions of the present invention may comprise a safe and effective amount of a compound described herein as the active pharmaceutical ingredient, and a pharmaceutically-acceptable carrier.

As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of treatment, the nature of concurrent therapy, the particular pharmaceutically-acceptable carrier utilized, and like factors within the knowledge and expertise of the attending physician.

Pharmaceutical compositions for use in accordance with the present Disclosure may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Reminington's Pharmaceutical Sciences", (Meade Publishing Co., Easton, Pa.). Therapeutic compositions must typically be sterile and stable under the conditions of manufacture and storage.

The route by which compounds of present invention can be administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

The pharmaceutical formulations, include, but are not limited to, solutions, suspensions, aqueous liquid dispersions, self-emulsifying dispersions, solid solutions, liposomal dispersions, solid dosage forms, powders, immediate release formulation, controlled release formulations, fast melt formulations, tablets, capsules, pills, delayed release formulations, extended release formulations, pulsatile release formulations, multiparticulate formulations, and mixed immediate and controlled release formulations. Generally speaking, one will desire to administer an amount of a compound of invention that is effective to achieve a plasma level commensurate with the concentrations found to be effective in vivo for a period of time effective to elicit a therapeutic effect.

Carriers for systemic administration typically comprise at least one of the following excipient classes: a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All excipients are optional in the systemic compositions. The carrier can also be an encapsulating material.

Suitable diluents for solid dosage forms include sugars such as glucose, lactose, dextrose, trehalose, cellulose, and sucrose; diols such as propylene glycol; calcium carbonate; calcium phosphates, for example tricalcium phosphate or calcium hydrogen phosphate, sodium carbonate; sugar alcohols, such as glycerin; mannitol; and sorbitol. The amount of ingredient a) in the systemic or topical composition is typically about 50 to about 90%.

Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of ingredient b) in the systemic or topical composition is typically about 5 to about 10%. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used.

Suitable binders for solid dosage forms include polyvinyl pyrrolidone; magnesium aluminum silicate; starches such as corn starch, maize starch, wheat starch, rice starch, potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Suitable disintegrants for solid dosage forms include agar, alginic acid and the sodium salt thereof, effervescent mixtures, croscarmellose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%. Dye stuffs or pigments may be added to the tablets or dragee coatings, for example, for identification or in order to characterize combinations of active compound doses.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic or topical composition is typically about 1 to about 8%.

Ingredient o) is a wetting agent such as lecithin, polysorbate 80, and sodium lauryl sulfate.

Ingredient p) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and Mccutcheon's Volume 1, Emulsifiers & Detergents, 1994, North American Edition, pp. 236-239. The amount of ingredient o) in the systemic or topical composition is typically about 0.1% to about 5%.

The amounts of a compound of invention and the excipients or carriers in the systemic compositions may vary depending on the type of systemic composition prepared, the specific derivative selected as the compound of invention and the excipients and carriers. In general, systemic compositions comprise 0.01% to 50% of a compound of invention and 50% to 99.99% of the excipients and carriers together.

Compositions for parenteral administration typically comprise A) 0.1% to 10% of the compounds of the present invention and B) 90% to 99.9% of a carrier comprising a) a diluent and m) a solvent. In one embodiment, component a) comprises propylene glycol and m) comprises ethanol or ethyl oleate. The carrier and excipients may comprise a single ingredient or a combination of two or more ingredients.

Conventional pharmaceutical excipients are well known to those of skill in the art. In particular, one of skill in the art will recognize that a wide variety of pharmaceutically acceptable excipients can be used in admixture with the compounds of invention, including those listed in the Handbook of Pharmaceutical Excipients, Pharmaceutical Press 4th Ed. (2003), and Remington: The Science and Practice of Pharmacy, Lippincott Williams & Wilkins, 21st ed. (2005).

In other embodiments, the carrier comprises water, ethanol, isopropanol, propylene glycol, benzyl alcohol, glycerin, sorbitol, sucrose, carbopol, maltodextrin, lycasin (maltitol), sodium benzoate, sodium saccharide, lutrol E, F, methyl paraben, propyl paraben, citric acid, capryol 90, Tween 80 (polysorbate 80), Kollidon® CL-M, polyoxyl stearate, hydroxypropyl methyl cellulose, Cremophor® RH 40, Cremophor® EL, sodium carboxymethyl cellulose (CMC), hypromellose acetate succinate, guar gum, xanthan gum, polyethylene glycol, or polyvinyl pyrrolidone, or a mixture thereof.

In some embodiments, the carrier comprises magnesium carbonate, magnesium stearate, talc, lactose, sugar, pectin, dextrin, starch, tragacanth, methyl cellulose, sodium carboxymethyl cellulose, a low-melting wax, cocoa butter, and the like.

In further embodiments, the carrier comprises Soluplus® (polyvinylcaprolactam-polyvinyl acetate-polyethylene glycol graft copolymer.

Pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the Compound of the Disclosure is dissolved or suspended in suitable liquids, such as fatty oils, or liquid paraffin, optionally with stabilizers.

Fatty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In some embodiments, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX®. 355. Other triglycerides are caprylic-capric acid triglycerides such as known and commercially available under the trade name MYRITOL, including the product MYRITOL 813. Further triglycerides of this class are CAPMUL MCT, CAPTEX®. 200, CAPTEX®. 300, CAPTEX®. 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS).

In another embodiment, the carrier comprises Labrafil®, Labrasol®, Gelucire®, Labrafac®, Lauroglycol™ 90, Peceol™, Transcutol®, Compritol®, Geloil®, Geleol™, or Precirol®, or a mixture thereof.

In another embodiment, the carrier comprises Lauroglycol 90, Phosal 53 MCT, polysorbate 80, Crillet 1 HP, Isopropyl myristate, Oleic acid, and/or PEG 400 NF, Acconon® or PL90G.

In another embodiment, the carrier comprises DYNACERIN®, DYNACET®, DYNASAN, GALENOL®, IMWITOR (Glyceryl Monooleate, Stearate, Caprylate), ISOFOL® (long chain alcohols), LIPDXOL® (Macrogol), MASSA ESTARINUM (Hydrogenated Coco-Glycerides), MIGLYOL (Caprylic/Capric Triglyceride), NACOL®, Nafol (alcohols), SOFTIGEN®, SOFTISAN®, WITEPSOL (Hydrogenated Coco-Glycerides), or WITOCAN® (Hydrogenated Coco-Gly), or a mixture thereof.

In some embodiments, the present invention provides a topical composition. In such topical compositions, the carrier comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

In addition to excipient types (a) through (p) listed above, the carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5% to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0% to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0% to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0% to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0% to about 95%.

Ingredient v) is a powder. The amount of ingredient v) in the topical composition is typically 0% to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically about 0% to about 0.5%, particularly, about 0.001% to about 0.1%.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this disclosure include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this disclosure include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0% to about 10%. For ocular applications a pigment is generally not used.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the skin. Component B may further comprise one or more optional components.

The oral solid dosage formulations described herein include particles of a compound of invention in crystalline form, amorphous form, semi-crystalline form, semi-amorphous form, or mixtures thereof.

Compositions may contain from 0.01% to 99% by weight of a compound of invention, e.g., about 0.01%, about 1%, about 2%, about 3%, about 4%, about 5%, about 6%, about 7%, about 8%, about 9%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. The amount in any particular composition will depend upon the effective dose, that is, the dose required to elicit the desired level of gene expression.

In another aspect, the present disclosure provides micronized compounds of invention, and compositions thereof. In one embodiment, the average particle size distribution of the micronized form of a compound of invention is about 20 mm or less, e.g., about 19 mm, about 18 mm, about 17 mm, about 16 mm, about 15 mm, about 14 mm, about 13 mm, about 12 mm, or about 11 mm, or less. In another embodiment, the average particle size distribution is about 10 mm or less, e.g., about 9 mm, about 8 mm, about 7 mm, about 6 mm, or about 5 mm, or less. In another embodiment, the average particle size distribution is about 5 mm or less, e.g., about 4 mm, about 3 mm, about 2 mm, or about 1 mm, or less. In another embodiment, the average particle size distribution is about 1 mm or less, e.g., about 0.9 mm, about 0.8 mm, about 0.7 mm, about 0.6 mm, about 0.5 mm, about 0.4 mm, about 0.3 mm, about 0.2 mm, about 0.1 mm, about 0.09 mm, about 0.08 mm, about 0.07 mm, about 0.06 mm, about 0.05 mm, about 0.04 mm, about 0.03 mm, about 0.02 mm, or about 0.01 mm or less.

Dosage Forms

A dose to treat human patients may range from about 0.1 mg to about 1000 mg of a compound described herein. A typical dose may be about 1 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50% to about 95% of component B), and more particularly, from about 50% to about 75%

The selection of ingredients in the carrier for oral compositions depends on secondary considerations like taste, cost, and shelf stability, which are not critical for the purposes of this disclosure. One skilled in the art would know how to select appropriate ingredients without undue experimentation.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

Oral

The pharmaceutical formulations, include, but are not limited to, solutions, suspensions, aqueous liquid dispersions, self-emulsifying dispersions, solid solutions, liposomal dispersions, solid dosage forms, powders, immediate release formulation, controlled release formulations, fast melt formulations, tablets, capsules, pills, delayed release formulations, extended release formulations, pulsatile release formulations, multiparticulate formulations, and mixed immediate and controlled release formulations. Generally speaking, one will desire to administer an amount of a Compound of the Disclosure that is effective to achieve a concentration level in the target tissue that is commensurate with the concentrations found to be effective in vivo for a period of time effective to elicit a therapeutic effect.

In one embodiment, the pharmaceutical compositions described herein are formulated into any suitable dosage form, including but not limited to, aqueous oral dispersions, solid oral dosage forms, fast melt formulations, lyophilized formulations, tablets, capsules, extended release formulations, and IV formulations.

In one embodiment, a Compound of the Disclosure is formulated into an immediate release form that provides for once-a-day administration.

Tablets

In some embodiments, the solid dosage forms described herein are in the form of a tablet, (including an immediate release tablet, an extended release tablet, a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, multiparticulate dosage forms, pellets, or granules.

In powders, the carrier is a finely divided solid, which is in a mixture with the finely divided active component. In tablets, the active component is mixed with the carrier having the necessary binding properties in suitable proportions and compacted in the shape and size desired.

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes.

Tablets can be compressed, tablet triturates, enteric-coated, sugar-coated, film-coated, or multiple-compressed. Tablets typically comprise a Compound of the Disclosure, and a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc.

Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Soft and Hard Filled Gelatin Capsules

In one embodiment, a capsule is prepared. In some embodiments, the formulations (nonaqueous suspensions and solutions) are placed in a soft gelatin capsule. In other embodiments, the formulations are placed in standard gelatin capsules or non-gelatin capsules such as capsules comprising HPMC.

Solid compositions of a similar type may also be employed in soft and hard filled gelatin capsules. Preferred materials, therefore, include lactose or milk sugar and high molecular weight polyethylene glycols.

Capsules (including implants, time release and sustained release formulations) typically comprise A Compound of the Disclosure, and a carrier comprising one or more a) diluents disclosed above in a capsule comprising gelatin. Granules typically comprise Compound of the Disclosure, and preferably further comprise k) glidants such as silicon dioxide to improve flow characteristics. Implants can be of the biodegradable or the non-biodegradable type. Implants may be prepared using any known biocompatible formulation.

The solid compositions may also be coated by conventional methods, typically with pH or time-dependent coatings, such that the Compound of the Disclosure is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Liquids

Liquid dosage forms for oral administration include, but are not limited to, pharmaceutically acceptable aqueous oral dispersions, emulsions, solutions, and syrups. See, e.g., Singh et ah, Encyclopedia of Pharmaceutical Technology, 2nd Ed., pp. 754-757 (2002).

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Suspensions or elixirs. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise a Compound of the Disclosure and a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Food

In addition to or together with the above modes of administration, Compounds of the Disclosure, or compositions thereof, can be added to food consumed by a subject. In one embodiment, a compound of invention, or a composition thereof, is combined, blended, or admixed with food material to provide a "food product." The term "food material" is used in its broadest possible sense, and includes any form, e.g., solid, emulsion, liquid, of ingestible materials consumed by an animal, e.g., a human. Food products may be formulated so the subject takes in an appropriate quantity of a Compound of the Disclosure, or composition thereof, with its diet. In another embodiment, a Compound of the Disclosure, or composition thereof, is formulated as a premix for addition to food material. In one embodiment, the food product or premix comprises a Compound of the Disclosure, or composition thereof, and one or more lipids.

Parenteral Dosage Form

Formulations for injection are optionally presented in unit dosage form (e.g., in ampoules or vials) or in multi dose containers. In some embodiments, a parenteral formulations is stored in powder form or in a freeze-dried (lyophilized) condition requiring only the addition of the sterile liquid carrier, for example, saline or sterile pyrogen-free water, immediately prior to use.

In some embodiments, a parenteral formulation disclosed herein is formulated as a depot preparation. Such long acting formulations may be administered by implantation (for example subcutaneously or intramuscularly) or by intramuscular injection. Thus, for example, the compounds may be formulated with suitable polymeric or hydrophobic materials (e.g., as an emulsion) or ion exchange resins, or as sparingly soluble derivatives, for example, as a sparingly soluble salt.

Sublingual, Buccal and Nasal.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methyl cellulose. Such compositions may further comprise b) lubricants, e) colorants, f) flavors, g) sweeteners, h) antioxidants, and k) glidants.

Suppository

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Topical Dosage Forms

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, a Compound of the Disclosure, and component B, a carrier. The carrier of the topical composition preferably aids penetration of the compounds into the skin. Component B may further comprise one or more optional components.

The exact amounts of each component in the topical composition depend on various factors. The amount of component A) depends on the binding affinity or inhibition potency (IC50) of the disclosed compound selected. The amount of component A) added to the topical composition is up to 10% of the total, but more typically is from about 0.01% to about 1%.

The topical composition further comprises 1 to 20% of an optional activity enhancer (component C), and a sufficient amount of component B) such that the amounts of components A), B), and C), combined equal 100%. The amount of carrier B) is sufficient to provide a practical quantity of material for administration per unit dose of the compound. Techniques and compositions for making dosage forms useful in the methods of this disclosure are described in the following references: Modern Pharmaceutics, $5^{th}$ Ed., Florence and Siepmann, eds. (2016); Lieberman & Lachman, Pharmaceutical Dosage Forms: Tablets, $3^{rd}$ Ed., (1989); and Allen, L., Ansel's Pharmaceutical Dosage Forms and Drug Delivery Systems, $10^{th}$ Ed., (2013).

The carrier, Component B), may comprise a single component or a combination of two or more components. Typical carriers for component B) in the topical compositions include water, alcohols, aloe vera gel, allantoin, glycerin, vitamin A and E oils, mineral oil, propylene glycol, PPG-2 myristyl propionate, dimethyl isosorbide, combinations thereof, and the like. Preferred carriers include water.

The carrier of the topical composition may further comprise one or more ingredients selected from the group consisting of (q) emollients, (r) propellants, (s) solvents, (t) humectants, (u) thickeners, (v) powders, and (w) fragrances.

Ingredient (q) is an emollient. The amount of ingredient (q) in the topical composition is typically 5 to 95%. Suitable emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl 1 palmitate, polydimethylsiloxane, di-n-butyl sebacate, iso-propyl myristate, iso-propyl palmitate, iso-propyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Preferred emollients include stearyl alcohol and polydimethylsiloxane.

Ingredient (r) is a propellant. The amount of ingredient (r) in the topical composition is typically 5 to 95%. Suitable propellants include propane, butane, iso-butane, dimethyl ether, carbon dioxide, nitrous oxide, and combinations thereof. However, in a topical eyedrop no propellant is used.

Ingredient(s) is a solvent. The amount of ingredient(s) in the topical composition is typically 5 to 95%. Suitable solvents include water.

Ingredient (t) is a humectant. The amount of ingredient (t) in the topical composition is typically 5 to 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient (u) is a thickener. The amount of ingredient (u) in the topical composition is typically 0 to 95%.

Ingredient (v) is a powder. The amount of ingredient (v) in the topical composition is typically 0 to 95%. Suitable powders include chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient (w) is a fragrance. The amount of ingredient (w) in the topical composition is typically 0.001 to 0.5%, preferably 0.001 to 0.1%.

Examples of Component C), the optional activity enhancer, include 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, iso-propyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-2-hyroxyoctanoic acid, dimethyl sulphoxide, N,N-dimethyl acetamide, N,N-dimethyl formamide, 2 pyrrolidone, 1-methyl-2-pyrrolidone, 5-methyl-2-pyrrolidone, 1,5-dimethyl-2-pyrrolidone, 1-ethyl-2 pyrrolidone, phosphine oxides, sugar esters, tetrahydrofurfural alcohol, urea, diethyl-m-toluamide, 1-dodecylazacyloheptan-2-one, and combinations thereof. Component C), the optional activity enhancer, is typically 1 to 5%.

Container-Closures/Kits for Oral, Parenteral, and Topical Dermal Administration

In some embodiments, the present invention provides an article of manufacture, or "kit", containing materials useful for the treatment of the diseases and disorders described above is provided. In one embodiment, the kit comprises a container comprising a compound of the disclosure, or a stereoisomer, tautomer, or pharmaceutically acceptable salt thereof. The kit may further comprise a label or a package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of the disclosure. Alternatively, or additionally, the article of manufacture may further comprise a second container comprising a pharmaceutically diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of the disclosure, such as tablets or capsules. Such a kit can include a number of unit dosages. An example of such a kit is a "blister pack".

Blister packs are well known in the packaging industry and are widely used for packaging pharmaceutical unit dosage forms.

According to one embodiment, a kit may comprise (a) a first container with a compound of the disclosure contained therein; and optionally (b) a second container with a second pharmaceutical formulation contained therein, wherein the second pharmaceutical formulation comprises a second compound with anti-glaucoma activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Ocular Formulation

Preferably, the pharmaceutical compositions according to the present invention is formulated as solutions, suspensions and other dosage forms for ocular topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, emulsion, ointment, cream, lotion, gel, colloidal dispersion, spray, insert, or other types of solid or semi-solid compositions or combinations thereof.

Ophthalmic formulations described herein deliver kinase inhibitors to the ophthalmic tissues of a mammal. In certain instances, localized ocular administration of a kinase inhibitor reduces or eliminates side-effects associated with systemic administration of kinase inhibitors.

In some embodiments, described is an ophthalmic formulation comprising a compound described herein and at least one suitable pharmaceutically acceptable excipient, wherein the formulation is in a form suitable for administration to the eye of a mammal. In some embodiments, a compound of the present invention is provided in an amount effective for the treatment of an ophthalmic disease or condition in a mammal. In some embodiments, the ophthalmic disease or condition is a disease or condition described herein. In some embodiments, the ophthalmic formulation is in the form of a solution, suspension, viscous or semi-viscous gel, emulsion, ointment, cream, lotion, gel, colloidal dispersion, spray, insert, or other types of solid or semi-solid compositions or combinations thereof.

In particular embodiments, formulations of the present invention comprise a compound described herein and one or more excipients selected from: a mucoadhesive, a tear substitute, pH adjusting agents, a viscosity enhancing agent, a demulcent, a tonicity enhancer, a solubilizer, a wetting agent or surfactant, an emulsifier, a penetration enhancer, a preservative, a sequestering agent, co-solvents, and a filler. The amount and type of excipient added is in accordance with the particular requirements of the formulation and is generally in the range of from about 0.0001% to 90% by weight.

Compositions may contain from 0.01% to 99% by weight of a compound of invention, e.g., about 0.01%, about 0.02%, about 0.05%, about 0.1%, about 0.2%, about 0.3%, about 0.4%, about 0.5%, about 0.75%, about 1%, about 2%, about 3%, about 4%, about 5%, about 6%, about 7%, about 8%, about 9%, about 10%, about 15%, or about 20%.

In some embodiments, the aqueous solutions, suspensions, or emulsions described herein remain in a homogenous state, as defined in The USP Pharmacists' Pharmacopeia (2005 edition, chapter 905), for at least 4 hours. In one embodiment, an aqueous suspension is resuspended into a homogenous suspension by physical agitation lasting less than 1 minute (e.g., by shaking a eye-drop dispenser). In still another embodiment, no agitation is necessary to maintain a homogeneous aqueous dispersion.

In some embodiments, the ophthalmic formulations described herein are stable (e.g., with respect to pH, active ingredient) over a period of any of at least about 1 day, at least about 2 days, at least about 3 days, at least about 4 days, at least about 5 days, at least about 6 days, at least about 1 week, at least about 2 weeks, at least about 4 weeks, at least about 6 weeks, at least about 8 weeks, at least about 4 months, at least about 5 months, or at least about 6 months. In other embodiments, the formulations described herein are stable over a period of at least about 1 week to about 1 month, or at least about 1 month to about 6 months.

In certain embodiments, the ophthalmic formulations described herein are designed for minimal ophthalmic toxicity, irritation and/or allergic challenge to ocular tissues and include, for example, low amounts of excipients such as surfactants, preservatives and/or cosolvents.

Ocular Excipients.

In some embodiments, formulations of the Compound of the Disclosure comprise one or more pharmaceutically acceptable excipients. The term excipient as used herein broadly refers to a biologically inactive substance used in combination with the active agents of the formulation. An excipient can be used, for example, as a mucoadhesive, a tear substitute, pH adjusting agents, a viscosity enhancing agent, a demulcent, a tonicity enhancer, a solubilizer, a wetting agent or surfactant, an emulsifier, a penetration enhancer, a preservative, a sequestering agent, co-solvents, and a filler. Preferably, at least one excipient is chosen to provide one or more beneficial physical properties to the formulation, such as increased stability and/or solubility of the active agent(s). A "pharmaceutically acceptable" excipient is one that has been approved by a state or federal regulatory agency for use in animals, and preferably for use in humans, or is listed in the U.S. Pharmacopia, the European Pharmacopia or another generally recognized pharmacopia for use in animals, and preferably for use in humans.

Examples of excipients that may be used in the formulations of the present disclosure include water, mixtures of water and water-miscible solvents, such as C1- to C7-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100,000 times the concentration of the active ingredient.

Further examples of excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN®, PLURONICS®, or a polyethylene glycol (PEG) designated 200, 300, 400, or 600; a Carbowax designated 1000, 1500, 4000, 6000, and 10000;

carbohydrates such as glucose, sucrose, mannose, maltose, trehalose, and dextrins, including cyclodextrins; polyols such as mannitol and sorbitol; chelating agents such as EDTA; and salt-forming counter-ions such as sodium. The amount and type of excipient added is in accordance with the particular requirements and is generally in the range of from approximately 0.0001 to approximately 90% by weight.

Mucoadhesives

In a particular embodiment, the excipient is a polymeric, mucoadhesive vehicle. Examples of mucoadhesive vehicles suitable for use in the methods or formulations of compounds of the disclosure include but are not limited to aqueous polymeric suspensions comprising one or more polymeric suspending agents including without limitation dextrans, polyethylene glycol, polyvinylpyrolidone, poly (acrylic acid) (PAA), polysaccharide gels, Gelrite®, cellulosic polymers, methylcellulose (MC), and carboxy-containing polymer systems. Other non-limiting examples of mucoadhesive polymers include carboxymethylcellulose, carbomer (acrylic acid polymer), poly(methylmethacrylate), polyacrylamide, acrylic acid/butyl acrylate copolymer, and sodium alginate. In a particular embodiment, the polymeric suspending agent comprises a crosslinked carboxy-containing polymer (e.g., polycarbophil). In another particular embodiment, the polymeric suspending agent comprises polyethylene glycol (PEG). Examples of cross-linked carboxy-containing polymer systems suitable for use in the topical stable ophthalmic formulations of the Compound of the Disclosure include but are not limited to Noveon AA-1, Carbopol®, and/or DuraSite® (InSite Vision).

Tear Substitutes

The term "tear substitute" refers to molecules or compositions which lubricate, "wet," approximate the consistency of endogenous tears, aid in natural tear build-up, or otherwise provide temporary relief of dry eye signs or symptoms and conditions upon ocular administration. A variety of tear substitutes are known in the art and include, but are not limited to: monomeric polyols, such as, glycerol, propylene glycol, and ethylene glycol; polymeric polyols such as polyethylene glycol; cellulose ethers such as methylcellulose ethylcellulose; cellulose esters such hydroxypropylmethyl cellulose, carboxymethyl cellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. Many such tear substitutes are commercially available, which include, but are not limited to cellulose esters such as Bion Tears®, Celluvisc®, Genteal®, OccuCoat®, Refresh®, Systane®, Teargen II®, Tears Naturale®, Tears Natural II®, Tears Naturale Free®, and TheraTears®; and polyvinyl alcohols such as Akwa Tears®, HypoTears®, Moisture Eyes®, Murine Lubricating®, and Visine Tears®, Soothe®. Tear substitutes may also be comprised of paraffins, such as the commercially available Lacri-Lube® ointments. Other commercially available ointments that are used as tear substitutes include Lubrifresh PM®, Moisture Eyes PM® and Refresh PM®.

In some embodiments, the tear substitute comprises hydroxypropylmethyl cellulose (Hypromellose or HPMC). According to some embodiments, the concentration of HPMC ranges from about 0.1% to about 2% w/v, or any specific value within said range. According to some embodiments, the concentration of HPMC ranges from about 0.5% to about 1.5% w/v, or any specific value within said range. According to some embodiments, the concentration of HPMC ranges from about 0.1% to about 1% w/v, or any specific value within said range. According to some embodiments, the concentration of HPMC ranges from about 0.6% to about 1% w/v, or any specific value within said range. In a preferred embodiments, the concentration of HPMC ranges from about 0.1% to about 1.0% w/v, or any specific value within said range (i.e., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

For example, without limitation, a tear substitute which comprises hydroxypropyl methyl cellulose is GenTeal® lubricating eye drops. GenTeal® (CibaVision-Novartis) is a sterile lubricant eye drop containing hydroxypropylmethyl cellulose 3 mg/g and preserved with sodium perborate. Other examples of an HPMC-based tear are provided.

In another preferred embodiment, the tear substitute comprises carboxymethyl cellulose sodium. For example, without limitation, the tear substitute which comprises carboxymethyl cellulose sodium is Refresh® Tears. Refresh® Tears is a lubricating formulation similar to normal tears, containing a, mild non-sensitizing preservative, stabilised oxychloro complex (Purite®)), that ultimately changes into components of natural tears when used.

In a preferred embodiment, the tear substitute, or one or more components thereof, is an aqueous solution having a viscosity in a range which optimizes efficacy of supporting the tear film while minimizing blurring, lid caking, etc. Preferably, the viscosity of the tear substitute, or one or more components thereof, ranges from 1-150 centipoise (cpi), e.g., 5-150 cpi, 5-130 cpi, 30-130 cpi, 50-120 cpi, 60-115 cpi (or any specific value within said ranges). In a particular embodiment, the viscosity of the tear substitute, or one or more components thereof, is about 70-90 cpi, or any specific value within said range (for example without limitation, 85 cpi).

Viscosity may be measured at a temperature of 20° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec). Alternatively, viscosity may be measured at 25° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec).

In some embodiments, the tear substitute, or one or more components thereof is buffered to a pH 5.0 to 9.0, preferably pH 5.5 to 7.5, more preferably pH 6.0 to 7.0 (or any specific value within said ranges), with a suitable salt (e.g., phosphate salts). In some embodiments, the tear substitute further comprises one or more ingredients, including without limitation, glycerol, propyleneglycerol, glycine, sodium borate, magnesium chloride, and zinc chloride.

Salts, Buffers, and Preservatives

The formulations of the present disclosure may also contain pharmaceutically acceptable salts, buffering agents, or preservatives.

Salts

Examples of such salts include those prepared from the following acids: hydrochloric, hydrobromic, sulfuric, nitric, phosphoric, maleic, acetic, salicylic, citric, boric, formic, malonic, succinic, and the like. Such salts can also be prepared as alkaline metal or alkaline earth salts, such as sodium, potassium or calcium salts, including sodium chloride and potassium chloride. Other salts are mono-, di- and trisodium phosphate, tris(hydroxymethyl)aminomethane hydrochloride, and combinations thereof.

Buffers

For the adjustment of the pH, preferably to a physiological pH, buffers may especially be useful. The pH of the present solutions should be maintained within the range of 4.0 to 8.0, more preferably about 5.5 to 7.5, more preferably about 6.0 to 7.0. Suitable buffers may be added, such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride, potassium citrate, citric acid, TRIS, 2-(N-morpholino) ethanesulfonic acid (MES). Additional buffers are various mixed phosphate buffers (including combinations of Na2HPO4, NaH2PO4 and KH2PO4) and mixtures thereof. Borate buffers are preferred. Generally, buffers will be used in amounts ranging from about 0.05 to 2.5 percent by weight, and preferably, from 0.1 to 1.5 percent.

Preservatives

In certain embodiments, the topical formulations additionally comprise a preservative. A preservative may typically be selected from a quaternary ammonium compound such as benzalkonium chloride, benzoxonium chloride or the like. Benzalkonium chloride is better described as: N-benzyl-N—(C8-C18 alkyl)-N,N-dimethylammonium chloride, cetyltrimethylammonium bromide, and cetylpyridinium chloride. Further examples of preservatives include antioxidants such as vitamin A, vitamin E, vitamin C, retinyl palmitate, and selenium; the amino acids cysteine and methionine; citric acid and sodium citrate; sodium thiosulfate and sodium metabisulfite; and synthetic preservatives such as thimerosal, and alkyl parabens, including for example, methyl paraben and propyl paraben. Other preservatives include benzoic acid, p-hydroxybenzoates, octadecyldimethylbenzyl ammonium chloride, hexamethonium chloride, benzethonium chloride, phenol, catechol, resorcinol, cyclohexanol, 3-pentanol, m-cresol, phenylmercuric nitrate, phenylmercuric acetate or phenylmercuric borate, sodium perborate, sodium chlorite, alcohols, such as chlorobutanol, butyl or benzyl alcohol or phenyl ethanol, guanidine derivatives, such as chlorohexidine or polyhexamethylene biguanide, sodium perborate, Polyquad®, Germal®II, sorbic acid and stabilized oxychloro complexes (e.g., Purite®), metal chelating agents, thiol containing compounds and other general stabilizing agents. Preferred preservatives are quaternary ammonium compounds, in particular benzalkonium chloride or its derivative such as Polyquad (see U.S. Pat. No. 4,407,791), alkyl-mercury salts, parabens and stabilized oxychloro complexes (e.g., Purite®). Where appropriate, a sufficient amount of preservative is added to the ophthalmic composition to ensure protection against secondary contaminations during use caused by bacteria and fungi.

In particular embodiments, the formulations of the Compound of the Disclosure comprise a preservative selected from among the following: benzalkonium chloride, 0.001% to 0.05%; benzethonium chloride, up to 0.02%; sorbic acid, 0.01% to 0.5%; polyhexamethylene biguanide, 0.1 ppm to 300 ppm; polyquaternium-1 (Omamer M)-0.1 ppm to 200 ppm; hypochlorite, perchlorite or chlorite compounds, 500 ppm or less, preferably between 10 and 200 ppm); stabilized hydrogen peroxide solutions, a hydrogen peroxide source resulting in a weight % hydrogen peroxide of 0.0001 to 0.1% along with a suitable stabilizer; alkyl esters of p-hydroxybenzoic acid and mixtures thereof, preferably methyl paraben and propyl paraben, at 0.01% to 0.5%; chlorhexidine, 0.005% to 0.01%; chlorobutanol, up to 0.5%; and stabilized oxychloro complex (Purite®) 0.001% to 0.5%.

In another embodiment, the topical formulations of the Compound of the Disclosure do not include a preservative. Such formulations would be useful for patients who wear contact lenses, or those who use several topical ophthalmic drops and/or those with an already compromised ocular surface (e.g. dry eye) wherein limiting exposure to a preservative may be more desirable.

Viscosity Enhancing Agents and Demulcents

In certain embodiments, viscosity enhancing agents may be added to formulations of the Compound of the Disclosure. Examples of such agents include polysaccharides, such as hyaluronic acid and its salts, chondroitin sulfate and its salts, dextrans, various polymers of the cellulose family, vinyl polymers, and acrylic acid polymers.

In some embodiments, a topical formulation for administration to an eye comprises an ophthalmically acceptable demulcent or viscosity enhancer (e.g., a thermo-sensitive or pH sensitive gelling polymer). In certain instances, a viscosity enhancer increases the time a formulation disclosed herein remains in an eye. In certain instances, increasing the time a formulation disclosed herein remains in the eye allows for greater drug absorption and effect. In certain embodiments, formulations of the Compound of the Disclosure comprise ophthalmic demulcents and/or viscosity enhancing polymers selected from one or more of the following: cellulose derivatives such as carboxymethycellulose (0.01 to 5%) hydroxyethylcellulose (0.01% to 5%), hydroxypropyl methylcellulose or hypromellose (0.01% to 5%), and methylcelluose (0.02% to 5%); dextran 40/70 (0.01% to 1%); gelatin (0.01% to 0.1%); polyols such as glycerin (0.01% to 5%), polyethylene glycol 300 (0.02% to 5%), polyethylene glycol 400 (0.02% to 5%), polysorbate 80 (0.02% to 3%), propylene glycol (0.02% to 3%), polyvinyl alcohol (0.02% to 5%), and povidone (0.02% to 3%); hyaluronic acid (0.01% to 2%); and chondroitin sulfate (0.01% to 2%).

Viscosity of the stable ophthalmic Compound of the Disclosure formulations of the invention may be measured according to standard methods known in the art, such as use of a viscometer or rheometer. One of ordinary skill in the art will recognize that factors such as temperature and shear rate may effect viscosity measurement. In a particular embodiment, viscosity of the is measured at 20° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec). In another embodiment, viscosity of the ophthalmic formulations of the invention is measured at 25° C.+/−1° C. using a Brookfield Cone and Plate Viscometer Model VDV-III Ultra+ with a CP40 or equivalent Spindle with a shear rate of approximately 22.50+/−approximately 10 (1/sec), or a Brookfield Viscometer Model LVDV-E with a SC4-18 or equivalent Spindle with a shear rate of approximately 26+/−approximately 10 (1/sec).

According to some embodiments, the ophthalmic formulations of the present invention has a viscosity that ranges from about 30 to about 150 centipoise (cpi), preferably about 50 to about 120 cpi, even more preferably about 60 to about 115 cpi (or any specific value within said ranges). According to preferred embodiments, the ophthalmic formulations of the present invention has a viscosity that ranges from about 60 to about 80 cpi, or any specific value within said range (i.e., about 60 cpi, about 61 cpi, about 62 cpi, about 63 cpi, about 64 cpi, about 65 cpi, about 66 cpi, about 67 cpi, about 68 cpi, about 69 cpi, about 70 cpi, about 71 cpi, about 72 cpi, about 73 cpi, about 74 cpi, about 75 cpi, about 76 cpi, about 77 cpi, about 78 cpi, about 79 cpi, or about 80 cpi).

Tonicity Enhancers

Tonicity is adjusted if needed typically by tonicity enhancing agents. Such agents may, for example be of ionic and/or non-ionic type. Examples of ionic tonicity enhancers are alkali metal or earth metal halides, such as, for example, $CaCl_2$, KBr, KCl, LiCl, NaI, NaBr or NaCl, $Na_2SO_4$, sodium thiosulfate, sodium bisulfite, ammonium sulfate or boric acid. Non-ionic tonicity enhancing agents are, for example, urea, glycerol, sorbitol, mannitol, propylene glycol, or dextrose. The aqueous solutions of the present invention are typically adjusted with tonicity agents to approximate the osmotic pressure of normal lachrymal fluids which is equivalent to a 0.9% solution of sodium chloride or a 2.5% solution of glycerol. An osmolality of about 225 to 400 mOsm/kg is preferred, more preferably 280 to 320 mOsm.

Solubilizing Agents

The topical formulation may additionally require the presence of a solubilizer, in particular if one or more of the ingredients tends to form a suspension or an emulsion. Suitable solubilizers include, for example, tyloxapol, fatty acid glycerol polyethylene glycol esters, fatty acid polyethylene glycol esters, polyethylene glycols, glycerol ethers, polysorbate 20, polysorbate 80 or mixtures of those compounds. In a preferred embodiment, the solubilizer is a reaction product of castor oil and ethylene oxide, for example the commercial products Cremophor EL® or Cremophor RH40®. Reaction products of castor oil and ethylene oxide have proved to be particularly good solubilizers that are tolerated extremely well by the eye. In another embodiment, the solubilizer is tyloxapol or a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient.

In some embodiments, a topical formulation for administration to an eye disclosed herein further comprises a solubilizing agent, for example, a glucan sulfate and/or a cyclodextrin. Glucan sulfates which can be used include, but are not limited to, dextran sulfate, cyclodextrin sulfate and □-1,3-glucan sulfate, both natural and derivatives thereof. Cyclodextrin derivatives that are used as a solubilizing agent include, but are not limited to, □-cyclodextrin, □-cyclodextrin, □-cyclodextrin, hydroxyethyl □-cyclodextrin, hydroxypropyl □-cyclodextrin, hydroxypropyl □-cyclodextrin, sulfated □-cyclodextrin, sulfated □-cyclodextrin, sulfobutyl ether □-cyclodextrin. The formulations described herein comprise from about 0.5 to 20% cyclodextrins. In some embodiments, the formulations described herein comprise from about 1 to about 10% cyclodextrins.

Surfactants

In some embodiments, the present invention provides an ophthalmic formulation for delivery to the eyes of a mammal that comprises one or more surfactants. "Surfactants" are wetting agents that lower the surface tension of a liquid. Examples of surfactants for ophthalmic formulations include and are not limited to oils derived from natural sources, such as, corn oil, olive oil, cotton seed oil and sunflower seed oil; sorbitan esters, such as Sorbitan trioleate available under the trade name Span 85, Sorbitan monooleate available under the trade name Span 80, Sorbitan monolaurate available under the trade name Span 20, Polyoxyethylene (20) sorbitan monolaurate available under the trade name Tween 20, Polyoxyethylene (20) sorbitan monooleate available under the trade name Tween 80; lecithins derived from natural sources such as those available under the trade name Epikuron particularly Epikuron 200. Oleyl polyoxyethylene (2) ether available under the trade name Brij 92, Stearyl polyoxyethylene (2) available under the trade name Brij 72, Lauryl polyoxyethylene (4) ether available under the trade name Brij 30, Oleyl polyoxyethylene (2) ether available under the trade name Genapol 0-020, Block copolymers of oxyethylene and oxypropylene available under the trade name Synperonic, Oleic acid, Synthetic lecithin, Diethylene glycol dioleate, Tetrahydrofurfuryl oleate, Ethyl oleate, Isopropyl myristate, Glyceryl trioleate, Glyceryl monolaurate, Glyceryl mono-oleate, Glyceryl monostearate, Glyceryl monoricinoleate, Cetyl alcohol, stearyl alcohol, polyethylene glycol 400, cetyl pyridinium chloride, and semifluorinated alkanes.

Emulsifiers

In some embodiments, a topical formulation for administration to an eye disclosed herein further comprises an emulsifier such as ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Penetration Enhancers

In some embodiments, a topical formulation for administration to an eye disclosed herein further comprises a penetration enhancer such as Gelucire 44/14, cyclodextrins, BAC, EDTA, surfactants, heteroglycosides, bile salts, polycarbophil-cysteine conjugates and boric acid.

Advanced Formulations

In some instances an ophthalmic formulation described herein comprises nanoparticles of a Compound of the Disclosure. In some instances ophthalmic formulations described herein comprise crystalline particles. In some embodiments, ophthalmic formulations described herein comprise amorphous particles. In some embodiments, ophthalmic formulations described herein comprise nano-structured formulations. Advanced formulations with structural features on the nano-scale may increase ocular bioavailability, modulate solution viscosity, and improve corneal penetration. Advanced ophthalmic formulations of the Compounds of the Disclosure comprise nanoparticles, nanoemulsion, nanomicelles, core-shell nanoparticles, nanostructured lipid carriers, surface-modified nanoparticles, chitosan-coated nanoparticle, nanovesicular carriers (liposomes & niosomes), cationic, anionic, and neutral liposomes, light-sensitive gold nanoparticle-loaded liposomes, lipid nanoparticles (solid lipid nanoparticles, nanostructured lipid carriers), chitosan nanoparticles, polycarboxylic acid nanoparticles, PLA nanoparticles, PLG nanoparticles, $(Ca)_3(PO_4)_2$ nanoparticles, Eudragit nanoparticles, PLGA-PLA microspheres and nanospheres, core-shell nanoassemblies, nanoparticle compact films, polymeric nanoparticles, nanoparticles encapsulated in a polymer (nanocapsule), nanoparticles dispersed in the polymer matrix (nanosphere), discomes, cubosomes, hydrogels, dendrimers, poly(amidoamine) dendrimers, micro-encapsulating particles, encapsulating microspheres, microemulsions, microparticles, (optionally with concomitant administration of spreading enzymes such as hyaluronidase and collagenase), polymeric nanogels and hydrogels, light-sensitive hydrogels, in situ gelling systems, fibrin sealants (e.g. form a gel-based semisolid structure, which sustains drug release), in situ gelling formulations, cationic emulsions, non-mesoporous biodegradable silica matrix technology, biodegradable or non-biodegradable PRINT particles (Particle Replication in Non-wetting Templates), mucus penetrating particles (MPP, Kala Pharmaceuticals), and synthetic vitreous humor.

Ocular Dosage Forms

In one embodiment of the disclosure, the compounds of the present invention are topically administered. Topical compositions that can be applied locally to the eye may be in any form known in the art, non-limiting examples of which include solids, liquid drops, gellable drops, sprays, ointments, or a sustained or non-sustained release unit placed in the conjunctival cul-du-sac of the eye or another appropriate location. In some embodiments, the ophthalmic formulation is administered via implantation, insertion, injection, spraying, washing, or combinations thereof.

Solutions

Described herein is an ophthalmic formulation comprising a Compound of the Disclosure wherein the ophthalmic formulation is in the form of a solution. In certain instances, delivery of a Compound of the Disclosure is achieved by administration of an ocular solution formulation as drops to the eye of a mammal. In certain instances, the solution is administered as an eye wash to the eyes of a mammal.

In certain instances, the solution comprises a Compound of the Disclosure or a salt thereof dissolved in sterile water and/or 0.9% sodium chloride solution. Small quantities of an alcohol or glycerin are optionally used to solubilize the Compound of the Disclosure compound. The quantities of alcohol and/or glycerin are kept as low as possible to minimize irritation to the eye upon administration. Any irritation to ocular tissues results in excessive tearing and washing away of the administered formulation.

In some instances, the solutions comprise a pH modifying agent to solubilize the Compound of the Disclosure. In certain instances, a pH-modifying agent maintains a solution pH of 5-8 and solubilizes the Compound of the Disclosure (e.g., an acid salt of a Compound of the Disclosure). In certain instances, the solution further comprises a preservative and/or a stabilizer. In certain instances, sterile solutions are obtained in the absence of a preservative and/or a stabilizer using filtration systems (e.g., 0.2μ filtration systems) and/or heat treatment. The preservative and/or stabilizer is present in an amount from about 0.001% to about 5% of the total weight of the formulation. In some embodiments, the ocular solutions described herein further comprise tonicity agents. Examples of tonicity agents that are compatible with the formulations described herein include and are not limited to sodium borate, boric acid, sodium chloride, potassium chloride, mannitol, dextrose, glycerin, propylene glycol or mixtures thereof. The solutions are designed for isotonicity with physiological fluids (e.g., osmolality of the solution compositions is about 300 mOsm).

In some embodiments, a topical formulation for administration to an eye disclosed herein is administered or delivered to the posterior segments of an eye (e.g., to the retina, choroid, vitreous and optic nerve). In some embodiments, an ophthalmic formulation described herein is applied to the surface of the eye or in the lacrimal sac or under the eyelid.

Suspensions and Emulsions

Described herein, in certain embodiments, is an ophthalmic formulation comprising a Compound of the Disclosure wherein the ophthalmic formulation is in the form of an emulsion or a suspension. The ophthalmic formulation that is in the form of an emulsion a suspension is administered topically as eye drops in a mammal. The formulations further comprise pH-modifying agents, preservatives and/or stabilizers. In certain instances, sterile formulations are obtained in the absence of a preservative and/or a stabilizer using filtration systems (e.g., 0.2μ filtration systems) and/or heat treatment. In certain embodiments, the suspensions or emulsions comprise a surfactant to enhance solubility of a Compound of the Disclosure. In certain embodiments, the surfactant concentration is kept as low as possible to minimize foaming that might interfere with proper administration. In certain instances, the liquid phase (e.g., a cosolvent) of a suspension or emulsion has a density similar to the density of the suspensoid. In certain instances, the liquid phase is a cosolvent that partially dissolves or does not dissolve the Compound of the Disclosure, thus minimizing particle size growth resulting from the dissolved compound crystallizing out onto crystals present in the suspenoid.

In some embodiments the suspensions or emulsions are aqueous suspensions or emulsions. The aqueous suspensions optionally comprise suspending agents, such as for example, sodium carboxymethylcellulose, methylcellulose, hydroxypropyl-methylcellulose, sodium alginate, polyvinylpyrrolidone, gum tragacanth, gum acacia or the like or mixtures thereof.

In some embodiments, the suspensions or emulsions are oil-in-water suspensions or emulsions. The oily phase is a vegetable oil, (e.g., olive oil, castor oil, soy oil, sesame oil, coconut oil) or a mineral oil (e.g., liquid paraffin). Such suspensions or emulsions optionally contain a thickening agent, for example beeswax, hard paraffin or cetyl alcohol.

The oil-in-water suspensions or emulsions optionally comprise emulsifying agents such as naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate, or the like.

In certain embodiments, an ophthalmic formulation described herein is isotonic with physiological fluids (e.g., osmolality of about 290 mOsm). In certain instances, the suspensions, emulsions or colloidal dispersions comprise tonicity agents (e.g., sodium chloride, potassium chloride or the like) that render the formulation isotonic with physiological fluids. In certain instances, an ophthalmic formulation described herein is a hypotonic formulation. Hypotonic formulations allow for absorption of the Compound of the Disclosure from the lacrimal sac.

Ointments

In some embodiments, the ophthalmic formulation is in the form of a solution that is administered to the mammal in the form of an eye ointment.

Disclosed herein, in certain embodiments, is a topical formulation for administration to an eye wherein the topical formulation for ocular administration is in the form of an ointment. In certain instances, ointments are semisolid (e.g., soft solid or thick liquid) formulations that include a Compound of the Disclosure dispersed in an oil-in-water emulsion or a water-in-oil emulsion. In some embodiments, the hydrophobic component of an ointment is derived from an animal (e.g., lanolin, cod liver oil, and ambergris), plant (e.g., safflower oil, castor oil, coconut oil, cottonseed oil, menhaden oil, palm kernel oil, palm oil, peanut oil, soybean oil, rapeseed oil, linseed oil, rice bran oil, pine oil, sesame oil, or sunflower seed oil), or petroleum (e.g., mineral oil, or petroleum jelly). In certain instances, ointments are semi-solid preparations that soften or melt at body temperature (including the temperature of an eye and/or a tissue related thereto). In certain instances, ointments re-hydrate a tissue and are thus useful for ophthalmic disorders characterized by loss of moisture or dryness in the eye.

Gels

Often there is difficulty in instilling eye drops in the eye. Ophthalmic drops also cause unpleasant side effects of tearing, eyelid crusting and/or vision blurring. The tearing causes difficulty in applying an appropriate amount of a Compound of the Disclosure to the eye due to rapid loss of drug through the lacrimal drainage system. Ophthalmic gels provide for good ocular retention, while avoiding burst release of a Compound of the Disclosure. In some instances, an ophthalmic formulation is designed for controlled release of the Compound of the Disclosure in order to provide increased delivery efficiency, and maximum therapeutic effect.

Described herein, in certain embodiments, is an ophthalmic formulation comprising a Compound of the Disclosure wherein the ophthalmic formulation is in the form of a liquid that gels upon administration to the eye. The formulation is a liquid at room temperature and comprises Compound of the Disclosure eye causes rapid gellation of the polymer (i.e. a transition from liquid phase to solid phase) thereby preventing tearing and washing away of the Compound of the Disclosure.

Ophthalmic formulations comprising thermosensitive gelling polymers are liquids at room temperature and gel at body temperature (i.e., in situ gelling systems). Thermally-sensitive gelling polymers include alkyl cellulose, hydroxyalkyl cellulose, cellulosic ethers, Pluronic polymers, Tetronic polymers or the like, or mixtures thereof. Ophthalmic formulations described comprising pH-sensitive gelling polymers gel upon mixing with aqueous tear fluid. pH sensitive gelling polymers include acidic and crosslinked acidic polymers such as those containing carboxyl groups (e.g., carboxy vinyl polymers such as polyacrylates, cross-linked polyacrylate acid, methacrylic acid, ethacrylic acid, □-methylacrylic acid, cis-□-methylcrotonic acid, trans-□-methylcrotonic acid, □-butylcrotonic acid, □-phenylacrylic acid, □-benzylacrylic acid, □-cyclohexylacrylic acid, and the like or mixtures thereof.

Solids

In some embodiments, the ophthalmic drug delivery system is in the form of a solid or a formulation-impregnated solid matrix. Such drug delivery systems would comprise drug-eluting contact lenses that are soaked with a Compound of the Disclosure (optionally using cyclodextrins or other container molecules), particle-laden, nanoparticle-laden, molecularly-imprinted, ion-exchanged with a compound of the disclosure, microemulsion-laden, or micelle-laden, wherein, the loading particle, emulsion, or micelle contains a compound of the disclosure. An example of a drug-eluting matrix is Lacrisert®.

In some embodiments, the ophthalmic drug delivery system is in the form of a mini-tablet, comprising cellulose derivatives, chitosan acrylates, Amioca, drum-dried waxy maize starch, or Carbopol. An example of a mini-tablet is PROLOC from Encompass Pharma.

In some embodiments, the ophthalmic drug delivery system comprises bioadhesive ophthalmic drug inserts, collagen shields, gelfoams, minidiscs (ocular therapeutic system), polyvinyl alcohol flag devices, mucoadhesive microdiscs, or soluble ocular inserts.

Ocular Injection

In some embodiments, a formulation of a Compound of the Disclosure for administration to a tissue of the eye is administered or delivered via injection to a target site of the eye, where it releases a Compound of the Disclosure over a defined period of time. In certain embodiments, a formulation of a Compound of the Disclosure is administered by intravitreal injection. In some embodiments, a formulation of a Compound of the Disclosure is administered by subtenon injection. In some embodiments, a formulation of a Compound of the Disclosure is administered by suprachoroidal injection. In certain embodiments, a formulation of a Compound of the Disclosure is administered by retrobulbar injection. In some embodiments, the formulation for injection of a Compound of the Disclosure is a solution formulation. In certain embodiments, the formulation for injection of a Compound of the Disclosure is a suspension formulation. In some embodiments, a formulation of a Compound of the Disclosure is injected using microneedles.

Ocular Inserts

In some embodiments, a formulation of a Compound of the Disclosure for administration to an eye is administered or delivered via a device that can be inserted between an eye and eyelid or in the conjunctival sac, where it releases the Compound of the Disclosure. In certain embodiments, a Compound of the Disclosure is released into the lacrimal fluid that bathes the surface of the cornea, or directly to the cornea itself, with which the solid device is generally in intimate contact. In certain embodiments, a suitable device for administration to an eye is used with a Compound of the Disclosure (e.g., Lacrisert®, topical ophthalmic drug delivery device (TODD™) of Amorphex Therapeutics).

In some embodiments, a depot preparation for insertion in the eye is formulated by forming microencapsulated matrices (also known as microencapsule matrices) of a Compound of the Disclosure in biodegradable polymers. In some embodiments, a depot preparation is formulated by entrapping a Compound of the Disclosure in liposomes or microemulsions.

In some embodiments, it is envisioned that a compound of the disclosure is delivered though a drug-loaded polymer disc (e.g., minidisc ocular therapeutic system (OTS) by Bausch & Lomb), a sustained-release rod-shaped device (e.g., Ocufit SR® (Escalon® Medical Corp)), or a poly (vinylalcohol) (PVA) film flag (e.g., new ophthalmic delivery system (NODS®), Smith & Nephew Pharmaceutical Ltd).

Ocular Implants

In some embodiments, a Compound of the Disclosure for administration to an eye is administered or delivered via an injectable or implantable depot preparation. As used herein, a depot preparation is a controlled-release formulation enclosed within a device that is implanted in an eye or a tissue related thereto (e.g., the sclera) (for example subcutaneously, intramuscularly, intravitreally, subconjunctivally, episclerally, or intrasclerally). The ratio of the Compound of the Disclosure to controlled-release matrix and the nature of the matrix employed control the rate of drug release.

In some embodiments, a Compound of the Disclosure is eluted from a biodegradable implant matrix comprising polylactic acid (PLA), polyglycolic acid (PGA), or polylactic-co-glycolic acid (PLGA). Examples of biodegradable implants are Ozurdex®, Surodex®, Medidur®, or the Zordera nanoporous membrane film. In other embodiments, the implant comprises polyortho-ester gels, collagen matrix gels, or PLGA film.

In other embodiments, a Compound of the Disclosure is eluted from a non-biodegradable implant matrix comprising polyvinyl alcohol (PVA), ethylene vinyl acetate (EVA), polysulfone capillary fiber (PCF), or micronised particles of oxidised meso-porous silicon. Examples of non-biodegradable implants are Vitrasert®, Retisert®, Iluvien®, I-vation™, and Ocusert®.

In other embodiments, a Compound of the Disclosure is eluted from an encapsulated cell implant, ocular ring, or a drug-eluting intraocular lenses.

Other Delivery Methods

In other embodiments of the disclosure, a Compound of the Disclosure is delivered to an eye tissue via a punctal plugs, intracanalicular refillable drug reservoirs, microcannulation, solid or hollow microneedles, micropumps, iontophoresis (e.g. Ocuphor®, EyeGate® and Visulex®-related systems), or ultrasound.

Container Closures/Kits for Ocular Administration

The formulations of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is generally unnecessary.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP") and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing.")

The use of a single dose packaging arrangement eliminates the need for an antimicrobial preservative in the compositions, which is a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single dose packaging arrangements currently available, such as small volume plastic vials prepared by means of a process known as "form, fill and seal", have several disadvantages for manufacturers and consumers. The principal disadvantages of the single dose packaging systems are the much larger quantities of packaging materials required, which is both wasteful and costly, and the inconvenience for the consumer. Also, there is a risk that consumers will not discard the single dose containers following application of one or two drops to the eyes, as they are instructed to do, but instead will save the opened container and any composition remaining therein for later use. This improper use of single dose products creates a risk of microbial contamination of the single dose product and an associated risk of ocular infection if a contaminated composition is applied to the eyes.

While the formulations of this disclosure are preferably formulated as "ready for use" aqueous solutions, alternative formulations are contemplated within the scope of this disclosure. Thus, for example, the active ingredients, surfactants, salts, chelating agents, or other components of the ophthalmic solution, or mixtures thereof, can be lyophilized or otherwise provided as a dried powder or tablet ready for dissolution (e.g., in deionized, or distilled) water. Because of the self-preserving nature of the solution, sterile water is not required.

The present disclosure provides a pharmaceutical pack or kit comprising one or more containers filled with a liquid or lyophilized formulation of the Compound of the Disclosure (i.e., a formulation comprising Compound of the Disclosure alone or in combination with an additional active agent as described herein). In one embodiment, the formulation is an aqueous formulation of Compound of the Disclosure. In one embodiment, the formulation is lyophilized. In preferred embodiments the liquid or lyophilized formulation is sterile. In one embodiment, the kit comprises a liquid or lyophilized formulation of the compound of the disclosure, in one or more containers, and one or more other prophylactic or therapeutic agents. The one or more other prophylactic or therapeutic agents may be in the same container as the Compound of the Disclosure or in one or more other containers. Preferably, the Compound of the Disclosure is formulated at a concentration of from about 0.05% (w/v) to about 1.0% (w/v) and is suitable for topical ocular administration. In certain embodiments, the Compound of the Disclosure is formulated with an additional active agent. In certain embodiments, the kit contains the Compound of the Disclosure in unit dosage form.

In certain embodiments, the kit further comprises instructions for use (e.g., using the Compound of the Disclosure alone or in combination with another prophylactic or therapeutic agent), as well as side effects and dosage information for one or more routes of administration. Optionally associated with such container(s) is a notice in the form prescribed by a governmental agency regulating the manufacture, use or sale of pharmaceuticals or biological products, which notice reflects approval by the agency of manufacture, use or sale for human administration. While the instructional materials typically comprise written or printed materials they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g. CD ROM), and the like. Such media may include addresses to internet sites that provide such instructional materials In another embodiment, this disclosure provides kits for the packaging and/or storage and/or use of the formulations described herein, as well as kits for the practice of the methods described herein. The kits can be designed to facilitate one or more aspects of shipping, use, and storage.

Methods of Treatment

In one embodiment, the compounds of invention are used in the preparation of medicaments for the treatment of rho kinase-dependent or rho kinase-mediated diseases or conditions. In addition, a method for treating any of the diseases or conditions described herein in a subject in need of such treatment, involves administration of pharmaceutical compositions that include at least one Compounds of the Disclosure or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

For systemic modes of administration, generally speaking, one will desire to administer an amount of a Compound of the Disclosure that is effective to achieve a plasma level commensurate with the concentrations found to be effective in vivo for a period of time effective to elicit a therapeutic effect. Doses employed for adult human treatment are typically in the range of 0.01 mg-5000 mg per day or from about 1 mg to about 1000 mg per day. In one embodiment, the desired dose is conveniently presented in a single dose or in divided doses.

In some embodiments, formulations provide a therapeutically effective amount of a Compound of the Disclosure, or a pharmaceutically acceptable salt thereof, enabling, for example, once a week, twice a week, three times a week, four times a week, five times a week, once every other day, once-a-day, twice-a-day (b.i.d.), or three times a day (t.i.d.) administration if desired. In one embodiment, the formulation provides a therapeutically effective amount of a rho kinase inhibitor, or a pharmaceutically acceptable salt thereof, enabling once-a-day administration.

Also disclosed herein, are ophthalmic formulations of the compounds of invention wherein the ophthalmic formulation is administered for prophylactic and/or therapeutic treatments. In certain instances, amounts effective for this use will depend on the severity and course of the disease, disorder or condition, previous therapy, the subject's health status and response to the drugs, and the judgment of the treating physician.

In some embodiments, where a rho kinase-dependent or rho kinase-mediated disease or condition does not improve, an ophthalmic formulation disclosed herein is administered chronically (i.e., for an extended period of time, including throughout the duration of the subject's life). In some embodiments, where a rho kinase-dependent or rho kinase-mediated disease or condition does improve, an ophthalmic formulation disclosed herein is given continuously; alternatively, the dose of active agent being administered is temporarily reduced or temporarily suspended for a certain length of time (i.e., a "drug holiday"). In some embodiments, a drug holiday lasts between 2 days and 1 year, including all intermediate time intervals. In some embodiments, the dose reduction during a drug holiday is from about 10% to about 100%, including all intermediate values.

In some embodiments, where a rho kinase-dependent or rho kinase-mediated disease or condition does improve, an ophthalmic formulation disclosed herein is administered as a maintenance dose. In some embodiments, where a rho kinase-dependent or rho kinase-mediated disease or condition does improve, an ophthalmic formulation disclosed herein is administered with reduced frequency or at a reduced dose.

In some embodiments, where an individual is suspected of having a rho kinase-dependent or rho kinase-mediated disease or condition, an ophthalmic formulation disclosed herein is administered as a prophylactic dose prior to onset of disease symptoms. In some embodiments, a prophylactic dose is a reduced dose compared to a therapeutic dose.

Para-Ocular Diseases/Conditions

In another embodiment, a compound of invention, or a composition thereof, is administered to a subject to treat a "para-ocular rho kinase-modulated disease, disorder, injury, or condition" in the subject.

The term "para-ocular rho kinase-modulated disease, disorder, injury, or condition" refers to general physiological conditions for which rho kinase exerts a regulatory or contributing role, but which do not necessarily have ocular effects. Such diseases or conditions include, but are not limited to:

Cardiovascular diseases e.g., angina (e.g., angina pectoris, vasospastic angina, stable effort angina), atherosclerosis, stroke, cerebrovascular disease (e.g., cerebral thrombosis, cerebral embolism, and cerebral hemorrhage), cardiac fibrosis and cardiac hypertrophy, myocardial hypertrophy, ischemia/reperfusion injury, reperfusion cardiomyopathy, atherosclerosis, transplant arteriosclerosis, congestive heart failure, coronary artery disease, myocardial infarction, peripheral vascular disease, stenosis (e.g., coronary artery stenosis, aortic stenosis, restenosis, postangioplasty restenosis, pulmonary stenosis), vasospasm (e.g., cerebral artery vasospasm, coronary artery vasospasm), hypertension (e.g., pulmonary artery hypertension, systemic arterial hypertension)), vasospasms leading to vasoconstriction and ischemia (both cerebral and coronary), ischemic stroke, cerebral venospasms, Reynaud's phenomenon Smooth muscle related disorders e.g., glaucoma, erectile dysfunction, bronchial asthma), Immune and autoimmune disorders e.g., immune hemolytic anemia, immune hepatitis, Berger's disease or IgA nephropathy, Celiac Sprue, chronic fatigue syndrome, Crohn's disease, irritable bowel syndrome, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, psoriasis vulgaris, rheumatic fever, rheumatic arthritis, scleroderma, Sjorgren syndrome, systemic lupus erythematosus, type 1 diabetes, ulcerative colitis, vitiligo, tuberculosis, systemic sclerosis, and inflammation, Inflammatory disorder e.g., asthma, psoriasis, rheumatoid arthritis, osteoarthritis, psoriatic arthritis, inflammatory bowel disease (Crohn's disease, ulcerative colitis), ankylosing spondylitis, sepsis, vasculitis, and bursitis, autoimmune diseases such as Lupus, Polymyalgia, Rheumatica, Scleroderma, Wegener's granulomatosis, temporal arteritis, cryoglobulinemia, and multiple sclerosis, transplant rejection, osteoporosis, cancer, including solid tumors (e.g., lung, CNS, colon, kidney, and pancreas), Alzheimer's disease, atherosclerosis, viral (e.g., HIV or influenza) infections, and chronic viral (e.g., Epstein-Barr, cytomegalovirus, herpes simplex virus) infection, Respiratory disease: e.g., asthmatic conditions including allergen-induced asthma, exercise-induced asthma, pollution-induced asthma, cold-induced asthma, and viral-induced-asthma; asthma-related diseases such as airway hyperreactivity and small airway disease; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchiolitis, bronchioectasis, cystic fibrosis, pigeon fancier's disease, farmer's lung, acute respiratory distress syndrome, pneumonia, pneumonitis, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus, hypoxia, dyspnea, hypercapnea, hyperinflation, hypoxemia, and cough, Allergic disorders: e.g., delayed type hypersensitivity reaction, allergic contact dermatitis, allergic rhinitis, and chronic sinusitis, Neurological disorders: e.g., neuronal degeneration, spinal-cord injury, Alzheimer's disease, Parkinson's disease, stroke, multiple sclerosis, neuropathic pain, AIDS-related dementia, cachexia, Sydenham's chorea, Huntington's disease, Parkinson's Disease, amyotrophic lateral sclerosis (ALS), multiple sclerosis, Korsakoffs syndrome, and imbecility relating to a cerebral vessel disorder, neuropathies of the central and peripheral nervous system (including, for example, IgA neuropathy, membranous neuropathy and idiopathic neuropathy), chronic inflammatory demyelinating polyneuropathy, transverse myelitis, Gullain-Barre disease, encephalitis, and cancers of the nervous system, sleeping disorders, schizophrenia, depression, depression or other symptoms associated with Premenstrual Syndrome (PMS), and anxiety, Cancer: e.g., hematological malignancies, hepatocellular carcinoma, colorectal cancer, and cancer of the breast, brain, liver, lung, ovary, prostate, bladder, cervix and skin, neoplasias including but not limited to brain cancer, bone cancer, leukemia, lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers, Granulomatosus disorders: e.g., sarcoidosis, Wegener's granulomatosus, Acute macrophage-mediated diseases e.g., adult respiratory distress syndrome, organ failure, chronic kidney disease, renal disease, renal failure, and encephalomyelitis.

metabolic disorders: e.g., metabolic syndrome, dyslipidemia, insulin resistance, diabetes complications.

Miscellaneous: wound healing, chronic kidney disease, encephalomyelitis, osteoporosis.

Ocular Diseases/Conditions

In one aspect, presented herein are compounds that inhibit rho kinase, and are useful as agents for the treatment or prevention of ocular diseases or conditions or diseases or conditions in which ocular tissues are affected. In some embodiments, such diseases or conditions will benefit from inhibition of rho kinase, such as diseases in which rho kinase participates, is involved in the etiology or pathology of the disease, or is otherwise associated with at least one symptom of the disease.

In another embodiment, a Compound of the Disclosure, or composition thereof, is administered to a subject to treat an "ocular disease, disorder, injury, or condition" in the subject.

In another embodiment, a Compound of the Disclosure, or composition thereof, is administered to a subject to treat an "ocular disease, disorder, injury, or condition" in the subject.

Retinopathies (for example, cystoid macular edema, central serous choroidopathy and presumed ocular histoplasmosis syndrome), radiation retinopathy, proliferative vitreoretinopathy (PVR), retinopathy of prematurity (ROP), endophthalmitis, thyroid associated orbitopathy, retinopathy of prematurity, familial exudative vitreoretinopathy (FEVR), diabetic retinopathy Retinal artery occlusions, retinal vein occlusions, retinal vascular disease (for example, Coat's disease and retinal arterial macroaneurysm), prevention and treatment of macular thickening related to photocoagulation, idiopathic polypoidal choroidal vasculopathy, epiretinal macular membranes, Macular edema associated with inherited retinal disease, chronic retinal macular edema, Usher syndrome, Bardet-Biedl syndrome (BBS), branch retinal vein occlusion (BRVO), central retinal vein occlusion (CRVO), Neovascularization: corneal graft rejection, and retrolental fibroplasia, epidemic keratoconjunctivitis, Vitamin A deficiency, contact lens overwear, atopic keratitis, superior limbic keratitis, pterygium keratitis sicca, Sjogren's disease, acne rosacea, phylectenulosis, neovascularization due to syphilis, Mycobacteria infections, lipid degeneration, chemical burns, bacterial ulcers, fungal ulcers, Herpes simplex infection, Herpes zoster infections, protozoan infections, Kaposi's sarcoma, Mooren's ulcer, Terrien's marginal degeneration, marginal keratolysis, systemic lupus, polyarteritis, trauma, Wegener's syndrome, sarcoidosis, scleritis, Stevens-Johnson's disease, pemphigoid, and radial keratotomy, Uveitis: anterior uveitis, posterior uveitis, chronic uveitis/vitritis, uveitis syndromes (for example, chronic iridocyclitis or chronic endophthalmitis), Refsum disease, rod-cone dystrophy, cone-rod retinal dystrophy, Oguchi Disease, Malattia Leventinese, blue-cone monochromacy, retinoschisis, choroideremia, vitelliform macular dystrophy (Best disease), choroidal neovascularization, vascular leak, and/or retinal edema, keratic precipitates, inflammation response after intraocular lens implantation, Retinal vasculitis (for example, as seen in rheumatoid arthritis, juvenile rheumatoid arthritis, systemic lupus erythymatosus, progressive systemic sclerosis, polyarteritis nodosa, Wegener's granulomatosis, termporal arteritis, Adamantiades Bechcet disease, Sjorgen's, relapsing polychondritis and HLA-B27 associated spondylitis), Retinal detachment, retinal detachment following penetrating injury) post-surgical macular edema, chronic retinal detachment, Sarcoidosis, Eales disease, acute retinal necrosis, Vogt Koyanaki Harada syndrome, occular toxoplasmosis, Orbital pseudotumor, pigment dispersion syndrome, scleritis, episcleritis choroidopathies (for example, "white-dot" syndromes including, but not limited to, acute multifocal posterior placoid), Thyroid eye disease, or fibrosis associated with keratoprosthesis procedure, Sickle cell anemia, sarcoidosis, pseudoxanthoma elasticum, Paget's disease, vein occlusion, artery occlusion, carotid obstructive disease, mycobacteria infections, Lyme's disease, systemic lupus erythematosus, Eales' disease, Behcet's disease, infections causing retinitis or choroiditis, presumed ocular histoplasmosis, myopia, optic pits, Stargardt's disease, pars planitis hyperviscosity syndromes, toxoplasmosis, trauma and post-laser complications, diseases associated with rubeosis (neovascularization of the angle), diseases caused by the abnormal proliferation of fibrovascular or fibrous tissue, including all forms of prolific vitreoretinopathy, Dry eye: dry eye syndrome (for example, dry eye observed in hypolacrimation, alacrima, xerophthalmia, Stevens-Johnson syndrome, ocular pemphigoid, marginal blepharitis, diabetes and the like, dry eye observed after cataract operation, dry eye in conjunction with allergic conjunctivitis and the like, and dry eye due to hypolacrimation caused by increased VDT (visual display terminal) work, dry room with air conditioning and the like), keratoconjunctivitis sicca (KCS) or keratitis sicca episcleral fibrosis leading to trabeculectormy (bleb) failure after glaucoma filtration surgery, Sjogren syndrome, inflammation following ocular surgery, keratoconjuctivitis, pterygia, non-specific orbital inflammation, Cataracts: cataracts (post-surgical scarring), corneal scarring, scarring associated with cular ciatricial pemphigoid, glaucoma filtration surgery, Conjunctivitis: bacterial conjunctivitis, fungal conjunctivitis, viral conjunctivitis, allergic conjunctivitis, keratoconjunctivitis, vernal keratoconjunctivitis, blepharoconjunctivitis, conjunctival melanoma, intraocular melanoma, contact lens-associated giant papillary conjunctivitis, anterior segment scarring, cicatricial pemphigoid, episcleritis, reticular gliosis, Graves' ophthalmopathykeratitis, pain, Pinguecula, post-surgical pain, pterygia, scarring, scleritis, blepharitis, Eye cancer, radiation induced corneal scarring, laser-assisted in situ keratomileusis, ocular fibrosis, corneal ulcers, Corneal transplant related disease or condition, trabeculectomy related disease or condition, cicatricial pemphigoid, corneal endothelial disorders, Fuchs corneal dystrophy, and pterygia.

"Ocular disease, disorder, injury, or conditions" also include but are not limited to "neurodegenerative ocular disease, disorder, injury, or conditions", as defined below.

1. Neurodegenerative Ocular Diseases/Conditions

In another embodiment, a Compound of the Disclosure, or composition thereof, is administered to a subject to treat a "neurodegenerative ocular disease, disorder, injury, or condition" in the subject.

The term "neurodegenerative ocular disease, disorder, injury, or condition" refers to conditions for which the neurological function of the eye is physiologically compromised or diminished. Such diseases or conditions include, but are not limited to:

Glaucoma & neuropathies: Glaucoma including Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma, Post-Traumatic Glaucoma, Steroid-Induced Glaucoma, Sturge-Weber Syndrome Glaucoma, and Uveitis-Induced Glaucoma, ocular glaucomas (for example, inflammatory glaucomas), pigmentary glaucoma, neovascular glaucoma, Macular degeneration: dry age related macular degeneration, geographic atrophy, wet age related macular degeneration (wet AMD), wet AMD with neovascularization, wet AMD with foveal thickening, Retinopathy: diabetic retinopathy, diabetic retinopathy with retinal edema, diabetic retinopathy with neovascularization, hypertensive retinopathy, genetic retinopathy, macular oedema, retinitis pigmentosa and related retinal degenerative diseases, Neuropathy & neuritis: ischemic optic neuropathy (e.g., anterior ischemic optic neuropathy, posterior ischemic optic neuropathy, radiation optic neuropathy), optic neuritis (e.g., Single isolated optic neuritis (SION), relapsing isolated optic neuritis (RION), chronic relapsing inflammatory optic neuropathy (CRION), the neuromyelitis optica (NMO) spectrum disorder, multiple sclerosis associated optic neuritis (MSON), nclassified optic neuritis (UCON) forms, Arteritic ischemic optic neuropathy (AION), Non-arteritic ischemic optic neuropathy (NAION)), compressive optic neuropathy (due to e.g. optic gliomas, infiltrative optic neuropathy (Inflammatory (non-demyelinating) optic neuropathy, Paraneoplastic optic neuropathy), traumatic optic neuropathy, mitochondrial optic neuropathies, nutritional optic neuropathies, toxic optic neuropathies, hereditary optic neuropathies (Leber's hereditary optic neuropathy (LHON), dominant optic atrophy, Behr's syndrome, Berk-Tabatznik syndrome), ocular symptoms associated with Parkinsons's disease and Alzheimer's disease, Meningiomas, hemangiomas, lymphangiomas, dermoid cysts, carcinoma, lymphoma, multiple myeloma, inflammatory orbital pseudotumor, and thyroid ophthalmopathy).

In another embodiment, a compound of invention, or a composition thereof, is administered to a subject to treat "glaucoma" in the subject.

The term "glaucoma" refers to diseases or conditions that include, but are not limited to . . . Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma, Post-Traumatic Glaucoma, Steroid-Induced Glaucoma, Sturge-Weber Syndrome Glaucoma, and Uveitis-Induced Glaucoma, ocular glaucomas (for example, inflammatory glaucomas), pigmentary glaucoma, and neovascular glaucoma.

In some embodiments, the ocular disease or condition is an ocular disease or condition affecting the posterior segment of the eye, the anterior segment of the eye, or both the posterior segment of the eye and the anterior segment of the eye.

In some embodiments, the ocular disease or condition is an ocular disease or condition affecting the posterior segment of the eye.

In some embodiments, the ocular disease or condition is an ocular disease or condition affecting the anterior segment of the eye.

Combination Therapy

The compounds of invention may be administered to a subject in conjunction with other pharmaceutically active compounds. It will be understood by those skilled in the art that pharmaceutically active compounds to be used in combination the compounds of invention will be selected in order to avoid adverse effects on the recipient or undesirable interactions between the compounds.

The additional therapeutic agent or agents may be administered simultaneously or sequentially with the compounds of invention. Sequential administration includes administration before or after the Compounds of the Disclosure. In some embodiments, the additional therapeutic agent or agents may be administered in the same composition as the Compounds of the Disclosure. In other embodiments, there may be an interval of time between administration of the additional therapeutic agent and the Compounds of the Disclosure.

In some embodiments, the administration of an additional therapeutic agent with a Compound of the Disclosure may enable lower doses of the other therapeutic agents and/or administration at less frequent intervals.

Para-Ocular Medications

In some embodiments, a Compound of the Disclosure may be used in combination with another pharmaceutically active compound from the list comprising, but not limited to:

- AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflammatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine H.sub.2 receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, *porphyria* agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media.

Ocular

Compounds of the Disclosure may be administered to a subject in conjunction with other pharmaceutically active compounds, proteins, or gene therapy products that treat ophthalmic conditions or diseases. It will be understood by those skilled in the art that pharmaceutically active treatments to be used in combination the Compound of the Disclosure will be selected in order to avoid adverse effects on the recipient or undesirable interactions between the compounds. Examples of other pharmaceutically active treatments which may be used in combination a Compound of the Disclosure, are:

- Antibiotics (e.g., polymyxin B sulfate/bacitracin zinc, polymyxin B/neomycin/gramicidin, polymyxin B/trimethoprim, polymyxin B/bacitracin, fluoroquinolones (e.g., ciprofloxacin, moxifloxacin, ofloxacin, gatifloxacin, levofloxacin), aminoglycosides (e.g.
- tobramycin, azithromycin, gentamicin, erythromycin, bacitracin),
- Anti-fungal agents (e.g., amphotericin B, intraconazole, fluconazole, voriconazole),
- Antiviral agents (e.g., acyclovir, vidarabine, trifluridine).
- Steroid anti-inflammatory agents (e.g. betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, ulobetasol),

- Nonsteroidal anti-inflammatory agents (NSAID, e.g., nepafenac, ketorolac, bromfenac, diclofenac, ketorolac, ketotifen),
- Mast cell stabilizers, e.g., lodoxamide tromethamine, nedocromil sodium, cromolyn sodium, pemirolast potassium,
- Antihistamines, e.g., amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine, and triprolidine. In some embodiments, antihistamines include, but are not limited to, emedastine, olopatadine, epinastine, azelastine, ketotifen,
- Immunosuppresive agents, e.g., cyclosporine and tacrolimus,
- Leukotriene modulators, e.g. 5-LO inhibitors, FLAP inhibitor compounds,
- Leukotriene receptor antagonist, e.g. CysLTi receptor antagonists,
- Anti-angiogenesis agents, e.g., pegaptanib sodium, ranibizumab, verteporfin, bevacizumab, aflibercept,
- Antimetabolites (e.g. methotrexate).

Glaucoma

In additional embodiments, a Compound of the Disclosure may be used in combination with a glaucoma medication from the list comprising, but not limited to:

- prostaglandin-like compounds, e.g. latanoprost (XALATAN®), bimatoprost (LUMIGAN®), and travoprost (TRAVATAN™), tafluprost, unoprostone,
- beta- Adrenergic blockers, e.g., levobunolol (BETAGAN®), timolol (BETIMOL®, TIMOPTIC®), betaxolol (BETOPTIC®), metipranolol (OPTIPRANOLOL®), levobunolol hydrochloride, carteolol hydrochloride, timolol maleate, and timolol hemihydrate, metipranolol,
- alpha- adrenergic agonists, e.g., apraclonidine (IOPIDINE®) and brimonidine (ALPHAGAN®),
- carbonic anhydrase inhibitors, e.g., dorzolamide (TRUSOPT®) and brinzolamide (AZOPT®) acetazolamide,
- miotic or cholinergic agonists, e.g., pilocarpine (ISOPTO CARPINE®, PILOPINE®) and carbachol (ISOPTO CARBACHOL®, acetylcholine chloride, echothiophate,
- Sympathomimetics, e.g. dipivefrin (PROPINE®), phenylephrine
- Rho kinase inhibitors, e.g., netarsudil,
- A1 adenosine receptor agonists, e.g., trabodenoson.

Neuroprotective Combinations

In another embodiment, Compounds of the Disclosure may be combined with medicinal agents including small molecules, proteins, or gene therapy products, which reduce oxidative stress in RGC and glial cells, sustain or promote mitochondrial energy production, modulate the immune response, modulate ocular perfusion pressure (OPP), modulate autophagic pathway in RGCs, modulate the biomechanical behavior of the connective tissues of the optic nerve head, or in other ways synergize the compounds of the disclosure. The medicinal agents that may be combined with compounds of the disclosure are:

- Endothelin Receptor, ETB inhibitors, e.g. BQ-788, bosentan,
- Endothelin Receptor, ETA inhibitors, e.g. BQ-123,
- Rho kinase inhibitors,
- Cannabinoid receptor CB1 agonists, e.g. WIN 55,212-2,
- MAP3K12 inhibitors, e.g. tozasertib, crizotinib, foretinib, axitinib,
- c-Jun kinase inhibitors, e.g. SP600125, D-JNKI-1, L-JNKI-1,
- EGFR kinase inhibitors, e.g. tyrphostin,
- Erythropoietin,
- ATP-sensitive K+ channel activators, e.g. diazoxide, nicorandil, cromakalim,
- NMDA-sensitive glutamate receptor inhibitors, memantine, riluzole, dextromethorphan & its major metabolite,
- ATP-sensitive K+ channel activators, e.g. diazoxide, nicorandil, cromakalim,
- mTOR inhibitors, e.g. rapamycin,
- A1AR agonists, e.g. trabodenoson, capadenoson,
- A1AR antagonists, e.g. caffeine,
- A2AAR agonists and antagonists,
- A2BAr antagonists,
- A3AR agonists,
- Cyclin-dependent kinase 5 (Cdk5) inhibitors,
- Ciliary neurotrophic factor (CNTF), [Brain 131:250-263],
- Signal transducer and activator of transcription 3 (STAT3) [Neural Regen. Res. 2015, 10, 12, 1949; Cell Death Dis 4: e734.],
- DP2 receptor antagonists,
- Complement C1q inhibitors,
- Small interfering RNAs (e.g. bevasiranib),
- Actin-disrupting agents,
- Serotonin modulators,
- Oxidative stress reducers,
- Receptor tyrosine kinase inhibitors,
- Neuroprotectants,
- Vaccination, e.g. glial cell-line derived neurotrophic factor, and
- mechanism unknown, e.g. brimonidine, glatiramer.

Assays

The ROCK inhibitors, prepared by the methods described herein, are screened for biophysical, biochemical, pharmacodynamics, and pharmacokinetic properties by a selection of the assays outlined in Table 1. Chemical structure assignment is performed by any of a number of methods known to those skilled in the art, including $^{1}H$ NMR, $^{13}C$ NMR, 2D NMR methods, LC-MS, elemental analysis, infra-red spectroscopy, and ultraviolet spectroscopy. In vitro biophysical characterizations such as solubility, log P, permeability, and metabolic stability are performed by established methods, specifically those described in Di & Kerns (2016). Biophysical methods specifically related to the ophthalmological context are reviewed or described in Gukasyan et. al. (2008) and Pepić et. al. (2014). Kinase inhibitor profiling assays of a number of different designs are reviewed in the cited references in Table 1. Many of these can be accessed at commercial vendors, as indicated in the Table. Additionally, a specific ROCK assay is described in Sturdivant (2016). Likewise, characterization as transporter substrates or inhibitors, pharmacodynamics characterization, and pharmacokinetic characterization are performed at the vendors or by the methods cited in Table 1. An assay cascade (Table 2) is performed in the approximate assay order as appears in Table 1 (below).

TABLE 1

Assays for identification and characterization of ROCK inhibitors, optionally bearing a transportophore.

| Category | Assay Type | Assay | Method |
| --- | --- | --- | --- |
| in silico | Calculations | logP<br>polar surface area (PSA: for AEI, BDDCS classification)<br>RO5 counts | |
| In vitro | Chemical ID verification | NMR, LC-MS | |
| In vitro | Pro-drug release | aqueous stability<br>biophase stability (pro-moiety release by lipase, peptidase, etc.) | Di & Kerns (2016) |
| In vitro | Physical properties<br>Biophysical properties | solubility<br>logP<br>PAMPA<br>metabolic stability (CYP) | Di & Kerns (2016) |

TABLE 1-continued

Assays for identification and characterization of ROCK inhibitors, optionally bearing a transportophore.

| Category | Assay Type | Assay | Method |
| --- | --- | --- | --- |
| | | melanin binding; relevant tissue protein binding | |
| In vitro | Permeability, cellular | Primary cell culture model: Conjunctiva<br>rabbit conjunctival epithelial cell (RCEC)<br>Chang cell line; IOBA-NHC cell line<br>Cornea<br>Primary cell culture model: HCE-T cell line<br>Retinal Pigment epithelium<br>ARPE-19 cell line | Gukasyan et. al. (2008)<br>Pepić et. al. (2014) |

ROCK = Rho-associated protein kinase

TABLE 2

Ocular ROCK inhibitor assay cascade.

| Category | Assay Type | Assay | Method |
| --- | --- | --- | --- |
| In vitro | Kinase profiling<br>ROCK Target engagement | inhibition of other kinases, especially relevant to ocular & tox<br>ROCK inhibition<br>Porcine and human trabecular meshwork cell assays | General kinase assays:<br>Zegzouti, et.al. (2016)<br>Jester et.al. (2012)<br>Jia et. al. (2008)<br>Glickman et. al. (2004-12)<br>ROCK:<br>Sturdivant (2016) |
| In vitro | Transporter<br>Human ocular transporters identified in Mol. Pharmaceutics, 2013,10,650:<br>SLC15A1 (PEPT1)<br>SLC22A1 (OCT1)<br>SLC22A2 (OCT2)<br>SLC22A3 (OCT3)<br>SLC22A5 (OCTN2)<br>SLC22A6 (OAT1)<br>SLC22A7 (OAT2)<br>SLC22A8 (OAT3)<br>SLC47A1 (MATE1)<br>SLC47A2 (MATE2)<br>SLCO1A2 (OATP1A2)<br>SLC10A1 (NTCP)<br>SLC10A2 (ASBT)<br>SLCO1B1 (OATP1B1)<br>SLCO1B3 (OATP1B3)<br>SLCO2B1 (OATP2B1) | influx (substrate)<br>efflux (inhibitor)<br>Monolayer Assays (vectorial transport)<br>Bidirectional cell monolayer transwell permeability methods<br>Plated cell monolayer uptake methods<br>Cell suspension oil spin method<br>Sandwich-cultured hepatocyte method<br>Media loss method<br>inverted vesicle assay<br>Oocyte uptake method<br>ATPase assay for ABC transporters<br>Calcein AM assay for P-gp inhibitors | Di & Kerns (2016)<br>Zdrazil et. al. (2014)<br>Jani et. al. (2014) |
| In vitro | Norepinephrine transporter (NET) | Norepinephrine transporter (NET) membrane radioligand binding assay | deLong et. al. (2015) |

TABLE 2-continued

Ocular ROCK inhibitor assay cascade.

| Category | Assay Type | Assay | Method |
|---|---|---|---|
| In vitro | SERT target engagement | serotonin transporter (SERT) membrane radiological binding assay | deLong et. al. (2015) |
| In vitro | Ocular PD | Human trabecular meshwork (PTM) assay porcine trabecular meshwork (PTM) assay | deLong et. al. (2015) Sturdivant (2016) |
| Ex vivo (Tissue explants) | Ocular PK | Cornea Excised cornea-Franz diffusion cell-porcine, human Conjunctiva Excised conjunctival tissue-Us sing chamber-rabbit, porcine, bovine, human Retinal pigment epithelium (RPE) Excised RPE-perfusion system-rabbit, porcine, bovine, human Other Tissues Sclera (human) Sclera-choroid-Bruch's membrane (porcine) Sclera-choroid-RPE (rabbit, human, porcine, bovine) Choroid-RPE-neural retina (porcine) Isolated perfused eye system (ovine, bovine) | Pepić et. al. (2014) |
| Simulated Ex vivo | | Bioengineered 3D equivalent of human cornea Organ-on-a-chip (when become available for ocular) | Pepić et. al. (2014) |
| In vivo | Ocular PK | Biodistribution to ocular tissues | Mainolfi (2013) many other references |
| In vivo | Ocular PD | Intraocular pressure rabbit intraocular pressure (IOP), tonometric Neuroprotection/regeneration Optic nerve crush and quantification of regenerating axons Immunofluorescence staining and survival quantification of RGCs Western blot analysis-Rock target protein phosphorylation Immunohistochemistry of retinal and optic nerve cross-sections | Sturdivant et. al. (2016) Shaw et.al. (2016) |
| In vivo | Transporter | Genetic knockout animals Chemical knockout methods | |

ROCK = Rho-associated protein kinase

1. General Assay Selection and SOPs a. L. Di, E. H. Kerns, Drug-Like Properties: Concepts, Structure Design and Methods from ADME to Toxicity Optimization 2nd Ed., 2016, Academic Press.

b. Assay Guidance Manual E-Book, Eli Lilly & Co. and the National Center for Advancing Translational Sciences, Bethesda (MD); 2004;

www.ncbi.nlm.nih.gov/books/NBK53196; Bookshelf ID: NBK53196; PMID: 22553861.

2. BDDCS a. Barton P., Riley R. J., A new paradigm for navigating compound property related drug attrition, Drug Discovery Today, 2016, 21, 1, 72-81.

3. Kinase Inhibitor Assays a. Zegzouti, H., Goueli, S. A., Eds., Kinase Screening and Profiling: Methods and Protocols (Methods in Molecular Biology) 1st ed. 2016, Humana Press.

b. Jester B. W., Gaj A, Shomin C. D., Cox K. J., Ghosh I., Testing the promiscuity of commercial kinase inhibitors against the AGC kinase group using a split-luciferase screen, J. Med. Chem. 2012, 55, 4, 1526. doi: 10.1021/jm201265f.

c. Jia Y, Quinn C M, Kwak S, Talanian R V., Current in vitro kinase assay technologies: the quest for a universal format, Curr. Drug Discov. Technol. 2008, 5, 1, 59, PMID: 18537568.

d. Glickman J F, Assay Development for Protein Kinase Enzymes, in Assay Guidance Manual [Internet], Sittampalam G S, Coussens N P, Nelson H, Arkin M, Auld D, Austin C, Bejcek B, Glicksman M, Inglese J, Iversen P W, Li Z, McGee J, McManus O, Minor L, Napper A, Peltier J M, Riss T, Trask O J Jr., Weidner J, Eds.; Bethesda (MD): Eli Lilly & Company and the National Center for Advancing Translational Sciences; 2004-2012.

4. ROCK Inhibitors for Glaucoma: In Vitro, In Vivo PK & PD a. Jill M. Sturdivant, et. al., Discovery of the ROCK inhibitor netarsudil for the treatment of open-angle glaucoma; Bioorganic & Medicinal Chemistry Letters 2016, 26, 2475.

b. P. Shaw, et. al., Topical administration of a Rock/Net inhibitor promotes retinal ganglion cell survival and axon regeneration after optic nerve injury, Experimental Eye Research 2016, 16, 30181, http://dx.doi.org/10.1016/j.exer.2016.07.006.

Intraocular pressure (IOP) measurement (Intraocular pressure (IOP) was measured using a TonoLab Tonometer)

Optic nerve crush and quantification of regenerating axons

Immunofluorescence staining and survival quantification of RGCs

Western blot analysis-Rock target protein phosphorylation

Immunohistochemistry of retinal and optic nerve cross-sections c. deLong, M. A., Sturdivant, J. M., Royalty, S. M., Dual mechanism inhibitors for the treatment of disease, US-2015/0175549.A1, 2015.

5. Transporters In vitro a. B. Zdrazil, C. Chichester, L. Z. Balderud, O. Engkvist, A. Gaulton, J. P. Overington, Transporter assays and assay ontologies: useful tools for drug discovery; Drug Discovery Today: Technologies, 2014, 12, e47.

b. Márton Jani, Péter Krajcsi, In vitro methods in drug transporter interaction assessment; Drug Discovery Today: Technologies, 2014, 12, e105.

c. deLong, M. A., Sturdivant, J. M., Royalty, S. M., Dual mechanism inhibitors for the treatment of disease, US-2015/0175549.A1, 2015.

6. Ocular Pharmacokinetics a. H. J. Gukasyan, K.-J. Kim, V. H. L. Lee, The Conjunctival Barrier in Ocular Drug Delivery, in Drug Absorption Studies, Springer, 2008, pp 307-320.

Tissue: Excised conjunctival tissue-Ussing chamber b. Ivan Pepić et. al., Toward the practical implementation of eye-related bioavailability prediction models, Drug Discovery Today, 2014, 19, 1 31.

c. Nello Mainolfi, et. al., An Effective Prodrug Strategy to Selectively Enhance Ocular Exposure of a Cannabinoid Receptor (CB1/2) Agonist, J. Med. Chem. 2013, 56, 5464-5472.

EXAMPLES

Example 1

General Experimental Procedures

Abbreviations

AQ=aqueous
Bpin=pinacolato-boronate group
CR=crude
DIOL=Diol bonded phase media for flash chromatography
DIPEA=di-isopropylethylamine
DMSO=dimethyl sulfoxide
FA=formic acid
HILIC=hydrophilic interaction liquid chromatography
ML=mother liquor
SM=starting material
P, PROD=product
PMA=phosphomolybdic acid
RM=raw material
RP=reverse phase
TEA=triethylamine
TLC=thin layer chromatography
Xtal, X=crystal Solvent Abbreviations H=hexane, hexanes
E=ether
EA=ethyl acetate
DCM=dichloromethane, methylene chloride
M=methanol
THF=tetrahydrofuran
W=water Solvents Solvents were reagent or chromatography grade unless otherwise stated. Solvents were generally purchased from Fisher, VWR, and Aldrich. Anhydrous solvents were purchased from Acros or Aldrich, packaged in each vendor's specialized sealed glass bottles: Acroseal or SureSeal, respectively.

Reagents

Reagents were generally obtained from these manufacturers: Aldrich, Acros, Alfa-Aesar, Allychem, Arkpharm, Bachem, Fisher, Gelest, Manchester, Oakwood, Oxchem, TCI, VWR. Reagents were purchased directly or alternatively through distributors Fisher and VWR.

Temperature Measurement

Temperature was measured with non-mercury thermometers purchased from Ace Glass. Thermometers were generally placed inside of the reaction vessels rather than in the bath surrounding the vessel. During the course of the experiments, it was suspected, but not proven, that low-temperature thermometers may have occasionally lost their calibration. To the extent possible, this was addressed by replacing the thermometer. In all cases, temperatures reported are those read directly from the thermometer.

Ultrasonication

Ultrasonication was performed in a Skymen JP-010B bath: 2 L capacity, 60 W, 40 KHz, no heater.

Melting Points

Melting points were not obtained.

Thin Layer Chromatography, TLC:

Analytical TLC plates were purchased from Macherey-Nagel:

| | | |
|---|---|---|
| Silica: | Polygram ® Sil G/$UV_{254}$ 0.2 mm plates | Cat #805021 |
| Alumina: | Polygram ® ALOX/$UV_{254}$ 0.2 mm plates | Cat #802021 |
| Reverse phase RP18 | Alugram ® RP18-W/$UV_{254}$ 0.15 mm plates | Cat #818144 |
| CYANO | Alugram ® Nano Sil CN/$UV_{254}$ 0.2 mm plates | Cat #818184 |
| AMINO | Alugram ® Nano Sil NH2/$UV_{254}$ 0.2 mm plates | Cat #818182 |

TLC plate visualization was performed by:

Short wavelength (254 nm) UV. Model UVG-11, Mineralight lamp, Ultraviolet Products Inc. Spectraline cM-10A Cabinet.

Long wavelength (366 nm) UV. Model UVL-56, Ultraviolet Products Inc. Spectraline cM-10A Cabinet.

Phosphomolybdic acid staining with heat gun heating was used to visualize UV-non-active substances. Solution: 8 g PMA in 100 mL EtOH+1 mL $H_2SO_4$.

Alizarin staining was used to demonstrate the presence or absence of a boron-containing moiety. Solution: 24 mg alizarin in 100 mL acetone. Alizarin staining was optionally enhanced by subsequent treatment of the plate with ammonia vapor in a closed chamber using aqueous ammonia solution. Visualization was performed both under ambient lighting and 366 nm as described above.

Most plates were visualized primarily by short wavelength UV.

Flash Column Chromatography:

Flash chromatography was performed on a Teledyne-ISCO Combiflash Rf instrument (ID #625230006), using the manufacturer's Redisep® disposable silica columns or reusable RP or HILIC columns. The latter were conditioned and stored according to the manufacturer's recommendations.

The mobile phase solvent system identified by the ISCO software is not always accurate. Refer to the lab notebook entries and the hand-written annotations on ISCO print-outs.

Sample Preparation and Salt/Solvate Assignment

Samples for screening were generally dried under high vacuum without heating. Solvate and salt assignments were made based on synthesis provenance, 1H NMR chemical shifts, and 1H NMR integrations.

$^1$H NMR Spectra $^1$H NMR spectroscopy was performed by Novatia LLC, Newtown, PA on a Bruker 500 MHz multinuclear, variable temperature NMR spectrometer with a Prodigy Cryoprobe. Source raw data files were obtained from Novatia and maintained separately from the hard copy notebook.

LC-MS

LC-MS was performed by Novatia LLC, Newtown, PA:

Instrument: Michrom Bioresources Paradigm MS4B with external dynamic mixer, and CTC HTS-PAL autosampler with 500 uL sample loop PDA Detector: Thermo Accela PDA, 1 cm light pipe, monitoring 200-300 nm MS Instrument: Thermo LTQ Orbitrap Discovery Ionization mode: Electrospray ionization (ESI), Positive Mode Detection Mode: Ion Trap MS Scan range: 150-1200 u Source conditions: +3.0 kV Sheath gas flow rate: 30 AU (arbitrary units)

Aux gas flow rate: 5 AU

Sweep gas flow rate: 2 AU

Capillary temperature: 300° C.

Injection volume: 10 uL

The chromatography conditions were as follows, unless otherwise indicated:

Column: Waters X-Bridge C-18, 2.1×50 mm

Flow: 0.5 mL/min

Solvents: A) 10 mM aqueous ammonium acetate B) acetonitrile

General Scheme 1

SYNTHESIS OF Teoc-$NHCH_2OCH_3$ (COMPOUND 4)

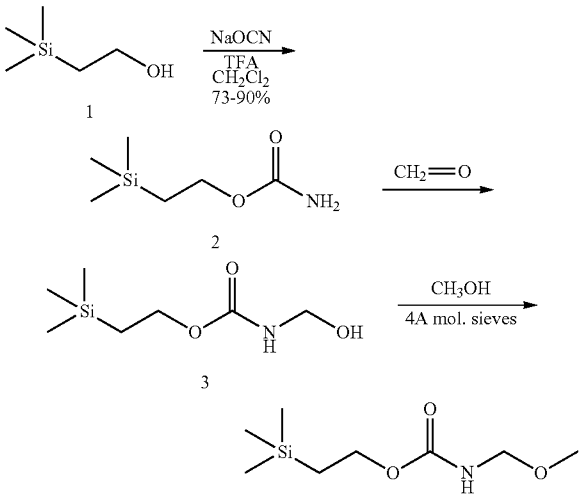

1

2

3

4

General Scheme 2
SYNTHESIS OF COMPOUND 10 & 10-2HCl
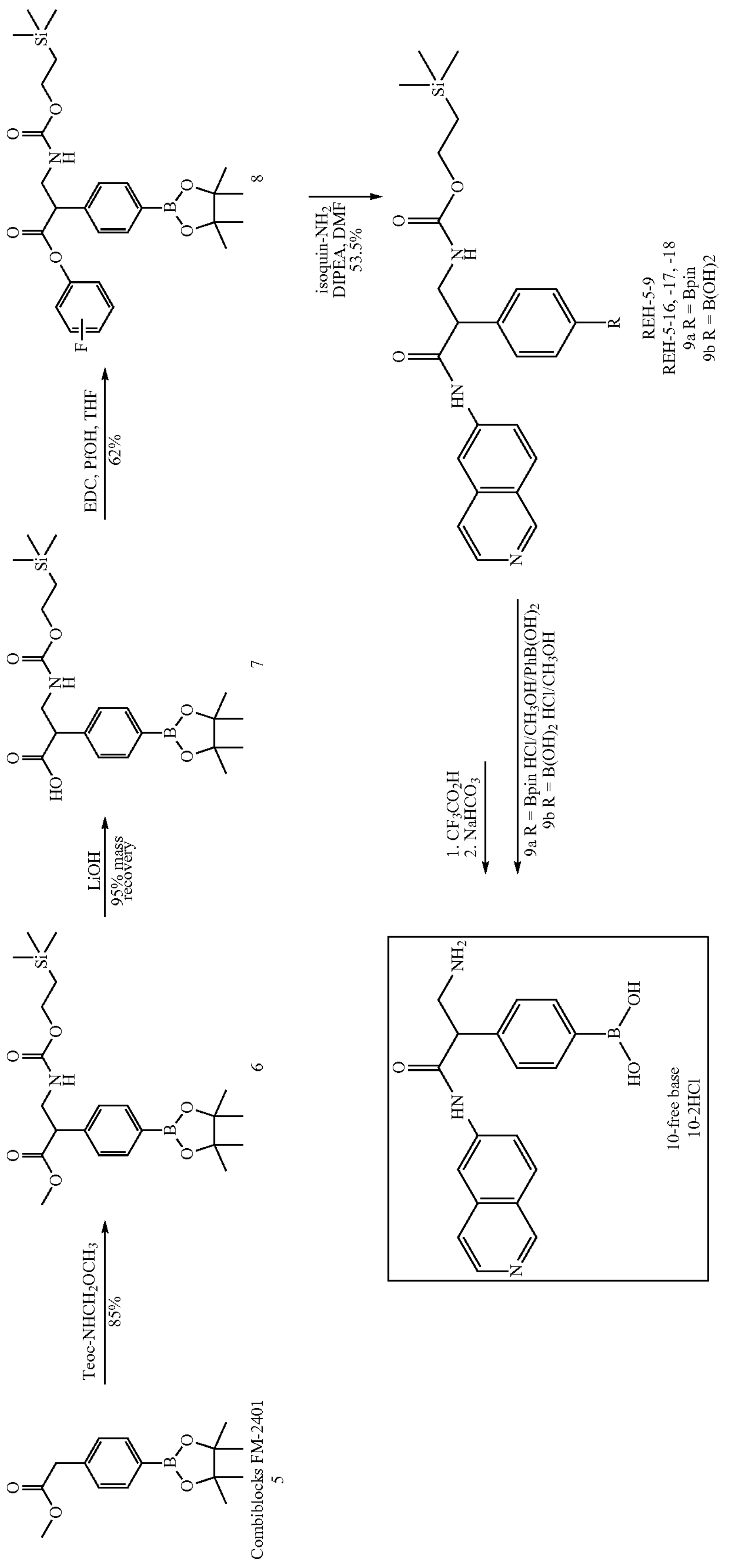

Preparation of 2-Trimethylsilylethyl Carbamate, Compound 2

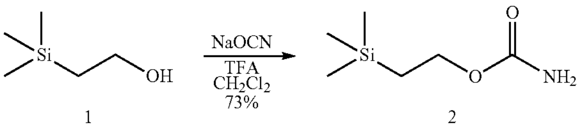

1 2

Trimethylsilylethanol (50.85 g, 430 mmol, Gelest) and 450 mL dichloromethane were added to a 2 L round-bottom flask equipped with thermometer, magnetic stirring, and nitrogen inlet. With magnetic stirring and under $N_2$ atmosphere, sodium cyanate (NaOCN, 55.08 g, 847 mmol, 1.97 eq.) was added as a powder. Neat trifluoroacetic acid (102.96 g, 903 mmoles, 2.1 eq) was added in an intermittent stream with over a period of 20 min with occasional ice bath chilling to maintain the temperature at 19-23 C. An additional 30 mL dichloromethane was used to rinse reagent vessels and added to the mixture. The granular undissolved NaOCN disappeared and a flocculant precipitate appeared. Gas evolved. After 4.75 hours, water was added (220 mL). The lower organic layer was collected, and the aqueous layer was washed twice with 100 mL dichloromethane, adding water as necessary to differentiate the phases. The organic fractions were combined, washed with brine, dried over $MgSO_4$, and filtered through paper. Solvent was removed in vacuo to provide 64.7 g of a white crystalline solid. This material was recrystallized from 150 mL pentane at refrigerator temperature and careful/rapid washing with 100 mL ice-cold pentane to provide 46.1 g brilliant white flakes. A second crop of 4.32 g was obtained from pentane at freezer temperature and washing with chilled pentane for a total of 50.4 g, 72.7% yield of 2-trimethylsilylethyl carbamate. $^1H$ NMR (500 MHz, DMSO): δ 6.35 (br, 2H), 3.98 (t, 2H), 0.90 (t, 2H), 0.02 (s, 9H) ppm; $^1H$ NMR (500 MHz, $CDCl_3$): δ 4.52 (br, 2H), 4.11 (t, 2H), 0.95 (t, 2H), 0.00 (s, 9H) ppm. TLC (1:1 hexanes:ethyl acetate, phosphomolybdic acid staining) Rf=0.54.

Preparation of Trimethylsilylethyl N-(hydroxymethyl)carbamate, Compound 3

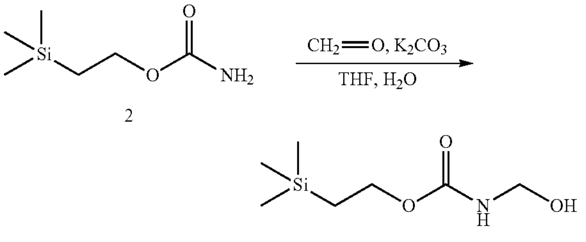

2

3

2-Trimethylsilylethyl carbamate (20 g, 124 mmoles) was dissolved or suspended in 50 mL THF in a 500 mL, 3-necked, round-bottom flask equipped with thermometer and magnetic stirring. Water (80 mL) and formaldehyde (10.6 mL, 3.91 g, 130 mmoles of a commercial 37% solution in 10-15% $CH_3OH$, 48-53% water) were added. Finally, potassium carbonate (428 mg, 3.1 mmoles dissolved in 4 mL water) was added. The reaction was stirred at room temp 15 min and then heated at 60-65 C. for 2 HR 10 min., monitoring by TLC. The mixture was allowed to cool. Ether was added. The aqueous phase was removed and extracted twice with ether. The combined organic phases were dried with brine and then solid MgSO4, and then filtered. Solvent was removed in vacuo at 55 C., using hexanes and pentane to drive off THF and methanol. A light, colorless oil was obtained, 24.18 g. The crude material was purified by crystallization from pentane at freezer temperature (−13 C.) and washing with chilled (ca. −5 C.) pentane. Both crystallized and non-crystallized crude product were further purified by silica gel chromatography using a hexanes-ethyl acetate gradient. Yield: White, slightly waxy solid, 13.4 g, 56.5% yield. $^1H$ NMR (500 MHz, $CDCl_3$): δ 5.85 (br, 1H), 4.69 (t, 2H), 4.17 (t, 2H), 3.08 (br, 1H), 0.98 (t, 2H), 0.02 (s, 9H) ppm. TLC (1:1 hexanes:ethyl acetate, phosphomolybdic acid staining) Rf=0.39.

Preparation of 2-Trimethylsilylethyl N-(methoxymethyl)carbamate, Compound 4

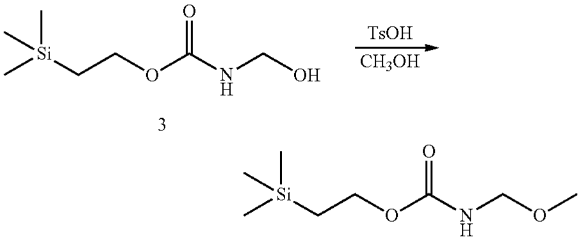

3

4

2-Trimethylsilylethyl N-(hydroxymethyl) carbamate (8.0 g, 41.8 mmoles) was dissolved in ether (180 mL) and methanol (30 mL) in a 500 ml Erlenmeyer flask with cap. 4 Å molecular sieves (3.89 g) and p-toluenesulfonic acid (0.184 g, 0.97 mmoles) were added. The reaction mixture was stirred for 3 hours, and monitored by TLC (1:1 hexanes: ethyl acetate, $I_2$ staining). The mixture was filtered through a small pad of ether-wetted Celite in a plastic fritted funnel. The solvent was removed in vacuo at 55° C. Ether (5×) and pentane (1×) were added and removed in vacuo so as to drive out residual methanol. The product was held under high vacuum for 5-10 min, providing 8.45 g (98.4%) 2-trimethylsilylethyl N-(methoxymethyl) carbamate as an off-white, slightly volatile oil. $^1H$ NMR (500 MHz, $CDCl_3$): δ 5.35 (br, 1H), 4.60 (d, 2H), 4.17 (t, 2H), 3.31 (s, 3H), 0.97 (t, 2H), 0.02 (s, 9H) ppm. TLC (1:1 hexanes:ethyl acetate, $I_2$ staining) Rf=0.6.

Preparation of 2-Trimethylsilylethyl N-2-methoxycarbonyl, 2-(4,4,5,5-tetramethyl-[1,3,2]dioxaborolane-2-yl-phenyl)ethylcarbamate, Compound 6

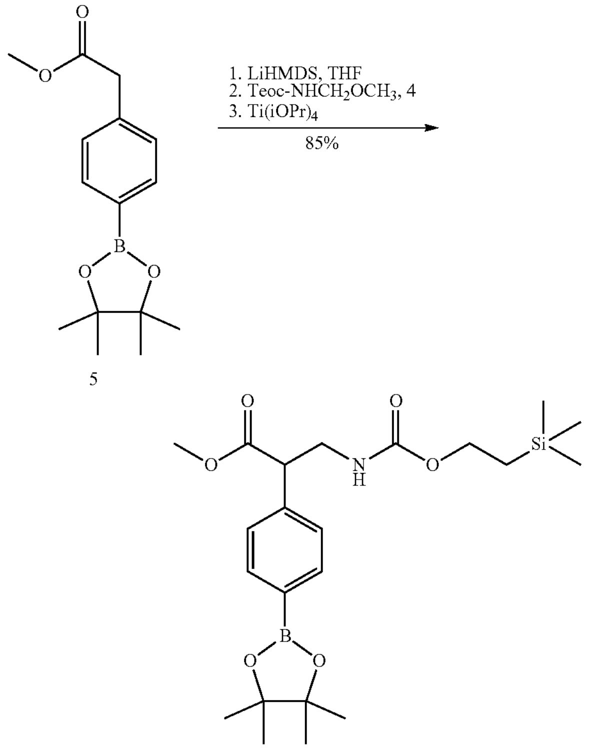

5

6

A 500 mL, round-bottom flask equipped with low-temperature thermometer, gas inlet, and oversized magnetic stir bar was dried under inert atmosphere. The flask was charged with 75 mL anhydrous THF and cooled to −20 C. using a dry ice/isopropanol bath. The flask was then charged with LiHMDS (94.9 mL of a 1M solution in THF, 94.9 mmoles) by syringe and the orange solution was chilled to −60 C. With vigorous stirring, the flask was then carefully charged over 25 min by syringe with (4-methoxycarbonylmethyl) phenylboronic acid pinacol ester (13.67 g, 49.4 mmoles, Combiblocks FM.2401) as a solution in 40 mL anhydrous THF, maintaining the temperature below −53 C., and adding 33 mL additional THF to maintain fluidity of the gelled reaction mixture. 2-trimethylsilylethyl N-(methoxymethyl) carbamate (8.45 g, 41.2 mmoles) was added by syringe over 10 min as a solution in THF (combined volume with 25 mL). The temperature was maintained at −57 to −60 C. during the addition. $Ti(OiPr)_4$ (26.05 g, 91.7 mmoles in THF, total volume of 66 mL) was added over 30 min, maintaining the temperature between −60 to −56 C. during the addition. The reaction mixture turned deep orange and remained opaque. The mixture was stirred for 1.5 hours at −64 to −60 C. Over approx. 30 min, the mixture rose to −7 C., at which time it became reddish brown in color. After another ca. 30 min, the temperature rose to 1 C., at which time the flask was placed in an ice/salt bath. After 15 min, the temperature rose to 4 C., at which time, the reaction was monitored by TLC and deemed to be nearly complete. The mixture was stirred another ca. 30 min at 4-5 C. The mixture was poured, with mixing, into 100 mL ice-chilled 10% HCl in a 1 L glass beaker. The organic phase was diluted with ether and separated. The aqueous phase was extracted twice with 200 mL ether. The organic phases were combined, washed twice with brine, and dried over $MgSO_4$. Solvent was removed in vacuo to yield 23.4 g crude product as an amber oil. Flash column chromatography on silica gel using a hexane/ethyl acetate gradient (0-50%), provided 15.68 g of a viscous oil, 84.7% yield. $^1H$ NMR (500 MHz, $CDCl_3$): δ 7.76 (d, 2H), 7.23 (d, 2H), 4.95 (br, 1H), 4.10 (m, 2H), 3.90 (m, 1H), 3.64 (s, 3H), 3.60 (m, 1H), 3.55 (m, 1H), 1.31 (s, 12H), 0.95 (m, 2H), 0.01 (s, 9H). TLC (4:1 hexanes:ethyl acetate, UV) Rf=0.26, Rf of starting Bpin ester=0.4.

Preparation of Compound 7

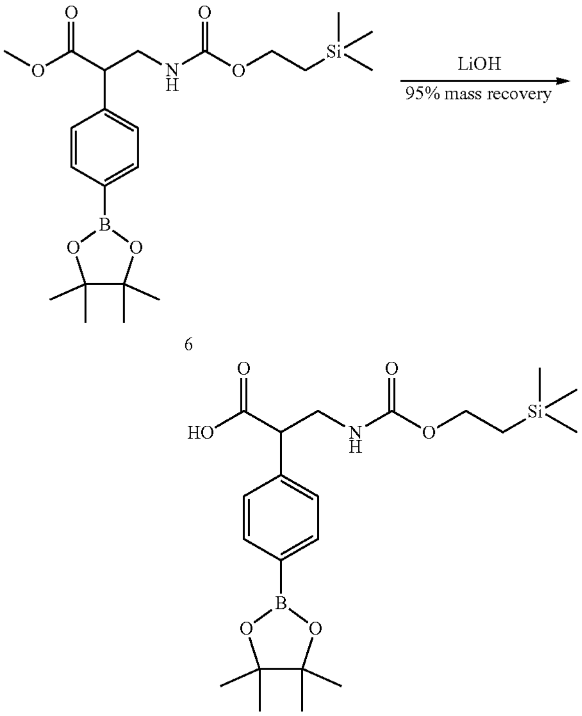

6

7

Ester 6 (15.05 g, 33.5 mmoles) was dissolved in 46 mL THF and chilled on ice. Aqueous lithium hydroxide (42 mL of a 2N solution, 84 mmoles) was added dropwise over 10 min. The bath was removed, and the mixture was stirred vigorously so as to create a fine emulsion. After ca. 20 min, the initial two-phase system became one transparent phase. The reaction was monitored by TLC. After 3 hours, the mixture was chilled on ice and carefully acidified with 40 mL 10% HCl. As product precipitated, ether (150 mL) was added to redissolve the precipitate. The organic phase was separated, and the aqueous phase was extracted twice with ether. The organic phases were combined, and dried with brine and then solid $MgSO_4$. The solution was decanted and solvent was removed in vacuo to provide 13.85 g (95% mass balance) of an electrostatic, flaky, white solid, approximately 90% pure by TLC. This material was used in the next step without purification. An analytical sample was purified by flash chromatography on a DIOL column. The product crystallizes out of hexanes containing 5-10% ethyl acetate. $^1H$ NMR (500 MHz, DMSO): δ12.5 (br, 1H), 7.64 (d, 2H), 7.28 (d, 2H), 7.09 (t, 1H), 3.99 (m, 2H), 3.79 (m, 1H), 3.51 (m, 1H), 3.31 (m, 1H), 1.30 (s, 12H), 0.86 (m, 2H), 0.01 (s, 9H) ppm. TLC (1:1 hexanes:ethyl acetate, UV, alizarin @ 366 nm, phosphomolybdic acid) $R_f$=0.53, $R_f$ of starting ester=0.7.

Preparation of Compound 8

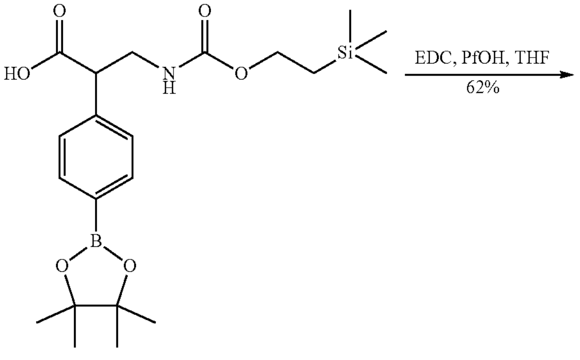

7

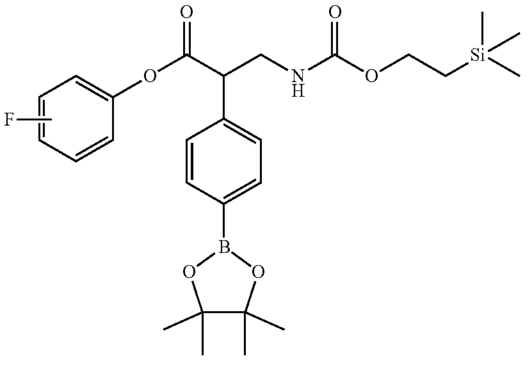

8

Carboxylic acid 7 (13 g, 29.9 mmoles) was dissolved in 40 mL dry THF. Dimethylaminopyridine (100 mg, 0.83 mmoles) as added, followed by a solution of pentafluorophenol (6.84 g, 37.2 mmoles) in 20 mL dry THF. The vessel was chilled in an ice bath and solid 1-ethyl-3-(3-dimethylaminopropyl) carbodiimide-HCl (7.53 g, 39.9 mmoles). An additional 20 mL THF was used to rinse the solids into the reaction mixture. The bath was removed and mixture was stirred at room temperature for 20 hours. Approximately 10 mL water and 150 mL ether were added. The organic phase was removed from the watery residue, which was extract twice more with ether. The organic phases were combined, washed with 5% HCl, 1N $NaHCO_3$, and finally brine. The solution was dried over $MgSO_4$ and solvent was removed in vacuo at 50 C., adding pentane to drive off residual THF. The crude product was obtained as a thick colorless oil, 20.35 g. The product was purified by flash chromatography on silica sing a 0/25% hexanes/ethyl acetate gradient to provide 11.11 g (61.8% yield) of a thick colorless oil. $^1$H NMR (500 MHz, $CDCl_3$): δ 7.80 (d, 2H), 7.31 (d, 2H), 4.95 (br t, 1H), 4.30 (br t, 1H), 4.13 (m, 2H), 3.20 (m, 1H), 3.12 (m, 1H), 1.31 (s, 12H), 0.94 (m, 2H), 0.01 (s, 9H) ppm. TLC (4:1 hexanes: ethyl acetate, alizarin @ ambient light or 366 nm, phosphomolybdic acid) $R_f$=0.32, $R_f$ of starting carboxylic acid=0.04.

Preparation of Compounds 9a and 9b

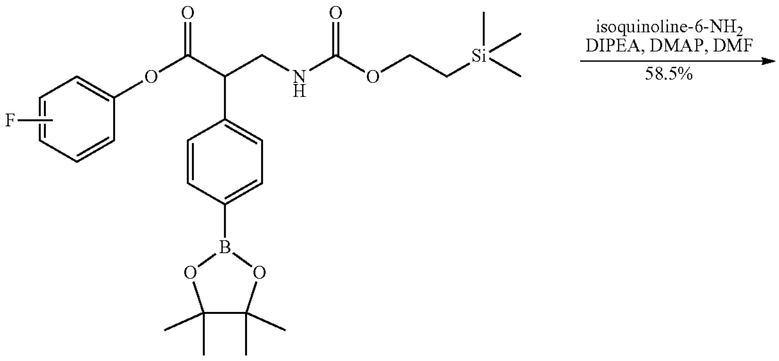

8

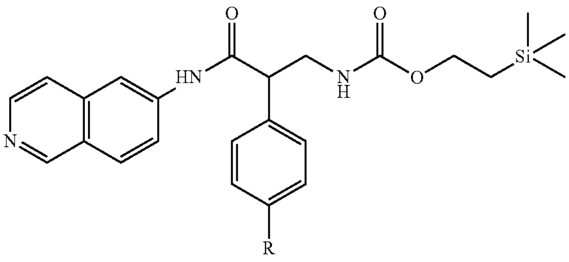

9a R = Bpin
9b R = $B(OH)_2$

A 20 mL vial was charged with isoquinoline-6-$NH_2$ (389.3 mg, 2.7 mmoles) and anhydrous DMF (3.67 g, 3.86 mL). The mixture was capped and sonicated to complete dissolution. Dimethylaminopyridine (3.5 mg, 0.028 mmoles) was added, followed by diisopropyl, ethylamine (695 mg, 5.38 mmoles), and again the mixture was gently agitated to achieve complete dissolution. A separate vial was charged with compound 8 (1.57 g, 2.68 mmoles) and a stir bar. With moderation of exotherm by use of a room temperature water bath, the DMF solution was slowly added to neat 8. The vial was tightly capped and the mixture was stirred for 5 days at room temperature. A fine precipitate formed. The reaction mixture was diluted to homogeneity with 10 mL ether, and added dropwise to aqueous phosphate buffer (0.5M, pH 6-7, 40 mL) and ether (5 mL) in an Erlenmeyer flask with stir bar, in a room temperature water bath. The biphasic mixture was stirred vigorously for 40 min. a fine light-yellow precipitate developed in the ether phase. Stirring was stopped, the aqueous phase was removed, and replaced with fresh 20 mL 0.5M phosphate buffer. Stirring was resumed for another 20 min, during which time, an emulsion of the precipitate and the aqueous phase developed. Hexanes (20 mL) were added and mixing was continued for another 40 min. The precipitate grew more voluminous and the emulsion partially resolved. The mixture was filtered through a plastic fritted funnel. The collected solids were washed portionwise with ca. 30 mL water, followed by a total of 30 mL 1:1 hexanes:ether in 3 portions. A fine off-white powder was collected, which after drying in air, provided a mixture of predominantly 9a with 9b as a minor constituent (860 mg, 58.5%). Additional product could be obtained from the filtrate by extraction of the secondary wash aqueous phases with dichloromethane and ether, concentration and redissolution to ether alone, washing repeatedly with phosphate buffer, and precipitation or crystallization from pentane/ether mixtures. Compounds 9a and 9b were purified and separated from one another in both analytical and semi-preparative quantities by flash chromatography, although this is not strictly necessary for subsequent use in synthesis. A HILIC DIOL column was employed using a 0-100% hexanes-ethyl acetate gradient, followed by step up to 100% methanol. The substances were also purified by reverse-phase chromatography. $^1H$ NMR (500 MHz, DMSO) Compound 9a: δ 10.58 (s, 1H), 9.15 (s, 1H), 8.38 (m, 2H), 8.02 (m, 1H), 7.66 (m, 2H), 7.64 (d, 2H), 7.41 (d, 2H), 7.29 (t, 1H), 4.15 (m, 1H), 4.0 (t, 2H), 3.62 (m, 1H), 3.32 (m, 1H), 1.27 (s, 12H), 0.87 (m, 2H), 0.03 (s, 9H) ppm. Compound 9b: δ 10.56 (s, 1H), 9.16 (s, 1H), 8.39 (s, 2H), 8.03 (d, 1H), 7.99 (s, 2H), 7.70 (m, 2H), 7.75 (d, 2H), 7.37 (d, 2H), 7.3 (t, 1H), 4.10 (m, 1H), 4.01 (t, 2H), 3.60 (m, 1H), 3.33 (m, 1H), 0.86 (t, 2H), 0.02 (s, 9H) ppm. TLC (ethyl acetate, UV-254 & 366 nm, alizarin @ 366 nm) Rf=0.48 (9a), 0.29 (9b), Rf of starting Pf ester=0.71, Rf of isoquinoline-6-NH2=0.18. The product has a distinct pinkish hue @366 nm with alizarin staining Preparation of Compound 10 from Compound 9a.

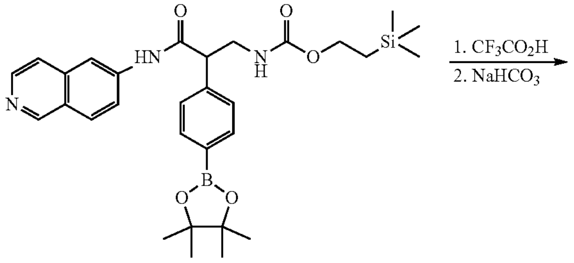

9a

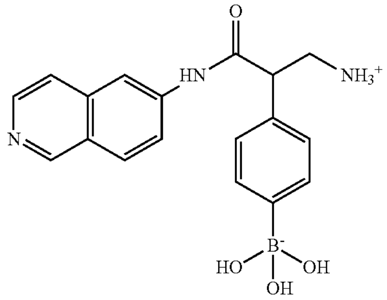

10

Compound 9a/9b (ca. 1:1) (46.3 mg, 0.078 mmoles) was dissolved in 745 mg trifluoroacetic acid and stirred at room temperature for 2½ hours. The mixture was chilled on ice. Aqueous 1N $NaHCO_3$(ca. 10 mL) was added TO the reaction mixture until it became cloudy and the pH was brought up to 8, as checked by pH paper. After stirring 15 min, a solid formed and was collected in a small filtration funnel. This solid was dissolved in methanol. Slow evaporation resulted in tan, spar-like crystals of a first lot of compound 10 (7.7 mg). In the meantime, more solids precipitated from the aqueous filtrate. This secondary solid was allowed to settle and washed twice with distilled water. After exposure to high vacuum, a second lot of compound 10 was collected (5.4 mg) as a white, electrostatic powder. $^1H$ NMR (500 MHz, DMSO): δ10.5 (br s, 1H), 9.15 (s, 1H), 8.40 (s, 2H), 8.02 (m, 2H), 8.01 (s, 1H), 7.73 (d, 2H), 7.70 (m, 2H), 7.36 (d, 2H), 3.80 (m, 1H), 3.30 (m, 1H), 2.84 (m, 1H), 2.54 (s, 1H) ppm. LC-MS: 336 (M+1). TLC (methanol/1% TEA, UV-254 & 366 nm, alizarin @366 nm) Rf=0.12. Compound 10 has a distinct pinkish hue @366 nm with alizarin staining.

Preparation of Compound 10•2HCl from Compound 9b

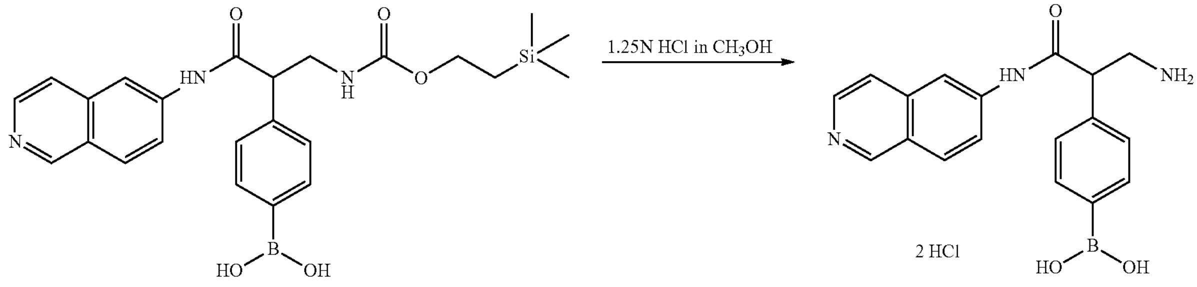

9b 10-2HCl

Compound 9b (18.3 mg, 0.038 mmoles) was dissolved in 747 mg 1.25M HCl in methanol, and heated at 60 C. for 3 hours. The solvent as evaporated under a stream of N2. The residue was triturated thrice from 1 mL ether both with the aid of a spatula and sonication. Brief centrifugation was used to assist precipitation of the solids. A powdery tan residue developed. This was crystallized from ether/methanol in a freezer (−13 C.) and washed with ether to yield compound 10-2HCl as a tan solid (9.1 mg, 58.4%). 1H NMR (500 MHz, DMSO): δ 11.55 (s, 1H), 9.65 (s, 1H), 8.70 (s, 1H), 8.55 (d, 1H), 8.42 (d, 1H), 8.31 (d, 1H), 8.2 (br s, 2H), 8.1 (br, 3H), 8.08 (d, 1H), 7.80 (d, 2H), 7.46 (d, 2H), 4.39 m, 1H), 3.58 (m, 1H), 3.11 (m, 1H) ppm. TLC (1:1 ethyl acetate:methanol, 0.5% FA, UV-254 & 366 nm, alizarin @ 366 nm) $R_f$=0.26. Compound 10-2HCl has a distinct pinkish hue @366 nm with alizarin staining.

Preparation of Compound 10•2HCl from Compound 9a.

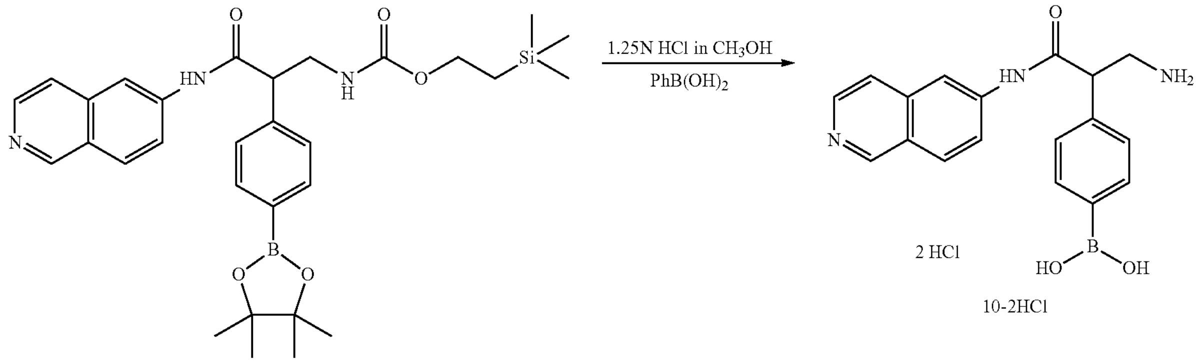

10-2HCl

9a

Compound 9a (40.7 mg, 0.072 mmoles) and phenylbornic acid (41 mg, 0.34 mmoles) were dissolved in 1.25M HCl in methanol (1.6 g, 1.92 mL) and heated at 60 C. The reaction was monitored by TLC. At 4.5 hours, additional phenylbornic acid (32.6 mg, 0.27 mmoles) and methanolic HCl (656 mg, 790 mL) were added. After 8 hours, the solvent was evaporated under a steam of N2. The crude product was triturated 4x with ether. The product was crystallized from ca. 2.5 ml 1.5:1 ether:methanol in the freezer (−13 C.) and washed with ether: Compound 10-2HCl was obtained as a tan solid (20.2 mg, 68% yield). TLC (1:1 ethyl acetate: methanol, 0.5% FA, UV-254 & 366 nm, alizarin @366 nm) $R_f$=0.26. TLC is identical to that of material prepared from 9b. Compound 10-2HCl has a distinct pinkish hue @ 366 nm with alizarin staining.

Example 2

A recrystallized sample of 10, prepared by $HCl/CH_3OH$ hydrolysis, and presumptively a double HCl salt was exposed to high vacuum for an extended period. 1H NMR integration indicated the presence of ⅓ unit methanol and ⅓ unit ether. This sample was subjected to CHN elemental analysis. Additionally, weight % chlorine was determined by titration and weight % boron was determined by ICP-OES (inductively coupled plasma optical emission spectrometry). Elemental Analysis Calculated for $10.2HCl \cdot 1/3Et_2O \cdot 1/3CH_3OH$ $C_{19.66}H_{24.66}BCl_2N_3O_{3.66}$:

C 53.26 H 5.61 B 2.44 Cl 15.99 N 9.48 O 13.23

Found:

C 52.67 H 5.60 B 2.59 Cl 15.99 N 9.43

Calculated for 10.2HCl as boroxine $C_{54}H_{54}B_3Cl_6N_9O_6$:

C 55.43 H 4.65 N 10.77

Found after drying to constant weight:

C 55.00 H 4.83 N 10.40

The elemental analysis of the undesolvated form was consistent with assignment as the double HCl salt, ⅓ etherate, ⅓ methanolate: $10.2HCl \cdot ⅓Et_2O \cdot ⅓CH_3OH$. On this basis, compounds of the disclosure have been assigned as double salts of either HCl or trifluoroacetic acid, unless neutralized after the final deprotection under acidic conditions. The elemental analysis of the form dried to constant weight was consistent with assignment as 10.2HCl in the boroxine form or as the double boronic anhydride ($C_{54}H_{56}B_3Cl_6N_9O_7$: C 54.58 H 4.75 N 10.61):

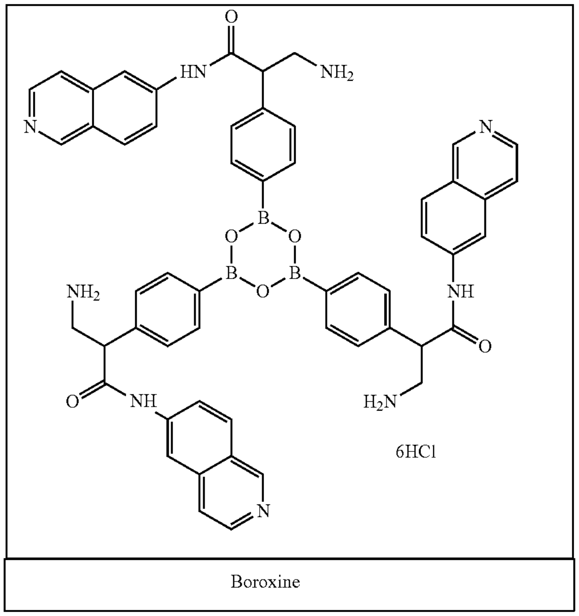

Boroxine

-continued

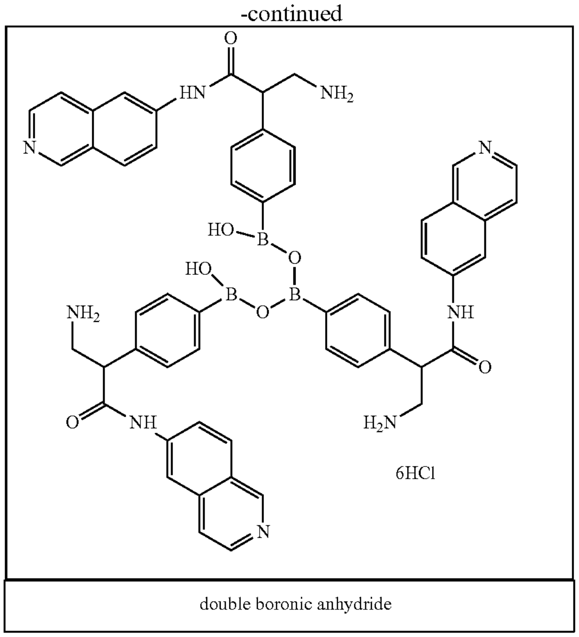

double boronic anhydride

Example 3. Preparation of Boronic Acids I (198-Racemic), II (215-Racemic), & III In this example, variation of the R group is demonstrated, with implications for stability of the Bpin group to hydrolysis, solubility of intermediate F during work-up, and robustness of recrystallization conditions for the final product I, II, & III.

Scheme 2b. Synthesis of Boronic Acids I, II, & III.
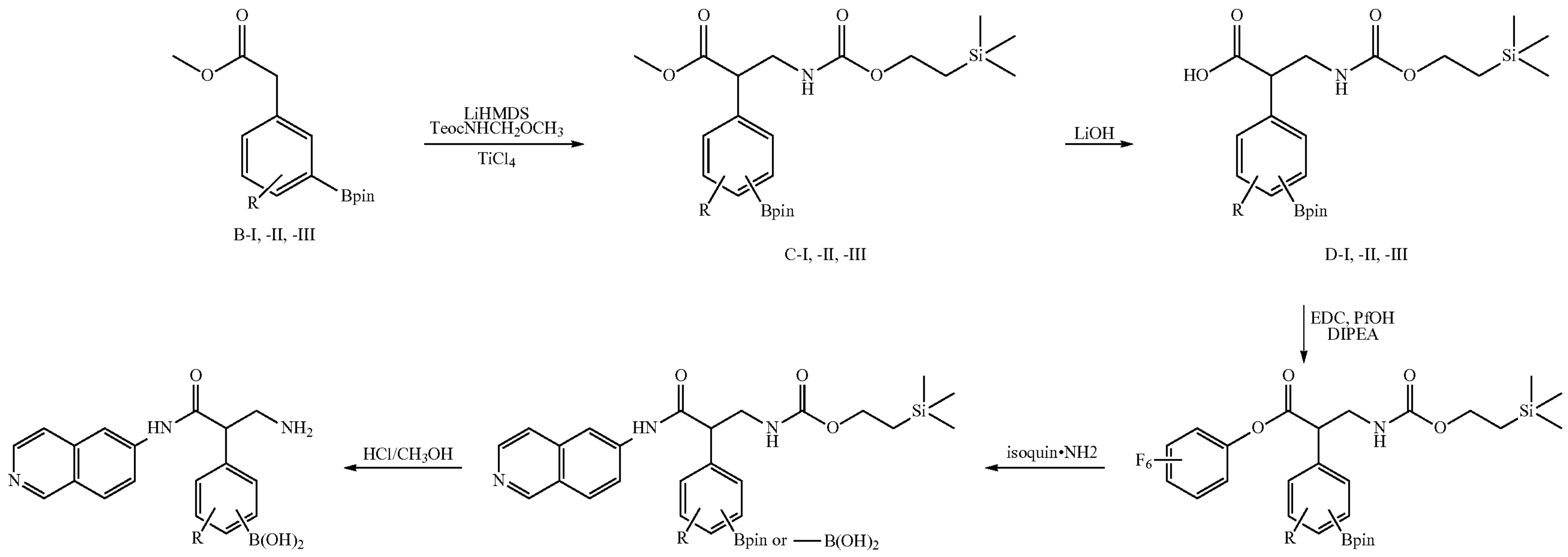
B-I, -II, -III
C-I, -II, -III
D-I, -II, -III
E-I, -II, -III
F-I, -II, -III
I, II, III General experimental procedures are as per Example 1.

3.1. Aminomethylation. Preparation of C-I, -II, & -III

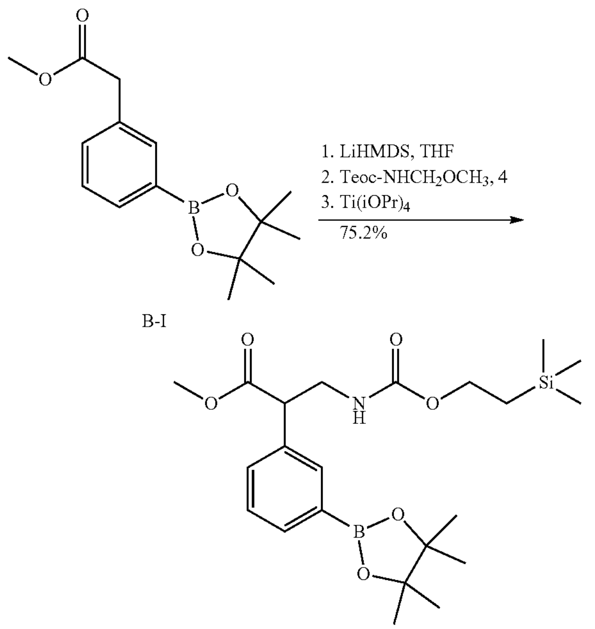

B-I

C-I

A dry 250 mL, 3-neck round-bottom flask equipped with magnetic stirring, low-temperature thermometer, and gas inlet was maintained under argon and charged with anhydrous THF (42 mL). The flask was chilled to −20° C. in a dry ice/isopropanol bath and lithium hexamethyldisilazide (35 mL, 1M in THF) was added. The solution was then chilled to −55° C. and a solution of ester B-I in anhydrous THF (4.93 g, 17.85 mmole, total volume including THF chases=16 mL) was added over 15 min with vigorous stirring, maintaining the temperature below −55° C. The dark orange mixture was stirred for 40 min at <−55° C. Next, a solution of aminal 4 (3.3 g, 16.07 mmole, total volume including THE chases=11.3 mL) was added over 10 min at <−55° C. A stirrable gel formed. THF (5 mL) was added to help break up the gel. The resultant orange-brown translucent solution was stirred for approx. 25 min. Next, $Ti(iOPr)_4$ in anhydrous THF (9.55 g, 33.6 mmole, total volume incl. THF chases=22 mL) was added over 12 min at <−55° C. The reaction mixture turned a deep brick red, and was stirred for another 35 min at <−55° C. The reaction mixture was allowed to warm slowly to −13° C. over a period of 30 min. The flask was then placed in an ice salt bath for 1 hr, during which time the temperature rose gradually to −4.5° C. and the color lightened to orange. The reaction mixture was placed in an ice bath and allowed to warm to 2.5° C. over approx. 30 min, during which time the color lightened further. A TLC check indicated approx. 9:1 product: starting material. After 40 min at 1.5-2.5° C., the ice bath was removed.

Work-Up. The reaction mixture was poured slowly, with stirring, into a slush of 50 mL 10% HCl and an approx. equal volume of ice, chilled in an ice bath. The pH was confirmed to be ca. 1. The organic phase was diluted with ether and removed while the aqueous phase was extracted twice with ether. The organic extracts were combined and dried first with brine and then with solid $MgSO_4$. Solvent was removed in vacuo, leaving the crude product as a yellow oil. The product was purified by silica gel flash chromatography using a 0-40% H:EA gradient. After solvent removal in vacuo, C-I was obtained as a colorless viscous oil (5.37 g, 75.2%). TLC (4:1 H:EA) $R_f$=0.28, visualization by PMA superior to $UV_{254}$.

TABLE 3

Characterization of certain embodiments of synthesis intermediate C.

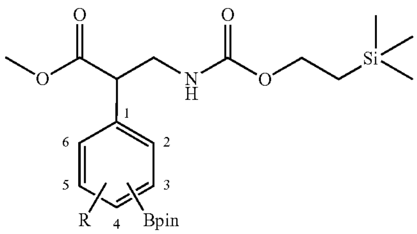

| R | Starting Bpin-Ester (B) | Product Teoc, Bpin-ester (C) | Yield | $^1$H NMR (500 MHz) |
|---|---|---|---|---|
| 3-Bpin | ArkPharm AK-84242 | C-I | Oil, 5.37 g, 75.2% | ($CDCl_3$) δ 7.70 (1H, m), 7.66 (1H, s), 7.32 (2H, m), 4.95 (1H, t), 4.10 (2H, m), 3.87 (1H, m), 3.65 (3H, s), 3.62 (1H, m), 3.55 (1H, m), 1.31 (12H, s), 0.95 (2H, t), 0.00 (9H, s) ppm |
| 3-$CH_3$, 4-Bpin | SynInnova SA-1308 | C-II | Oil, 1.2 g, 87.9% | (DMSO-$d_6$) δ 7.59 (1H, d), 7.15 (1H, t), 7.05 (2H, m), 4.0 (2H, t), 3.85 (1H, t), 3.59 (3H, s), 3.55 (1H, m), 3.30 (1H, m), 2.44 (3H, s), 1.29 (9H, s), 0.87 (2H, m), 0.01 (9H, s) ppm |
| 2-F, 4-Bpin | SynInnova SA-463 | C-III | Oil, 663 mg, 44.8% | ($CDCl_3$) δ 7.51 (1H, d), 7.46 (1H, d), 7.23 (1H, t), 5.05 (1H, t), 4.12 (2H, m), 4.12 (1H, m), 3.66 (3H, s), 3.66 (1H, m), 3.55 (1H, m), 1.31 (12H, s), 0.93 (2H, m), 0.01 99H, s) ppm |

3.2. Hydrolysis of Methyl Ester. Preparation of D-I, -II, & -III

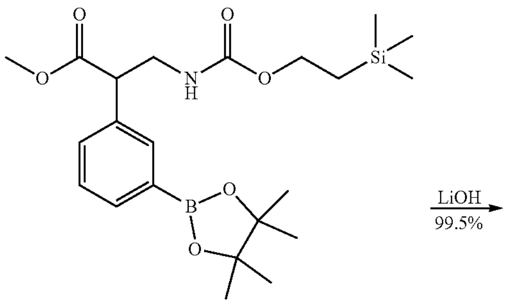

C-I

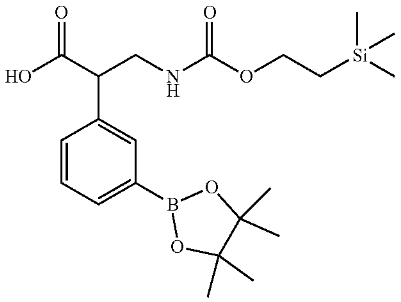

D-I

Ester C-I (4.42 g, 9.83 mmoles) was dissolved in 13.5 mL THF in a round-bottom flask with magnetic stirring and ice-bath cooling. A pre-chilled solution of aq. LiOH (12.3 mL, 2N) was added and the reaction was placed under an argon atmosphere. After an hour and 15 min, the ice bath was removed. The originally biphasic mixture become monophasic. At 2 hr and 15 min total reaction time, TLC indicated a nearly complete reaction. The mixture was chilled on ice and diluted with 30 mL ether. Aqueous 10% HCl (9 mL) was added dropwise to the stirred solution, resulting in a pH=1. The organic phase was removed and the aqueous phase was extracted twice with ether. The combined organic extracts were dried with two brine washes followed by solid $MgSO_4$.

The solution was decanted from the salts and solvent was evaporated in vacuo. Exposure to high vacuum resulted in a white semi-crystalline foam of D-I (4.26 g, 99.5%). An analytical sample was purified by flash chromatography on a DIOL column using a 0-100% H:EA gradient. TLC (1:1 H:EA) $R_f$=0.6, visualized with PMA.

TABLE 4

Characterization of certain embodiments of synthesis intermediate D.

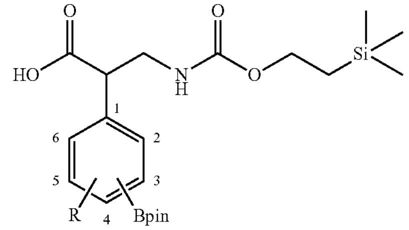

| R | Starting Teoc Bpin-Ester (C) | Product Teoc Bpin-acid (D) | Yield | $^1$H NMR (500 MHz, DMSO-$d_6$) |
|---|---|---|---|---|
| 3-Bpin | C-I | D-I | semi-solid, 4.26 g, 99.5% | δ 12.5 (1H, br), 7.58 (2H, d), 7.38 (2H, m), 7.10 (1H, t), 3.99 (2H, t), 3.79 (1H, t), 3.51 (1H, m), 3.26 (1H, m), 1.31 (12H, s), 0.87 (2H, t), 0.00 (9H, s) ppm |
| 3-$CH_3$, 4-Bpin | C-II | D-II | semi-solid, 960 mg, 102% mass balance | — |
| 2-F, 4-Bpin | REH-5-48 C-III | D-III | 602 mg, 96% | — |

3.3. Esterification to Pentafluorophenyl Ester. Preparation of Compound E-I, -II, -III

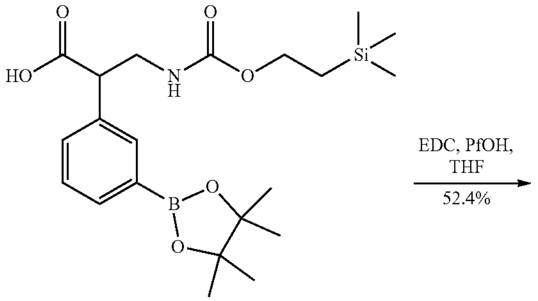

D-I

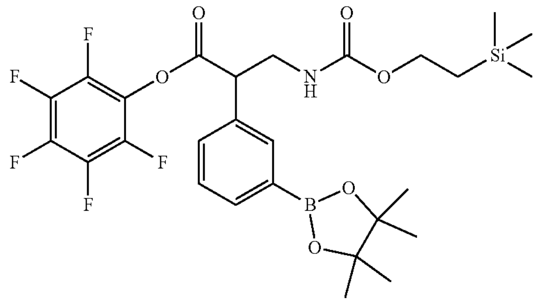

E-I

Carboxylic acid D-I (4.15 g, 9.52 mmole) was placed in a 250 mL round bottom flask with a magnetic stir bar. Dimethylaminopyridine (28 mg, 0.23 mmole) was added, followed by a solution of pentafluorophenol (2.31 g, 12.55 mmole) in 10 mL anhydrous THF. The solution was placed in an ice bath and EDC (2.55 g, 13.3 mmole) was added portion-wise with a spatula. The sides of the vessel were rinsed down with an additional 6 mL THF. The EDC did not entirely dissolve but remained as a white suspension until gummy reaction by-products began to appear. The reaction was placed under an argon atmosphere, the ice bath was removed, and the mixture was stirred overnight. The reaction was monitored by TLC.

Work-Up. After approximately 20 hr, ether (40 mL) and water (1.5 mL) were added with ice bath chilling and stirring. The biphasic mixture was stirred for 5-10 min and the ether phase was pipetted away from a viscous residue. The residue was extracted twice with ether. The organic extracts were combined, washed twice with 5% aq. HCl, and dried with brine followed by solid $MgSO_4$. Ether was removed in vacuo to yield 6.25 g of a thick colorless oil. The crude product was purified by silica gel flash chromatography using a 0-30% H-EA gradient. Solvent was removed in vacuo. E-I yield: 3.0 g (52.4%), thick colorless oil. TLC: (4:1 H:EA) $R_f$=0.44, yellow with alizarin staining @366 nm.

TABLE 5

Characterization of certain embodiments of synthesis intermediate E.

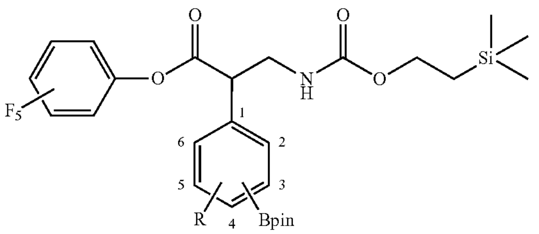

| R | Starting Teoc Bpin-Acid (D) | Product Teoc Bpin-Pf Ester (E) | Yield | 1 NMR (500 MHz) |
|---|---|---|---|---|
| 3-Bpin | D-I | E-i | Oil 3.0 g. 52.4% | (DMSO-$d_6$): δ 7.67 (1H, m), 7.49 (1H, d), 7.43 (1H, t), 7.31 (1H, t), 4.39 (1H, t), 4.02 (2H, m), 3.71 (1H, m), 3.39 (1H, m), 1.30 (12H, s), 0.87 (2H, m), 0.00 (9H, s) ppm |
| 3-$CH_3$-4-Bpin | D-II | E-II | Oil, 1.0 g, 76.2%: | (DMSO-$d_6$): δ 7.65 (1H, d), 7.33 (1H, t), 7.17 (1H, s), 7.16 (1H, d), 4.35 (1H, m), 4.02 (2H, m), 3.70 (1H, m), 3.39 (1H, m), 2.47 (3H, s), 1.29 (12H, s), 0.88 (2H, m), 0.00 (9H, s) ppm |
| 2-F, 4-Bpin | D-III | E-III | Oil, 238 mg, 28.9%: | (DMSO-$d_6$): δ 7.54 (1H, d), 7.47 (1H, t), 7.41 (1H, d),7.30 (1H, t), 4.63 (1H, t), 4.00 (2H, m), 3.8 (1H, m), 3.5 (1H, m), 1.30 (12H, s), 0.86 (2H, m), 0.01 (9H, s) ppm |

3.4. Amide Coupling Using Pentaflurophenyl Ester. Preparation of F-I, -II, -III

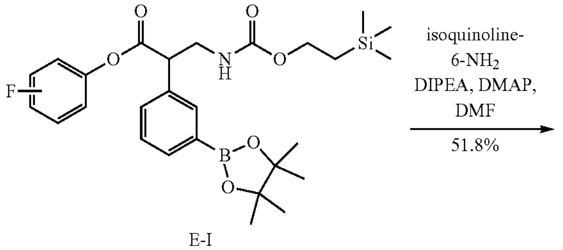

E-I

-continued

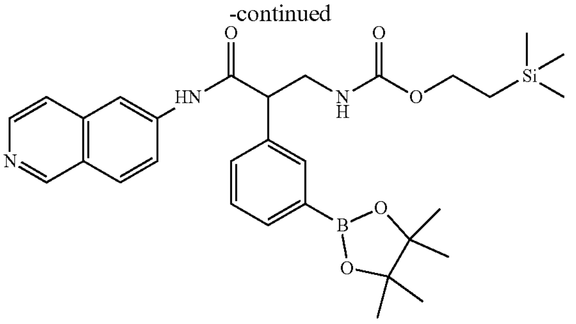

F-I

To a 40 mL capped vial with stir bar were added pentafluorophenyl ester E-I (3.0 g, 4.99 mmole), isoquinoline-6-$NH_2$ (702 mg, 4.87 mmole), DMF (anhydrous, 6.35 g), dimethylaminopyridine (7.3 mg, 0.056 mmole), and diisopropylethylamine (1.23 g, 9.5 mmole). Solids were dissolved with the aid of sonication. The vial was placed in a room temp water bath to dampen any exotherm. The sides of the vial were rinsed down with 200 mL DMF and the reaction mixture was stirred magnetically for 3.5 days at room temperature.

Work-Up: Ether (20 mL) was added to the stirred solution, resulting in slight haziness. This diluted reaction mixture was then partitioned 3× between 0.5M aq. phosphate buffer (pH 6-7, total 140 mL) and ether (25 mL) so as to remove DMF, isoquinoline-6-$NH_2$, and pentafluorophenol. Mixing was achieved by gentle magnetic stirring over 20-45 min periods for each extraction. Pentane (80 mL) was added to the ethereal solution, resulting in precipitation of a gum. This was vigorously triturated with a spatula and sonication to yield a granular solid. The solid was transferred to a Chemrus plastic fritted funnel and washed thrice with a total of 80 mL water and thrice with a total of 40 mL 2:1 pentane:ether. The solid was collected and allowed to dry on the open bench for several days. A fine, light yellow powder was obtained: 1451 mg, 51.8% yield. The product contains 20-30% of the corresponding boronic acid, as ascertained by TLC and NMR. TLC (EA) $R_f$=0.5, boronic acid $R_f$=0.1; (2:1 EA:M, 0.5% formic acid) $R_f$=0.81.

An analytical sample of F-I as well as preparatory samples of F-II & F-III were purified on a DIOL column using a 0-100% H:EA gradient, optionally followed by $CH_3OH$.

TABLE 6

Characterization of certain embodiments of synthesis intermediate F.

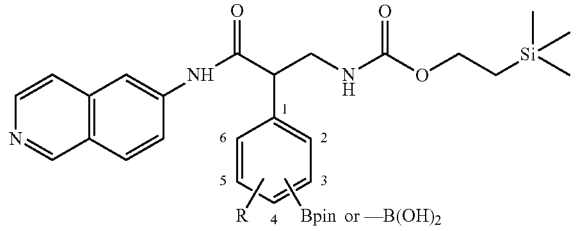

| R | Starting Teoc Bpin-Pr Ester (E) | Product Teoc Bpin-Isoquinoline (F) | Yield | $^1$H NMR (500 MHz, DMSO-$d_6$) |
|---|---|---|---|---|
| 3-Bpin | E-I | F-I | powder, 1451 mg, 51.8% | δ 10.60 (1H, s), 9.18 (1H, s), 8.44 (2H, d), 8.06 (1H, d), 7.78 (1H, s), 7.73 (1H, d), 7.68 (1H, d), 7.59 (1H, d), 7.55 (1H, d), 7.40 (1H, t), 7.33 (1H, t), 4.15 (1H, m), 4.05 (2H, m), 3.65 (1H, m), 3.35 (1H, m), 1.33 (12H, s), 0.88 (2H, m), 0.01 (9H, s) ppm (Sample REH-5-46-1) |
| 3-$CH_3$, 4-Bpin | E-II | F-II | solid, 150 mg, 57.5% | δ 10.58 (1H, s), 9.18 (1H, s), 8.43 (2H, m), 8.06 (1H, d), 7.73 (1H, d), 7.69 (1H, d), 7.62 (1H, d), 7.31 (1H, t), 7.23 (2H, m), 4.03 (3H, m), 3.61 (1H, m), 3.30 (1H, m), 2.46 (3H, s), 1.30 (12H, s), 0.89 (2H, m), 0.00 (9H, s) ppm |
| 2-F, 4-Bpm | E-III | F-III | solid, 29 mg, 14% | δ 10.65 (1H, s), 9.19 (1H, s), 8.43 (2H, d), 8.07 (1H, d), 7.74 (2H, m), 7.52 (2H, m), 7.39 (1H, m), 4.45 (1H, m), 4.03 (2H, m), 3.65 (1H, m), 3.4 (1H, m), 1.32 (12H, s), 0.88 (2H, m), 0.01 (9H, s) ppm |

3.5. Teoc and Bpin Deprotection. Preparation of I, II, and III

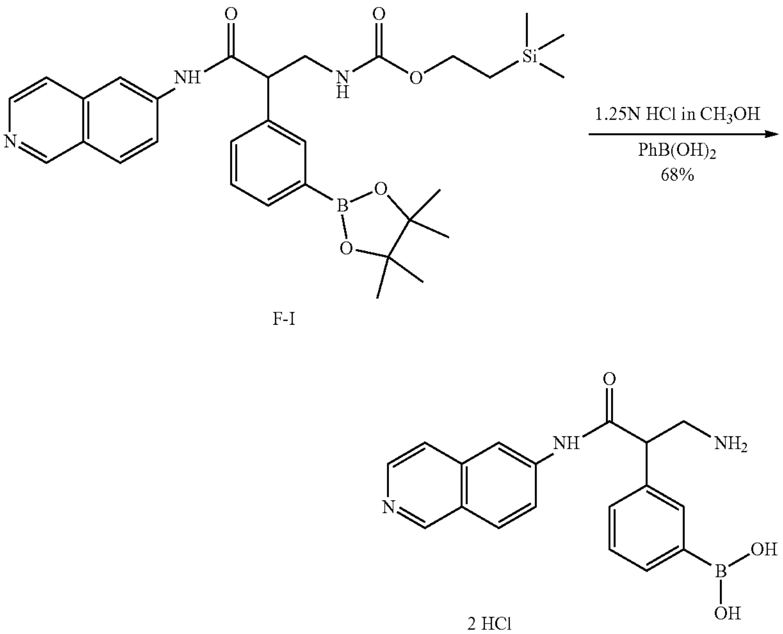

F-I

2 HCl

I.2HCl
(198-racemic)

A 100 mL round bottom flask was charged with 500 mg (0.89 mmoles) F-I, 1089 mg (8.9 mmoles) phenylboronic acid, and finally, 34 mL 1.25M HCl in $CH_3OH$. The mixture was stoppered so as to permit pressure relief, and heated at 60° C. in a water bath for a total of 17.5 hr, while monitoring by TLC. A total of 18 mL $HCl/CH_3OH$ was added portion-wise at regular time intervals.

The solvent was removed in vacuo in a 65° C. water bath, using ether chases to drive off methanol. Residual solvent was evaporated with a stream of argon to provide a light orange paste. This solid was triturated with sonication 6× with ether to remove phenylboronic acid. The solid residue was taken up in approximately 5 mL methanol at room temperature, drawn away from solid contaminants, and transferred to a screw-cap vial. Ether (ca. 5 ml) was added dropwise with swirling, during which time, precipitation commenced. After 5 min at room temp, the vial was capped and placed in a freezer. After >16 hr, solids were collected. In this manner, several recrystallizations from methanol/ether were conducted. Separately as a final step, two crops of the product were each washed with ether and dried under high vacuum to provide a total of 258.5 mg (68%) I.2HCl as an off-white powder. TLC (2:1 EA:M, 0.5% formic acid) $R_f$=0.15, yellow by alizarin staining under ambient light, pink @366 nm.

TABLE 7

Characterization of certain embodiments of the invention.

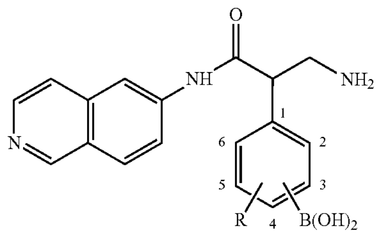

| R/ $B(OH)_2$ | Starting Teoc Bpin-Isoquinoline (F) | Product $NH_2$, $B(OH)_2$, isoquinoline | Yield | $^1H$ NMR (500 MHz, DMSO-$d_6$) |
|---|---|---|---|---|
| 3-$B(OH)_2$ | F-I | I•2HCl 198-racemic | solid, 258 mg, 68% | δ 11.52 (1H, s), 9.63 (1H, s), 8.67 (1H, s), 8.49 (1H, d), 8.38 (1H, d), 8.28 (1H, d), 8.21 (3H, br), 8.05 (1H, d), 7.81 (1H, s), 7.68 (1H, d), 7.53 (1H, d), 7.28 (1H, t), 4.34 (1H, m), 3.54 (1H, m), 3.02 (1H, m) ppm |
| 3-CH, 4-$B(OH)_2$ | F-II | II•2HCl 215-racemic | solid, 35 mg, 32% | δ 11.61 (1H, 2s), 9.69 (1H, s), 8.74 (1H, s), 8.56 (1H, d), 8.45 (1H, d), 8.35 (1H, d), 8.26 (3H, br), 8.12 (1H, d), 7.45 (1H, d), 7.25 (1H, d), 7.24 (1H, s), 4.35 (1H, m), 3.62 (1H, m), 3.06 (1H, m), 2.40 (3H, s) ppm |
| 2-F, 4-$B(OH)_2$ | F-III | III•2HCl | solid, 2 mg, 10% | δ 11.46 (1H, s), 9.70 (1H, s), 8.81 (3H, br), 8.73 (1H, s), 8.56 (1H, d), 8.44 (1H, d), 8.36 (1H, m), 8.24 (2H, br) 8.07 (1H, d), 7.61 (2H, m), 7.43 (1H, t), 4.63 (1H, m), 3.11 (1H, m), 3.51 (1H, m) ppm |

Example 4

This example demonstrates preparation of starting aryl Bpin compounds, direct amide coupling using the BOP coupling agent, generation of a target compound using HCl without a boronic acid scavenger, and generation of a target compound using trifluoroacetic acid.

Scheme 2c. Synthetic of Boronic Acids IV, V, VI, & VII.

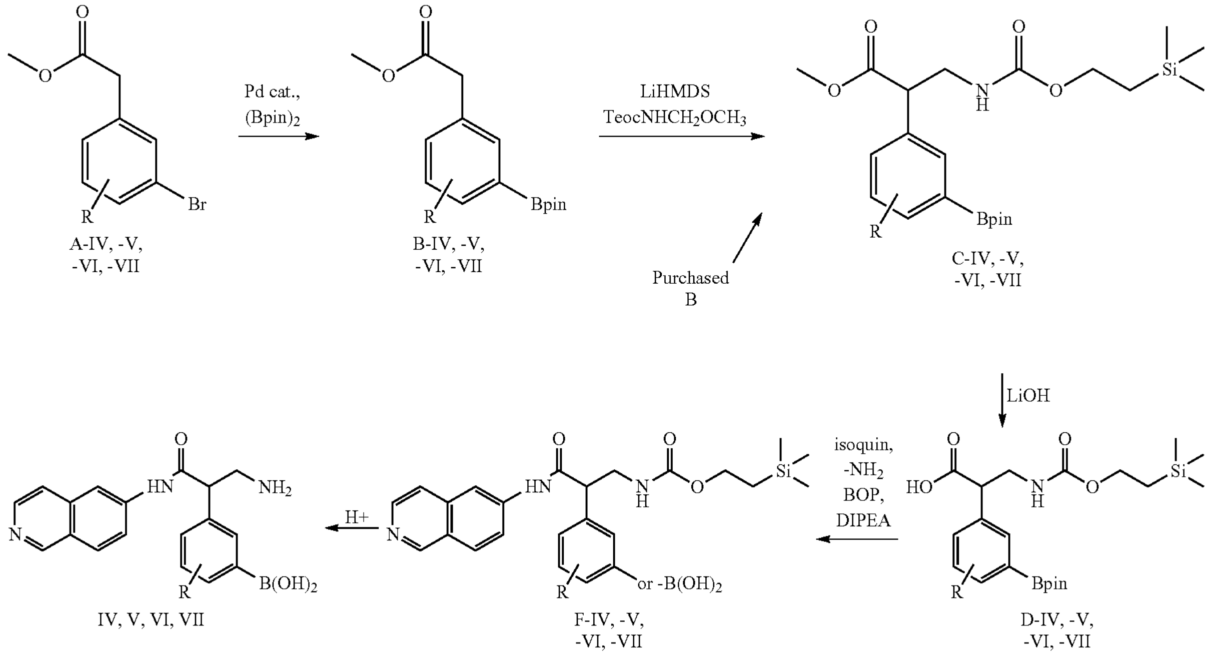

$^1$H NMR Spectra

A 600 MHz spectrum of compound C-V was taken on a Bruker Avance instrument. Otherwise, 1H NMR spectroscopy was performed by Novatia LLC, Newtown, PA on a Bruker 500 MHz NMR spectrometer.

LC-MS

LC-MS was performed using a PE SCIEX API 150 EX, by ESI ionization.

4.1 Esterification. Preparation of methyl 2-(3-bromo-4-methylphenyl)acetate

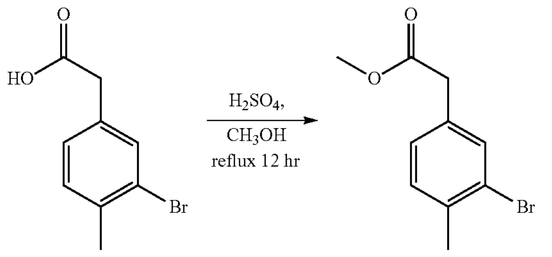

A-IV

A mixture of 2-(3-bromo-4-methylphenyl) acetic acid (2 gm, Combi-blocks HB-7249) in methanol (30 mL) and 0.2 ml conc. $H_2SO_4$ was heated at 65° C. for 12 hr. The reaction was monitored by TLC. The mixture was allowed to cool to room temperature. The solvent was removed in vacuo at 45° C. and diluted with 10 mL solution of saturated sodium bicarbonate and 100 mL of ethyl acetate. The aqueous layer was separated and back-extracted with 50 mL of ethyl acetate, and the combined organic layers were dried over $MgSO_4$, filtered into a 500 mL, round-bottom flask, and concentrated on a rotary evaporator under reduced pressure to yield 2.05 g of ester A-IV as a viscous oil, TLC (4:1 H:EA, UV) $R_f$=0.65, $R_f$ of starting carboxylic ester=0.20.

4.2. Bpinylation. Preparation of B-IV, -V, -VI, & -VII

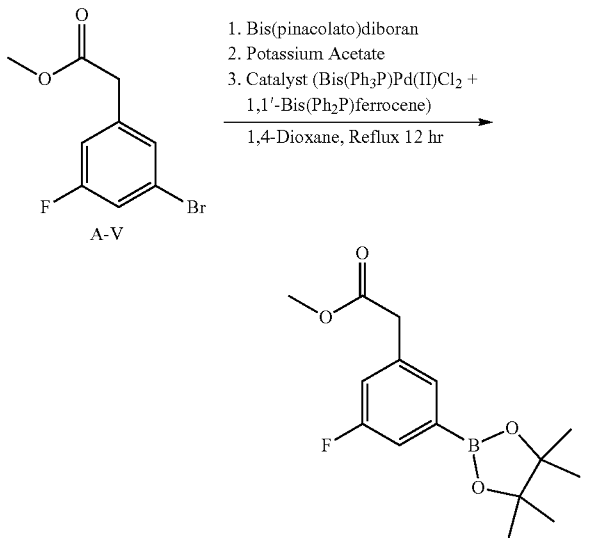

B-V

A 500-mL, round-bottom flask equipped with a magnetic stir bar was charged with methyl (3-bromo-5-fluorophenyl) acetate (A-V) (10 g, 40.5 moles, Combi-blocks; CA-5875), bis(pinacolato)diborane (12.34 g, 48.6 mmoles), potassium acetate (8 g, 0.81 mmoles), and 150 mL of 1,4-dioxane. Bis(triphenyl-phosphine)palladium (II) dichloride (100 mg, 1% by wt. of A) and 1,1'-Bis(diphenylphosphino)-ferrocene ((100 mg, 1% by wt. of A) were added. The mixture was degassed using vacuum/nitrogen back-fill, and then was heated to 95° C. for 12 hr with vigorous stirring under inert atmosphere. The reaction was monitored by TLC. The mixture was allowed to cool to room temperature, and filtered through a small pad of ether-wetted Celite in a plastic fritted funnel. The filtrate solvent was removed in vacuo at 65° C., and the residue was taken up in 50 mL of water and 150 mL of ethyl acetate. The aqueous layer was separated and back-extracted with 50 mL of ethyl acetate. The combined organic layers were dried over $MgSO_4$, filtered into a 500 mL round-bottom flask, and concentrated on a rotary evaporator under reduced pressure to yield 10.4 g crude product as brown syrup. Flash column chromatography on silica gel using a H-EA gradient (0-40%), provided 7.5 g of B-V a viscous oil, 75% yield by wt. TLC (4:1 H:EA, UV) $R_f$=0.65, $R_f$ of starting carboxylic ester=0.70.

TABLE 8

Characterization of certain embodiments of synthesis intermediate B.

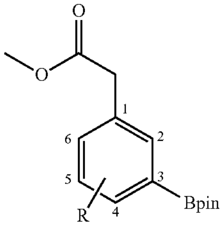

| R | Starting Br-Ester | Product Bpin-ester (B) | Yield | $^1$H NMR (500 MHz, $CDCl_3$) | LC-MS (M+1)/ Parent Exact Mass |
|---|---|---|---|---|---|
| 4-$CH_3$ | A-IV | B-IV | Oil, 2.3 g, 76% | δ 7.68 (1H, s), 7.28 (1H, d), 7.17 (1H, d), 3.70 (3H, s), 3.63 (2H, s), 2.55 (3H, s), 1.37 (12H, s) ppm | 291.3/ 290.17 |
| 5-F | Combi-blocks CA-5875, 10 g | B-V | Oil, 7.5 g, 75% | δ 7.48 (IH, s). 7.39 (1H, d), 7.12 (1H, d), 3.71 (3H, s), 3.64 (2H, s), 1.35 (12H, s) ppm | 295.2/ 294.14 |
| 6-OCH | Combi-blocks HB 3115, 5 g | B-VI | Solid, 3.6 g, 72% | δ 7.75 (1H, d), 7.64 (1H, s), 6.88 (1H, d), 3.85 (3H, s), 3.69 (3H, s), 3.65 (3H, s), 1.35 (12H, s) ppm | 307.2/ 306.16 |
| 4-$OCH_3$ | Oakwood 099447, 10 g | B-VII | Solid, 6.8 g, 68% | δ 7.56 (IH, s). 7.32 (1H, d), 6.82 (IH, d), 3.81 (3H, s), 3.67 (3H, s), 3.56 (2H, s), 1.35 (12H, s) ppm | 307.3 / 306.16 |

4.3. Aminomethylation. Preparation of C-IV, -V, -VI & -VII

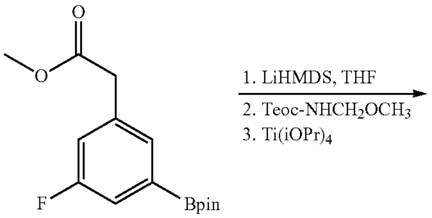

B-V

-continued

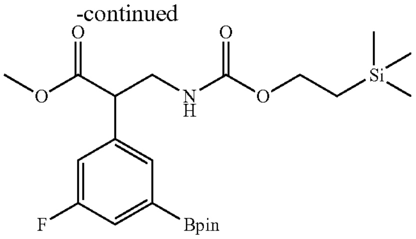

C-V

A 500 mL, round-bottom flask equipped with a low-temperature thermometer, gas inlet, and oversized magnetic stir bar was dried under inert atmosphere. The flask was charged with 40 mL anhydrous THF and cooled to −20° C. using a dry ice/isopropanol bath. The flask was then charged with LiHMDS (17.85 mL of a 1M solution in THF, 17.85 mmoles) by syringe and the orange solution was chilled to −60° C. With vigorous stirring, the flask was then carefully charged over 25 min by syringe with the arylacetate B-V (2.5 g, 8.5 mmoles,) as a solution in 10 mL anhydrous THF, maintaining the temperature below −53° C., and adding 5 mL additional THF to maintain fluidity of the gelled reaction mixture. 2-trimethylsilylethyl N-(methoxymethyl) carbamate, 4 (1.5 g, 7.3 mmoles) was added by syringe over 10 min as a solution in THF (combined volume with THF=5 mL). The temperature was maintained at −57 to −60° C. during the addition. The reaction mixture was then stirred at −30 to −35° C. for 30 min. $Ti(OiPr)_4$ (5.07 g, 17.85 mmoles in THF) was added over 30 min, maintaining the temperature between −60 to −56° C. during the addition. The reaction mixture turned deep orange and remained opaque. The mixture was stirred for 1.5 hours at −64 to −60° C. Over approx. 30 min, the mixture rose to −7° C., at which time it became reddish brown in color. After another ca. 30 min, the temperature rose to 1° C., at which time the flask was placed in an ice/salt bath. After 15 min, the temperature rose to 4° C., at which time, the reaction was monitored by TLC and deemed to be nearly complete. The mixture was stirred another ca. 30 min at 4-5° C. The mixture was poured, with mixing, into 20 mL ice-chilled 10% HCl in a 1 L glass beaker. The organic phase was diluted with ether and separated. The aqueous phase was extracted twice with 50 mL ether. The organic phases were combined, washed twice with brine, and dried over $MgSO_4$. Solvent was removed in vacuo to yield 5.6 g crude product as an amber oil. Flash column chromatography on silica gel using a H-EA gradient (0-50%), provided 2.8 g of C-V as a viscous oil, 70.5% yield. TLC (4:1 H:EA, UV) $R_f$=0.26, Rf of starting Bpin ester=0.4.

TABLE 9

Characterization of certain embodiments of synthesis intermediate C.

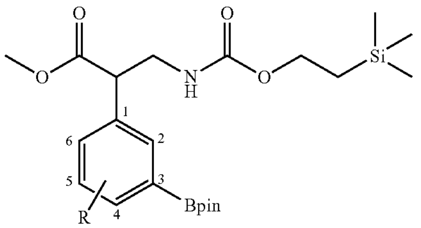

| R | Starting Bpin-Ester (B) | Product Teoc, Bpin-ester (C) | Yield | $^1$H NMR (500-600 MHz, $CDCl_3$) | LC-MS (M + 1)/ Parent Exact Mass |
|---|---|---|---|---|---|
| 4-$CH_3$ | B-IV, 2.0 g | C-IV | Oil, 1.6 g | — | 464.7 463.26 |
| 5-F | B-V, 2.5 | C-V | Oil, 2.8 g, 70.5% | (600 MHz, CDCl3) δ 7.45 (1H, s), 7.4, (1H, d), 7.05 (1H, d), 5.0 (1H, t), 4.1 (2H, m), 3.9 (1H, m), 3.65 (1H, m), 3.65 (3H, s), 3.5, 1H, m), 1.3 (12H, s), 0.9 (2H, m), 0.0 (9H, s) ppm | 467.4/ 467.23 |
| 6-$OCH_3$ | B-VI, 2.5 g | C-VI | Oil, 2.4 g | (500 MHz, CDCl3) δ 7.7 (1H, d), 7.57 (1H, s), 6.84 (1H, d), 5.18 (1H, t), 4.10 (2H, m), 4.06 (1H, m), 3.80 (3H, s), 3.64 (1H, m), 3.63 (3H, s), 3.5 (1H, m), 1.29 (12H, s), 0.9 (2H, m), 0.0 (9H, s) ppm | 480.4/ 479.25 |
| 4-$OCH_3$ | B-VII, 2.5 g | C-VII | Oil, 2.7 g, oil | (500 MHz, CDCl3) δ 7.50 (1H, s), 7.25 (1H, d), 6.78 (1H d), 4.97 (1H, t), 4.10 (2H, m), 3.80 (1H, m), 3.78 (3H, s), 3.63 (3H, s), 3.6 (1H, m), 3.5 (1H, m), 1.32 (12H, s), 0.95 (2H, m), 0.00 (9H, s) ppm | 480.1/ 479.25 |

4.4. Ester Hydrolysis. Preparation of Compound D-IV, -V, -VI, & -VII

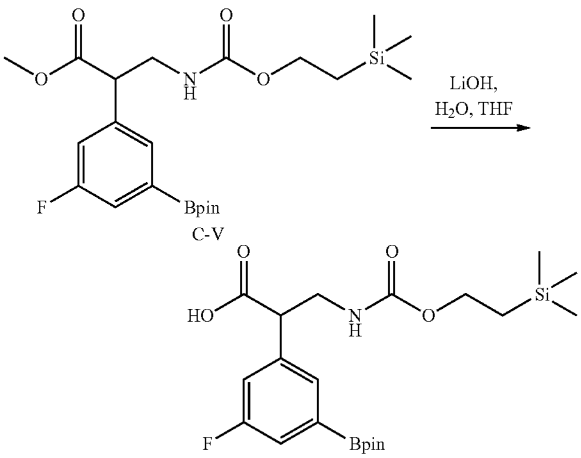

C-V

D-V

Ester C-V (2.5 g, 5.3 mmoles) was dissolved in 10 mL THF and chilled on ice. Aqueous lithium hydroxide (8 mL of a 2N solution, 16 mmoles) was added dropwise over 10 min. The bath was removed, and the mixture was stirred vigorously so as to create a fine emulsion. After ca. 20 min, the initial two-phase system became one transparent phase. The reaction was monitored by TLC. After 3 hours, the mixture was chilled on ice and carefully acidified with 8 mL 10% HCl. Product was extracted with 50 mL ethyl acetate. The organic phase was separated, and the aqueous phase was extracted twice with ethyl acetate. The organic phases were combined, and dried with brine and then solid $MgSO_4$. The solution was decanted and solvent was removed in vacuo to provide 2.1 gm of acid D-V as syrup, approximately 85% pure by TLC. This material was used in the next step without purification. TLC (1:1 H:EA, UV, alizarin @ 366 nm, phosphomolybdic acid) $R_f$=0.53, $R_f$ of starting ester=0.75.

TABLE 10

Characterization of certain embodiments of synthesis intermediate D.

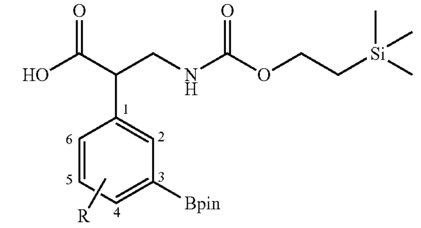

| R | Starting Teoc Bpin-Ester (C) | Product Teoc Bpin-acid (D) | Yield | $^1$H NMR (500 MHz, $CDCl_3$) | LC-MS (M + 1)/ Parent Exact Mass |
|---|---|---|---|---|---|
| 4-$CH_3$ | C-IV, 1.6 g | D-IV | Oil, 1.4 g | δ 7.65 (1H, s), 7.23 (1H, br s), 7.12 (1H, d), 6.96 + 5.12 (1H, br t), 4.13 (2H, m), 3.6 + 3.7 (1H, m), 3.5-3.8 (2H, m), 2.49, (3H, s), 1.32 (12H, s), 0.95 (2H, m), 0.00 (9H, m), ppm. | 450.5/ 449.24 |
| 5-F | C-V, 2.5 g | D-V | Oil, 2.1 g | δ 7.47 (1H, s), 7.4 (1H, d), 7.1 (1H, d), 5.3 (1H, br), 3.5-4.2 (5H, br), 1.31 (12H, s), 0.9 (2H, m), 0.00 (9H, s) ppm | 454.4/ 453.22 |
| 6-$OCH_3$ | C-VI, 2.4 g | D-VI | Oil, 2.15 g | δ 7.70 (1H, d), 7.60 (1H, s), 6.85 (1H, d), 5.32 (1H, br s), 4.09 (2H, + 1H, m), 3.80 (3H, s), 3.4-3.2 (2H, br), 1.20 (12H, s), 0.9 (2H, m), 0.0 (9H, s) ppm | 466.6/ 465.24 |
| 4-$OCH_3$ | C-VII, 2.7 g | D-VII | Oil, 2.3 g | δ 7.54 (1H, s), 7.30 (1H, d), 6.80 (1H, d), 4.2 (1H, br), 4.15 (2H, m), 3.75 (3H, s), 3.4-3.6 (2H, br), 1.32 (12H, s), 0.9 (2H, m), 0.0 (9H, s) ppm | 466.7/ 465.24 |

4.5 Amide Coupling Using Carboxylic Acid. Preparation of F-IV, -V, -VI, & -VII

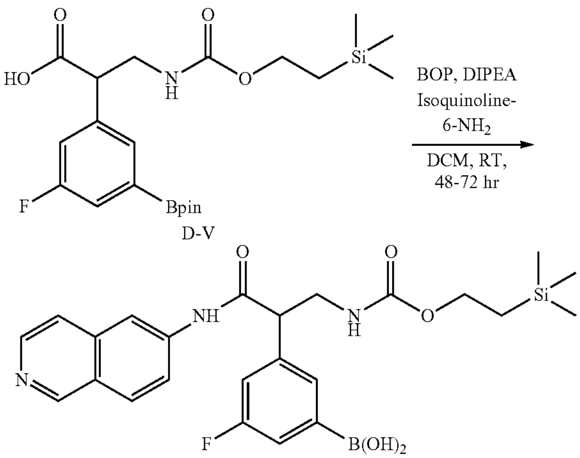

D-V

F-V

A 250 mL, round-bottom flask was charged with carboxylic acid D-V (2.0 gm, 2.7 mmoles) and dichloromethane (50 mL) followed by diisopropyl, ethylamine (695 mg, 5.38 mmoles) and BOP (benzotriazol-1-yloxytris(dimethylamino)phosphonium hexafluorophosphate). The mixture was stirred to complete dissolution at 25° C. for 30 min. Isoquinoline-6-NH2 (389.3 mg, 2.7 mmoles) was added, and the mixture was stirred for 2-3 days under inert atmosphere at room temperature. The reaction was monitored by TLC. Solvent was removed in vacuo to yield crude product as an amber oil. The —Bpin and —$B(OH)_2$ products were purified and separated from one another by flash chromatography, using a 0-100% H-EA gradient, followed by step up to 40% methanol-ethyl acetate gradient. In the case of F-V, the Bpin product was converted to the corresponding boronic acid on silica gel to obtain 320 mg F-V.

TABLE 11

Characterization of certain embodiments of synthesis intermediate F.

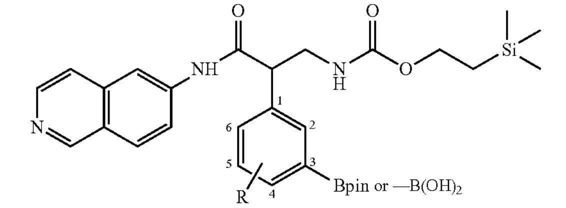

| R | Starting Teoc Bpin-Acid (D) | Product Teoc Bpin/$B(OH)_2$-isoquinoline (F) | Yield | Product Variant (Bpin/$BOH)_2$) | LC-MS (M + 1)/ Parent Exact Mass |
|---|---|---|---|---|---|
| 4-$CH_3$ | D-IV, 1.3 g | F-IV | 320 mg, solid | Bpin | 576.9/ 575.3 |
| 5-F | D-V, 2.0 g | F-V | 320 mg, solid | $B(OH)_2$ | 498.5/ 497.2 |
| 6-$OCH_3$ | D-VI, 2.0 g | F-VI | 230 mg, solid | Bpin | 592.9/ 591.29 |
| 4-$OCH_3$ | D-VII, 2.0 g | F-VII | 130 mg, solid | $B(OH)_2$ | 510.7/ 509.22 |

F-IV: (500 MHz, DMSO-$d_6$) δ 10.56 (1H, s), 9.17 (1H, s), 8.43 (2H, m), 8.05 (1H, d), 7.47 (2H, d), 7.45 (1H, d), 7.42 (1H, d), 7.3 (1H, t), 7.18 (1H, d), 4.1 (1H, m), 4.05 (2H, m), 3.6 (1H, m), 3.3 (1H, m), 2.45 (3H, s), 1.33 (12H, s), 0.89 (2H, t), 0.01 (9H, s) ppm.

F-V: (500 MHz, DMSO-$d_6$) δ 10.7 (1H, s), 9.2 (1H, s), 8.45 (2H, m), 8.28 (2H, s), 8.08 (1H, d), 7.76 (2H, m), 7.69 (1H, s), 7.5 (1H, d), 7.35 (1H, t), 7.25 (1H, d), 4.17 (1H, t), 4.05 (2H, t), 4.0 (1H, br), 3.7 (1H, m), 0.9 (2H, t) 0.0 (9H, s) ppm.

F-VI: (500 MHz, DMSO-$d_6$) δ 10.38 (1H, s), 9.18 (1H, s), 8.44 (2H, m), 8.05 (1H, d), 7.76 (2H, m), 7.72 (1H, s), 7.65 (1H, d), 7.15 (1H, t), 7.07 (1H, d), 4.42 (1H, m), 4.05 (2H, m), 3.89 (3H, s), 3.6 (1H, m), 3.3 (1H, m), 1.30 (12H, s), 0.88 (2H, m), 0.0 (9H, s) ppm.

F-VII: (500 MHz, DMSO-$d_6$) δ 10.6 (1H, br), 9.23 (1H, br), 8.44 (1H, m), 8.1 (1H, m), 7.35-7.85 (3H, m), 6.75-7.35 (3H, m), 4.05 (2H, m), 3.5-3.9 (6H, m), 0.9 (2H, m), 0.0 (9H, s) ppm.

4.6. Teoc and Bpin Deprotection. Preparation of IV.2TFA

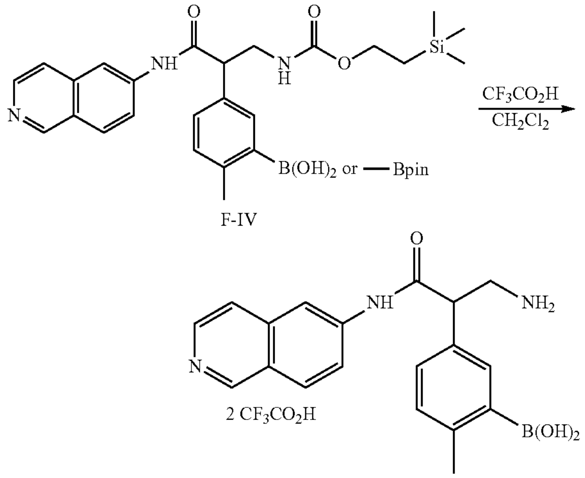

F-IV

IV.2TFA
(206-racemic)

The Bpin compound F-IV was treated with trifluoroacetic acid in dichloromethane at room temperature. Product IV.2TFA was isolated by trituration with ether.

4.7 Teoc and Bpin Deprotection. Preparation of V & VII (208-Racemic)

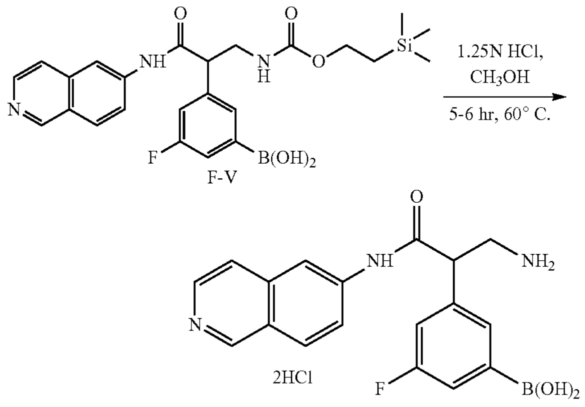

F-V

V.2HCl

Boronic acid F-V (300 mg, 0.060 mmoles) was dissolved in 2 ml of 1.25M HCl in methanol, and heated at 60° C. for 5 hours. The solvent was evaporated under a stream of $N_2$. The residue was triturated thrice from 1 mL ether both with the aid of a spatula and sonication. Brief centrifugation was used to assist precipitation of the solids. A powdery tan residue developed. This was crystallized from ether/methanol in a freezer (−13° C.) and washed with ether to yield V.2HCl as a tan solid (185 mg).

TABLE 12

Characterization of certain embodiments.

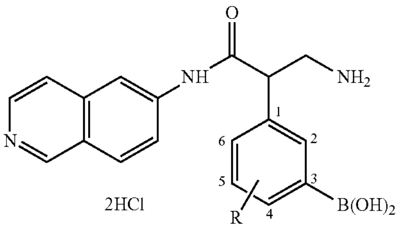

2HCl

| R | Starting Teoc Boronic Acid (F) | Product $NH_2$, $B(OH)_2$, isoquinoline | Yield | Salt Form | LC-MS (M + 1)/ Parent Exact Mass |
|---|---|---|---|---|---|
| 5-F | F-V, 300 mg | V•2HCl | 185 mg, 68% | 2HCl | 354.4/ 353.13 |
| 4-$OCH_3$ | F-VII, 12 mg | VII•2HCl 208-racemic | 5 mg, solid | 2HCl | 366.0/ 365.15 |

V: (500 MHz, DMSO-$d_6$) δ 11.62+11.33 (1H, 2s), 9.66 (1H, s), 8.73 (1H, 2s), 8.55 (1H, d), 8.44 (1H, d), 8.32 (1H, m), 8.23 (3H, br), 8.10 (1H, m), 7.71 (1H, s), 7.52 (1H, d), 7.50 (1H, d), 6.98 (1H, t), 4.45+4.25 (1H, 2t), 3.6 (1H, m), 3.15+3.07 (1H, 2m) ppm.

VII: (500 MHz, DMSO-$d_6$) δ 11.31+11.28 (1H, 2s), 9.62 (1H, s), 8.69 (1H, s), 8.55 (1H, d), 8.41 (1H, d), 8.30 (1H, d), 8.1 (3H, br), 8.02 (1H, d), 7.65 (1H, d), 7.51 (1H, d), 7.01 (1H, d), 4.25 (1H, m), 3.80 (3H, s), 3.55 (1H, m) 3.05 (1H, m) ppm.

4.8. Teoc and Bpin Deprotection. Preparation of IV (206-Racemic) and VI

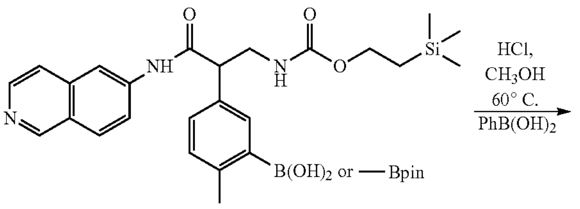

F-IV

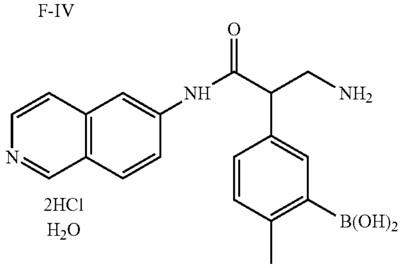

2HCl
$H_2O$

IV.2HCl
206-racemic

Compound F-IV (50 mg, 0.087 mmoles) and phenylboronic acid (41 mg, 0.34 mmoles) were dissolved in 1.25M HCl in methanol (3 mL) and heated at 60° C. The reaction was monitored by HPLC. At 4.5 hours, additional phenylboronic acid (32.6 mg, 0.27 mmoles) and methanolic HCl (656 mg, 790 mL) were added. After 8 hours, the solvent was evaporated under a steam of $N_2$. The crude product was triturated 4× with ether. The product was crystallized from ca. 2.5 ml 1.5:1 ether:methanol in the freezer (−13° C.) and washed with ether: Compound IV was obtained as a tan solid (21.5 mg, 68% yield).

TABLE 13

Characterization of certain embodiments.

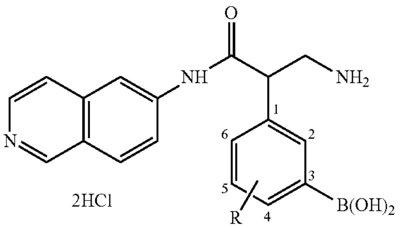

2HCl

| R | Starting Teoc Bpin-Add (F) | Product $NH_2$, $B(OH)_2$, isoquinoline | Yield | Salt Form | LC-MS (M + 1)/ Parent Exact Mass |
|---|---|---|---|---|---|
| 4-$CH_3$ | F-IV, 50 mg | IV.2HCl 206-racemic | 21.5 mg, 68% | 2HCl | 350.3/ 349.16 |
| 6-$OCH_3$ | F-VI, 15 mg as $RB(OH)_2$ | VI.2HCl | 8 mg, solid | 2HCl | 366.3/ 365.15 |

IV: (500 MHz, DMSO-$d_6$) δ 11.36 (1H, s), 9.64 (1H, s), 8.70 (1H, s), 8.55 (1H, d), 8.41 (1H, d), 8.30 (1H, d)

8.15 (3H, br), 8.04 (1H, d), 7.54 (1H, s), 7.34 (1H, d), 7.14 (1H, d), 4.26 (1H, m), 3.6 (1H, m), 3.05 (1H, m), 2.37 (3H, s) ppm.

VI: (500 MHz, DMSO-$d_6$) δ 10.95 (1H, s), 9.61 (1H, s), 8.70 (1H, s), 8.54 (1H, d), 8.40 (1H, d), 8.25 (1H, s), 8.1 (3H, br s), 8.0 (1H, d), 7.8 (1H, d), 7.7 (1H, s), 7.1 (1H, d), 4.52 (1H, m), 3.89 (3H, s), 3.55 (1H, m), 3.0 (1H, m) ppm.

Example 5

5.1. Preparation of $B(OCMePh)_2$ Esters VIII & IX

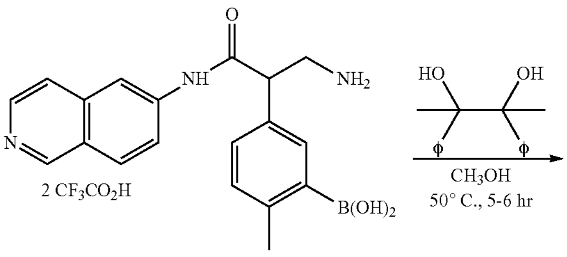

2 $CF_3CO_2H$

IV.2TFA

-continued

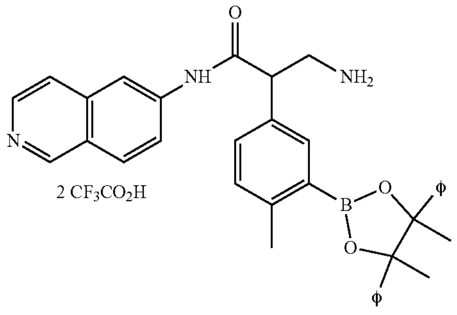

VIII.2TFA

Compound IV.2TFA (25 mg, 0.06 mmoles), and 2,3-diphenyl-butane-2,3-diol (20 mg, 0.08 mmoles, Millipore Sigma; S280402) were dissolved in methanol (5 mL) and heated at 50° C. for 5-6 hr. The reaction was monitored by HPLC. After 6 hours, the solvent was evaporated under a stream of $N_2$. The crude product was triturated 4× with ether. The product was crystallized from ca. 2.0 ml 1.5:1 ether: methanol in the freezer (−13° C.) and washed with ether: Compound VIII.2TFA was obtained as a white solid (20 mg).

TABLE 14

Characterization of certain embodiments.

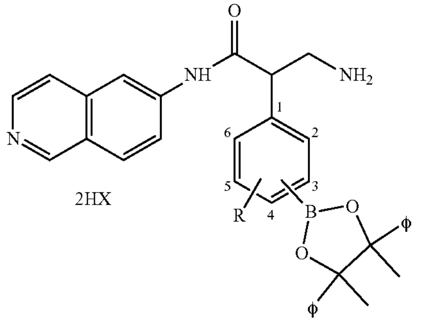

| R | Boronic position | Starting $NH_2$, $B(OH)_2$, isoquinoline (G) | Product $NH_2$, $B(OCMePh)_2$, isoquinoline | Yield | Salt Form | LC-MS (M + 1)/ Parent Exact Mass |
|---|---|---|---|---|---|---|
| 4-$CH_3$ | 3 | IV.2TFA, 25 mg | VIII.2TFA | 20 mg, solid | 2TFA | 556.4/ 555.27 |
| H | 4 | 10.2HCl, 25 mg | IX.2HCl | 20 mg, solid | 2HCl | 542.6/ 541.25 |

VIII: (500 MHz, DMSO-$d_6$) δ 11.0 (1H, s), 9.47 (1H, s), 8.57 (1H, s), 8.51 (1H, d), 8.29 (1H, d), 8.1 (1H, d), 8.02 (1H, s), 8.0 (3H, br), 7.87 (1H, d), 7.51 (1H, d), 7.37 (1H, d), 7.0 (10H, m), 4.2 (1H, m), 3.6 (1H, m), 3.2 (1H, m), 2.61 (3H, s), 1.90 (6H, s) ppm.

IX: (500 MHz, DMSO-$d_6$) δ 11.64 (1H, s), 9.66 (1H, s), 8.74 (1H, s), 8.56 (1H, d), 8.43 (1H, d), 8.33 (1H, d), 8.25 (3H, br), 8.11 (1H, d), 7.97 (2H, d), 7.66 (2H, d), 7.48+7.46 (1H, 2t), 6.98 (10H, s), 4.5 (1H, m), 3.65 (1H, m), 3.2 (1H, m), 1.87 (6H, s) ppm.

Example 6. Preparation of Boronate Esters X, XI, and XII (212-Racemic)

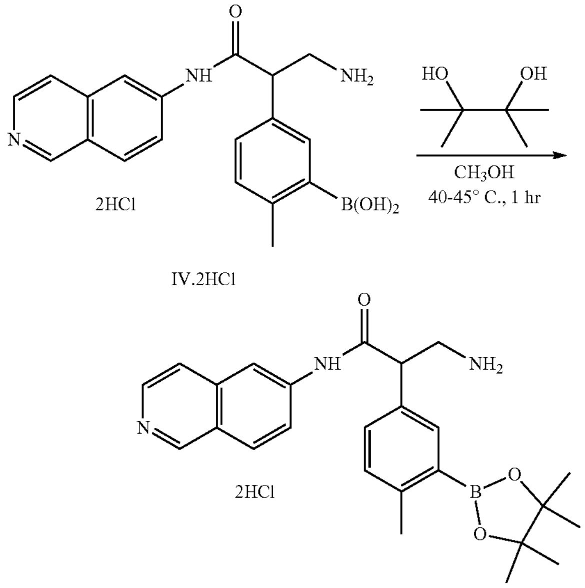

X.2HCl

Compound IV.2HCl (25 mg, 0.06 mmoles) and pinacol (10 mg, 0.085 mmoles, Oakwood 166700) were dissolved in methanol (5 mL) and heated at 45° C. for 1 hr. The reaction was monitored by HPLC. After 1 hour, the solvent was evaporated under a stream of $N_2$. The crude product was triturated 4× with ether. The product was crystallized from ca. 2.0 ml 1.5:1 ether:methanol in the freezer (−13° C.) and washed with ether: Compound X.2HCl was obtained as a solid (20 mg).

TABLE 15

Characterization of certain embodiments.

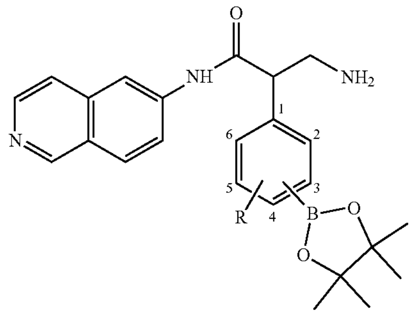

| R | Boronic position | Starting $NH_2$, $B(OH)_2$, isoquinoline | Product $NH_2$, $B(OCMePh)_2$, isoquinoline | Yield | Salt Form | LC-MS (M + 1)/ Parent Exact Mass |
|---|---|---|---|---|---|---|
| 4-CH3 | 3 | IV.2HCl 25 mg | X | 20 mg, solid | 2HCl | 432.5/ 431.24 |
| 6-OCH3 | 3 | VI.2HCl 15 mg | XI | 10 mg, solid | 2HCl | 448/ 447.23 |
| H | 4 | 10.2HCl 22 mg | XII 212-racemic | 18 mg, solid | 2HCl | 418.3/ 417.22 |

X: (500 MHz, DMSO-$d_6$) Δ 11.43 (1H, s), 9.68 (1H, s), 8.71 (1H, s), 8.55 (1H, d), 8.45 (1H, d), 8.35 (1H, d), 8.2 (3H, br), 8.05 (1H, d), 7.72 (1H, s), 7.47 (1H, d), 7.21 (1H, d), 4.32 (1H, m), 3.55 (1H, m), 3.05 (1H, m), 2.44 (3H, s), 1.31 (12H, s) ppm.

XI: (500 MHz, DMSO-$d_6$) Δ 10.94 (1H, s), 9.64 (1H, br), 8.68 (1H, s), 8.56 (1H, s), 8.42 (1H, d), 8.32 (1H, s), 8.08 (3H, br), 8.00 (1H, d), 7.68 (1H, d), 7.55 (1H, s), 7.11 (1H, d), 4.49 (1H, m), 3.88 (3H, s), 3.4 (1H, m), 3.0 (1H, m), 1.25 (12H, s) ppm.

XII: (500 MHz, DMSO-$d_6$) Δ 11.60 (1H, s), 9.66 (1H, s), 8.71 (1H, s), 8.55 (1H, d), 8.43 (1H, d), 8.33 (1H, d), 8.22 (3H, br), 8.08 (1H, d), 7.70 (2H, d), 7.52 (2H, d), 4.44 (1H, m), 3.6 (1H, m), 3.1 (1H, m), 1.28 (12H, s) ppm.

Example 7. Rho Kinase (ROCK) and Protein Kinase A (PKA) Enzyme Inhibition Assays The use of Rho Kinase (ROCK) inhibitors as therapeutic agents is well established and discussed in many publications (Feng Y et al., Rho Kinase (ROCK) Inhibitors and Their Therapeutic Potential, J Med Chem. 2016 Mar. 24; 59 (6): 2269-300; and Defert and Boland, Rho kinase inhibitors: a patent review (2014-2016), Expert Opin Ther Pat. 2017 April; 27 (4): 507-515). We measured ROCK and PKA kinase enzyme activity inhibition by compounds using commercially available ROCK1 (Promega Corporation, cat #V9581), ROCK2 (Promega, cat #V4045), and PKA kinase (Promega, cat #V4247) ADP-Glo™ assay kits. ADP-Glo™ Kinase Assay is a luminescent ADP detection assay that provides a homogeneous method to measure kinase activity by quantifying the amount of ADP produced during a kinase reaction. The assay is performed in two steps. First, after the kinase reaction, an equal volume of ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer. A complete protocol is included with the kits and is also available at the Promega website. The assay is briefly described below.

1. Diluted enzyme, substrate, ATP, and compounds (inhibitors) in Kinase Buffer (40 mM Tris, 7.5, 20 mM $MgCl_2$, 0.1 mg/ml BSA, 50 μM DTT).
2. Added 1 μl of inhibitor, 2 μl of enzyme and 2 μl of substrate/ATP mix to the wells of 384-well low volume nonbinding assay plate A series of three-fold dilution of inhibitor was prepared and assayed for each inhibitor.
3. Incubated at room temperature for 60 minutes.
4. Added 5 μl of ADP-Glo™ Reagent.
5. Incubated at room temperature for 60 minutes.
6. Added 10 μl of Kinase Detection Reagent
7. Incubated at room temperature for 30 minutes.

Recorded luminescence (Integration time 1 second) using a plate-based luminometer.

Calculated Percent Enzyme Activity: First subtract the signal of the negative control (no enzyme and no inhibitor) from each sample's signal. Then use the mean relative light units (RLU) values for the 0% kinase activity (neither inhibitor nor enzyme) and the 100% kinase activity (no compound) to calculate the other percent enzyme activities remaining in the presence of the different dilutions of inhibitor.

Plotted percent enzyme activity and inhibitor concentration dose response curve to estimate 50% inhibitory concentration ($IC_{50}$).

For comparison we also assayed the following ROCK inhibitors purchased from vendors: Netarsudil.2HCl (AR-13324, Selleckchem, cat #S8226), Netarsudil.2HCl (AR-13324, Apex Bio, cat #B7807), Fasudil (HA-1077, Apex bio, cat #B3523), Ripasudil (K-115, Apex bio, cat #B4809), Dimethyl Fasudil (H-1152P, Enzo Lifesciences, cat #ALX-270-423-M005), SLx-2199 (KD025, Ark Pharm, cat #AK341023), and Y-27632 (Ark Pharm, cat #AK546557). Chemical structures of inhibitors are given in Table 16. Inhibitor stock solutions of 10 mM are made in DMSO and stored at −20° C. Dilutions were made in assay buffer immediately before use.

The synthesis of Netarsudil and Netarsdil-M1-racemate.2HCl salts have been described in Sturdivant et al., Discovery of the ROCK inhibitor netarsudil for the treatment of open-angle glaucoma, Bioorg Med Chem Lett. 2016 May 15; 26 (10): 2475-2480; Lin et al., Discovery and Preclinical Development of Netarsudil, a Novel Ocular Hypotensive Agent for the Treatment of Glaucoma, J Ocul Pharmacol Ther. 2018 January/February; 34 (1-2): 40-51; and WIPO patent publication #WO 2101/127329, Dual-action inhibitors and methods of using same.

TABLE 16

| Chemical Structures. | | | |
|---|---|---|---|
| Structure | CAS# | Trade/Code Name | Vendor |
| 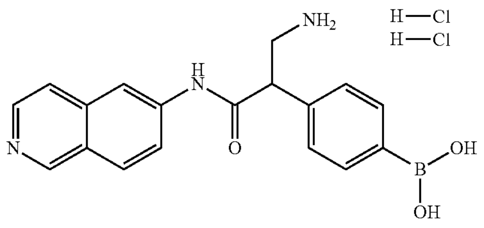 MW = 353.2 (free base) MW = 408.1 (2HCl) | none | Compound #10 | — |

TABLE 16-continued

Chemical Structures.

| Structure | CAS# | Trade/Code Name | Vendor |
|---|---|---|---|
| 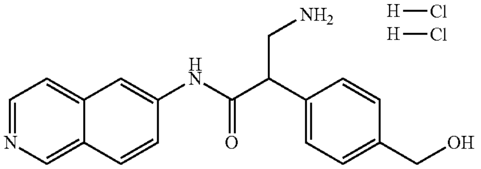 MW = 321.38 (free base) MW = 393.1 (2HCl) | — | Netarsdil-M1- (racemic) | — |
| 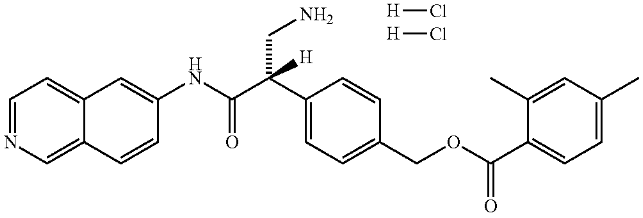 MW = 453.54 (free base) MW = 526.45 (2HCl) | 1254032-66-0 (free base) 1253952-02-1 (2HCl salt) | Netarsudil AR-13324 | Selleckchem, #S8226, 2HCl salt ApexBio, #B7807, 2HCl salt |
| 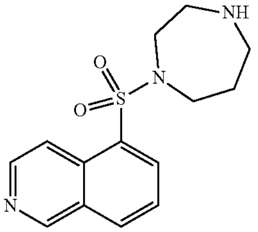 [SMILES: O=S(=O)(c1cccc2cnccc12)N1CCCNCC1] MW = 291.37 (free base) | 103745-39-7 (free base) | Fasudil HA-1077 | Apex Bio, #B3523, free base |
| 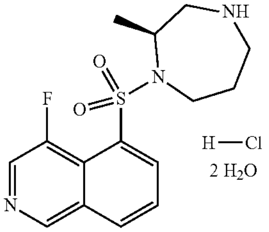 MW = 323.39 (free base) MW = 395.87 (2H20, HCl) | 887375-67-9 (2H2O, HCl) | Ripasudil K-115 | Apex Bio, #B4809, HCl dihydrate |
| 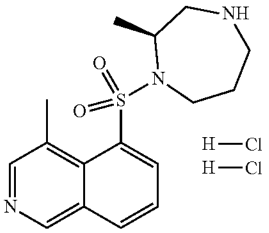 MW = 319.42 (free base) MW = 392.34 (2HCl) | 451462-58-1 (free base) 871543-07-6 (2HCl salt) | H-1152P dimethylfasudil | Axxora/Enzo, #ALX-270-423-M005, 2HCl salt |

TABLE 16-continued

| Chemical Structures. | | | |
|---|---|---|---|
| Structure | CAS# | Trade/Code Name | Vendor |
| 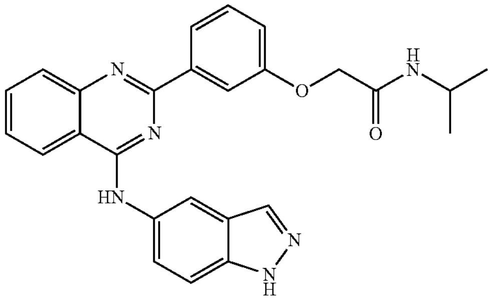 [SMILES: CC(C)NC(=O)COc1cccc(-c2nc(Nc3ccc4[nH]ncc4c3)c3ccccc3n2)c1] MW = 452.5 (free base) | 911417-87-3 (free base) | SLx-2119 KD025 | ArkPharm, #AK341023, free base |
| 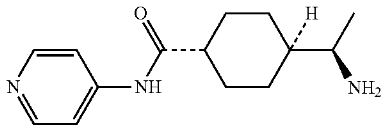 MW = 247.3 (free base) | 146986-50-7 (free base) | Y-27632 | ArkPharm, #AK546557, free base |
| 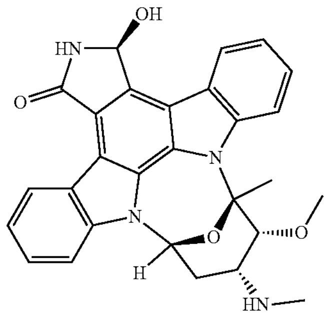 [SMILES: CN[C@@H]1C[C@H]2O[C@@](C)([C@@H]1OC)n1c3ccccc3c3c4c(c5c6ccccc6n2c5c31)C(=O)N[C@H]4O] MW = 482.5 (free base) | 112953-11-4 (free base) | Staurosporine | Apex Bio, #A8192, |

As shown in Table 17, two independent lots of compound 10 and compound 10.2HCl had an average $IC_{50}$ estimate of 25 nM against ROCK2 and 84 nM against ROCK1. These $IC_{50}$ estimates are slightly higher than observed for Netarsudil.2HCl and similar to Netarsdil-M1-racemate.2HCl. $IC_{50}$ estimates for ROCK2 and ROCK1 of other ROCK inhibitors tested are higher than compounds 10 and 10.2HCl. Compounds 10 and Netarsudil-M1-racemate.2HCl also inhibited PKA at nanomolar concentration. In vitro ROCK1, ROCK2 and PKA enzyme inhibition assays demonstrate that compounds 10 and 10.2HCl have significant inhibitory activity against ROCK and PKA.

TABLE 17

$IC_{50}$ estimates of compounds 10 and 10•2HCl, and ROCK inhibitors

| Compound | ROCK2 $IC_{50}$(Exp #1) | ROCK2 $IC_{50}$(Exp #2) | ROCK2 $IC_{50}$(Exp #3) | ROCK1 $IC_{50}$ | PKA$IC_{50}$ |
|---|---|---|---|---|---|
| Compound 10, lot 1 | 27 nM | 26 nM | 26 nM | 137 nM | 52 nM |
| Compound 10, lot 2 | NT | NT | 15 nM | 62 nM | NT |
| Compound 10•2HCl | NT | NT | 28 nM | 54 nM | NT |
| Netarsudil-M1-racemate•2HCl | NT | 66 nM | 15 nM | NT | 23 nM |
| Netarsudil•2HCl (Selleckchem) | 13 nM | 29 nM | 6 nM | 102 nM | 322 nM |
| Netarsudil•2HCl (Apex Bio) | NT | 18 nM | NT | NT | NT |
| Fasudil | NT | 1643 nM | 522 nM | 3192 nM | >1000 nM |
| Ripasudil | NT | 90 | NT | NT | >1000 nM |
| Dimethyl Fasudil | 10 nM | 81 | NT | NT | >1000 nM |
| SLx-2119 | 265 nM | 295 | NT | NT | >1000 nM |
| Y-27632 | 316 nM | NT | NT | NT | >1000 nM |

NT: Not Tested.

Example 8. Kinase Selectivity Profiling of Compound 10.2HCl w/AGC Family Kinases ROCK1 (also called ROCK I, ROKβ, Rho-kinase β, or p160ROCK) and ROCK2 ((also known as ROCK II, ROKα, or Rho kinase) belong to AGC family of serine/threonine kinases. The group of AGC kinases consists of 63 evolutionarily related serine/threonine protein kinases comprising PDK1, PKB/Akt, SGK, PKC, PRK/PKN, MSK, RSK, S6K, PKA, PKG, DMPK, MRCK, ROCK, NDR, LATS, CRIK, MAST, GRK, Sgk494, and YANK, while two other families, Aurora and PLK, are the most closely related to the group (Leroux et al., AGC kinases, mechanisms of regulation and innovative drug development, Semin Cancer Biol. 2018 February; 48:1-17). We assayed inhibitory activity of compound 10.2HCl at a single dose of 1 μM against 16 AGC family kinases that are available as AGC Kinase Selectivity Profiling Systems from Promega Corporation (cat #V6859 and #V6931).

In the Kinase Selectivity Profiling Systems kits, kinase and substrate pairs organized in an easy-to-use 8-tube strip format.

Concentrated kinases and substrates/cofactor stocks were first diluted and then combined with test compound in a 384-well plate. After a 1-hour incubation, the ADP-Glo™ Assay was performed to measure kinase activity as described in example on Rho Kinase (ROCK) Enzyme Inhibition Assay.

If kinase reaction with compound produced a lower percent kinase activity than the no-compound control reaction, the compound inhibited the kinase, as seen by the lower percent kinase activities in the test wells when compared to the no-compound control percent kinase activities.

If the percent kinase activity of kinase reactions with compound is approximately equal to that of the no-compound control reaction, the compound had no effect on kinase activity.

As expected, compound 10.2HCl at 1 μM concentration inhibited ROCK1 and PKA at 96% and 98%, respectively, in the profiling assay (Table 18). Compound 10.2HCl also inhibited other AGC family kinases to varying levels. Compound 10.2HCl showed relatively higher inhibition of AKT1 and lower inhibition of PDK1 compared to Netarsudil.

TABLE 18

Percent enzyme activity inhibition of AGC family kinases in the presence of 1 μM compound: 10•2HCl or Netarsudil•2HCl.

| | AGC Panel | Compound 10•2HCl | Netarsudil•2HCl |
|---|---|---|---|
| 1 | AKT1 | 52 | 5 |
| 2 | p7056Kb | 56 | 52 |
| 3 | PDK1 | 19 | 77 |
| 4 | PKA | 98 | 88 |
| 5 | PKC | 83 | 96 |
| 6 | PRKG1 | 84 | 82 |
| 7 | ROCK1 | 96 | 88 |
| 8 | RSK2 | 67 | 65 |
| 9 | PKCa | 78 | 65 |
| 10 | PKCb II | 83 | 45 |
| 11 | PKCd | 94 | 75 |
| 12 | PKCe | 36 | 25 |
| 13 | PKCg | 63 | 36 |
| 14 | PKCi | 12 | 20 |
| 15 | PKCtheta | 79 | 51 |
| 16 | PKCz | 12 | 22 |

Example 9. Kinase Selectivity Profiling of Compound 10.2HCl on 23 Kinases Representing Different Kinase Families In addition to profiling AGC family, we also tested enzyme inhibition activity of compound 10.2HC on 23 kinases that represent different families of kinases to obtain information on specificity towards a specific kinase or group of kinases using Kinase Selectivity Profiling Systems—General Panel available from Promega Corporation (cat #V6928).

Similar to AGC family profiling system kit, the general panel kit includes kinase and substrate pairs organized in an easy-to-use 8-tube strip format.

We followed Promega protocol (available with the kit and at Promega website) without modifications.

Inhibitor (1 μM final), kinase, kinase specific substrate, ATP, and assay buffer were mixed and incubated at room temperature for 60 minutes. After this incubation, 5 μl of ADP-Glo™ reagent was added to 5 μl reaction and incubated for 40 minutes. Then, 10 μl of Kinase Detection Reagent added to all assay wells in the assay plate and incubated at room temperature for 30 minutes. Luminescence was measured using an integration time of 0.5 seconds per well in a plate luminometer.

The percent inhibition of kinases activity in the presence of 1 μM compound 10.2HCl is given in Table 19. AGC family kinases ROCK1, AKT1 and PKCa enzymes are also included in Promega General Panel kit. Percent inhibitor activity of these three kinases by compound 10.2HCl is similar to values obtained with AGC family panel assay kit (see Table 18), suggesting reproducibility of assay on different days with different kits. As a control, we included staurosporine, a potent, non-selective inhibitor of protein kinases. Among the non-AGC family kinases tested, significant inhibitory activity of compound 10.2HCl is observed for kinases FGFR1, AMPK A1/B1/G2, and MAPKAPK2 (Table 19).

TABLE 19

Percent enzyme activity inhibition of 23 kinases in the presence of 1 μM Compound 10•2HCl and Staurosporin.

| | General Panel | Compound 10•2HCl | Staurosporine |
|---|---|---|---|
| 1 | FGFR1 | 35 | NT |
| 2 | JAK3 | 0 | NT |
| 3 | LCK | 0 | NT |
| 4 | SYK | 2 | NT |
| 5 | MINK1 | 3 | NT |
| 6 | PAK1/CDC42 | 0 | NT |
| 7 | IRAK4 | 0 | NT |
| 8 | CDK2/CyclinE1 | 11 | 98 |
| 9 | GSK3b | 0 | 96 |
| 10 | p38a | 0 | 13 |
| 11 | AMPKA1/B1/G2 | 58 | 99 |
| 12 | CAMK4 | 7 | 80 |
| 13 | CHK1 | 21 | 99 |
| 14 | DAPK1 | 20 | 94 |
| 15 | MAPKAPK2 | 30 | 70 |
| 16 | AKT1 | 55 | 99 |
| 17 | PKCa | 72 | 100 |
| 18 | ROCK1 | 98 | 59 |
| 19 | Aurora A | 21 | 99 |
| 20 | CK2a1 | 3 | 31 |
| 21 | IKKb | 0 | 67 |
| 22 | CK1a1 | 0 | 55 |
| 23 | CK1g1 | 0 | 51 |

NT: Not tested

Example 10. Inhibition of MYPT1 Phosphorylation in Human Trabecular Meshwork (hTM) Cells by Compound 10.2HCl The outflow of aqueous humor across the trabecular meshwork (TM) is regulated by, among other factors, actomyosin contraction of the TM cells and altered extracellular matrix. ROCK is known to inhibit the phosphatase activity of myosin light chain phosphatase (MLCP) by phosphorylating MYPT1 at amino acids Thr696 and Thr853. We investigated inhibition of MYPT1 at Thr853 by incubating hTM cells with Compound 10.2HCl, Netarsudil.2HCl, or Netarsudil-M1-racemate.2HCl and measuring inhibition of phosphorylation using an antibody that specifically detects Phospho-MYPT1 Thr853 in western blotting assay.

1. Primary hTM cells, passage 2 were purchased from ScienCell Research Laboratories (cat #6590) and cultured in TM cell medium (ScienCell, cat #6591) on poly-L-lysine (ScienCell, cat #0403) coated cell culture plates according to included directions.
2. A day before assays, passage 4 cells were plated in T75 flasks coated with gelatin (Corning, cat #354488) such that cells reach ~80% confluence in 24 hours. On the day of inhibitor addition, 12 ml of culture medium in each flask was replaced with 12 ml media containing 10 μM inhibitors or DMSO (0.01%) and incubated for 7 hours at 37° C. and 5% CO2.
3. In another experiment, passage 4 cells were plated in 6-well plates coated with poly-L-lysine and exposed to 2.5 μM inhibitors.
4. Media with inhibitors was suctioned off, wells washed 2 times with cold PBS pH 7.4 buffer, and attached cells were scrapped off with 500 μl (T75 flasks) or 100 μl (6-well plates) SDS-PAGE sample buffer, and collected into 1.5 ml microcentrifuge tubes.
5. Samples were sonicated 30 seconds on ice to break DNA and lyse cells and heated at 70° C. for 10 minutes before loading on 4-12% SDS-PAGE gel.
6. The ThermoFisher suggested protocol for SDS-PAGE was followed without any changes using the following material: Bolt™ 4-12% Bis-Tris Plus Gels, 15-well (cat #NW04125BOX), Bolt™ Mini Gel Tank (cat #A25977), 20× Bolt™ MES SDS Running Buffer (cat #B000202), 4× Bolt® LDS Sample Buffer (cat #B0008), and 10× Bolt® Sample Reducing Agent (cat #B0009).
7. An equal volume of cell lysate (20 μl/lane) of different treatments was separated on 4-12% gel by running at 165V constant for 45 minutes.
8. The gel was blotted to 0.2 micron PVDF membrane at constant voltage of 20V for 1 hour using the material and methods from ThermoFisher: 20× Bolt® Transfer Buffer (cat #BT00061), Bolt® Antioxidant (cat #BT00061), 1× Transfer Buffer made with 10% Methanol and Antioxidant., Novex XCell II Blot Module (cat #EI9051), and Invitrolon™ PVDF/Filter Paper Sandwich, 0.2 μm pore size (cat #LC2005).
9. Phosphorylated MYPT1 on blot was detected using antibodies against Phospho-MYPT1 Thr853 (Cell Signaling Technology, cat #4563S). Briefly; blocked membrane with 5% milk powder in TBST (20 mM Tris pH 7.5, 150 mM NaCl, 0.05% Tween 20) at room temperature (RT) for 1 h, Incubated 1 st antibody at 1:1000 dilution in 12 ml 5% milk at 4° C. over night, washed 3×5 min with TBST at RT, incubated with anti-Rabbit-HRP conjugate (Cell Signaling Technology, cat #70745) at 1:2000 dilutions in 12 ml 5% milk at RT for 1 hour, washed 4×5 min with TBST, and detected signal using SuperSignal™ West Pico PLUS reagent (ThermoFisher, cat #34018) and capturing light signal with an imaging camera.
10. To detect endogenous levels of total MYPT1 protein, phosphor-MYPT1 Thr853 antibody was stripped off of blot using western blot stripping buffer (ThermoFisher, cat #21059) and then developed with MYPT1 (D6C1) Rabbit mAb (Cell Signaling, cat #8574).
11. β-actin, a "housekeeping" protein used as a loading control on western blot, was detected using β-Actin (C4) antibody conjugated to HRP (Santa Cruz Biotechnology, cat #sc-47778-HRP)

FIG. 1 shows western blot detection of phospho-MYPT1 Thr853, total MYPT1, and actin proteins in hTM cells incubated with 10 or 2.5 μM inhibitors. Compound 10.2HCl, Netarsudil.2HCl, or Netarsudil-M1-racemate.2HCl completely inhibited MYPT1 phosphorylation. MYPT1 is phosphorylated in control cells (0.1% DMSO) with a strong signal at expected molecular mass of 115 kDa (panels A). Detection of total MYPT1 (panel B) in all lanes suggests that lack of signal in panel A with phospho-MYPT1 Thr853 antibody is not due to lack of MYPT1 protein. Actin detection in panel C shows that all lanes have similar amount of protein loaded. Panel D of FIG. 1 shows hTM cells incubated with 2.5 μM inhibitors. Addition of compound 10.2HCl, Netarsudil.2HCl, or Netarsudil-M1-racemate.2HCl to media inhibited phosphorylation of MYPT1 also at 2.5 μM concentration.

Example 11. Kinase Inhibitor Potency of Compound 10.2HCl in Live HEK293 Cells To estimate occupancy of compound 10.2HCl in live cells as a kinase inhibitor we used a commercially available PKA-NanoBRET™ Target Engagement (TE) Intracellular Kinase Assay from Promega Corporation (Cat #NV1901). NanoBRET™ TE assay is based on the NanoBRET™ System, an energy transfer technique designed to measure molecular proximity in living cells. The NanoBRET™ TE assay measures the apparent affinity of test compounds by competitive displacement of the NanoBRET™ tracer, reversibly bound to a NanoLuc® luciferase-kinase fusions in cells. Using the NanoBRET™ TE Kinase Assay, a fixed concentration of tracer is added to cells expressing the desired NanoLuc® kinase fusion to generate a BRET signal. Introduction of competing compounds results in a dose-dependent decrease in BRET signal, which allows quantitation of the intracellular affinity of the target protein for the test compound.

1. Transiently transfect HEK293 suspension cells with PKA-NanoLuc fusion vector DNA and cultured at 37° C., 5% CO2 for 30 hours. HEK293 cells and media were purchased from ThermoFisher (cat #A14635) and cultured following suggested protocol.
2. Centrifuged culture, resuspended cells in fresh culture media, and dispense 85 ul in to wells of 96-well plate.
3. Dispensed 5 μl of 20× NanoBRET Tracer Reagent per well and mixed plate on an orbital shaker for 15 seconds at 700 rpm.
4. Added 10 μl of 10× serially diluted inhibitor compound per well containing cells with IX NanoBRET Tracer Reagent. Thoroughly mixed plate on an orbital shaker for 15 seconds at 700 rpm.
5. Incubated the plate at 37° C., 5% CO2 for 2 hours. Equilibrated plate to room temperature for ~15 minutes.
6. Added 50 μl of 3× NanoBRET Nano-Glo® Substrate and Incubated for 2-3 minutes at room temperature. Measured donor emission wavelength (450 nm) and acceptor emission wavelength (610 nm) using the GloMax® Discover System (Promega). To generate raw BRET ratio values, divided the acceptor emission value (610 nm) by the donor emission value (450 nm) for each sample.

Figure 2:
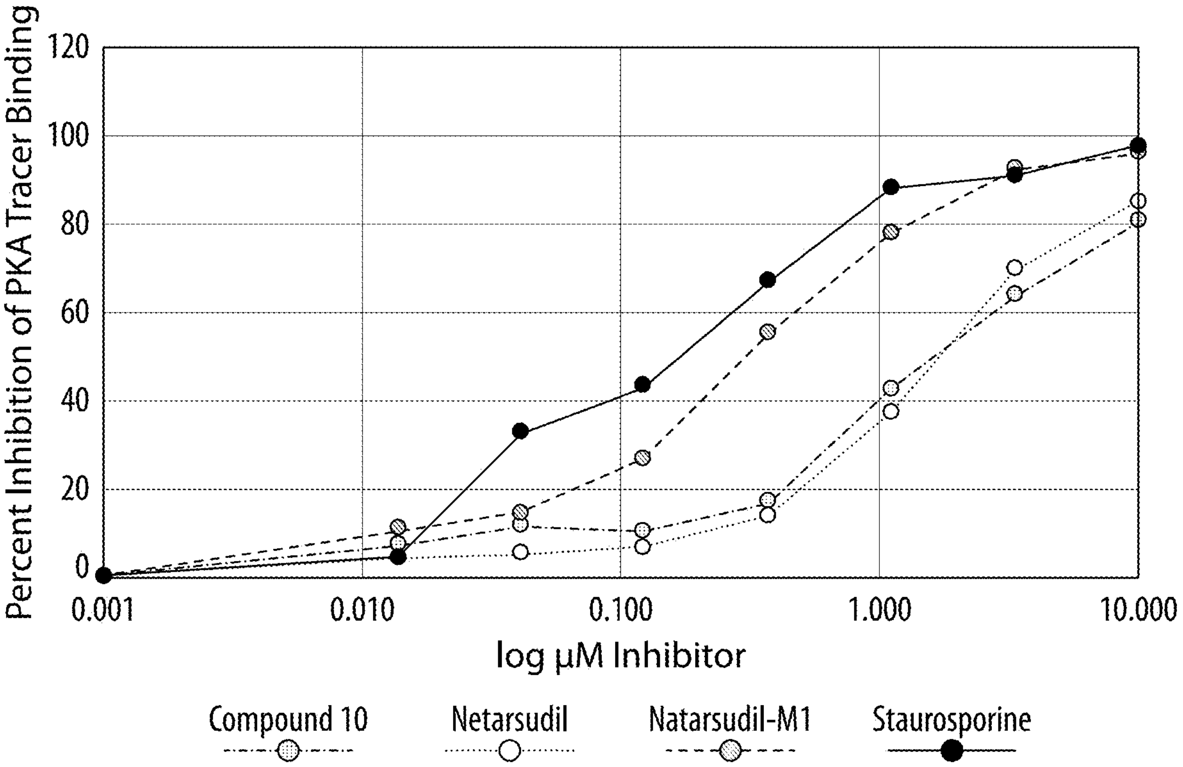
FIG. 2 NanoBRET tracer competition in transiently transfected HEK293 cells expressing PKA-NanoLuc® fusion protein. HEK293 cells expressing PKA-NanoLuc® fusion protein were resuspended in assay medium, seeded into 96-well plates and mixed NanoBRET Tracer K-5 (final 2 μM). Cells were treated with varying concentrations of compound 10.2HCl, Netarsudil.2HCl, Netarsudil-M1-racemate.2HCl, or Staurosporine as a competitive inhibitor for 2 hours before adding BRET substrate and measuring BRET.

Apparent intracellular NanoBRET tracer affinity in HEK293 cells transiently expressing PKA-NanoLuc® fusion protein in the presence of various concentrations of compound 10.2HCl, Netarsudil.2HCl, Netarsudil-M1-racemate.2HCl, or pan kinase inhibitor Staurosporine is given in FIG. 2. As compound 10.2HCl concentration increased from 0 to 10 uM, percent inhibition of tracer binding to PKA increased, that is, higher the concentration of compound 10.2HCl in culture media more of the tracer bound to PKA is displaced. The inhibition of tracer binding to PKA of Compound 10.2HCl and Netarsudil.2HCl are similar and are less than observed for Netarsudil-M1-racemate.2HCl and Staurosporin (FIG. 2). Estimated $IC_{50}$ values for compound 10.2HCl, Netarsudil.2HCl, Netarsudil-M1-racemate.2HCl, and Staurosporine are 1424 nM, 1524 nM, 360 nM, and 65 nM, respectively. BRET assay clearly indicates that compound 10.2HCl has kinase inhibitory potency in live HEK293 cells affirming inhibition of MYPT1 phosphorylation in hTM cells.

Example 12. Cell Viability Assay and Cell Morphology Changes to Estimate Cytotoxicity of Compound 10

Cell viability assay with various concentrations of compound is used to determine if the test compound has effects on cell proliferation or show direct cytotoxic effects that eventually lead to cell death. The measurement of ATP using firefly luciferase is the commonly applied method for estimating the number of viable cells. We used CellTiter-Glo® Luminescent Cell Viability Assay (Promega, cat #G7573) to determine the number of viable cells in culture based on quantitation of the ATP present, which signals the presence of metabolically active cells.

1. Prepared HEK293 suspension culture cells (ThermoFisher, cat #A14635) and added 50 μl cells in media (12,500 cells) to each well of a white, opaque-walled 96-well plate in triplicate.
2. Added inhibitors in 50 μl media to give 25, 2.5 or 0.25 μM final concentration.
3. Incubated at 37° C. and 5% CO2 for two days.
4. Added 100 μl of CellTiter-Glo® Reagent to each well and mix contents for 2 minutes on an orbital shaker to induce cell lysis.
5. Recorded luminescence using a plate luminometer.

Figure 3:
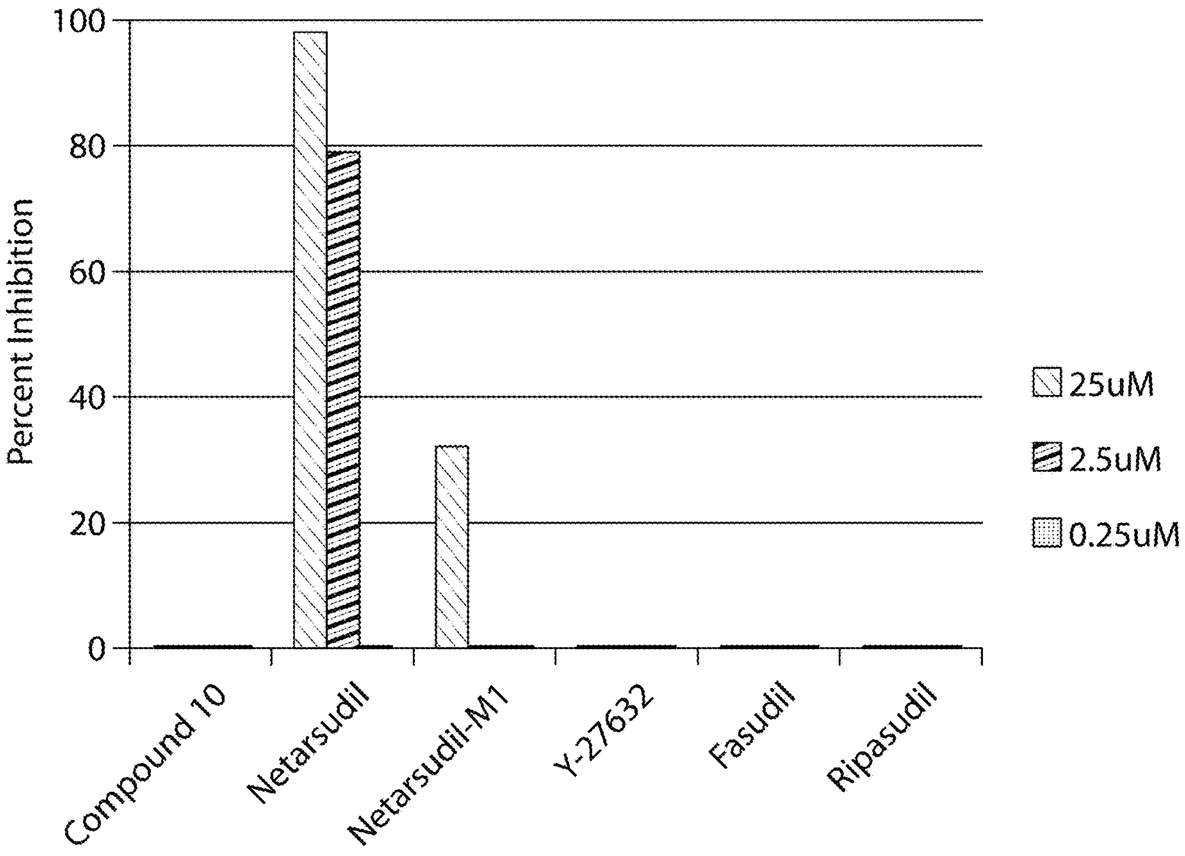
FIG. 3 CellTiter-Glo® Luminescent Cell Viability Assay of HEK293 cells incubated with 25, 2.5, or 0.25 μM compound 10.2HCl and other ROCK inhibitors.

HEK293 cells incubated with 25, 2.5, or 0.25 μM compound 10.2HCl for two days have same amount of ATP as cells without inhibitor (FIG. 3). Similar results are also observed for ROCK inhibitors Fasudil, Ripasudil, and Y-27632. In contrast, cell viability is very low when treated with Netarsudil.2HCl, 96% and 80% reduction in ATP levels at 25 μM and 2.5 μM, respectively (FIG. 3). Netarsudil-M1-racemate.2HCl inhibited cell growth only at 25 μM concentration.

Treatment of TM cells with ROCK inhibitors affects retraction and rounding of cell bodies as well as disruption of actin bundles (Kaneko et al., Effects of K-115, a novel ROCK inhibitor, on trabecular meshwork and Schlemm's canal endothelial cells, Sci Rep. 2016 Jan. 19; 6:19640). To visualize gross morphological changes in hTM, we incubated cells with 1.1, 3.3, or 10 μM compound 10.2HCl, Netarsudil.2HCl or Netarsudil-M1-racemate.2HCl and recorded changes in cell morphology with an inverted microscope. hTM were cultured on 8-well Chamber Slide (ThermoFisher, cat #154534PK) and when the cells reached ~80% confluency, media in chambers was replaced with fresh media containing inhibitors. Microscope images were taken after 20 hours of incubation with inhibitors.

Figure 4:
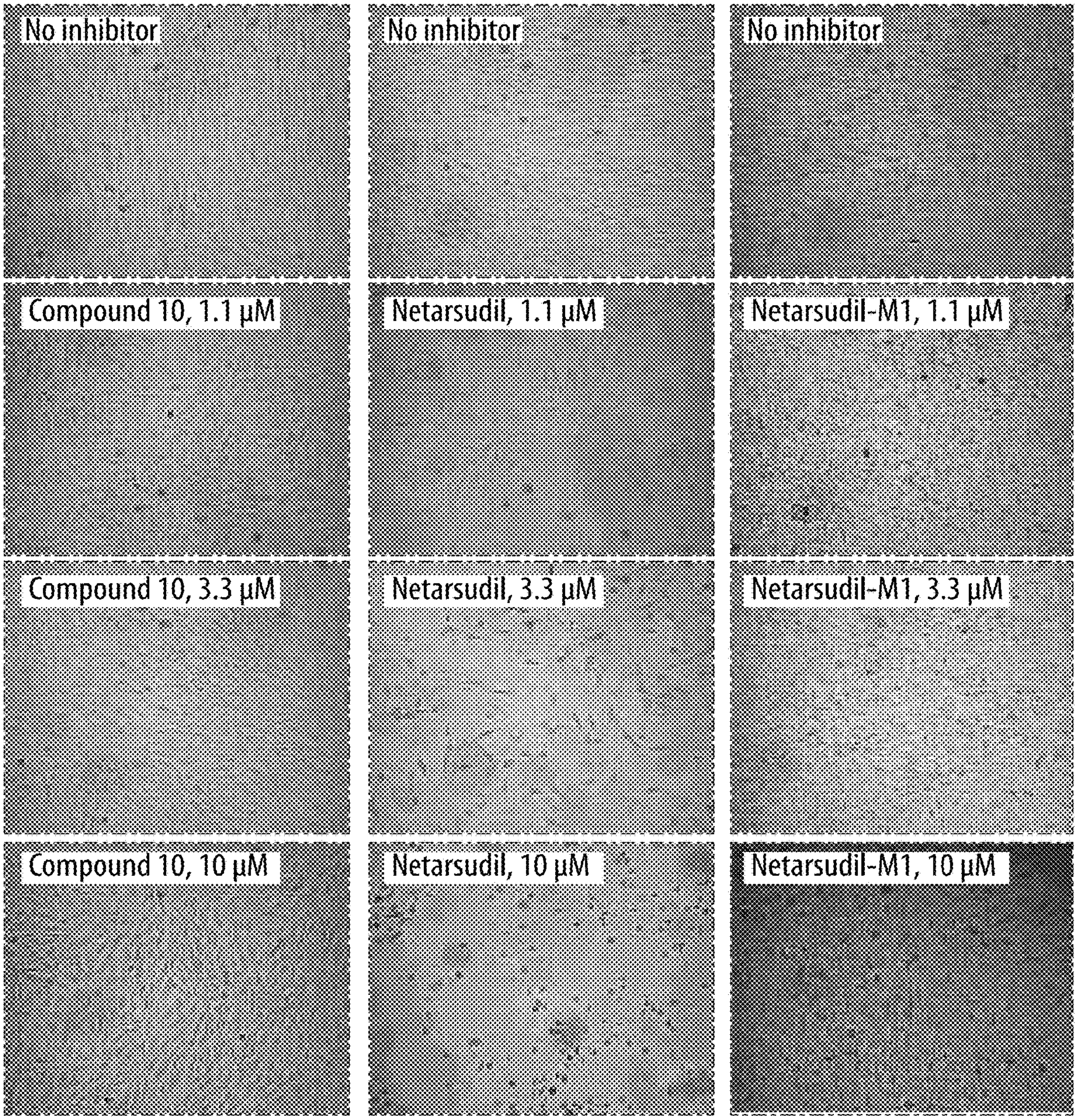
FIG. 4 Effect of compound 10.2HCl, Netarsudil.2HCl, and Netarsudil-M1-racemate.2HCl on hTM cell morphology.

As shown in FIG. 4, hTM cells incubated with 1.1 μM and 3.3 μM Netarsudil.2HCl started contracting and detaching from plate and became small and round at 10 μM. Cells incubated with 1.1 μM and 3.3 μM compound 10.2HCl and Netarsudil-M1-racemate.2HCl appeared to be similar to no inhibitor controls, and appeared slightly contracted at 10 μM. These results suggest that compound 10.2HCl does not affect hTM morphology at the concentrations tested.

Example 13. Stability of Compound 10.2HCl

Stability in Varied Buffers and Temperatures. The stability of compound 10.2HCl was tested by storage at 23° C. (room temperature), 37° C., 4° C., and −20° C. in water, 150 mM NaCl, pH 5 and 6 buffers, or buffers containing 150 mM NaCl. No visible precipitates were observed after storage. Samples were centrifuged at 16,000×g for 10 minutes at room temperature and supernatants were assayed for ROCK2 inhibition as described in Example 7. As shown in Table 20, compound 10.2HCl is stable for 4 months at both 37° C. and 4° C. in 150 mM NaCl. It is also stable in pH 5 and 7 buffers at room temperature for 15 days.

TABLE 20

Stability of compound 10•2HCl in various aqueous solutions at different temperatures and time periods, as measured by percent inhibition of ROCK2 activity.

| Buffer and (test article concentration) | Storage | % ROCK2 inhibition at 20 nM |
|---|---|---|
| 150 mM NaCl (2 mg/ml) | 120 days at 37° C. | 35 |
| 150 mM NaCl (2 mg/ml) | 120 days at 4° C. | 31 |
| 150 mM NaCl (0.5 mg/ml) | 15 days at 23° C. | 35 |
| 150 mM NaCl (0.5 mg/ml) | 0 days at 23 ° C. | 35 |
| Water (0.5 mg/ml) | 15 days at 23° C. | 34 |
| Water (0.5 mg/ml) | 15 days at −20° C. | 33 |
| 25 mM Borate pH 7 (0.5 mg/ml) | 15 days at 23° C. | 36 |
| 25 mM Borate, pH 7 (0.5 mg/ml) | 15 days at −20° C. | 34 |
| 25 mM Borate, pH 7, 150 mM NaCl (0.5 mg/ml) | 15 days at 23° C. | 32 |
| 25 mM Borate pH 5 (0.5 mg/ml) | 15 days at 23° C. | 31 |
| 25 mM Borate, pH 5 (0.5 mg/ml) | 15 days at −20° C. | 32 |
| 25 mM Borate, pH 5, 150 mM NaCl (0.5 mg/ml) | 15 days at 23° C. | 29 |

Stability in buffer, plasma, and blood. Study was conducted by Absorption Systems. Studies were carried out in pH 7.4 phosphate buffer, mixed-gender human plasma (Lot #HMN330460), and mixed-gender human whole blood (Lot #HMN 381096). The buffer was prepared by combining 50 mL of 0.2 M KH2PO4 with 150 mL of H2O, and then adjusting to pH 7.4 with 10 N NaOH (50 mM phosphate buffer). The plasma and blood were obtained from BioIVT and collected on sodium heparin. They were adjusted to pH 7.4 prior to initiating the experiments. A DMSO stock was first prepared for the compound 10.2HCl. Aliquots of the DMSO solution were dosed into 1 mL of matrix, which had been pre-warmed to 37° C., at a final concentration of 1 M. The vials were kept in a benchtop Thermomixer® for the duration of the experiment. Aliquots (100 μL) were taken at each time point (0, 15, 30, 60, and 120 minutes) and added to 96-well plates, which had been pre-filled with 300 μL of acetonitrile (ACN). Samples were stored at 4° C. until the end of the experiment. After the final time point was sampled, the plate was mixed and then centrifuged at 3,000 rpm for 10 minutes. Aliquots of the supernatant were removed, diluted 1:1 into distilled water, and analyzed by LC-MS/MS (Table 21). The peak area response ratio to internal standard (PARR) was compared to the PARR at time 0 to determine the percent of test article remaining at each time point. Half-lives were calculated using GraphPad software, fitting to a single-phase exponential decay equation.

TABLE 21

Stability of compound 10.2HCl in buffer, plasma, and blood as measured by LC-MS/MS.

| Matrix | Percent Remaining 0 min | 15 min | 30 min | 60 min | 120 min | Half-life (min) |
|---|---|---|---|---|---|---|
| Buffer | 100 | 102 | 97 | 101 | 93 | >120 |
| Plasma | 100 | 82 | 106 | 83 | 91 | >120 |
| Blood | 100 | 92 | 87 | 100 | 115 | >120 |

Stability in liver microsomes. Experiment was conducted by Absorption Systems. Mixed-gender human liver microsomes (Lot #1210347) were purchased from Xeno-Tech. The reaction mixture, minus NADPH, was prepared (Liver Microsomes 0.5 mg/mL, NADPH (cofactor) 1 mM, potassium phosphate, pH 7.4, 100 mM, MgCl2, 5 mM). The test article was added into the reaction mixture at a final concentration of 1 μM. The control compound, testosterone, was run simultaneously with the test article in a separate reaction. The reaction mixture (without cofactor) was equilibrated in a shaking water bath at 37° C. for 3 minutes. The reaction was initiated by the addition of the cofactor, and the mixture was incubated in a shaking water bath at 37° C. Aliquots (100 μL) were withdrawn at 0, 10, 20, 30, and 60 minutes. Test article and testosterone samples were immediately combined with 400 μL of ice-cold 50/50 acetonitrile (ACN)/H2O containing 0.1% formic acid and internal standard to terminate the reaction. The samples were then mixed and centrifuged to precipitate proteins. All samples were assayed by LC-MS/MS using electrospray ionization (Table 22). The peak area response ratio (PARR) to internal standard was compared to the PARR at time 0 to determine the percent remaining at each time point. Half-lives and clearance were calculated using GraphPad software, fitting to a single-phase exponential decay equation.

TABLE 22

Stability compound 10.2HCl in liver microsomes, as measured by LC-MS/MS.

| Species | % Remaining of Initial (n = 1) 0 min | 10 min | 20 min | 30 min | 60 min | Half-life (min) | $CL_{int}$ (mL/min/mg protein) |
|---|---|---|---|---|---|---|---|
| Human | 100 | 98.0 | 91.5 | 89.6 | 80.8 | >60 | <0.0231 |

Example 14. Solubility of Compound 10.2HCl

Solubility Assay #1. Experiment was conducted by Absorption Systems. The equilibrium solubility of compound 10.2HCl was measured in pH 7.4 aqueous buffer. The buffer was prepared by combining 50 mL of 0.2 M $KH_2PO_4$ with 150 mL of $H_2O$, and then adjusting to pH 7.4 with 10 N NaOH. At least 1 mg of powder was combined with 1 mL of buffer to make a ≥1 mg/mL mixture. The sample was shaken on Eppendorf Thermomixer® overnight at room temperature. The sample was then centrifuged for 10 minutes at 14,000 rpm. The supernatant was sampled and diluted in duplicate 10-, 100-, 1,000-, and 10,000-fold into a mixture of 1:1 buffer:acetonitrile (ACN) prior to analysis and assayed by LC-MS/MS using electrospray ionization against standards prepared in a mixture of 1:1 assay buffer:ACN. Standard concentrations ranged from 1.0 μM to 0.3 nM. Using this method solubility in phosphate buffer was estimated as 39.1 μM.

Figure 5:
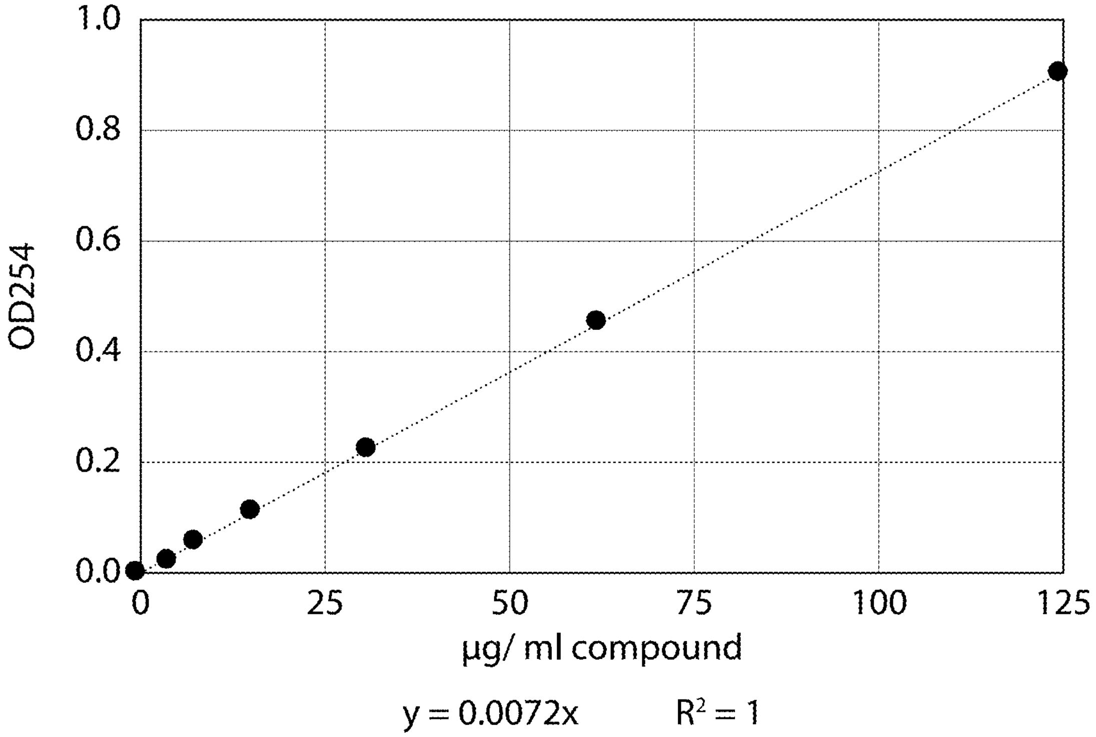
FIG. 5 Calibration curve for determining solubility of compound 10.2HCl in water. $OD_{254\ nm}$ was plotted against compound 10.2HCl standard to reveal a linear relationship.

Solubility assay #2. Solubility in water was determined by weighing 20 mg compound 10.2HCl into a glass vial and slowly adding ~0.18 ml ultrapure water such that the combined weight of compound 10.2HCl plus water was equal to 200 mg. The compound dissolved readily; no visible precipitate was observed at 2 h or overnight at room temperature. The solution was centrifuged at 16,000×g for 10 minutes at room temperature. The supernatant concentration was measured by absorbance at 254 nm. A calibration curve for UV 254 nm was constructed using a series of dilutions made from a separately prepared solution of compound 10.2HCl in water (1 mg/ml). A perfectly linear relationship was observed for standards of compound 10.2HCl at 3.9 μg/ml to 125 μg/ml (FIG. 5). Using this UV standard curve, the supernatant of a nominally 100 mg/ml solution was estimated as 108 mg/ml. Therefore, compound solubility in water is estimated as >100 mg/ml (>234 mM).

Solubility Assay #3. Qualitative solubility testing of compound 10.2HCl in borate and citrate buffers at a series of pH values indicated precipitation at approximately pH 8.5.

Example 15. Partition Coefficient (log D7.4) of Compound 10.2HCl

The octanol/buffer partition coefficient of compound 10.2HCl was measured by Absorption Systems. The buffer was prepared by combining 50 mL of 0.2 M solution of $KH_2PO_4$ with 150 mL of $dH_2O$, and then adjusting to pH 7.4 with 10 N NaOH. In a single incubation, 15 μL of a 10 mM DMSO solution of each test article was added to test tubes, which contained 0.75 mL of n-octanol and 0.75 mL of pH 7.4 phosphate buffer. Testosterone was also introduced to each tube as an internal control, also at a dosing concentration of 100 μM. These samples were gently mixed on a benchtop rotator for 1 hour at room temperature. The tubes were then removed from the rotator and the aqueous and organic phases were allowed to separate for 1 hour. An aliquot of the organic layer was taken and diluted 200-fold into a mixture of 1:1 buffer:acetonitrile (ACN). An aliquot of the aqueous layer was taken and diluted 2-fold, 10-fold, and 200-fold into a mixture of 1:1 buffer:ACN. All samples were assayed by LC-MS/MS using electrospray ionization. The log D at pH 7.4 of compound 10.2HCl was measured to be 0.822. As a methods control, the log D of testosterone was also measured at a satisfactory value.

Example 16. Permeability (Caco-2 and MDCK) of Compound 10.2HCl

Caco-2 Permeability. Experiment was conducted by Absorption Systems. Caco-2 cells (clone C2BBe1) were obtained from American Type Culture Collection (Manassas, VA). Cell monolayers were grown to confluence on collagen-coated, microporous membranes in 12-well assay plates. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 μM of test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. The flux of lucifer yellow was also measured post-experimentally for each monolayer to ensure no damage was inflicted to the cell monolayers during the flux period. All samples were assayed by LC-MS/MS using electrospray ionization. Permeability calculations were performed as per Absorption Systems protocol, Table 23.

TABLE 23

Permeability of compound 10.2HCl in Caco-2 cells.

| Test Article | Direction | Recovery (%) | Papp ($10^{-6}$ cm/s) R1 | R2 | Avg | Efflux ratio | Absorption Potential Classification | Significant Efflux |
|---|---|---|---|---|---|---|---|---|
| 10 | A to B | 108 | 0.209 | 0.176 | 0.192 | 2.58 | low | No |
| | B to A | 103 | 0.565 | 0.426 | 0.496 | | | |

Absorption potential classification: $P_{app}$(A to B) < 1 × $10^{-6}$ cm/s: low.
Papp(A-B) ≥ 1 × $10^{-6}$ cm/s: high MDR1-MDCK Permeability. Experiment was conducted by Absorption Systems. MDR1-MDCK cell monolayers were grown to confluence on collagen-coated, microporous membranes in 12-well assay plates. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 μM of test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. The flux of lucifer yellow was also measured post experimentally for each monolayer to ensure no damage was inflicted to the cell monolayers during the flux period. All samples were assayed by LC-MS/MS using electrospray ionization. Permeability calculations were performed as per Absorption Systems protocol, Table 24.

TABLE 24

Permeability of Compound 10.2HCl in MDCK cells.

| Test Article | Direction | Recovery (%) | Papp ($10^{-6}$ cm/s) R1 | R2 | Avg | Efflux ratio | Brain Penetration | Classification |
|---|---|---|---|---|---|---|---|---|
| 10 | A to B | 95.5 | <0.0566 | <0.0566 | <0.0566 | ND | low | |
| | B to A | 91.1 | <0..0772 | <0.0772 | <0.0772 | | | |

Absorption Potential Classification:
$P_{app}$(A to B)≥3×$10^{-6}$ cm/s and ER<3: high
$P_{app}$(A to B)≥3×$10^{-6}$ cm/s and 10>ER≥3: moderate
$P_{app}$(A to B)≥3×$10^{-6}$ cm/s and ER≥10, or $P_{app}$ (A to B)<3× $10^{-6}$ cm/s: low

Example 17. ROCK2 Inhibition by Compounds I to XII

We measured ROCK2 enzyme inhibition by compounds I to XII of the disclosure using commercially available ROCK2 ADP-Glo™ assay kit as described in Example 7. ROCK2 inhibitory potency quantitation results are summarized in Table 25. All 12 compounds inhibited ROCK2 in nanomolar quantity and compounds IV.2HCl and X.2HCl showed highest potency.

TABLE 25

$IC_{50}$ estimates of compounds 1 to XII.

| Compound | ROCK2 $IC_{50}$, nM |
|---|---|
| Compound I•2HCl | 18 |
| Compound II•2HCl | 47 |
| Compound III•2HCl | 58 |
| Compound IV•2HCl | 8 |
| Compound V•2HCl | 27 |
| Compound VI•2HCl | 217 |
| Compound VII•2HCl | 43 |
| Compound VIII•2TFA | 22 |
| Compound IX•2HCl | 56 |
| Compound X•2HCl | 8 |
| Compound XI•2HCl | 638 |
| Compound XII•2HCl | 34 |

Example 18. ROCK1, ROCK2, PKA, PKCtheta, and MRCKa Inhibition Assays

Experiment was conducted by Absorption Systems. IC50s of compounds 10.2HCl and I.2HCl, Netarsudil-M1-racemate.2HCl, and Netarsudil dimesylate (BOC Sciences, cat #B0084-475227) against five AGC family kinases (ROCK1, ROCK2, PKA, PKCtheta, and MRCKa) were estimated using radioisotope filter binding assay. The radioisotope filter binding assay is considered the gold standard for kinase profiling. The assay directly detects the true product without the use of modified substrates, coupling enzymes, or detection antibodies. Compounds are incubated with kinase, substrate, cofactors, and radioisotope-labeled ATP ($^{33}$P-Y-ATP). The reaction mixtures are then spotted onto filter papers, which bind the radioisotope-labeled catalytic product. Unreacted phosphate is removed via washing of the filter papers.

Assay Method:

Prepare kinase-specific substrate in freshly prepared Base Reaction Buffer (20 mM Hepes (pH 7.5), 10 mM MgCl2, 1 mM EGTA, 0.02% Brij35, 0.02 mg/ml BSA, 0.1 mM Na3VO4, 2 mM DTT, 10 UM ATP, and 1% DMSO).

Add kinase enzyme into the substrate solution and gently mix.

Add compounds in DMSO into the kinase reaction mixture by Acoustic technology (Echo550; nanoliter range), incubate for 20 minutes at room temperature.

Add $^{33}$P-ATP (specific activity 10 μCi/μl)) into the reaction mixture to initiate the reaction.

Incubate kinase reaction for 2 hours at room temperature.

Spot reactions onto P81 ion exchange paper.

Detect kinase activity by filter-binding method.

Compounds 10.2HCl and I.2HCl demonstrated significant inhibitory activity against PKA in addition to ROCK1 and ROCK2, and low potency against PKCtheta and MRCKa (Table 26) in filter binding assay. Compounds I.2HCl inhibitory activity is higher than Netarsudil dimesylate and Netarsudil-M1-racemate.2HCl, and similar to Staurosporine, a broad spectrum protein kinase inhibitor.

TABLE 26

$IC_{50}$ estimates (nM) of compounds 10•2HCl and I•2HCl, Netarsudil-M1-racemate•2HCl, Netarsudil dimesylate, and Staurosporine against 5 AGC class kinases using radioisotope filter binding assay.

| Kinase | Compound 10•2HCl | Compound I•2HCl | Netarsudil-M1-racemate• 2HCl | Netarsudil dimesylate | Staurosporine |
|---|---|---|---|---|---|
| ROCK1 | 10 | 4 | 15 | 41 | 5 |
| ROCK2 | 4 | 2 | 6 | 14 | 2 |
| PKA | 26 | 6 | 12 | 135 | 2 |
| PKCtheta | >10000 | 817 | 5128 | >10000 | 6 |
| MRCKa | >10000 | >10000 | >10000 | >10000 | 11 |

ROCK1, Rho-associated protein kinase 1;
ROCK2, Rho-associated protein kinase 2;
PKA, protein kinase A;
PKCT, protein kinase C theta; and
MRCKA, myotonic dystrophy kinase-related CDC42-binding kinase A.

Example 19. ROCK2 Inhibitory Activity of Compounds 10.2HCl, 1.2HCl, II.2HCl, and III.2HCl in Human Trabecular Meshwork (hTM) Cell-Based Assay Phosphorylation-dephosphorylation cycles mediated by kinases and phosphatases can exhibit dose response behaviors including graded response. Compounds 10.2HCl, I.2HCl, II.2HCl, III.2HCl, Netarsudil-M1-racemate.2HCl, and Netarsudil.2HCl were assayed in hTM for inhibition of phosphorylation MYPT1 (ROCK2 substrate) at concentration of 10 μM to 0.04 μM by western blotting following procedures described in Example 10. Two days before compound addition 6-well plates were seeded at a density of 75,000 cells/well. On the day of compound addition media was replaced with 3 ml fresh media containing compounds at different concentration. Fifteen hours after compound addition cells in each well were lysed with 0.2 ml extraction buffer (SDS-PAGE sample buffer containing phosphates and protease inhibitors) and extracts were collected. Equal volumes of cell extract (15 μl) were separated on SDS-PAGE and analyzed by western blotting using antibodies against Phospho-MYPT1 Thr853 (pMYPT1, Cell Signaling Technology, cat #4563S), MYPT1 (Cell Signaling Technology, cat #8574S) and GAPDH (Proteintech, cat #60004-1-1). Blots were first stained with Phospho-MYPT1 Thr853 antibody and bound antibodies were stripped off of blots using Thermo Scientific Restore Western Blot Stripping Buffer (cat #21059) before probing with MYPT1 and/or GAPDH antibodies.

Figure 6:
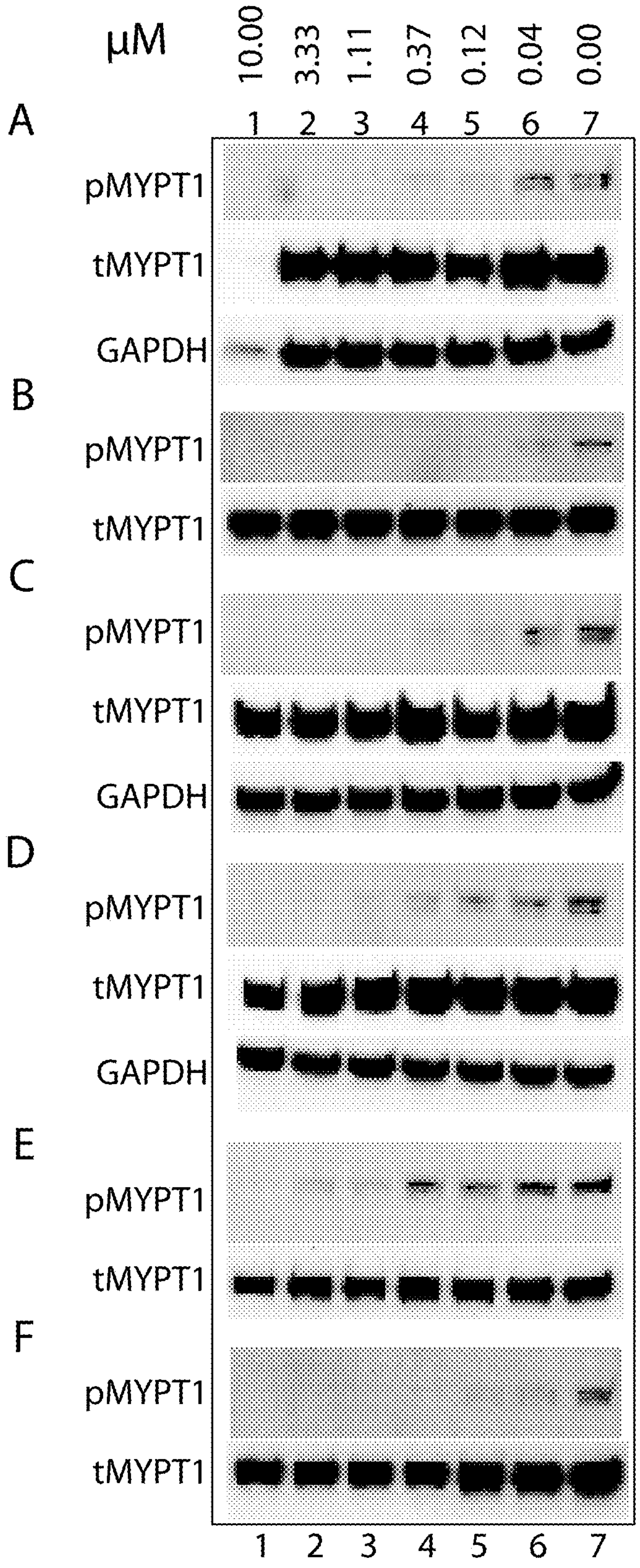
FIG. 6 Dose response of: (A) Netarsudil.2HCl; (B) Netarsudil-M1-racemate.2HCl; (C) compound I.2HCl; (D) compound 10.2HCl; (E) compound II.2HCl; and (F) compound III.2HCl in inhibition of pMYPT1 phosphorylation; pMYPT1; MYPT1 phosphorylated at Thr853; tMYPT1; total MYPT1 protein; and GAPDH; housekeeping protein for normalization.

Western blot images of dose response are shown in FIG. 6. No staining of pMYPT1 was observed at 10 μM concentration of all compounds assayed. Lane with cells incubated with Netarsudil.2HCl at 10 μM had much lower amount of protein because of toxicity at this concentration (FIG. 6, A). Western blotting is not a quantitative assay. However, comparison of pMYPT1 band intensities at different concentrations suggested that compound II.2HCl is less effective at lower concentrations in inhibiting MYPT1 phosphorylation compared other compounds (FIG. 6). Staining for total MYPT1 or GAPDH showed approximately equal amount of extract was loaded in wells.

Figure 7:
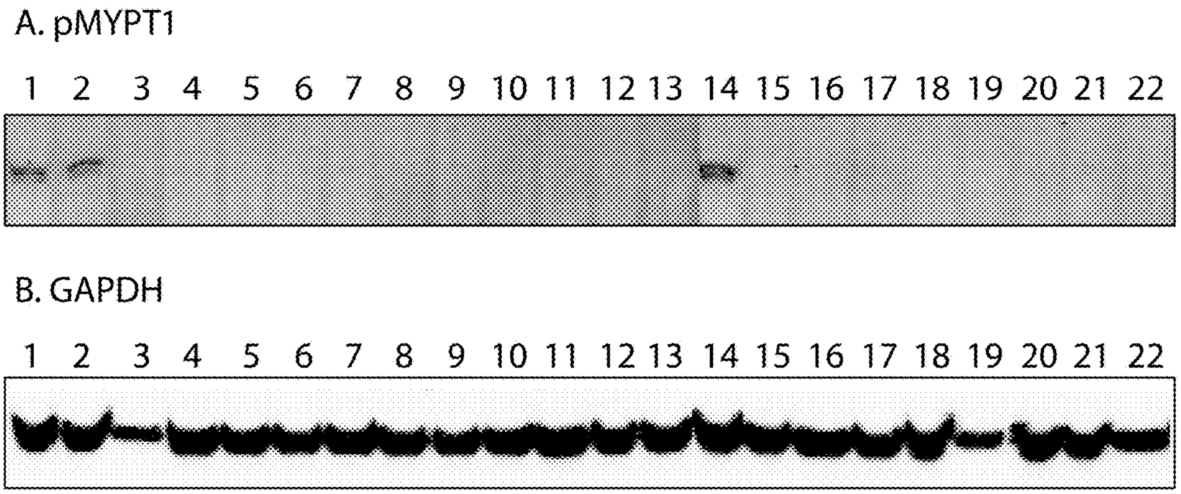
FIG. 7 (A) Inhibition of MYPT1 phosphorylation by 13 disclosed compounds and 6 ROCK inhibitors. (B) The same blot was stained with GAPDH antibody for normalization. Lanes 3 with cells incubated with Netarsudil dimesylate and lane 22 with cells incubated with Staurosporine have less protein than in other lanes due to toxicity, as seen with less intense GAPDH antibody staining.

In another experiment hTM cells were incubated with 19 compounds including 6 ROCK inhibitors at 10 UM concentration for 24 hours and measured their effect on inhibition of MYPT1 phosphorylation by western blotting. Compounds (10 μM) were added to hTM cells cultured in 60 mm plates and cell extracts collected after 24. Cells were lysed with 0.2 ml lysis buffer and 20 μl extract was loaded in each lane (FIG. 7). All 13 disclosed compounds inhibited phosphorylation of pMYPT1. Among the 6 ROCK inhibitors, only Fasudil did not inhibit MYP2 phosphorylation at 10 μM.

| Lane | Compound |
|---|---|
| 1 | DMSO control |
| 2 | Fasudil |
| 3 | Netarsudil dimesylate |
| 4 | Netarsudil-M1-racemate•2HCl |
| 5 | Compound I•2HCl |
| 6 | Compound 10•2HCl |
| 7 | Compound II•2HCl |
| 8 | Compound IIL2HCl |
| 9 | Compound IV•2HCl |
| 10 | Compound V•2HCl |
| 11 | Compound VI•2HCl |
| 12 | Compound VII•2HCl |
| 13 | Compound VIII•2TFA |
| 14 | DMSO control |

-continued

| Lane | Compound |
|---|---|
| 15 | Compound IX•2HCl |
| 16 | Compound X•2HCl |
| 17 | Compound XI•2HCl |
| 18 | Compound XII•2HCl |
| 19 | Netarsudil dimesylate |
| 20 | Ripasudil |
| 21 | Y27632 |
| 22 | Staurosporin |

Example 20. Cytotoxic Effect of Compounds 10.2HCl and 1.2HCl and Netarsudil.2HCl in hTM Cells Commercially available RealTime-Glo™ MT cell viability (Promega, catalog #G9712) and CellTox™ Green cytotoxicity (Promega, catalog #G8731) assays were used in assessing effect of compounds on primary hTM cell viability and cytotoxicity. The RealTime-Glo™ MT cell viability assay is a nonlytic, homogeneous, bioluminescent method that determines the number of viable cells in culture by measuring the reducing potential of cells and thus metabolism (MT). Viable cells reduce the proprietary pro-substrate to generate a substrate for NanoLuc® luciferase. This substrate diffuses from cells into the surrounding culture medium, where it is rapidly used by the NanoLuc® Enzyme to produce a luminescent signal. In a contrasting and complementary manner, CellTox™ Green cytotoxicity assay measures changes in membrane integrity that occur as a result of cell death. This assay system uses a proprietary asymmetric cyanine dye that is excluded from viable cells but preferentially stains the dead cells' DNA. The fluorescent signal produced by the dye binding to the dead-cell DNA is proportional to cytotoxicity.

Human™ cells were cultured and maintained as described in Example 12. Fifty μl cells (600 cells) in culture media containing compound, 25 μl media with RealTime-Glo™ MT cell viability assay reagent and 25 μl media with CellTox™ Green cytotoxicity assay reagent were plated in black, clear bottom 96-well plates. Light emitted by luciferase and fluorescence emitted by dye binding to DNA (excitation 485 nm and emission 525 nm) were measured at 24 h, 48 h, and 72 h after incubation using plate based luminescence and fluorescence plate readers. Manufacturer's suggested protocol was followed without any modifications.

Figure 8:
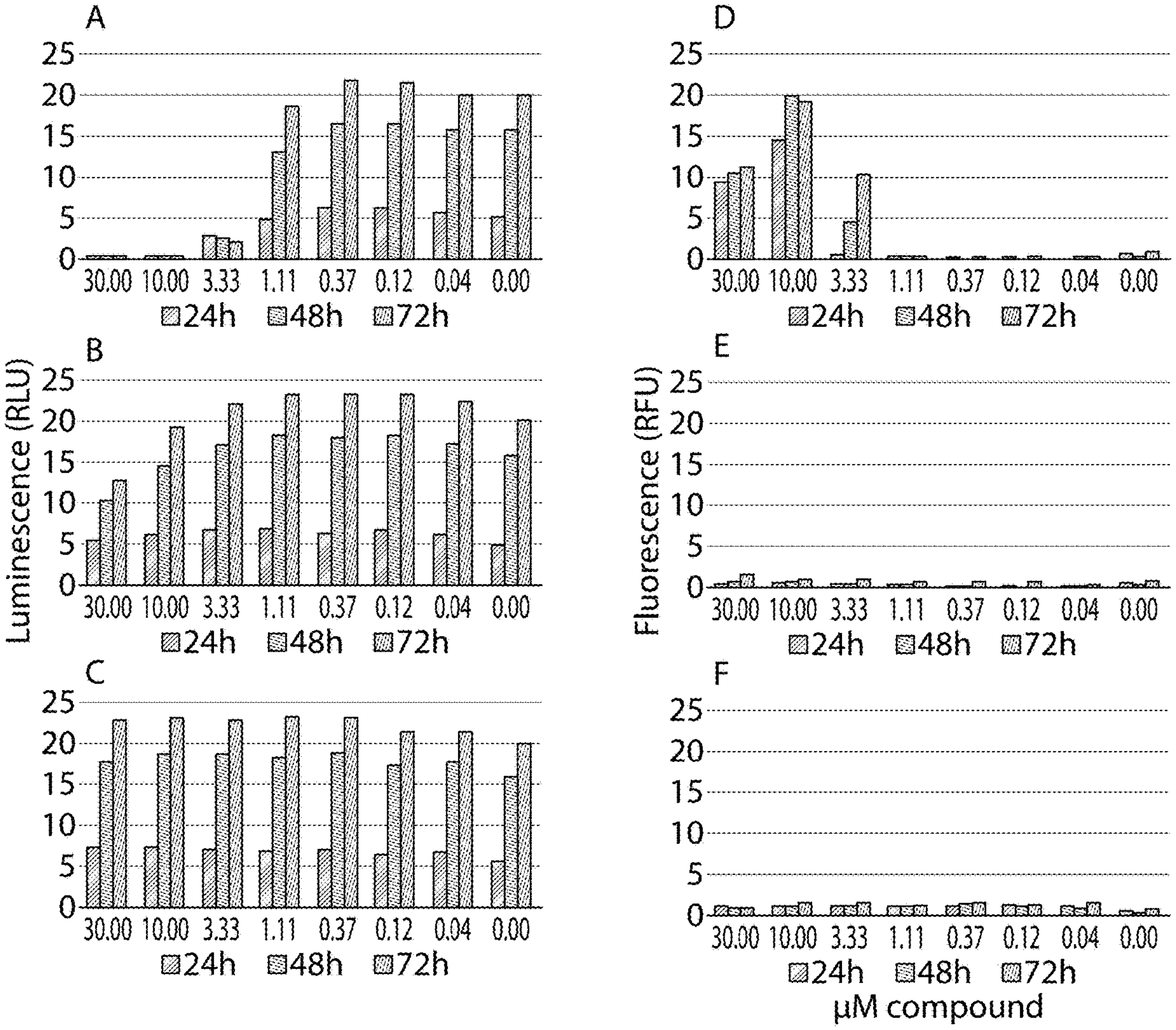
FIG. 8 Cell viability and cytoxicity performed in hTM cells. (A) Cell viability, cells incubated with Netarsudil.2HCl. (B) Cell viability, cells incubated with compound I.2HCl. (C) Cell viability, cells incubated with compound 10.2HCl. (D) Cytotoxicity, cells incubated with Netarsudil.2HCl. (E) Cytotoxicity, cells incubated with compound I.2HCl. (F) Cytotoxicity, cells incubated with compound 10.2HCl. Luminescence of RealTime-Glo™ MT assay and fluorescence of CellTox™ Green were monitored at 24 h, 48 h, and 72 h on Thermo Scientific Luminoskan luminometer and Molecular Devices SpectraMax Gemini fluorescence plate readers. RLU; relative light units, RFL; relative fluorescence units.

Luminescence associated with viability and fluorescence associated with cytotoxicity were concentration dependent for Netarsudil.2HCl (FIGS. 8, A and D). Cell viability was <2% within 24 h and <0.1% within 48 h at 30 UM and 10 μm concentrations compared to DMSO controls (FIG. 8, A). At 3.33 μm concentration, cell viability was 53%, 15% and 9% within 24 h, 48 h, and 72 h, respectively. A 10% reduction in viability was observed at 1.11 μM concentration. Cytotoxicity assay measuring complementary cell health by estimating fluorescence due to loss of membrane integrity correlated with viability (FIG. 8, D). Unlike Netarsudil.2HCl, compound 10.2HCl showed no effect on viability or membrane integrity at all concentrations and time points (FIGS. 8, C and F). Compound I.2HCl reduced viability by ~35% at 30 μM concentration only after 48 to 72 hours incubation (FIGS. 8, B and E).

Figure 9:
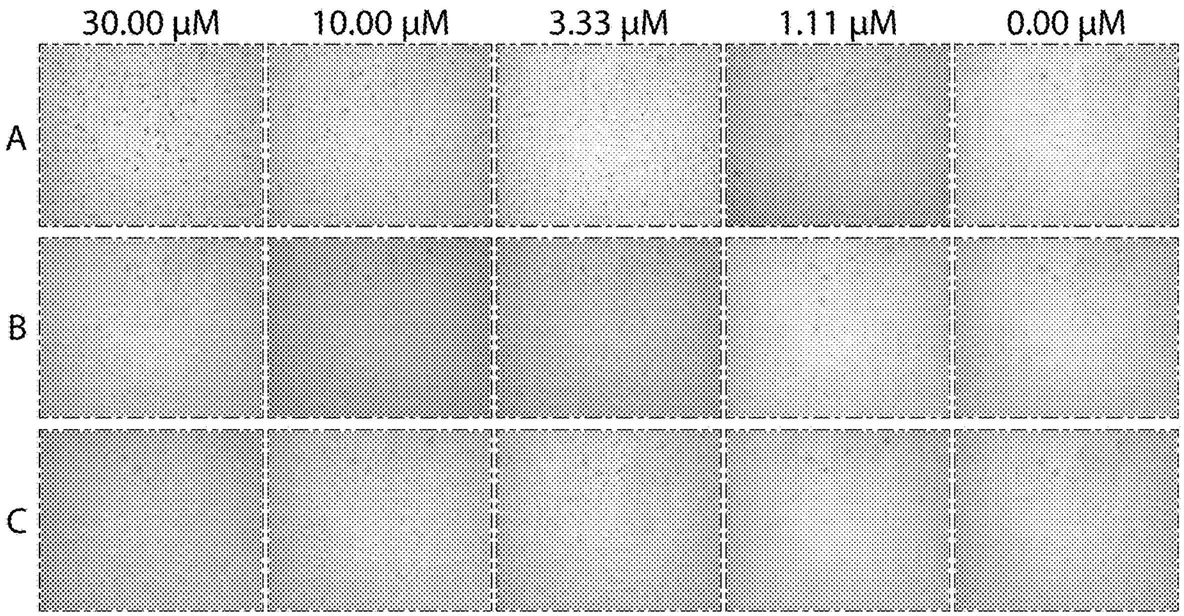
FIG. 9 Morphological changes in hTM cells after incubation with: (A) Netarsudil.2HCl; (B) compound I.2HCl; and (C) compound 10.2HCl, at indicated concentrations (μM) for 24 hours. Images (100×) were captured on a light microscope using a black and white digital camera.

To evaluate cellular morphological changes, hTM cells were incubated with 30, 10, 3.33, or 1.11 μM compound I.2HCl, compound 10.2HCl, or Netarsudil.2HCl in 24-well plates. Compounds diluted in culture media were added when cells reached 90% confluency and cells were observed 24 hours later. Netarsudil.2HCl affected cell morphology starting at 1.11 μM showing cell contraction and becoming round and small at 10 μM (FIG. 9). Cells incubated with 30 μM Netarsudil.2HCl were slightly larger than cells with 10 μM. This difference appeared to be due to lower solubility of Netarsudil.2HCl at 30 μM. In contrast, no cell morphological changes were observed with compound 10.2HCl at any concentration tested. Cells incubated with compound I.2HCl at 30 μM were beginning to show cell contraction. Cell viability, cytotoxicity, and morphology assays with primary hTM cells provided an indication that compounds 10.2HCl and I.2HCl have less potential to cause cell and tissue injury.

Example 21. Intraocular Pressure (IOP) Reduction in Rabbit

Efficacy of compounds 10.2HCl and I.2HCl in reducing intraocular pressure (IOP) was evaluated in rabbit models of (a) sodium hyaluronate-induced acute ocular hypertension, (b) phenol-induced chronic model of glaucoma, and (c) normotensive rabbits. For these efficacy studies methods were followed as described in (Jacob et al, A promising drug candidate for the treatment of glaucoma based on a P2Y6-receptor agonist, Purinergic Signal. 2018 September; 14 (3): 271-284). In all studies, male New Zealand White rabbits were acclimatized for one week before the study. Animals were given food and water ad libitum. Body weights of rabbits ranged from 2 to 3 kg. Animals were trained for the IOP measurement procedure during the acclimation period in order to reduce stress and obtaining more accurate measurements during the study. IOP measurements were taken using the Icare® TONOVET Plus tonometer. TONOVET Plus is a non-contact rebound tonometer and does not require local anesthesia. The technique of use of the non-contact tonometer in rabbits was described previously (Gloe et al, Validation of the Icare® TONOVET Plus Rebound Tonometer in Normal Rabbit Eyes, Exp Eye Res. 2019 August; 185:107698). IOP readings are obtained only when the tonometer is held an appropriate distance and in the correct plane relative to the ocular surface. Green light appears when the orientation is correct, thereby minimizing operator errors. Measurements were performed at the same time of day by the same person using the same instrument.

Figure 10:
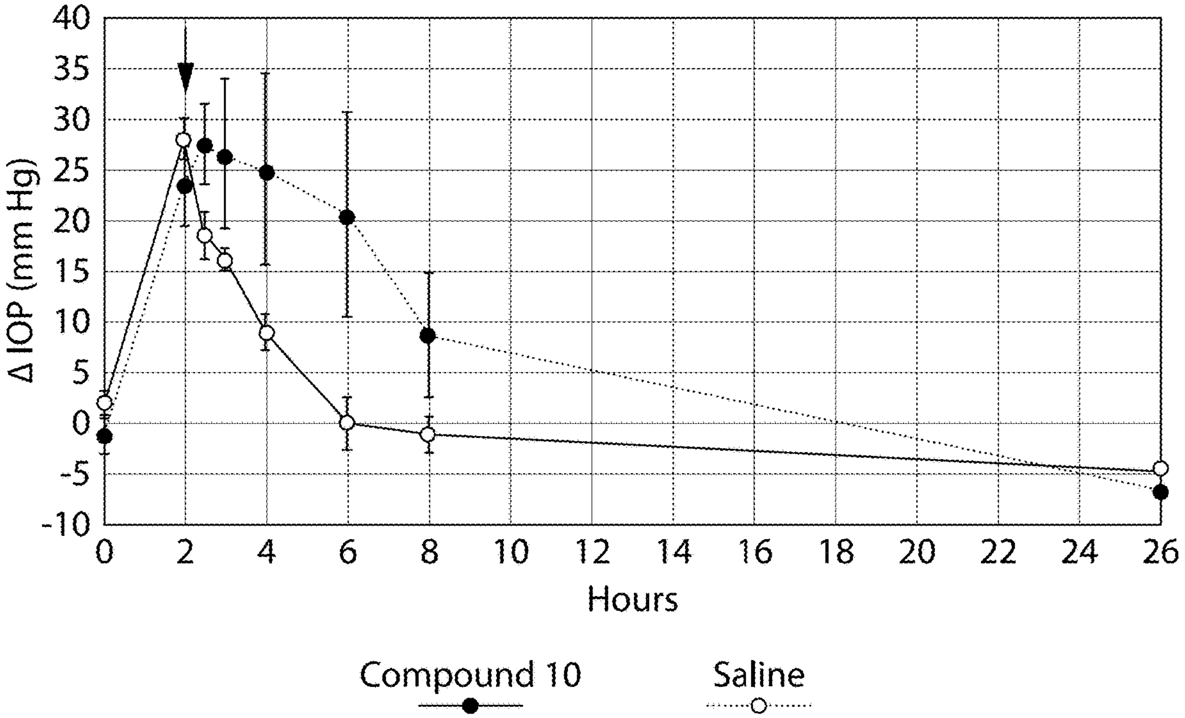
FIG. 10 Efficacy of compound 10.2HCl in acute hypertension rabbit model induced by unilateral injection of 2.3% sodium hyaluronate into the anterior chamber of the right eye. Two hours after injection 30 μl drops of compound 10.2HCl in saline (1 mg/ml, 2.34 mM) or saline (0.9% NaCl) were applied to right eye. Left eye of both groups received saline. Difference in right eye IOP from left eye at each measurement were compared. Arrow shows time of compound application. Each point and bar represent means±SEM of four rabbits.

Sodium hyaluronate-induced acute ocular hypertension study. Sodium hyaluronate injection into the anterior chamber of rabbit eye creates acute ocular hypertensive status. Rabbits were subjected to unilateral injection of 2.3% sodium hyaluronate into the anterior chamber of the right eye. Two hours after sodium hyaluronate injection, IOP increased in the injected right eye compared to IOP before injection. In experiment 1, the right eye of four rabbits with elevated IOP was treated by topical application with 30 μl of compound 10.2HCl prepared in normal saline (0.9% NaCl, vehicle). Another group of four animals with elevated IOP received saline only in right eyes. The left eyes of both groups were instilled topically with 30 μl saline eye drop. IOP was assessed in both eyes before compound application (0 h) and at 0.5, 1, 2, 4, 6, and 24 hours after application. As shown in FIG. 10, compound 10.2HCl decreased IOP significantly within 1 hour after application compared to the 'saline only' group. This effect lasted for 6 hours. The IOP reached to normal levels in all animals within 24 hours.

Figure 11:
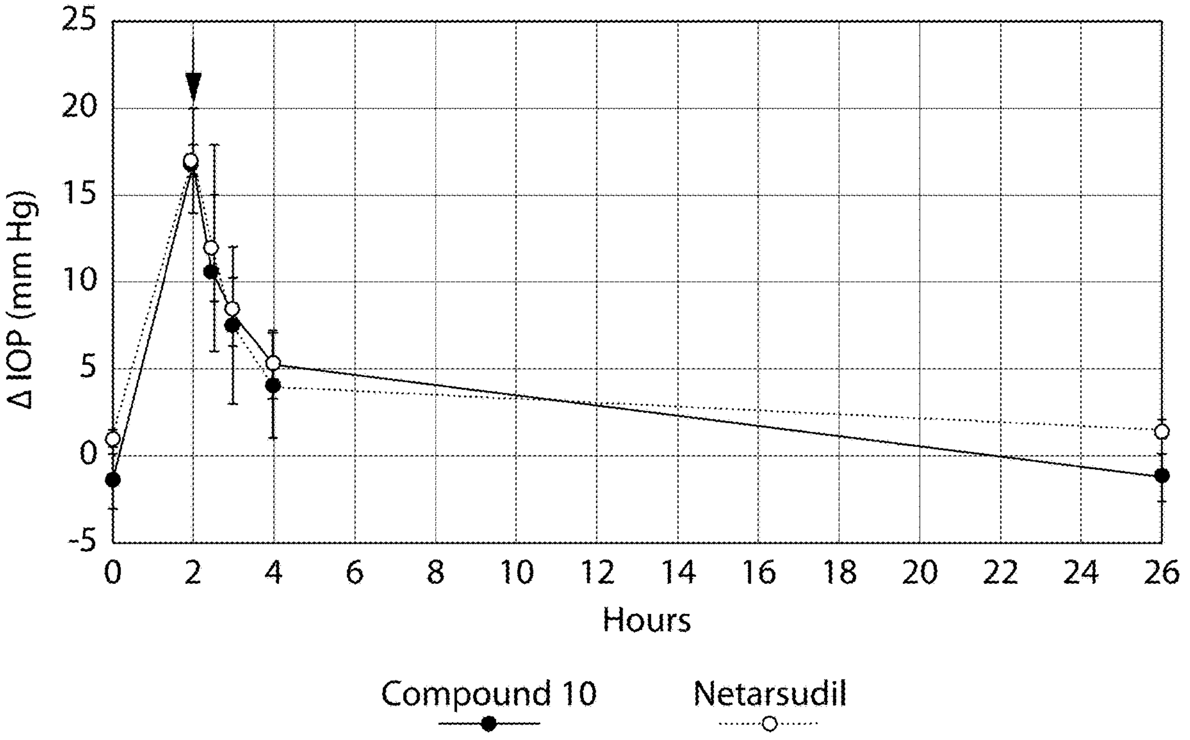
FIG. 11 Efficacy of compound 10.2HCl and Netarsudil.2HCl in acute hypertension rabbit model. Thirty μL eye drops were instilled 2 hours after hyaluronate injection in right eye, one group received compound 10.2HCl in saline (1 mg/ml, 2.34 mM) another group received compound Netarsudil.2HCl in saline (0.25 mg/ml, 0.47 mM). Left eye of both groups were instilled with 30 μL saline. Difference in right eye IOP from left eye at each measurement are compared. Arrow shows time of compound application. Each point and bar represent means±SEM of four rabbits.

In experiment 2 of the hyaluronate-induced acute model, compound 10.2HCl was compared with Netarsudil.2HCl. Both compounds showed a similar effect and reduced IOP significantly within 1 hour after eye drop application. The trend continued until IOP levels reached normal levels in 24 hours after application (FIG. 11).

Figure 12:
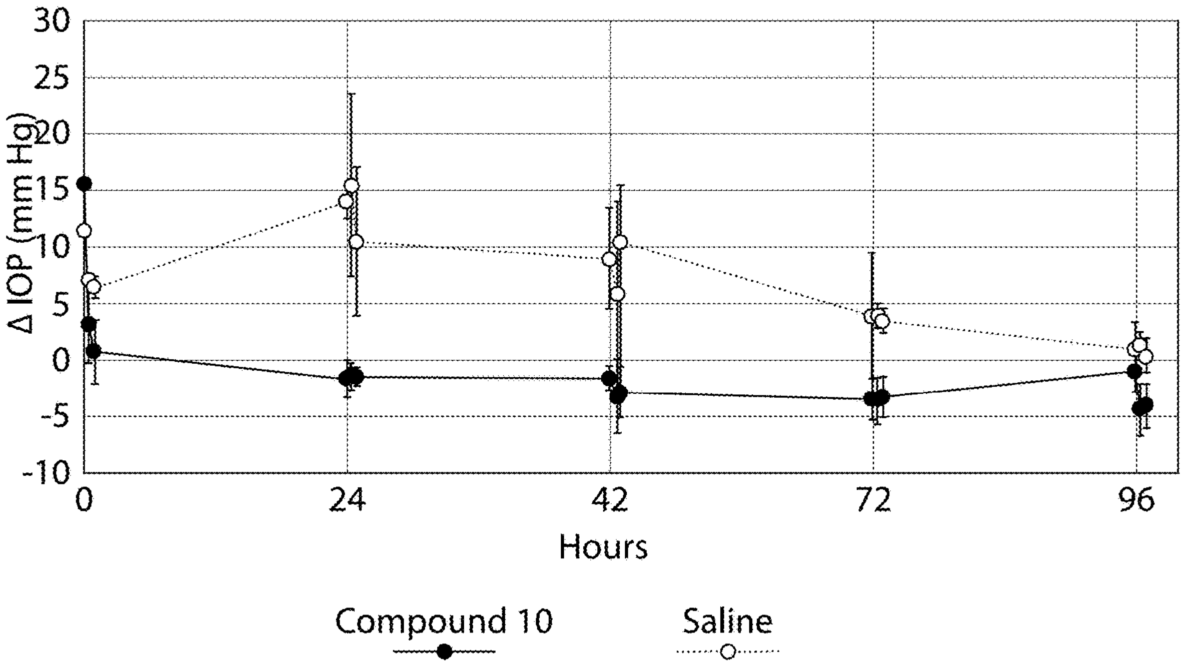
FIG. 12 Efficacy of compound 10.2HCl in chronic model of glaucoma induced by phenol injection. Thirty μL eye drop of compound 10.2HCl in saline (1 mg/ml, 2.34 mM) or saline alone was applied twice daily in right eye on days 8 to 12 after phenol injection. Time of compound or saline application on day 8 morning is shown as 0 hours. IOP measurements were taken on days 8 to 12 before compound application in the morning and 0.5 and 1 hour after morning application. The data are presented as the difference in IOP of right eye and left eye. Each point and bar represent mean±SEM of 5 rabbits for compound 10.2HCl and 2 rabbits for saline.

Phenol-induced chronic model of glaucoma. Subconjunctival injection of phenol was given into right eye and left eye served as control. IOP was measured daily after phenol injection and IOP doubled in 8 days after phenol injection. The right eye was instilled with compound 10.2HCl in saline (1 mg/ml, 2.34 mM) twice daily (8 AM and 5 PM) for 5 days (Days 8 to 12). Left eye of all animals received 30 μL saline and served as control. IOP readings were taken on mornings of days 8 to 12 before compound application and 0.5 and 1 hour after morning application. FIG. 12 shows IOP measurements expressed as differences from left eye over 5 days. Instilling compound 10.2HCl resulted in decrease of IOP to normal levels within 1 hour after application. Subsequent twice daily application maintained normal IOP. In comparison, IOP levels remained high for five days in saline treated rabbits.

Figure 13:
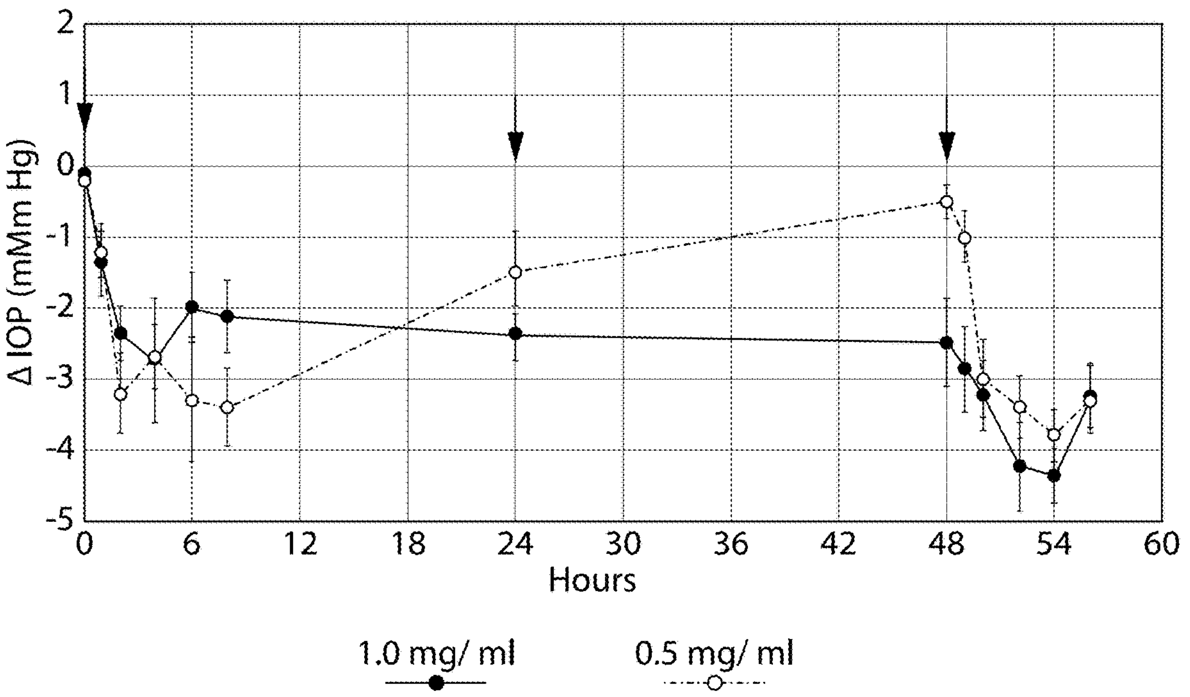
FIG. 13 Effect of compound I.2HCl on IOP in normotensive rabbits. Compound I.2HCl (1.0 or 0.5 mg/ml, 2.34 or 1.17 mM) in saline applied once daily as eye drop on days 1, 2 and 3. Contralateral left eye treated with saline served as control. Time dependent effect on IOP after compound addition is shown as the difference in IOP from control left eye. Arrows show time of compound application. All values are the means±SEM of 8 and 10 rabbits for 1 mg/ml and 0.5 mg/ml, respectively.

Normotensive rabbit studies. Compounds I.2HCl and 10.2HCl were evaluated in normotensive eyes. In experiment 1 of the normotensive study, the effect of compound I.2HCl was measured at two doses of 1 mg/ml (2.34 mM) and 0.5 mg/ml (1.17 mM). Compound I.2HCl prepared in saline was applied to the right eye, as a once daily, 30 μL eye drop application in the morning on days 1, 2 and 3. IOP measurements were taken before test article addition (0 h) and at 1, 2, 4, 6, and 8 hours after addition on days 1 and 3. On day 2, only a 0 h reading was taken. This was done to minimize stress on the animals and to compare day 2-0 h and day 3-0 h readings without handling rabbits between applications. Compound I.2HCl significantly reduced IOP with 2 hours after the instillation on day 1 at both doses (FIG. 13). Twenty four hours after the instillation, IOP increased but still remained below normal levels. At 1 mg/ml dose, the IOP remained lower than normal levels on day 3; compound application on day 3 further reduced IOP. At 0.5 mg/ml dose, the IOP reached normal levels by day 3 but IOP reduced to same levels as 1 mg/ml dose after compound instillation. Both doses markedly reduced IOP by ~35%.

Figure 14:
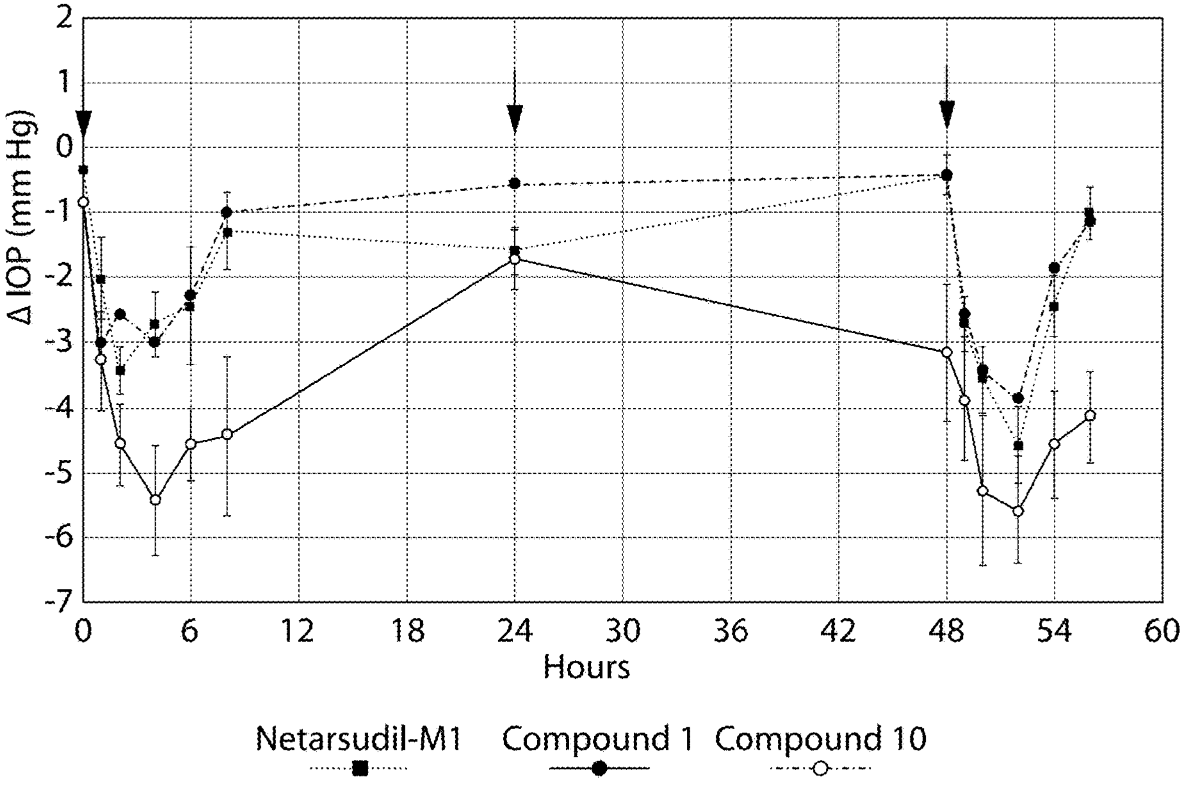
FIG. 14 Effect of compounds 10.2HCl and I.2HCl and Netarsudil-M1-racemate.2HCl on IOP in normotensive rabbit. Compounds were formulated in 0.5% carboxymethylcellulose (Refresh Tears™) at 0.83 mM and applied once daily as eye drop on days 1, 2 and 3. Contralateral left eye treated with Refresh Tears™ served as the control. Time dependent effect on IOP after compound addition is shown as the difference in IOP from the control left eye. Arrows show time of compound application. All values are the means±SEM of 7 rabbits.

In experiment 2 of normotensive study, compounds 10.2HCl and I.2HCl and Netarsudil-M1-racemate.2HCl were prepared in 0.5% carboxymethylcellulose by dissolving in over-the-counter Refresh Tears™ (Allergan Inc, Irvine, CA, USA) and tested at equimolar concentration of 0.83 mM. Similar to Experiment 1 of the normotensive study, compounds were applied once daily in the right eye in the morning on days 1, 2 and 3, whereas the left eye served as a control with application of Refresh Tears™. IOP measurements were taken at 0, 1, 2, 4, 6, and 8 hours on days 1 and 3, and 0 hours on day 2. All compounds reduced IOP significantly within 2 hours after application on day 1, the effect was much more pronounced with compound I.2HCl compared to compound 10.2HCl and Netarsudil-M1-racemate.2HCl (FIG. 14). Application on day 3 again reduced IOP significantly.

Efficacy studies in rabbit show that administration of novel compounds disclosed in this invention significantly reduce IOP in three different models tested.

Example 22. In Vivo Test for Acute Eye Irritation/Corrosion

The objective of the study was to assess the eye irritation/corrosion potential of compounds 10.2HCl and I.2HCl, Netarsudil-M1-racemate.2HCl, and Netarsudil.2HCl when applied to the eye of New Zealand White Rabbits. The study was performed in accordance with the Acute Eye irritation and OECD Guideline for Testing of Chemicals, No. 405: Acute Eye Irritation/Corrosion, 2017, and in compliance with Good Laboratory Practices.

Figure 15:
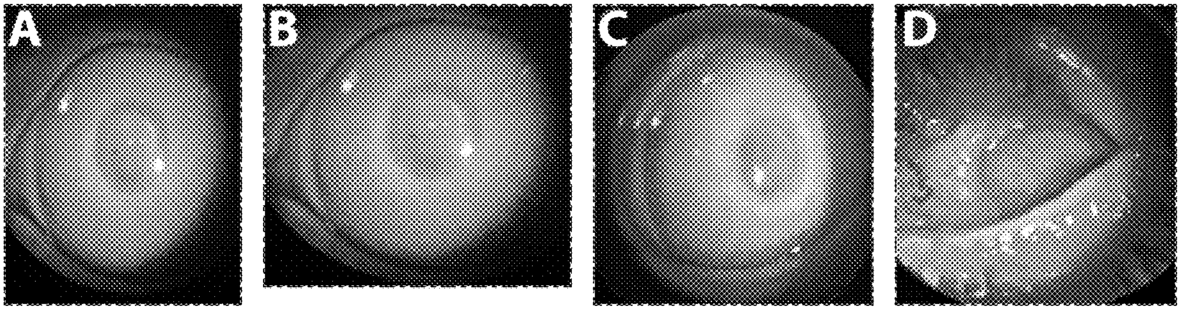
FIG. 15 Acute eye irritation in rabbits as per OECG 405 guidelines. A-D indicate representative eye of the animals used in the experiment 72 h after test article application. (A) Compound 10.2HCl; (B) Compound I.2HCl; (C) Netarsudil-M1-racemate.2HCl; and (D) Netarsudil.2HCl.

Compounds 10.2HCl and I.2HCl and Netarsudil-M1-racemate.2HCl (0.1 ml, 20 mg/ml in saline) were instilled using a micropipette into the conjunctival sac of left eye. The right eye that was not treated served as the control. Left eye of initial test animal did not exhibit ocular lesions at 24, 48 and 72 hours. To confirm the findings of the initial test, confirmatory test was conducted with two additional animals. The eyes of initial and confirmatory test animals were examined with slit lamp for ocular lesions. They were graded for mean score for conjunctival oedema (chemosis), conjunctival redness, iris and corneal opacity and scores as 0.0, 0.0, 0.0 and 0.0, respectively. The animals were also observed for clinical signs of toxicity, morbidity and mortality. No treatment-related adverse effects were noticed. The mean scores of initial and confirmatory test animals did not fall under any of the categories of the GHS classification and labeling of chemicals. Therefore, compounds 10.2HCl and I.2HCl and Netarsudil-M1-racemate.2HCl were classified to be non-irritating to the eye of New Zealand White Rabbits (FIG. 15).

Netarsudil.2HCl was not soluble in saline above 5 mg/ml. Therefore, 0.1 ml of 5 mg/ml was tested for eye irritation. Under the conditions OECD Guideline 405, Netarsudil.2HCl was graded for mean score for conjunctival oedema (chemosis), conjunctival redness, Iris and corneal opacity as 4.0, 3.0, 2.0 and 3.0, respectively. Netarsudil.2HCl was classified to be irritating to the eye of New Zealand White Rabbits (FIG. 15).

The foregoing presents particular embodiments of a system embodying the principles of the invention. Those skilled in the art will be able to devise alternatives and variations which, even if not explicitly disclosed herein, embody those principles and are thus within the scope of the invention. Although particular embodiments of the present invention have been shown and described, they are not intended to limit the scope of the invention. One skilled in the art will understand that various changes and modifications may be made without departing from the scope of the present invention as literally and equivalently covered by the following claims.

All patents and publications cited herein are fully incorporated by reference in their entirety.

What is claimed is:

1. A compound of Formula 1 or a pharmaceutically acceptable salt or solvate thereof:

Formula 1

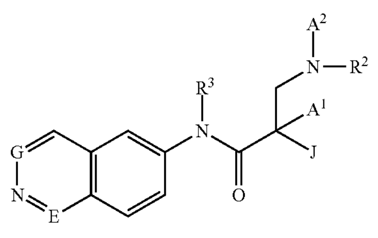

or a stereoisomer, tautomer, or pharmaceutically acceptable salt or solvate thereof, wherein:

E is selected from the group consisting of CH, C—OH, N, or NH,

G is CH, or, when E is NH, G is absent;

J is —$(CH_2)_n$-$A^6$, or

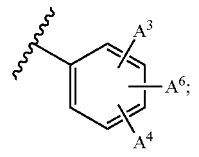

$A^1$, $A^2$, $R^2$ and $R^3$ are each —H or C1-C6 alkyl;

$A^3$ and $A^4$ are each selected from the group consisting of hydrogen, halo, C1-C6 alkyl, nitro, cyano, hydroxy, amino, optionally substituted alkyl, haloalkyl, hydroxyalkyl, alkoxy, alkylthio, alkoxyalkyl, alkylaminoalkyl, dialkylaminoalkyl, alkylaminoalkenyl, dialkylaminoalkenyl,

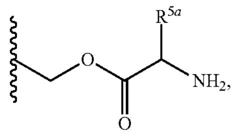

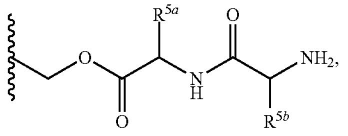

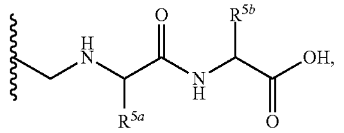

and

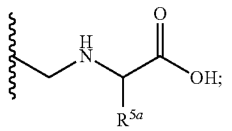

$R^{5a}$ and $R^{5b}$ are selected from a side chain of any natural amino acid, C1-C6 alkyl, trifluoro-C1-C6 alkyl, —$(CH_2)_nSH$, —$(CH_2)_n$NH—C(=NH)$NH_2$, —$(CH_2)_nCO_2H$, —$(CH_2)_nNH_2$, —$(CH_2)_nCH(NH_2)(CO_2H)$, —$(CH_2)_nSO_3H$, —$(CH_2)_nNR^6R^7$, —$(CH_2)_n$-pyridyl, —$(CH_2)_nONO_2$;

$A^6$ is —$(CR^6R^7)_nB(R^8R^9)$,

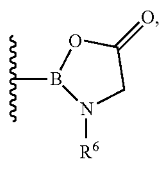

,

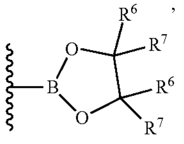

, or

-continued

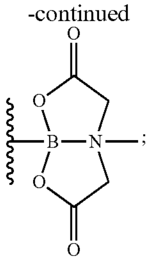

or $A^6$ together with either $A^3$ or $A^4$ form —$BR^8O(CR^6R^7)_nO$—, —$BR^8O(CR^6R^7)_nNR^6$—, —$BR^8O(CR^6R^7)_n$—, —$BR^8NR^6(CR^6R^7)_nO$—, —$BR^8NR^6(CR^6R^7)_nNR^6$—, —$BR^8NR^6(CR^6R^7)_n$—, —$B(R^8)_2N(R^6)_2(CR^6R^7)_nO$—, —$B(R^8)_2N(R^6)_2(CR^6R^7)_nNR^6$—, —$B(R^8)_2N(R^6)_2(CR^6R^7)_n$—, —$BR^8$—O—N=CH—, —$BR^8NR^6$N=CH—, —$B(R^8)_2N(R^6)_2$N=CH—, —$BR^8$—O—$CR^6$—N—, —$BR^8NR^6CR^6$—N—, —$BR^8$—O—C(=O)$NR^6$—, —$BR^8NR^6$C(=O)$NR^6$—, —$BR^8$—O—C($NR^6$)—N—, —$BR^8NR^6$C($NR^6$)=N—, —$B(R^8)_2N(R^6)_2CR^6$=N—, —$B(R^8)_2N(R^6)_2$C(=O)—N—, —$B(R^8)_2N(R^6)_2C(NR^6)$=N—, —$BR^8$—O—$NR^6$—, —B(OH)—O—NH—C(O)—, —B(OH)$NR^6$NHC(O)—, —$B(OH)_2N(R^6)_2$NHC(O)—, —$OBR^8$CH=CH—, —$NR^6BR^8$CH=CH—, —$N(R^6)_2$ $B(R^8)_2$CH=CH—, —$OBR^8(CR^6R^7)_nO$—, —$OBR^8(CR^6R^7)_nNR^6$—, —$OBR^8(CR^6R^7)_n$—, —$NR^6BR^8(CR^6R^7)_nO$—, —$NR^6BR^8(CR^6R^7)_nNR^6$—, —$NR^6BR^8(CR^6R^7)_n$, —$N(R^6)_2B(R^8)_2(CR^6R^7)_nO$—, —$N(R^6)_2B(R^8)_2(CR^6R^7)_nNR$—, —$N(R^6)_2B(R^8)_2(CR^6R^7)_n$—, —$BR^8$—O—CH=CH—, —$BR^8NR^6$CH=CH—, —$B(R^8)_2N(R^6)_2$CH=CH—;

$R^6$ and $R^7$ are each H, C1-C6 alkyl, C1-C6 alkenyl, C1-C6 alkynyl, trifluoro C1-C6 alkyl, acetyl, phenyl, C1-C6 alkylsulfonyl;

$R^8$ and $R^9$ are each fluoro, hydroxy or alkoxy; or —$B(R^8R^9)$ forms a fluoride adduct, hydroxy acid adduct, or an amino acid adduct;

n and m are each 0, 1, 2, 3, or 4.

2. The compound of claim 1, wherein Formula 1 is represented by Formula 2:

Formula 2

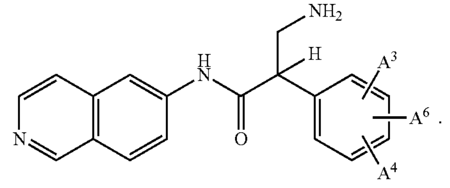

3. The compound of claim 2, wherein Formula 2 is represented by any of Formulae 3-11:

Formula 3

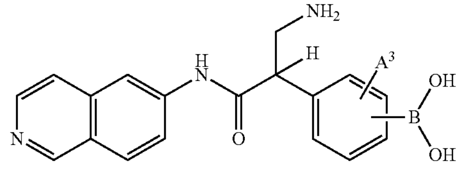

-continued
Formula 4
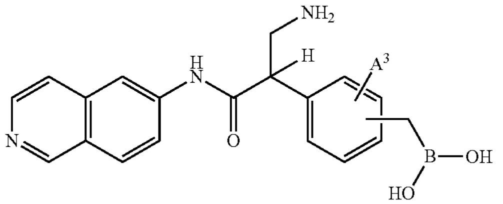
Formula 5
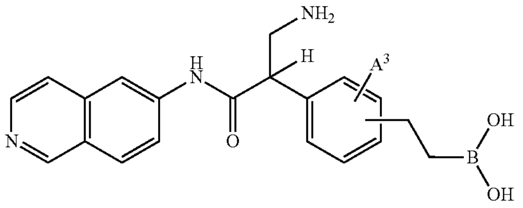
Formula 6
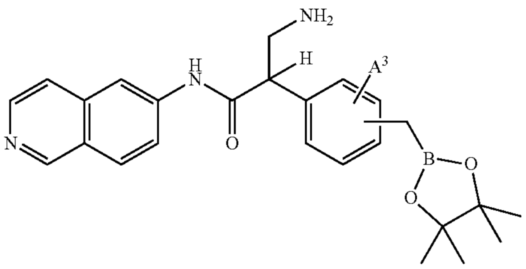
Formula 7
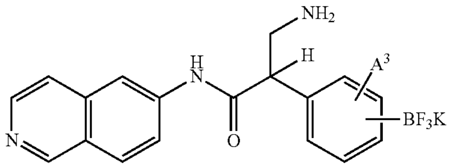
Formula 8
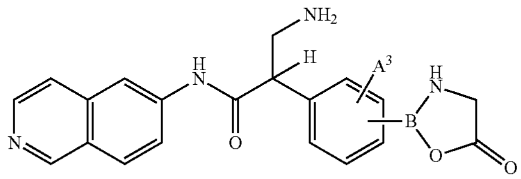
Formula 9
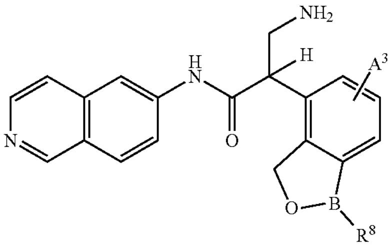
Formula 10
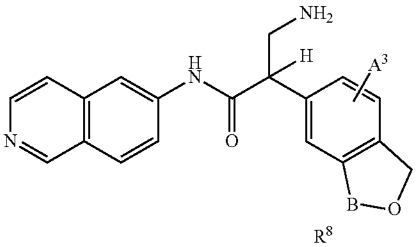
-continued
Formula 11
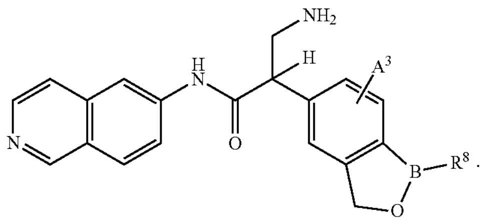
4. The compound of claim 2, wherein Formula 2 is represented by any of Formulae 12-17:
Formula 12
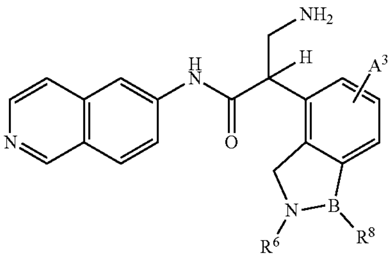
Formula 13
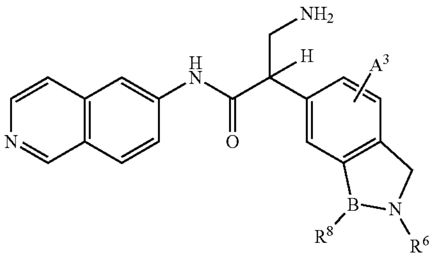
Formula 14
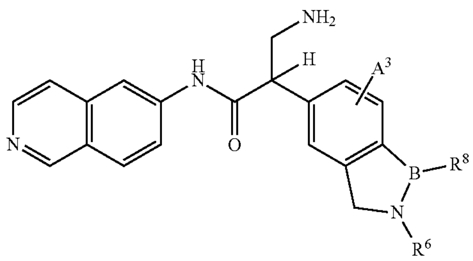
Formula 15
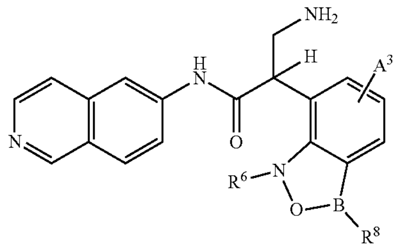

-continued
Formula 16
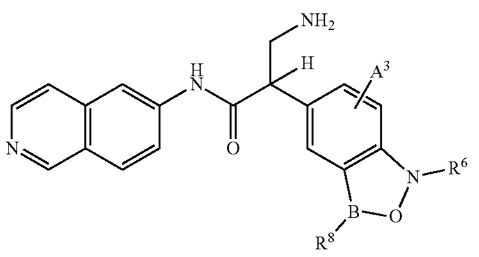
Formula 17
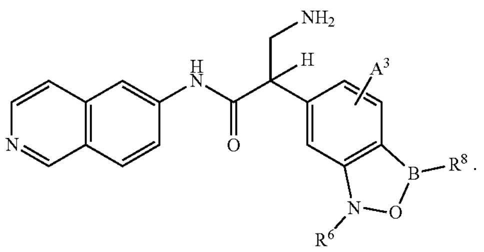
5. The compound of claim 2, wherein Formula 2 is represented by any of Formulae 18-23:
Formula 18
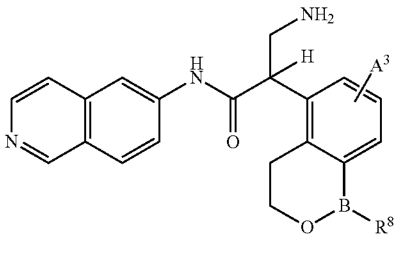
Formula 19
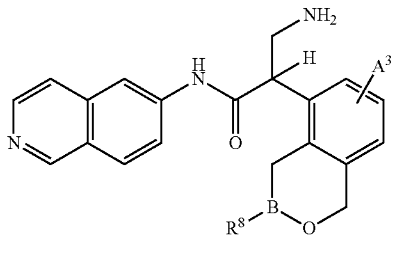
Formula 20
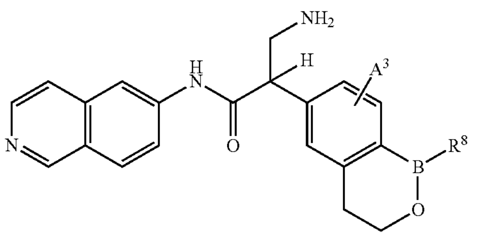
-continued
Formula 21
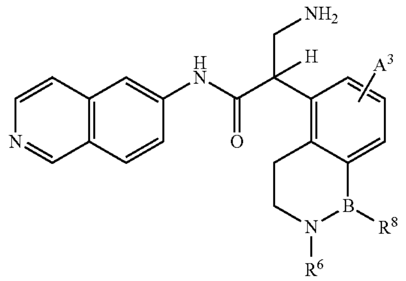
Formula 22
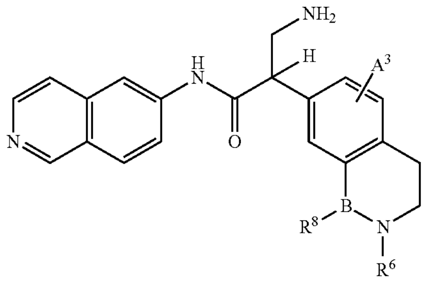
Formula 23
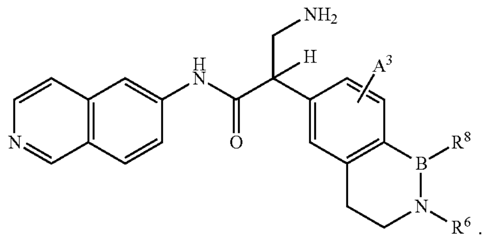
6. The compound of claim 2, wherein Formula 2 is represented by any of Formulae 24-26:
Formula 24
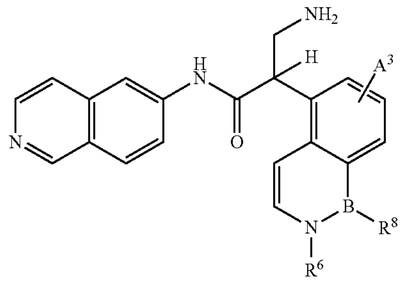
Formula 25
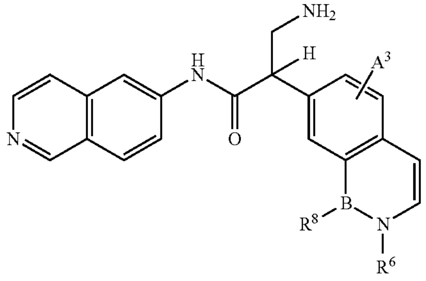

-continued
Formula 26
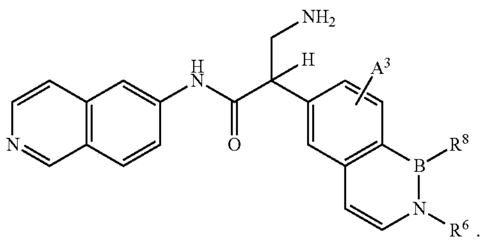
7. The compound of claim 2, wherein Formula 2 is represented by any of Formulae 27-32:
Formula 27
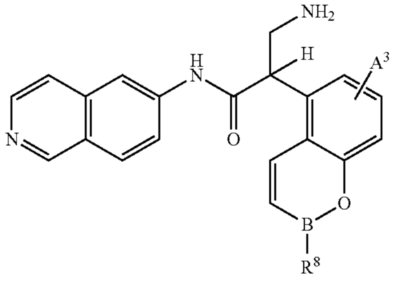
Formula 28
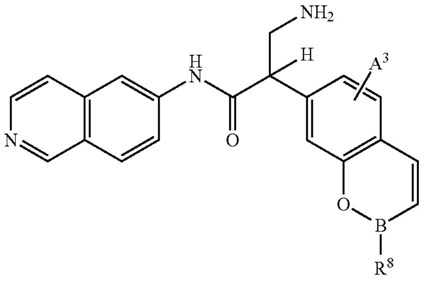
Formula 29
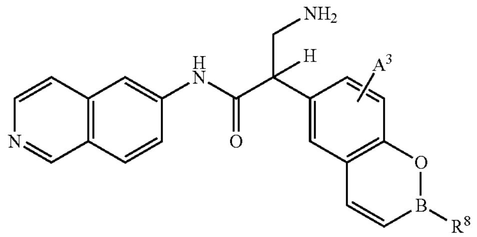
Formula 30
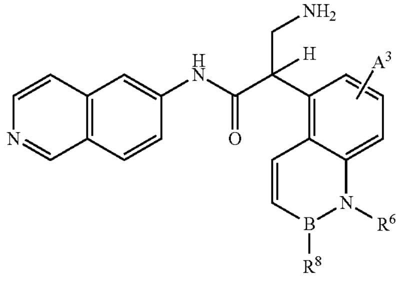
-continued
Formula 31
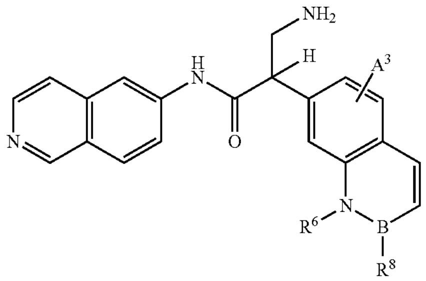
Formula 32
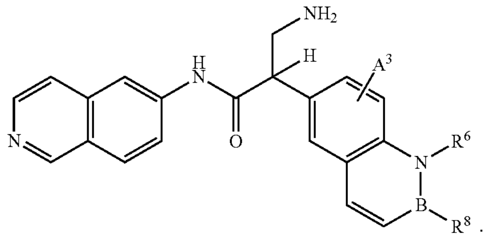
8. The compound of claim 2, wherein Formula 2 is represented by any of Formulae 33-38:
Formula 33
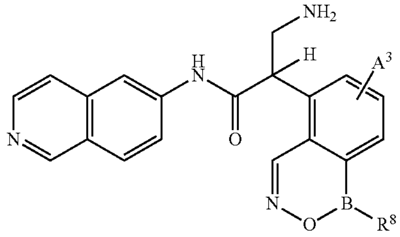
Formula 34
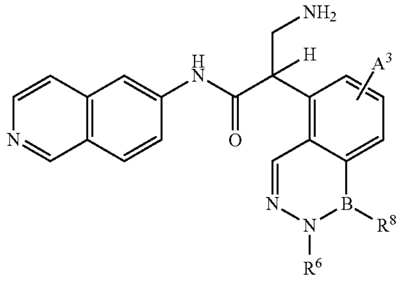
Formula 35
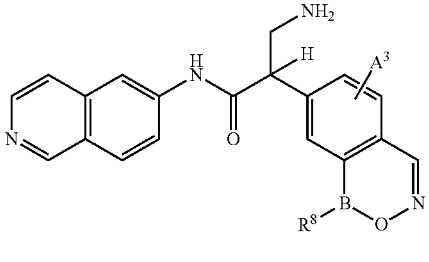

-continued
Formula 36
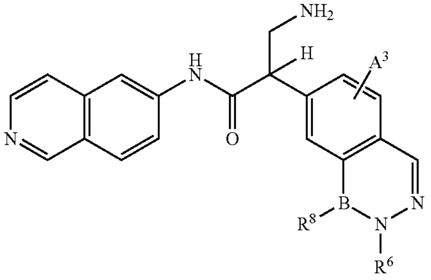
Formula 37
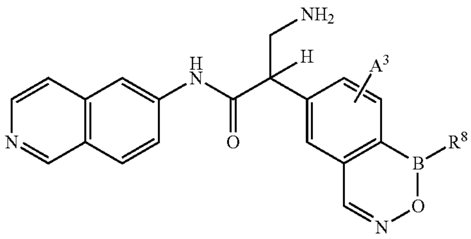
Formula 38
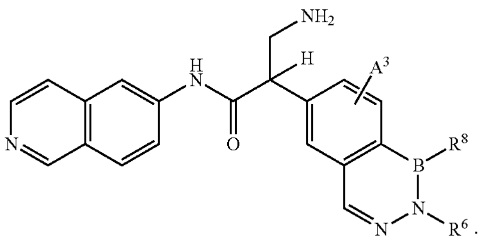
9. The compound of claim 2, wherein Formula 2 is represented by any of Formulae 39-41:
Formula 39
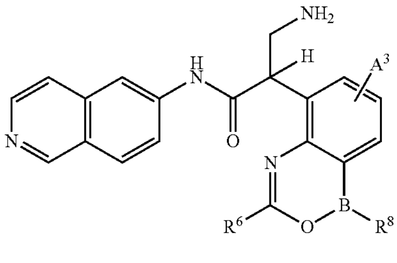
Formula 40
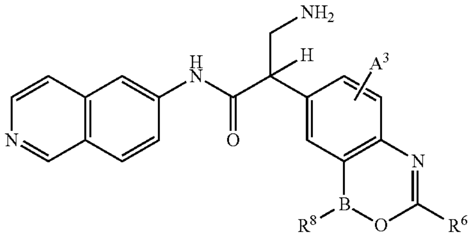
-continued
Formula 41
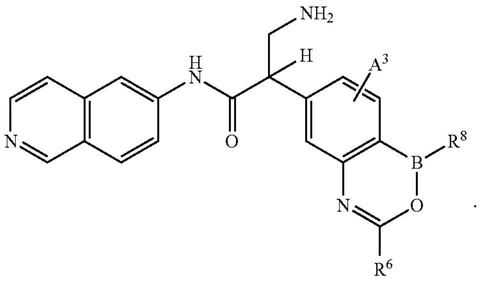
10. The compound of claim 2, wherein Formula 2 is represented by any of Formulae 42-47:
Formula 42
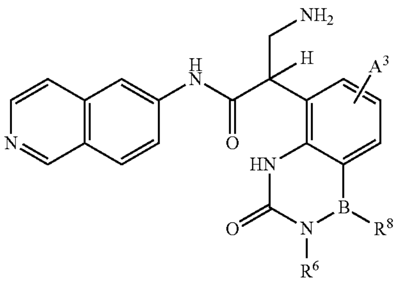
Formula 43
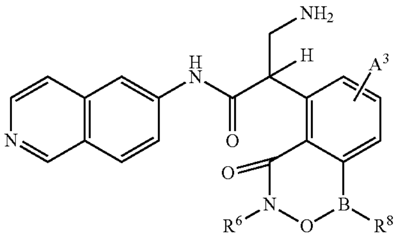
Formula 44
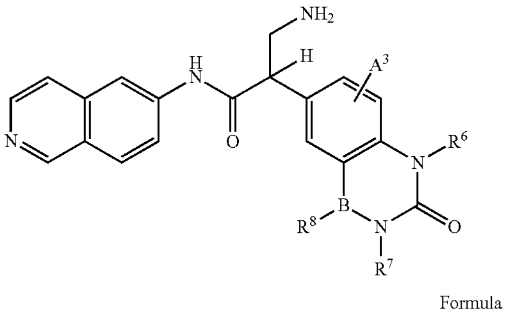
Formula 45
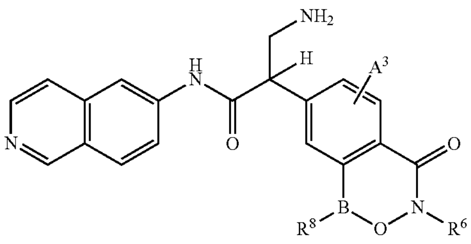

-continued
Formula 46
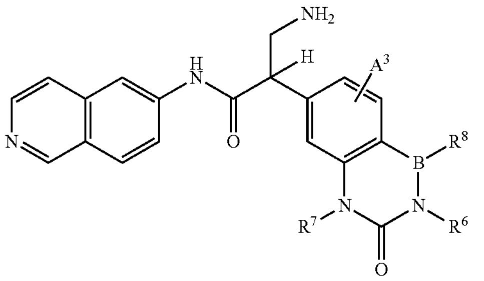
Formula 47
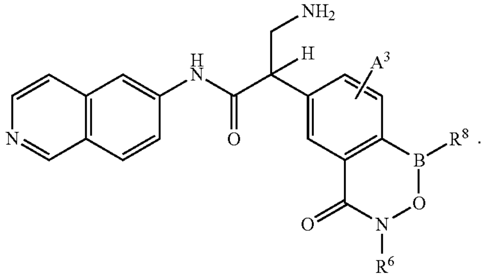
11. The compound of claim 2, wherein Formula 2 is represented by any of Formulae 48-56:
Formula 48
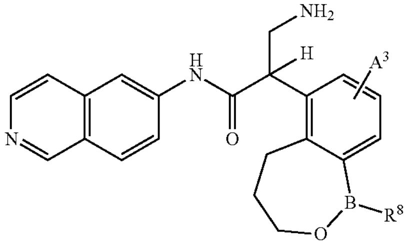
Formula 49
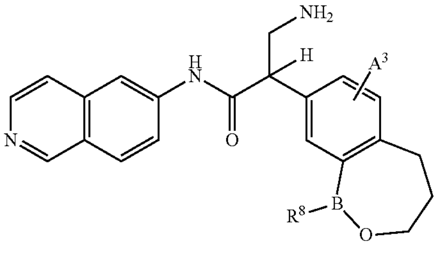
Formula 50
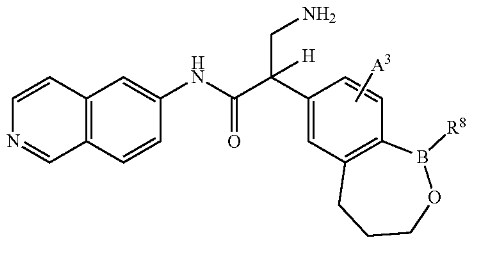
-continued
Formula 51
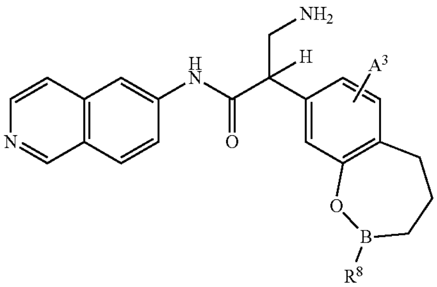
Formula 52
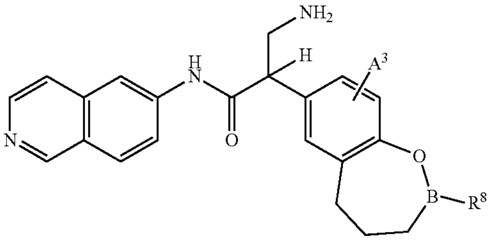
Formula 53
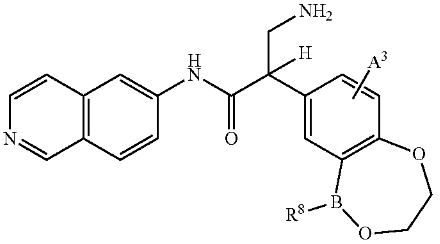
Formula 54
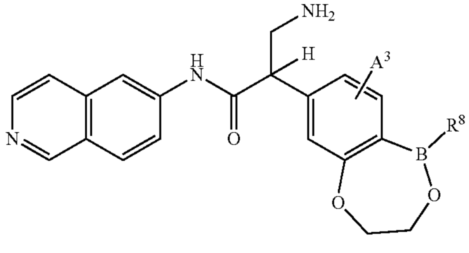
Formula 55
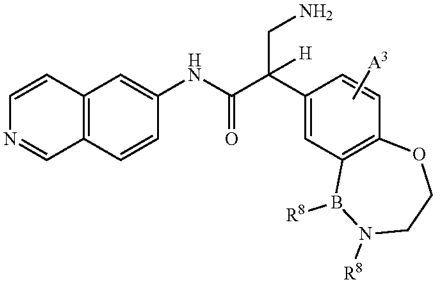

-continued
Formula 56
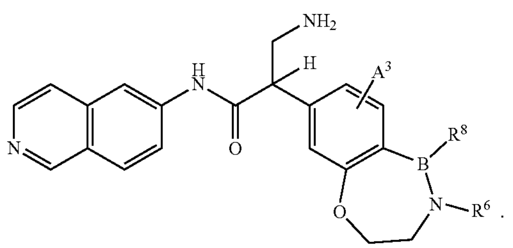
Formula 57
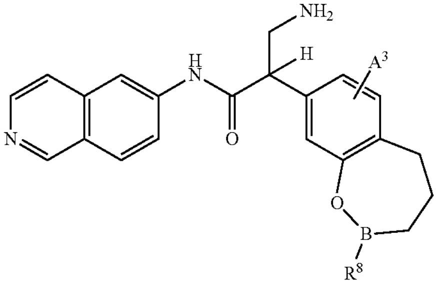
12. The compound of claim 1, wherein Formula 1 is represented by any of Formula 57 or Formulae 67:
Formula 57
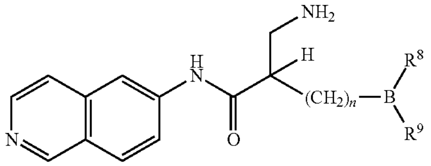
Formula 67
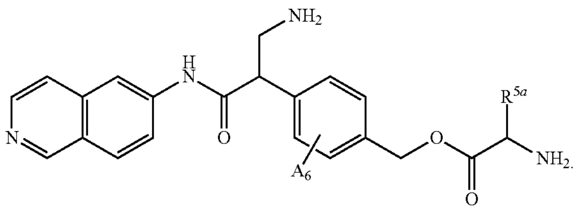
13. The compound of claim 2 selected from the group consisting of:
| # | Structure |
|---|---|
| 198 | 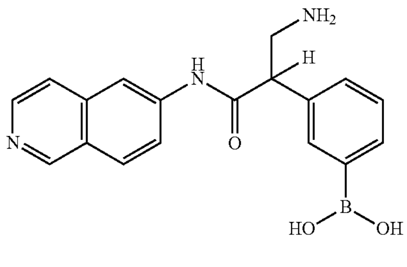 [SMILES: NCC(C(=O)Nc1ccc2cnccc2c1)c1cccc(B(O)O)c1] |
-continued
| # | Structure |
|---|---|
| 199 | 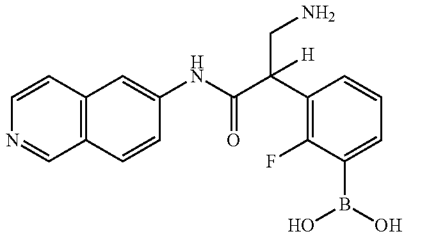 [SMILES: NCC(C(=O)Nc1ccc2cnccc2c1)c1cccc(B(O)O)c1F] |
| 200 | 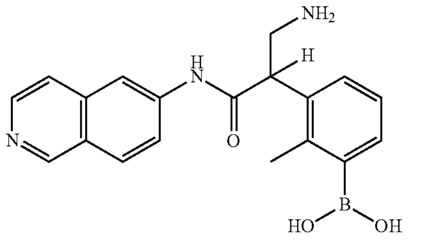 [SMILES: Cc1c(B(O)O)cccc1C(CN)C(=O)Nc1ccc2cnccc2c1] |
| 201 | 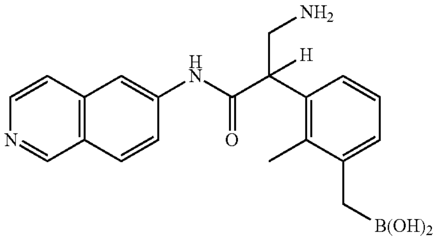 [SMILES: Cc1c(CB(O)O)cccc1C(CN)C(=O)Nc1ccc2cnccc2c1] |
| 202 | 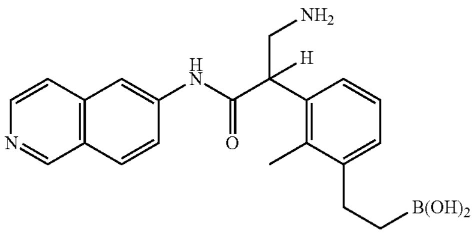 [SMILES: Cc1c(CCB(O)O)cccc1C(CN)C(=O)Nc1ccc2cnccc2c1] |
| 203 | 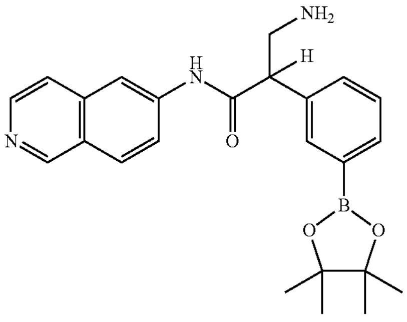 [SMILES: CC1(C)OB(c2cccc(C(CN)C(=O)Nc3ccc4cnccc4c3)c2)OC1(C)C] |
| 204 | 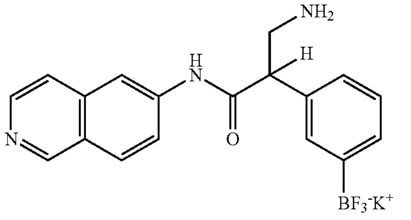 |

-continued
| # | Structure |
|---|---|
| 205 | 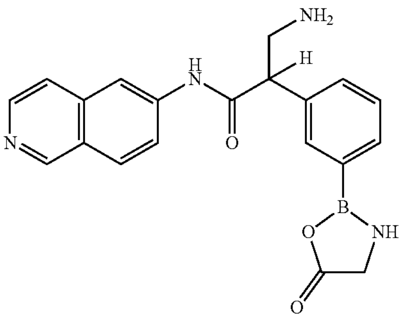 [SMILES: NCC(C(=O)Nc1ccc2cnccc2c1)c1cccc(B2NCC(=O)O2)c1] |
| 206 | 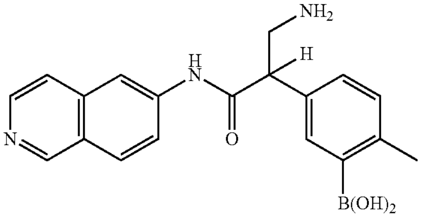 [SMILES: Cc1ccc(C(CN)C(=O)Nc2ccc3cnccc3c2)cc1B(O)O] |
| 207 | 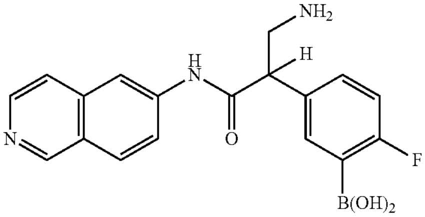 [SMILES: NCC(C(=O)Nc1ccc2cnccc2c1)c1ccc(F)c(B(O)O)c1] |
| 208 | 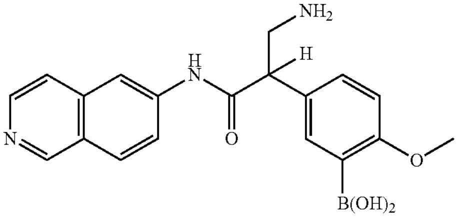 [SMILES: COc1ccc(C(CN)C(=O)Nc2ccc3cnccc3c2)cc1B(O)O] |
| 209 | 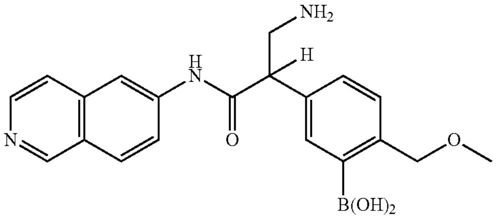 [SMILES: COCc1ccc(C(CN)C(=O)Nc2ccc3cnccc3c2)cc1B(O)O] |
| 210 | 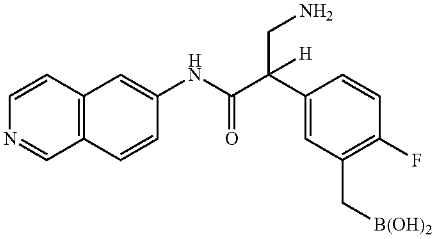 [SMILES: NCC(C(=O)Nc1ccc2cnccc2c1)c1ccc(F)c(CB(O)O)c1] |
-continued
| # | Structure |
|---|---|
| 211 | 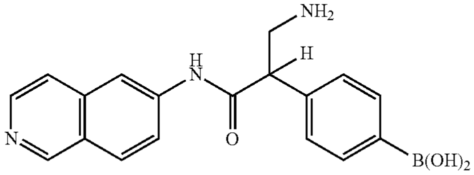 [SMILES: NCC(C(=O)Nc1ccc2cnccc2c1)c1ccc(B(O)O)cc1] |
| 212 | 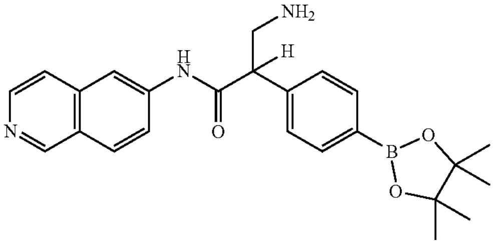 [SMILES: CC1(C)OB(c2ccc(C(CN)C(=O)Nc3ccc4cnccc4c3)cc2)OC1(C)C] |
| 213 | 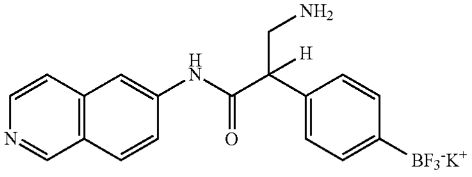 |
| 214 | 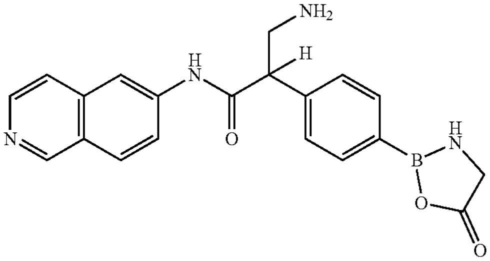 [SMILES: NCC(C(=O)Nc1ccc2cnccc2c1)c1ccc(B2NCC(=O)O2)cc1] |
| 215 | 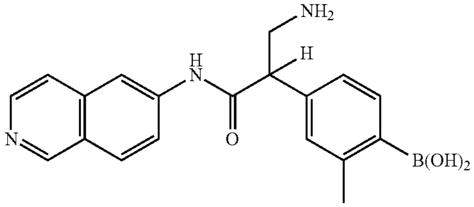 [SMILES: Cc1cc(C(CN)C(=O)Nc2ccc3cnccc3c2)ccc1B(O)O] |
| 216 | 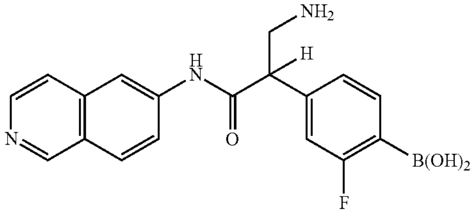 [SMILES: NCC(C(=O)Nc1ccc2cnccc2c1)c1ccc(B(O)O)c(F)c1] |
| 217 | 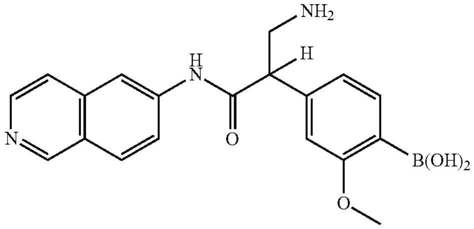 [SMILES: COc1cc(C(CN)C(=O)Nc2ccc3cnccc3c2)ccc1B(O)O] |

-continued
| # | Structure |
|---|---|
| 218 | 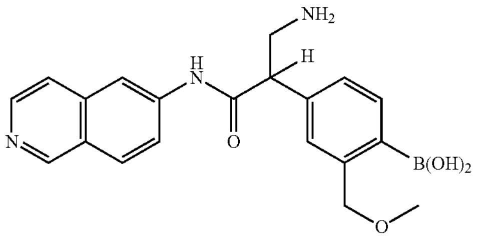 [SMILES: COCc1cc(C(CN)C(=O)Nc2ccc3cnccc3c2)ccc1B(O)O] |
| 219 | 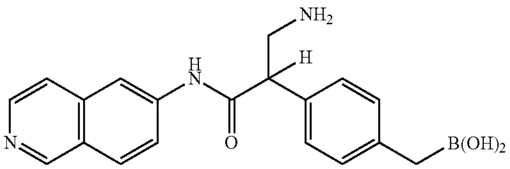 [SMILES: NCC(C(=O)Nc1ccc2cnccc2c1)c1ccc(CB(O)O)cc1] |
| 220 | 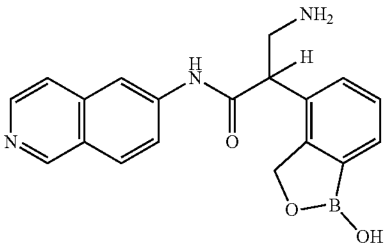 [SMILES: NCC(C(=O)Nc1ccc2cnccc2c1)c1cccc2c1COB2O] |
| 221 | 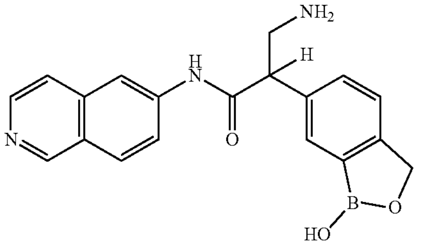 [SMILES: NCC(C(=O)Nc1ccc2cnccc2c1)c1ccc2c(c1)B(O)OC2] |
| 222 | 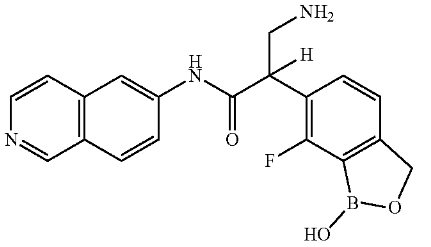 [SMILES: NCC(C(=O)Nc1ccc2cnccc2c1)c1ccc2c(c1F)B(O)OC2] |
| 223 | 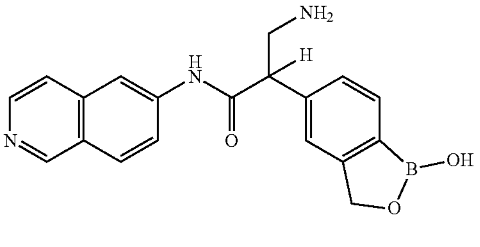 [SMILES: NCC(C(=O)Nc1ccc2cnccc2c1)c1ccc2c(c1)COB2O] |
-continued
| # | Structure |
|---|---|
| 224 | 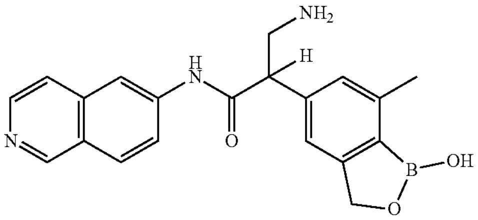 [SMILES: Cc1cc(C(CN)C(=O)Nc2ccc3cnccc3c2)cc2c1B(O)OC2] |
| 225 | 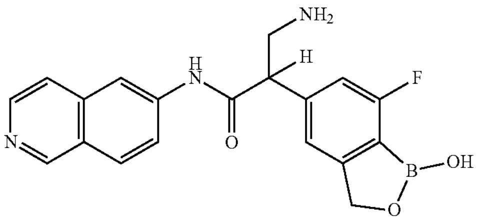 [SMILES: NCC(C(=O)Nc1ccc2cnccc2c1)c1cc(F)c2c(c1)COB2O] |
| 226 | 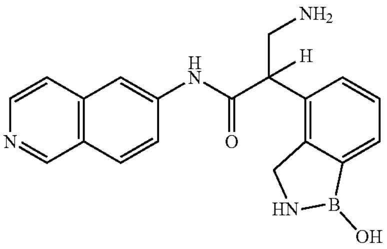 [SMILES: NCC(C(=O)Nc1ccc2cnccc2c1)c1cccc2c1CNB2O] |
| 227 | 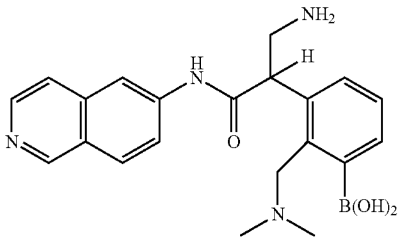 [SMILES: CN(C)Cc1c(B(O)O)cccc1C(CN)C(=O)Nc1ccc2cnccc2c1] |
| 228 | 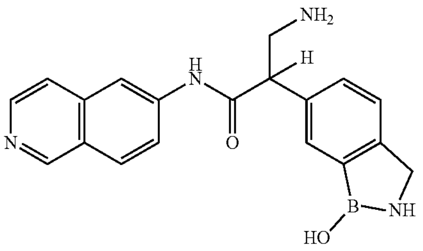 [SMILES: NCC(C(=O)Nc1ccc2cnccc2c1)c1ccc2c(c1)B(O)NC2] |
| 229 | 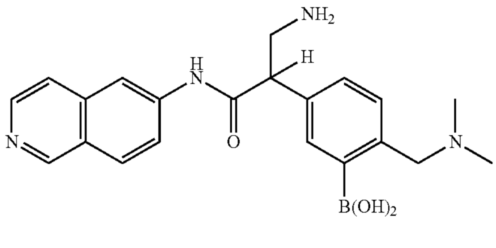 [SMILES: CN(C)Cc1ccc(C(CN)C(=O)Nc2ccc3cnccc3c2)cc1B(O)O] |

-continued
| # | Structure |
|---|---|
| 230 | 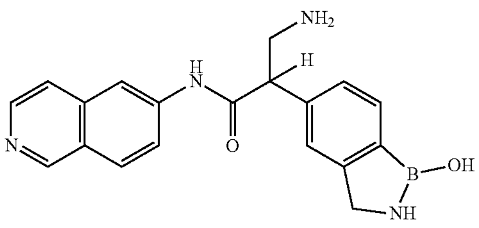 [SMILES: NCC(C(=O)Nc1ccc2cnccc2c1)c1ccc2c(c1)CNB2O] |
| 231 | 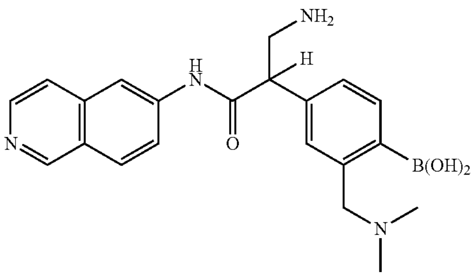 [SMILES: CN(C)Cc1cc(C(CN)C(=O)Nc2ccc3cnccc3c2)ccc1B(O)O] |
| 232 | 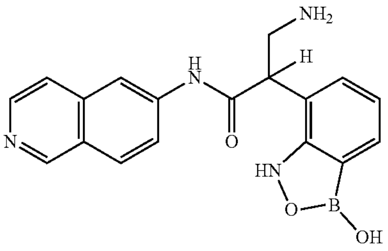 [SMILES: NCC(C(=O)Nc1ccc2cnccc2c1)c1cccc2c1NOB2O] |
| 233 | 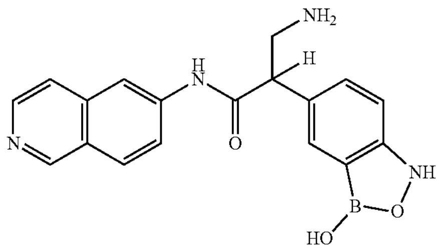 [SMILES: NCC(C(=O)Nc1ccc2cnccc2c1)c1ccc2c(c1)B(O)ON2] |
| 234 | 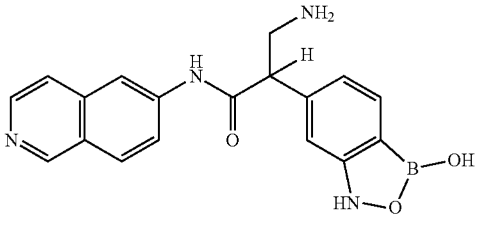 [SMILES: NCC(C(=O)Nc1ccc2cnccc2c1)c1ccc2c(c1)NOB2O] |
| 235 | 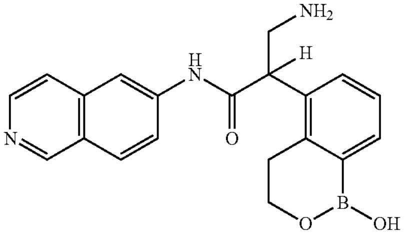 [SMILES: NCC(C(=O)Nc1ccc2cnccc2c1)c1cccc2c1CCOB2O] |
-continued
| # | Structure |
|---|---|
| 236 | 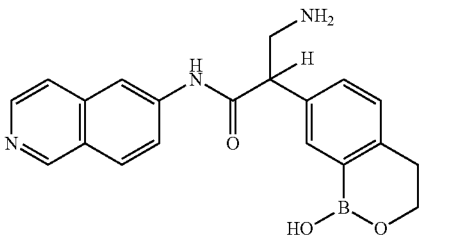 [SMILES: NCC(C(=O)Nc1ccc2cnccc2c1)c1ccc2c(c1)B(O)OCC2] |
| 237 | 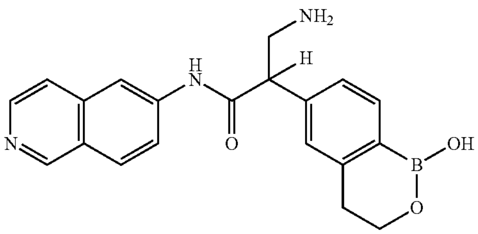 [SMILES: NCC(C(=O)Nc1ccc2cnccc2c1)c1ccc2c(c1)CCOB2O] |
| 238 | 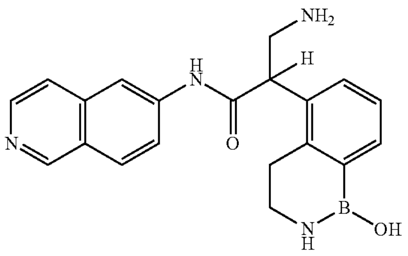 [SMILES: NCC(C(=O)Nc1ccc2cnccc2c1)c1cccc2c1CCNB2O] |
| 239 | 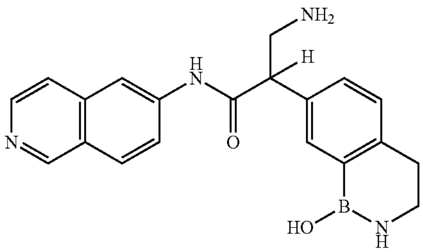 [SMILES: NCC(C(=O)Nc1ccc2cnccc2c1)c1ccc2c(c1)B(O)NCC2] |
| 240 | 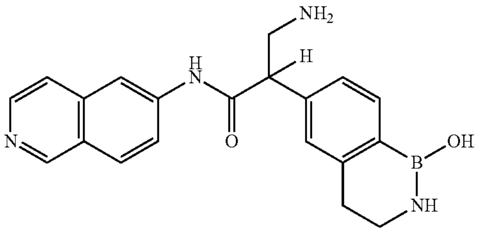 [SMILES: NCC(C(=O)Nc1ccc2cnccc2c1)c1ccc2c(c1)CCNB2O] |
| 241 | 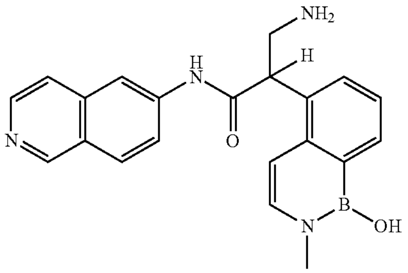 [SMILES: CN1C=Cc2c(cccc2C(CN)C(=O)Nc2ccc3cnccc3c2)B1O] |

-continued
| # | Structure |
|---|---|
| 242 | 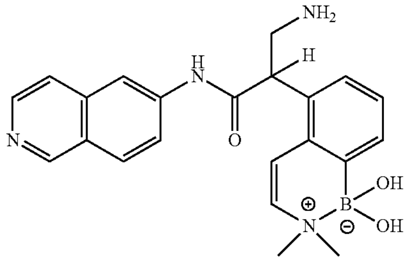 [SMILES: C[N+]1(C)C=Cc2c(C(CN)C(=O)Nc3ccc4cnccc4c3)cccc2[B-]1(O)O] |
| 243 | 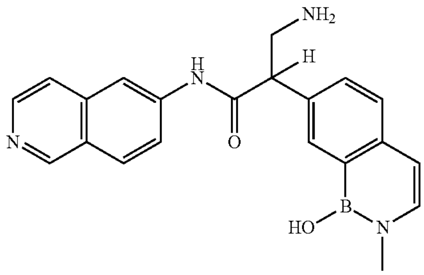 [SMILES: CN1C=Cc2ccc(C(CN)C(=O)Nc3ccc4cnccc4c3)cc2B1O] |
| 244 | 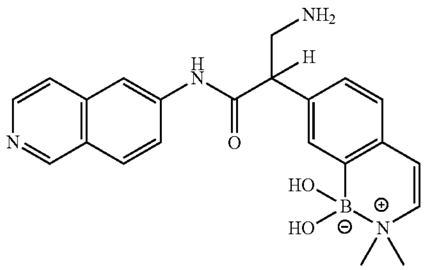 [SMILES: C[N+]1(C)C=Cc2ccc(C(CN)C(=O)Nc3ccc4cnccc4c3)cc2[B-]1(O)O] |
| 245 | 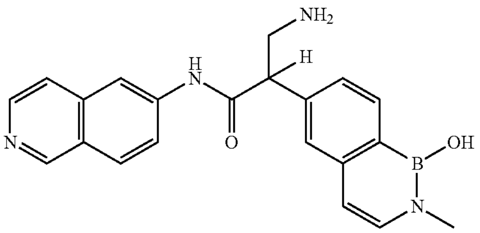 [SMILES: CN1C=Cc2cc(C(CN)C(=O)Nc3ccc4cnccc4c3)ccc2B1O] |
| 246 | 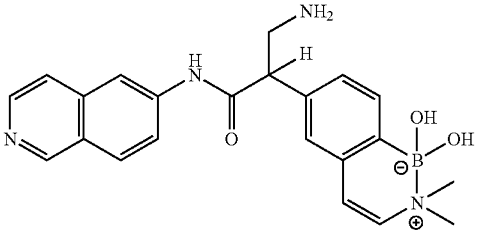 [SMILES: C[N+]1(C)C=Cc2cc(C(CN)C(=O)Nc3ccc4cnccc4c3)ccc2[B-]1(O)O] |
| 247 | 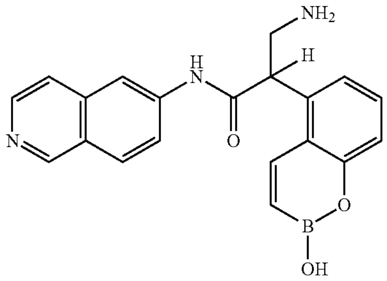 [SMILES: NCC(C(=O)Nc1ccc2cnccc2c1)c1cccc2c1C=CB(O)O2] |
-continued
| # | Structure |
|---|---|
| 248 | 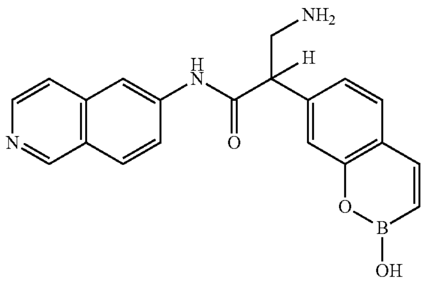 [SMILES: NCC(C(=O)Nc1ccc2cnccc2c1)c1ccc2c(c1)OB(O)C=C2] |
| 249 | 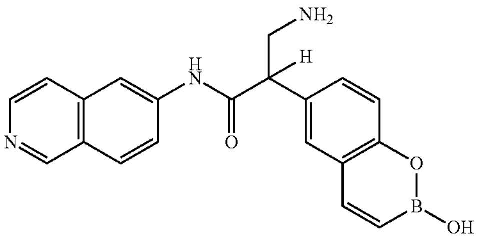 [SMILES: NCC(C(=O)Nc1ccc2cnccc2c1)c1ccc2c(c1)C=CB(O)O2] |
| 250 | 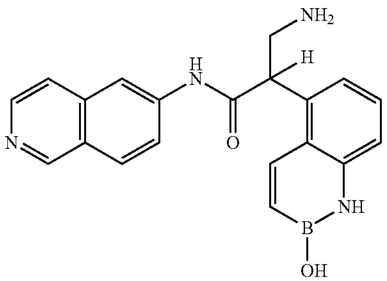 [SMILES: NCC(C(=O)Nc1ccc2cnccc2c1)c1cccc2c1C=CB(O)N2] |
| 251 | 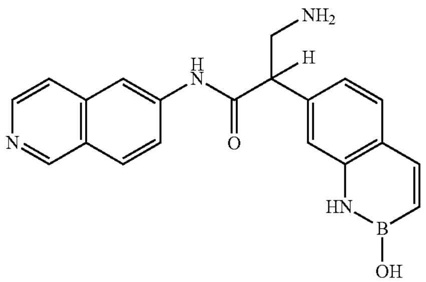 [SMILES: NCC(C(=O)Nc1ccc2cnccc2c1)c1ccc2c(c1)NB(O)C=C2] |
| 252 | 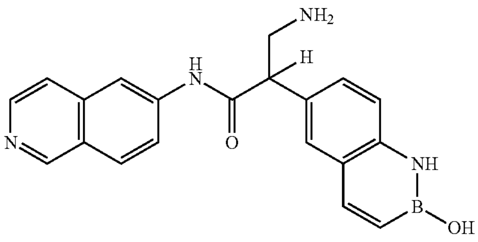 [SMILES: NCC(C(=O)Nc1ccc2cnccc2c1)c1ccc2c(c1)C=CB(O)N2] |

-continued
| # | Structure |
| --- | --- |
| 253 | 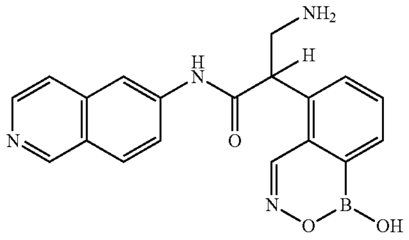 [SMILES: NCC(C(=O)Nc1ccc2cnccc2c1)c1cccc2c1C=NOB2O] |
| 254 | 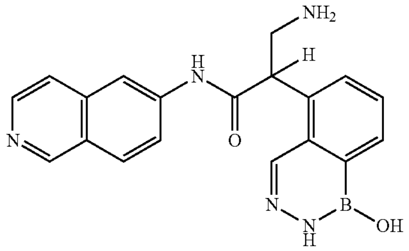 [SMILES: NCC(C(=O)Nc1ccc2cnccc2c1)c1cccc2c1C=NNB2O] |
| 255 | 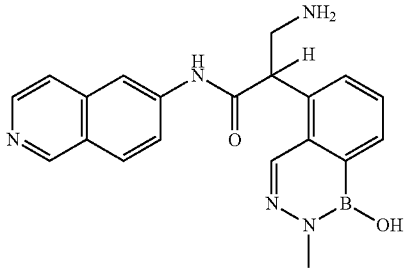 [SMILES: CN1N=Cc2c(cccc2C(CN)C(=O)Nc2ccc3cnccc3c2)B1O] |
| 256 | 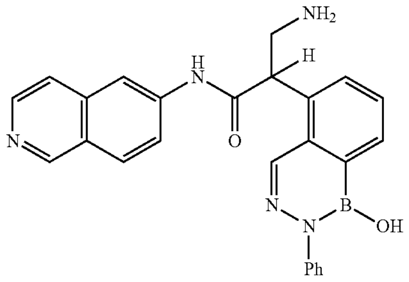 [SMILES: NCC(C(=O)Nc1ccc2cnccc2c1)c1cccc2c1C=NN(c1ccccc1)B2O] |
| 257 | 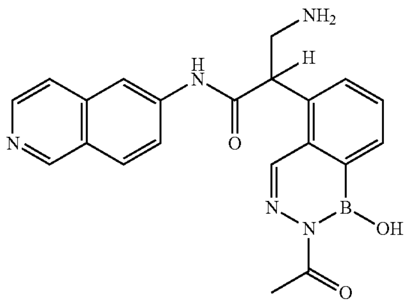 [SMILES: CC(=O)N1N=Cc2c(cccc2C(CN)C(=O)Nc2ccc3cnccc3c2)B1O] |
-continued
| # | Structure |
| --- | --- |
| 258 | 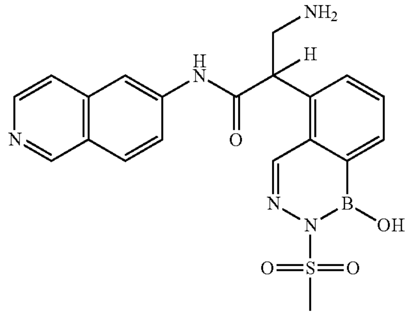 [SMILES: CS(=O)(=O)N1N=Cc2c(cccc2C(CN)C(=O)Nc2ccc3cnccc3c2)B1O] |
| 259 | 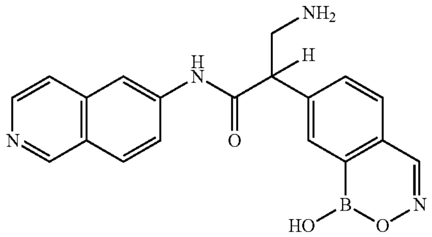 [SMILES: NCC(C(=O)Nc1ccc2cnccc2c1)c1ccc2c(c1)B(O)ON=C2] |
| 260 | 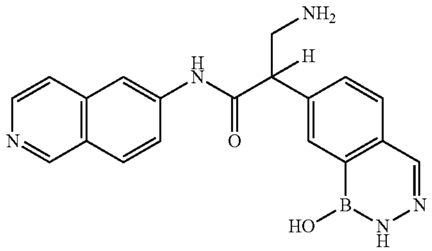 [SMILES: NCC(C(=O)Nc1ccc2cnccc2c1)c1ccc2c(c1)B(O)NN=C2] |
| 261 | 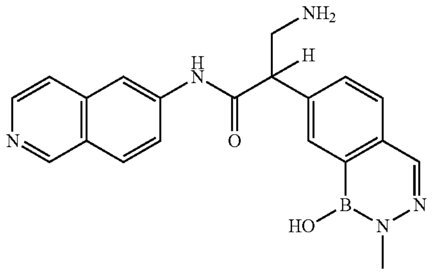 [SMILES: CN1N=Cc2ccc(C(CN)C(=O)Nc3ccc4cnccc4c3)cc2B1O] |
| 262 | 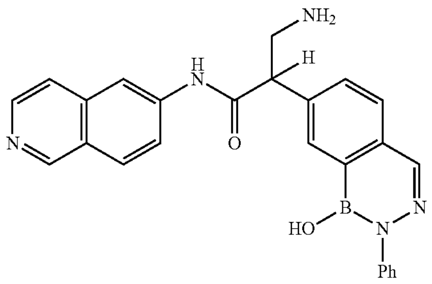 [SMILES: NCC(C(=O)Nc1ccc2cnccc2c1)c1ccc2c(c1)B(O)N(c1ccccc1)N=C2] |

-continued
| # | Structure |
|---|---|
| 263 | 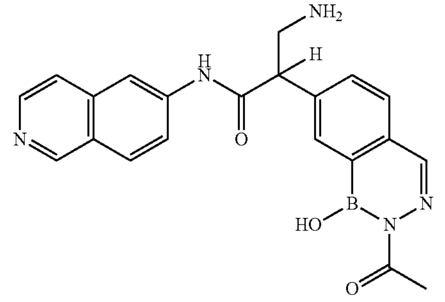 [SMILES: CC(=O)N1N=Cc2ccc(C(CN)C(=O)Nc3ccc4cnccc4c3)cc2B1O] |
| 264 | 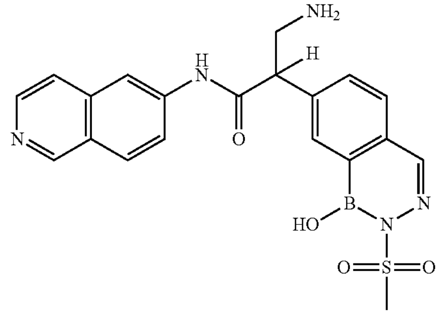 [SMILES: CS(=O)(=O)N1N=Cc2ccc(C(CN)C(=O)Nc3ccc4cnccc4c3)cc2B1O] |
| 265 | 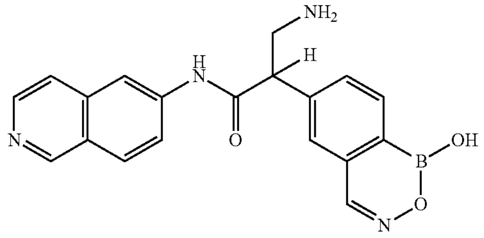 [SMILES: NCC(C(=O)Nc1ccc2cnccc2c1)c1ccc2c(c1)C=NOB2O] |
| 266 | 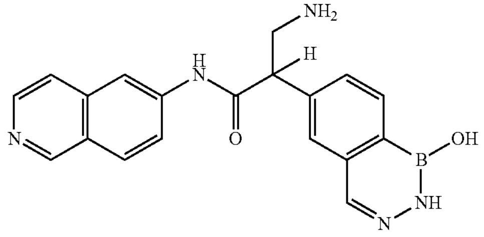 [SMILES: NCC(C(=O)Nc1ccc2cnccc2c1)c1ccc2c(c1)C=NNB2O] |
| 267 | 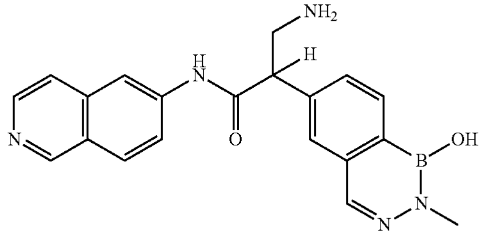 [SMILES: CN1N=Cc2cc(C(CN)C(=O)Nc3ccc4cnccc4c3)ccc2B1O] |
| 268 | 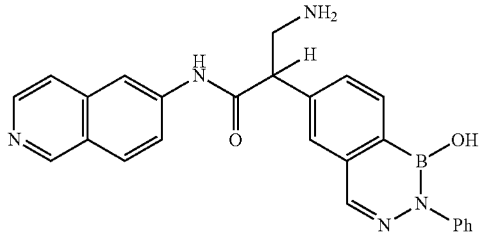 [SMILES: NCC(C(=O)Nc1ccc2cnccc2c1)c1ccc2c(c1)C=NN(c1ccccc1)B2O] |
-continued
| # | Structure |
|---|---|
| 269 | 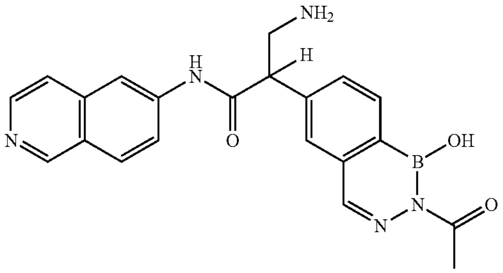 [SMILES: CC(=O)N1N=Cc2cc(C(CN)C(=O)Nc3ccc4cnccc4c3)ccc2B1O] |
| 270 | 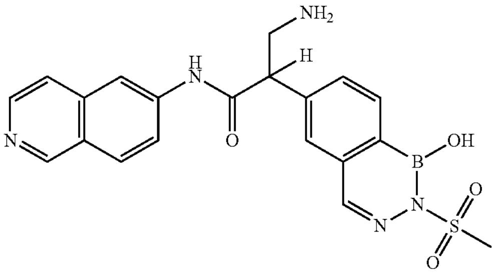 [SMILES: CS(=O)(=O)N1N=Cc2cc(C(CN)C(=O)Nc3ccc4cnccc4c3)ccc2B1O] |
| 271 | 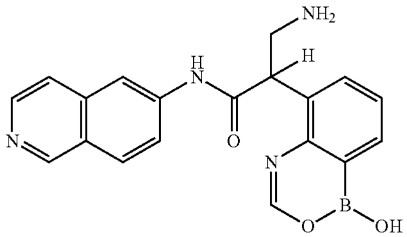 [SMILES: NCC(C(=O)Nc1ccc2cnccc2c1)c1cccc2c1N=COB2O] |
| 272 | 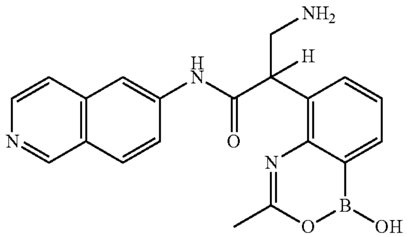 [SMILES: CC1=Nc2c(cccc2C(CN)C(=O)Nc2ccc3cnccc3c2)B(O)O1] |
| 273 | 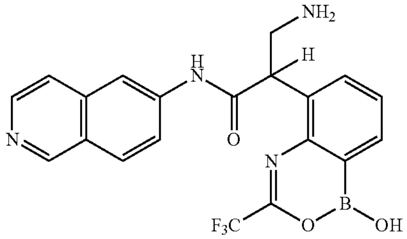 [SMILES: NCC(C(=O)Nc1ccc2cnccc2c1)c1cccc2c1N=C(C(F)(F)F)OB2O] |
| 274 | 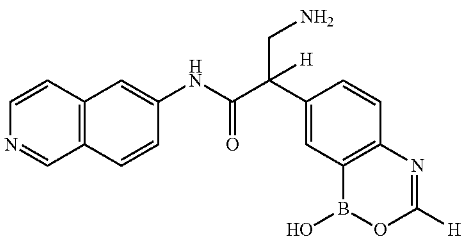 [SMILES: NCC(C(=O)Nc1ccc2cnccc2c1)c1ccc2c(c1)B(O)OC=N2] |

-continued
| # | Structure |
|---|---|
| 275 | 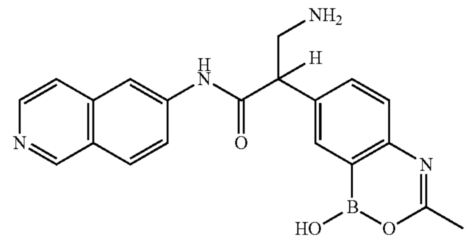 [SMILES: CC1=Nc2ccc(C(CN)C(=O)Nc3ccc4cnccc4c3)cc2B(O)O1] |
| 276 | 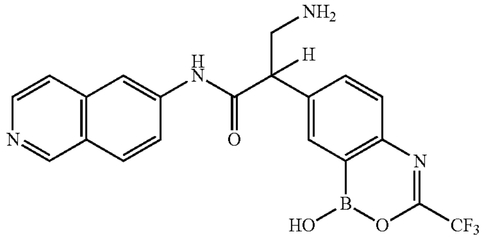 [SMILES: NCC(C(=O)Nc1ccc2cnccc2c1)c1ccc2c(c1)B(O)OC(C(F)(F)F)=N2] |
| 277 | 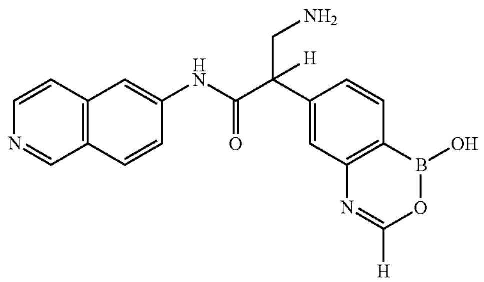 [SMILES: NCC(C(=O)Nc1ccc2cnccc2c1)c1ccc2c(c1)N=COB2O] |
| 278 | 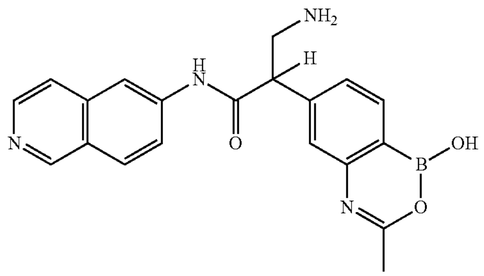 [SMILES: CC1=Nc2cc(C(CN)C(=O)Nc3ccc4cnccc4c3)ccc2B(O)O1] |
| 279 | 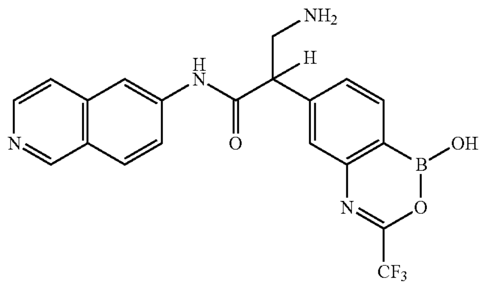 [SMILES: NCC(C(=O)Nc1ccc2cnccc2c1)c1ccc2c(c1)N=C(C(F)(F)F)OB2O] |
| 280 | 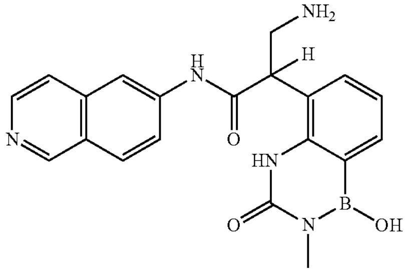 [SMILES: CN1B(O)c2cccc(C(CN)C(=O)Nc3ccc4cnccc4c3)c2NC1=O] |
| 281 | 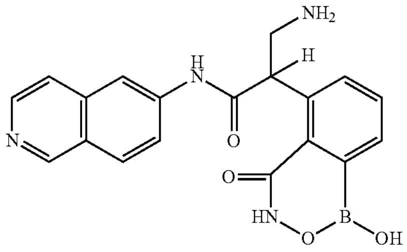 [SMILES: NCC(C(=O)Nc1ccc2cnccc2c1)c1cccc2c1C(=O)NOB2O] |
| 282 | 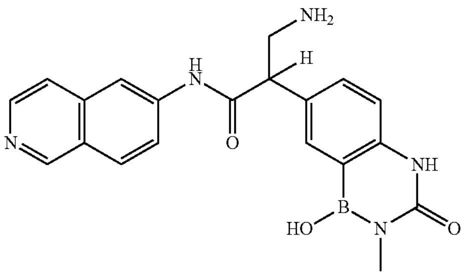 [SMILES: CN1B(O)c2cc(C(CN)C(=O)Nc3ccc4cnccc4c3)ccc2NC1=O] |
| 283 | 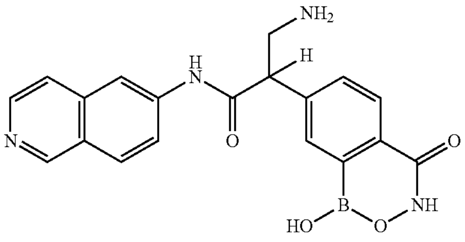 [SMILES: NCC(C(=O)Nc1ccc2cnccc2c1)c1ccc2c(c1)B(O)ONC2=O] |
| 284 | 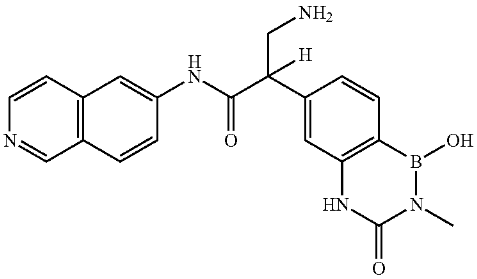 [SMILES: CN1B(O)c2ccc(C(CN)C(=O)Nc3ccc4cnccc4c3)cc2NC1=O] |
| 285 | 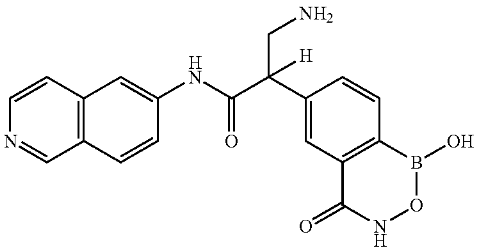 [SMILES: NCC(C(=O)Nc1ccc2cnccc2c1)c1ccc2c(c1)C(=O)NOB2O] |

-continued
| # | Structure |
|---|---|
| 286 | 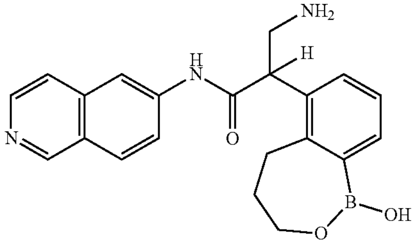 [SMILES: NCC(C(=O)Nc1ccc2cnccc2c1)c1cccc2c1CCCOB2O] |
| 287 | 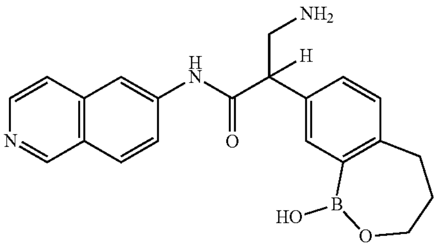 [SMILES: NCC(C(=O)Nc1ccc2cnccc2c1)c1ccc2c(c1)B(O)OCCC2] |
| 288 | 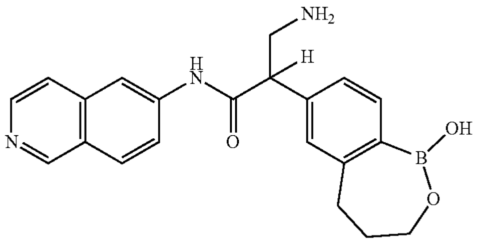 [SMILES: NCC(C(=O)Nc1ccc2cnccc2c1)c1ccc2c(c1)CCCOB2O] |
| 289 | 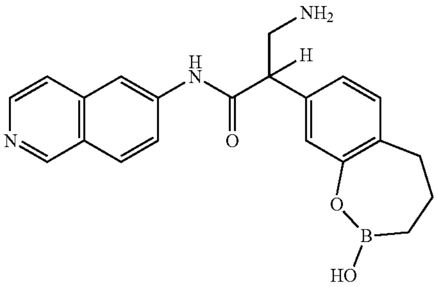 [SMILES: NCC(C(=O)Nc1ccc2cnccc2c1)c1ccc2c(c1)OB(O)CCC2] |
| 290 | 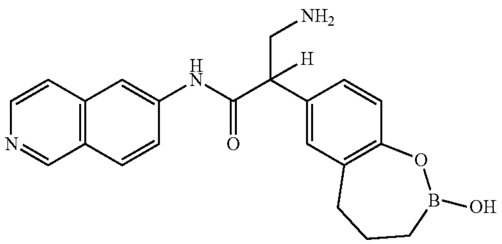 [SMILES: NCC(C(=O)Nc1ccc2cnccc2c1)c1ccc2c(c1)CCCB(O)O2] |
| 291 | 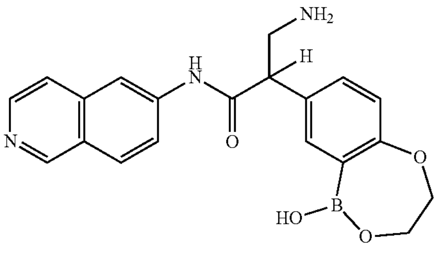 [SMILES: NCC(C(=O)Nc1ccc2cnccc2c1)c1ccc2c(c1)B(O)OCCO2] |
-continued
| # | Structure |
|---|---|
| 292 | 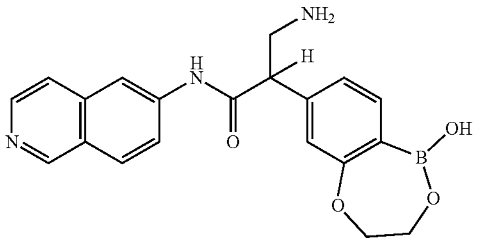 [SMILES: NCC(C(=O)Nc1ccc2cnccc2c1)c1ccc2c(c1)OCCOB2O] |
| 293 | 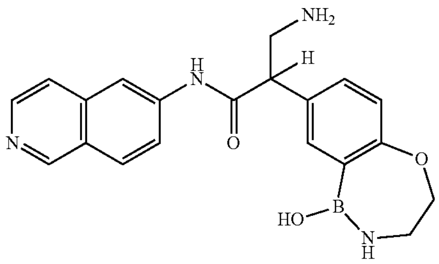 [SMILES: NCC(C(=O)Nc1ccc2cnccc2c1)c1ccc2c(c1)B(O)NCCO2] |
| 294 | 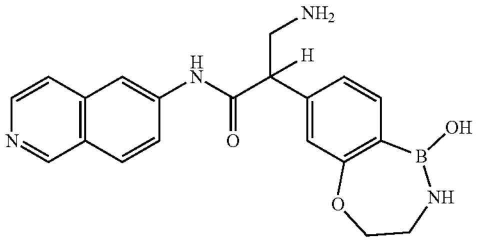 [SMILES: NCC(C(=O)Nc1ccc2cnccc2c1)c1ccc2c(c1)OCCNB2O] |
| | 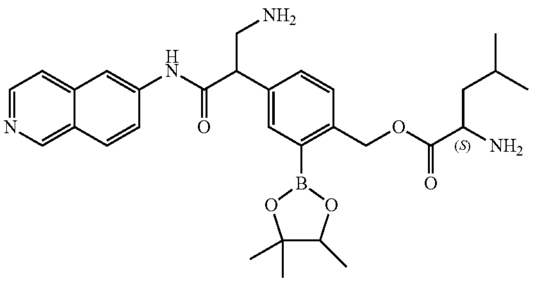 222-1 (Type I) |
| | f |
| | 222-2 (Type I) |
| | 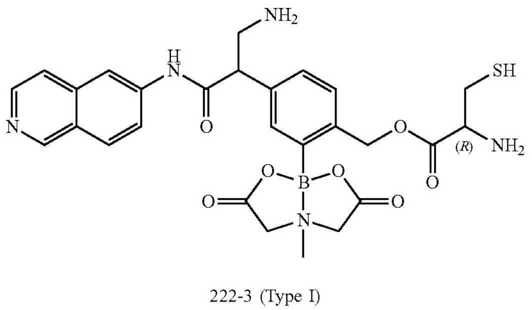 222-3 (Type I) |

14. The compound of claim 1, wherein Formula 1 is represented by Formula A:
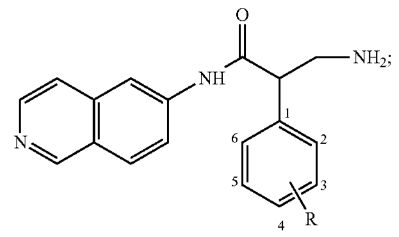
wherein:
R is selected from:
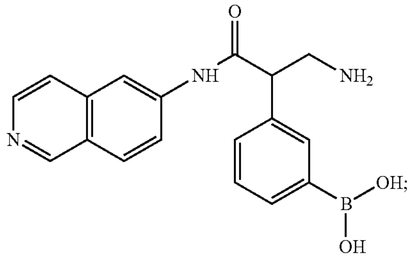
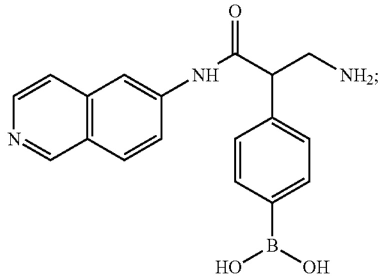
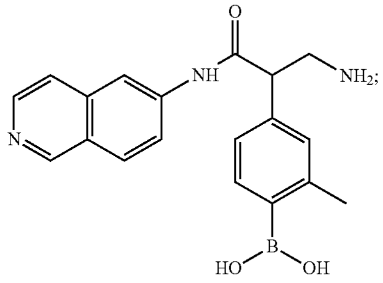
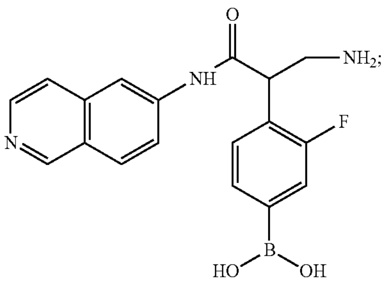
-continued
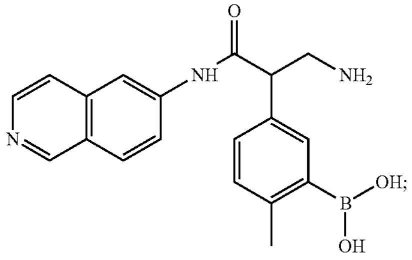
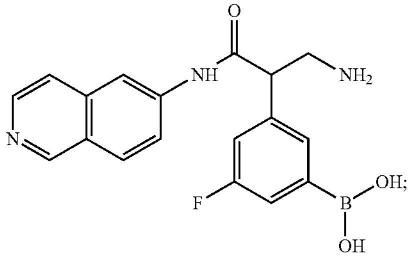
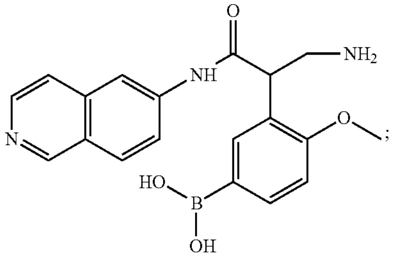
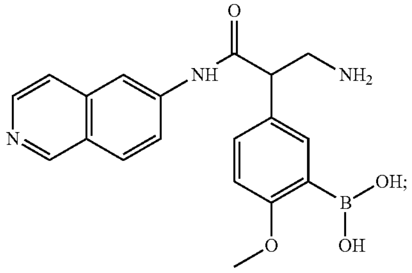
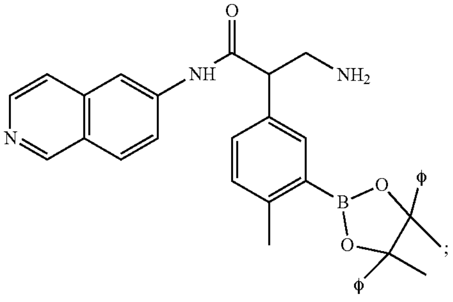
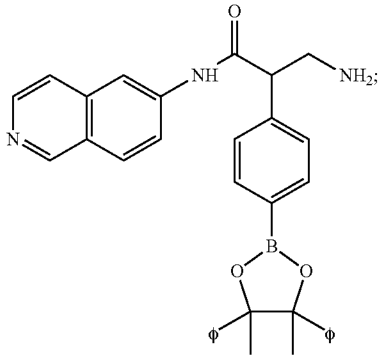

-continued

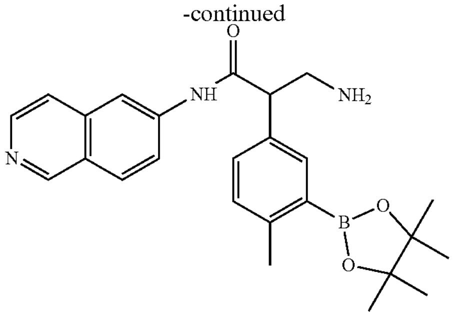

;

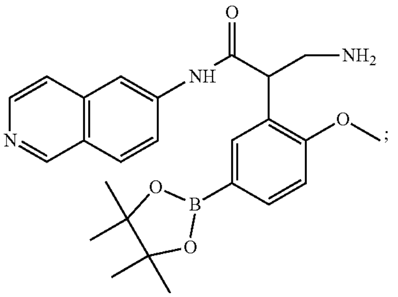

; and

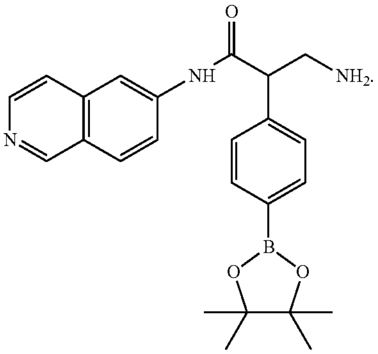

15. A compound according to claim 14, wherein R is selected from:

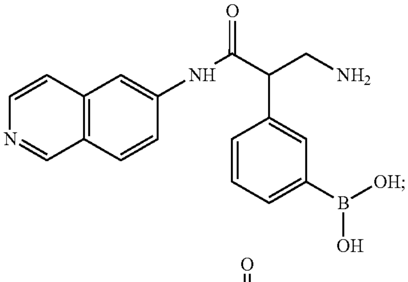

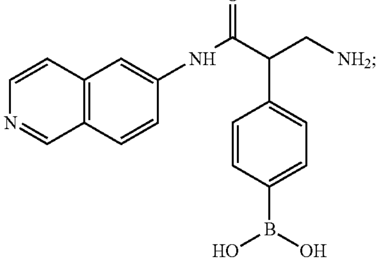

-continued

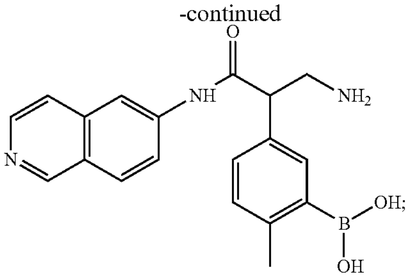

and

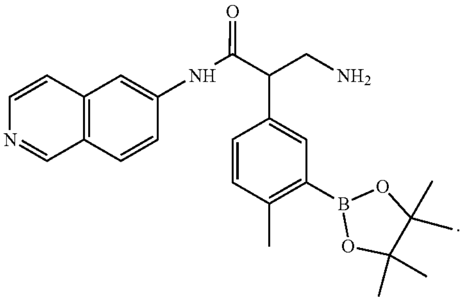

16. A pharmaceutical composition comprising the compound of claim 1, or a pharmaceutically acceptable salt or solvate thereof.

17. A method of treating an ocular disease, disorder, injury, or condition in a subject, comprising the steps of administering to the subject the compound of claim 1, or a pharmaceutically acceptable salt or solvate thereof.

18. The method of claim 17, wherein the compound is administered in conjunction with one or more additional therapeutic agents, wherein the additional therapeutic agent is selected from the group consisting of prostaglandin-like compounds, beta-adrenergic blockers, alpha-adrenergic agonists, carbonic anhydrase inhibitors, miotic or cholinergic agonists, sympathomimetics, Rho kinase inhibitors, and A1 adenosine receptor agonists.

19. A compound of Formula 68

Formula 68

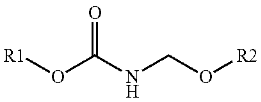

wherein $R^1$ is $—C(CH_3)_3$ and R2 is $CH_3$, or,

R1 is $—CH_2CH_2Si(CH_3)_3$ and R2 is either H or $CH_3$.

20. A compound of Formula 72

Formula 72

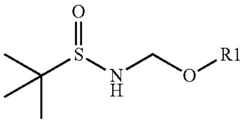

wherein $R^1$ is either H or $CH_3$.

* * * * *